(12) United States Patent
Hoflack et al.

(10) Patent No.: US 9,370,520 B2
(45) Date of Patent: Jun. 21, 2016

(54) MACROCYCLIC LRRK2 KINASE INHIBITORS

(71) Applicants: IPSEN PHARMA S.A.S., Boulogne-Billancourt (FR); ONCODESIGN S.A., Dijon (FR)

(72) Inventors: Jan Hoflack, Malle (BE); Petra Blom, Destelbergen (BE)

(73) Assignee: IPSEN PHARMA S.A.S., Boulogne-Billancourt (FR)

( * ) Notice: Subject to any disclaimer, the term of this patent is extended or adjusted under 35 U.S.C. 154(b) by 0 days.

(21) Appl. No.: 14/747,882

(22) Filed: Jun. 23, 2015

(65) Prior Publication Data

US 2015/0290198 A1    Oct. 15, 2015

Related U.S. Application Data

(62) Division of application No. 14/348,138, filed as application No. PCT/IB2012/002318 on Sep. 28, 2012, now Pat. No. 9,096,609.

(30) Foreign Application Priority Data

Sep. 30, 2011    (WO) ................. PCT/EP2011/067086

(51) Int. Cl.
| | |
|---|---|
| A61K 31/504 | (2006.01) |
| A61K 31/505 | (2006.01) |
| A61K 31/519 | (2006.01) |
| C07D 487/18 | (2006.01) |
| C07D 498/18 | (2006.01) |
| C07D 487/16 | (2006.01) |
| C07D 498/16 | (2006.01) |
| C07D 498/22 | (2006.01) |
| C07D 515/16 | (2006.01) |

(52) U.S. Cl.
CPC ............ A61K 31/519 (2013.01); C07D 487/16 (2013.01); C07D 487/18 (2013.01); C07D 498/16 (2013.01); C07D 498/18 (2013.01); C07D 498/22 (2013.01); C07D 515/16 (2013.01)

(58) Field of Classification Search
CPC ........................... A61K 31/504; A61K 31/505
See application file for complete search history.

(56) References Cited

U.S. PATENT DOCUMENTS

| 6,194,410 B1 | 2/2001 | Bös et al. |
| 6,369,086 B1 | 4/2002 | Davis et al. |
| 6,369,087 B1 | 4/2002 | Whittle et al. |
| 6,372,733 B1 | 4/2002 | Caldwell et al. |
| 6,372,778 B1 | 4/2002 | Tung et al. |
| 8,778,939 B2 | 7/2014 | Nichols et al. |

FOREIGN PATENT DOCUMENTS

| EP | 0729758 A2 | 9/1996 |
| EP | 1354884 A1 | 10/2003 |
| EP | 1908764 A1 | 4/2008 |
| WO | 9509615 A1 | 4/1995 |
| WO | 2006045392 A2 | 5/2006 |
| WO | 2006068492 A1 | 6/2006 |
| WO | 2009127652 A2 | 10/2009 |
| WO | 2011038572 A1 | 4/2011 |
| WO | 2012156756 A2 | 11/2012 |

OTHER PUBLICATIONS

Daniels et al., "Insight into the mode of action of the LRRK2 Y1699C pathogenic mutant," J. Neurochem (2011), vol. 116, No. 2, pp. 304-315.
Li, Y. et al., "Mutant LRRK2(R1441G) BAC transgenic mice recapitulate cardinal features of Parkinson's disease," Nature Neuroscience (2009), vol. 12, No. 7, pp. 826-828.
Zhao, Yi et al., "LRRK2 variant associated with Alzheimer's disease " Neurobiology of Aging (2011), vol. 32, pp. 1990-1993.
Zimprich, Alexander et al., "Mutations in LRRK2 Cause Autosomal-Dominant Parkinsonism with Pleomorphic Pathology" Neuron (2004), vol. 44, pp. 601-607.
Simon-Sanchez et al., *Nat Genet.*, 41:1308-1312 (2009).
Paisan-Ruiz et al., *Neuron*, 44:595-600 (2004).

*Primary Examiner* — Bruck Kifle
(74) *Attorney, Agent, or Firm* — Hunton & Williams LLP

(57) ABSTRACT

The present invention relates to novel macrocylic compounds and compositions containing said compounds acting as kinase inhibitors, in particular as inhibitors of LRRK2 (Leucine-Rich Repeat Kinase 2). Moreover, the present invention provides processes for the preparation of the disclosed compounds, as well as methods of using them, for instance as a medicine or diagnostic agent, in particular for the treatment and/or diagnosis of diseases characterized by LRRK2 kinase activity such as neurological disorders including Parkinson's disease and Alzheimer's disease.

9 Claims, 2 Drawing Sheets

MACROCYCLIC LRRK2 KINASE INHIBITORS

CROSS-REFERENCE TO RELATED APPLICATIONS

This application is a divisional application of U.S. patent application Ser. No. 14/348,138, filed Mar. 28, 2014, which is the U.S. National Phase of International Patent Application No. PCT/IB2012/002318, filed Sep. 28, 2012, which claims priority to International Patent Application No. PCT/EP2011/067086, filed Sep. 30, 2011, the contents of each are hereby incorporated by reference in their entireties.

FIELD OF THE INVENTION

The present invention relates to novel macrocylic compounds and compositions containing said compounds acting as kinase inhibitors, in particular as inhibitors of LRRK2 (Leucine-Rich Repeat Kinase 2). Moreover, the present invention provides processes for the preparation of the disclosed compounds, as well as methods of using them, for instance as a medicine or diagnostic agent, in particular for the treatment and/or diagnosis of diseases characterized by LRRK2 kinase activity such as neurological disorders including Parkinson's disease and Alzheimer's disease.

BACKGROUND OF THE INVENTION

Parkinson's disease is a degenerative disorder of the central nervous system. It results from the death of dopaminergic neurones in the midbrain. In the early stages of the disease the most obvious symptoms are movement-related such as shaking, slowness of movement and difficulty with walking. Later on also cognitive and behavioural problems arise, with dementia commonly occurring in the advanced stages of the disease. Although Parkinson's disease is generally considered to be sporadic, within the last decade, a few mutations in the LRRK2 (leucine rich repeat kinase 2) gene have been linked to Parkinson's disease (WO2006068492 and WO2006045392). LRRK2, also known as dardarin, is a member of the leucine-rich repeat kinase family having mixed-lineage kinase activity, in particular in the brain, but also in other tissues throughout the body. Researchers have identified over 20 LRRK2 mutations in families with late-onset Parkinson Disease. For example the G2019S mutation co-segregates with autosomal dominant Parkinsonism and accounts for about 6% of familial Parkinson's disease cases and 3% sporadic Parkinson's disease cases in Europe. The G2019S mutation occurs in the highly conserved kinase domain and it has therefore been postulated that the G2019S mutation may have an effect on kinase activity (WO2006068492). Furthermore, amino acid substitutions at a second residue R1441 are also associated with Parkinson's disease and have also been shown to elevate LRRK2 kinase activity. Over-expression of the mutant LRRK2 protein R1441G in transgenic mouse models (Li, Y et al. 2009, Nature Neuroscience 12:826-828) is associated with symptoms of Parkinson's disease as well as reduced dopamine release, suggesting that inhibitors of LRRK2 could also positively regulate dopamine release and have potential utility in treatment of conditions characterized by reduced dopamine levels, such as withdrawal sypmtoms/relapse associated with drug addiction; Tauopathy diseases such as Alzheimer's disease, argyrophilic grain disease, Pick's disease, corticobasal degeneration; inherited frontotemporal dementia; and Parkinson's disease. Two further mutations in LRRK have been clinically associated with the transition from mild cognitive impairment to Alzheimer's disease (WO200714979). These data further provide evidence that inhibitors of LRRK2 kinase activity could be useful for the treatment of dementias and related neurodegenerative disorders. Thus, pharmacological inhibition of LRRK2 kinase is an attractive strategy towards mechanism-based therapies in neurodegenerative disorders, such as Parkinson's disease and Alzheimer's disease. It was therefore an object of the present invention to provide compounds and compositions comprising said compounds, acting as inhibitors of LRRK2 kinases.

Until today several (non-macrocyclic) pyrazolopyrimidines have been suggested for the treatment of neuronal disorders, in particular Alzheimer's disease and/or Parkinson's disease (see for example EP1908764, U.S. Pat. No. 6,194,410, EP1354884, EP0729758 and U.S. Pat. No. 6,194,410). However, none of the compounds disclosed in said references have been shown to have LRRK2 inhibitory activity.

Furthermore, the currently developed LRRK2 kinase inhibitors, in particular those for the treatment of neuronal disorders, do not comprise macrocyclic pyrazolopyrimidine moieties (see for example WO2009127652, WO2011038572).

Nonetheless, there is a continuing need to design and develop LRRK2 kinase inhibitors for the treatment of neuronal disorders. We have now found that the macrocyclic pyrazolopyrimidines and pharmaceutically acceptable compositions according to this invention are useful for the treatment of several neuronal disorders associated with LRRK2 kinase activity.

SUMMARY OF THE INVENTION

We have surprisingly found that the macrocyclic compounds described herein act as kinase inhibitors, in particular LRRK2 kinase inhibitors.

In a first objective the present invention provides a compound of Formula I or a stereoisomer, tautomer, racemic, metabolite, pro- or predrug, salt, hydrate, N-oxide form, or solvate thereof,

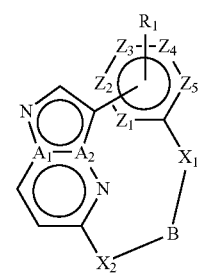

I

Wherein
$A_1$ and $A_2$ are selected from C and N; wherein when $A_1$ is C, then $A_2$ is N; and wherein when $A_2$ is C, then $A_1$ is N;
$R_1$ is selected from —H, -halo, —OH, —$C_{1-6}$alkyl, —$C_{3-6}$cycloalkyl, —O—$C_{1-6}$alkyl, —S—$C_{1-6}$alkyl, —$NR_9R_{10}$, —(C=O)—$R_4$, —$SO_2$—$R_4$, —CN, —$NR_9$—$SO_2$—$R_4$, -$Het_1$; wherein each of said $C_{1-6}$alkyl is optionally and independently substituted with from 1 to 3 substituents selected from -halo, —OH, —$NR_{11}R_{12}$, —O—$C_{1-6}$alkyl, —S—$C_{1-6}$alkyl;

$R_2$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, —(C=O)—$NR_{27}R_{28}$, -$Het_3$, —(C=O)-$Het_3$, —$SO_2$—$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, —$NR_{13}R_{14}$;

$R_3$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, -$Het_2$, —(C=O)-$Het_2$, —(C=O)—$NR_{29}R_{30}$, —$SO_2$—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, —$NR_{15}R_{16}$, -$Het_2$, —$Ar_4$;

$R_4$ is selected from -halo, —OH, —$C_{1-6}$alkyl, —O—$C_{1-6}$alkyl, —S—$C_{1-6}$alkyl, —$NR_{17}R_{18}$, -$Het_4$;

$R_5$ and $R_7$ are each independently selected from —H, -halo, —$C_{1-6}$alkyl, —$OC_{1-6}$alkyl, —S—$C_{1-6}$alkyl, -$Het_5$, —$Ar_1$, —$C_{3-6}$cycloalkyl, —$SO_2$—$Ar_3$, —$SO_2$, —$SO_2$—$C_{1-6}$alkyl, —(C=O), —(C=O)—$C_{1-6}$alkyl, —O—(C=O)—$C_{1-6}$alkyl, —(C=O)—O—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{23}R_{24}$;

$R_6$ is selected from —$SO_2$, —$SO_2$—$C_{1-6}$alkyl, —(C=O), —(C=S), —(C=O)—O—$C_{1-6}$alkyl, —(C=S)—O—$C_{1-6}$alkyl, —(C=O)—$C_{1-6}$alkyl, —(C=O)—$C_{2-6}$alkenyl, —(C=S)—$C_{1-6}$alkyl, —(C=S)—$C_{2-6}$alkenyl, —$C_{1-6}$alkyl-(C=O)—$NR_{31}R_{32}$, —$C_{1-6}$alkyl-(C=S)—$NR_{31}R_{32}$, —$C_{1-6}$alkyl-$NR_{33}$(C=O)—$NR_{31}R_{32}$, —$C_{1-6}$alkyl-$NR_{33}$(C=S)—$NR_{31}R_{32}$, —$SO_2$—$C_{3-5}$cycloalkyl, —(C=O)—$C_{3-5}$cycloalkyl, —(C=S)—$C_{3-5}$cycloalkyl, —(C=O)—$NR_{31}R_{32}$, —(C=S)—$NR_{31}R_{32}$, —(C=O)-$Het_5$, —(C=S)-$Het_5$, —(C=O)—$Ar_6$, —(C=S)—$Ar_6$, —(C=O)—$NR_{31}$—(C=O)—$R_{32}$; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{25}R_{26}$;

$R_8$ is selected from —$NR_{34}$—(C=O)—$R_{35}$, —$NR_{36}$—(C=O)—$NR_{34}R_{35}$, —$NR_{34}$—(SO2)-$R_{35}$, —$NR_{34}$—(C=O)—O—$R_{35}$, —O—(C=O)—$NR_{34}R_{35}$;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$, and $R_{40}$ are each independently selected from —H, -halo, —O, —OH, —O—$C_{1-6}$alkyl, —$C_{1-6}$alkyl, —$C_{3-6}$cycloalkyl or -$Het_1$; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_6$, —$Ar_5$;

$X_1$ is selected from —$C_{1-6}$alkyl-, —O—$C_{1-6}$alkyl-, —S—$C_{1-6}$alkyl-, —(C=O)—, —$NR_3$—(C=O)—, —$NR_3$—(C=O)—$C_{1-6}$alkyl, —(C=O)—$NR_3$—$C_{1-6}$alkyl-, —$NR_3$—$C_{1-6}$alkyl-, —$C_{1-6}$alkyl-$NR_3$—$C_{1-6}$alkyl-, —$SO_2$—$NR_3$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{37}R_{38}$;

$X_2$ is selected from —$C_{1-6}$alkyl-, —O—$C_{1-6}$alkyl-, —O—$C_{1-6}$alkyl-O—$C_{1-6}$alkyl-, —S—$C_{1-6}$alkyl-, —(C=O)—, —(C=O)—$NR_2$—, —$NR_2$—$C_{1-6}$alkyl-, —$NR_2$—, —$SO_2$—$NR_2$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{39}R_{40}$;

B is selected from —(C=O)—, —(C=N)—$R_3$—, —($SO_2$)—, —(C=O)—$NR_5$—, —(C=S)—$NR_5$—, —$NR_5$—(C=O)—$NR_7$—, —$NR_5$—(C=S)—$NR_7$—, —$SO_2$—$NR_5$—, —$NR_6$—, —$NR_5$—(C=O)—O—, —$NR_5$—(C=S)—O—, —$CHR_8$—;

$Ar_1$, $Ar_2$, $Ar_3$, $Ar_4$, $Ar_5$, and $Ar_6$ are each independently a 5- or 6-membered aromatic heterocycle optionally comprising 1 or 2 heteroatoms selected from O, N and S; each of said $Ar_1$, $Ar_2$, $Ar_3$, $Ar_4$, and $Ar_5$ being optionally and independently substituted with from 1 to 3 substituents selected from —$NR_{19}R_{20}$, —$C_{1-6}$alkyl, —O—$C_{1-6}$alkyl, —S—$C_{1-6}$alkyl;

$Het_1$, $Het_2$, $Het_3$, $Het_4$, $Het_5$, and $Het_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —$C_{1-6}$alkyl, —$OC_{1-6}$alkyl, —$SC_{1-6}$alkyl, —$NR_{21}R_{22}$; each of said —$C_{1-6}$alkyl being optionally substituted with from 1 to 3 -halo;

$Z_1$, $Z_2$, $Z_3$, $Z_4$ and $Z_5$ are each independently selected from C and N In particular, the present invention provides a compound of Formula I or a stereoisomer, tautomer, racemic, metabolite, pro- or predrug, salt, hydrate, N-oxide form, or solvate thereof, wherein $A_1$ and $A_2$ are selected from C and N; wherein when $A_1$ is C, then $A_2$ is N; and wherein when $A_2$ is C, then $A_1$ is N;

$R_1$ is selected from —H, -halo, —OH, —$C_{1-6}$alkyl, —$C_{3-6}$acycloalkyl, —O—$C_{1-6}$alkyl, —S—$C_{1-6}$alkyl, —$NR_9R_{10}$, —(C=O)—$R_4$, —$SO_2$—$R_4$, —CN, —$NR_9$—$SO_2$—$R_4$, -$Het_1$; wherein each of said $C_{1-6}$alkyl is optionally and independently substituted with from 1 to 3 substituents selected from -halo, —OH, —$NR_{11}R_{12}$, —O—$C_{1-6}$alkyl, —S—$C_{1-6}$alkyl;

$R_2$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, —(C=O)—$NR_{27}R_{26}$, -$Het_3$, —(C=O)-$Het_3$, —$SO_2$—$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, —$NR_{13}R_{14}$;

$R_3$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, -$Het_2$, —(C=O)-$Het_2$, —(C=O)—$NR_{29}R_{30}$, —$SO_2$—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, —$NR_{15}R_{16}$, -$Het_2$, —$Ar_4$;

$R_4$ is selected from -halo, —OH, —$C_{1-6}$alkyl, —O—$C_{1-6}$alkyl, —S—$C_{1-6}$alkyl, —$NR_{17}R_{18}$, -$Het_4$;

$R_5$ and $R_7$ are each independently selected from —H, -halo, —$C_{1-6}$alkyl, —$OC_{1-6}$alkyl, —S—$C_{1-6}$alkyl, -$Het_5$, —$Ar_1$, —$C_{3-6}$cycloalkyl, —$SO_2$—$Ar_3$, —$SO_2$, —$SO_2$—$C_{1-6}$alkyl, —(C=O), —(C=O)—$C_{1-6}$alkyl, —O—(C=O)—$C_{1-6}$alkyl, —(C=O)—O—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{23}R_{24}$;

$R_6$ is selected from —$SO_2$, —$SO_2$—$C_{1-6}$alkyl, —(C=O), —(C=S), —(C=O)—O—$C_{1-6}$alkyl, —(C=S)—O—$C_{1-6}$alkyl, —(C=O)—$C_{1-6}$alkyl, —(C=O)—$C_{2-6}$alkenyl, —(C=S)—$C_{1-6}$alkyl, —(C=S)—$C_{2-6}$alkenyl, —$C_{1-6}$alkyl-(C=O)—$NR_{31}R_{32}$, —$C_{1-6}$alkyl-(C=S)—$NR_{31}R_{32}$, —$C_{1-6}$alkyl-$NR_{33}$(C=O)—$NR_{33}R_{32}$, —$C_{1-6}$alkyl-$NR_{33}$(C=S)—$NR_{31}R_{32}$, —$SO_2$—$C_{3-5}$cycloalkyl, —(C=O)—$C_{3-5}$cycloalkyl, —(C=S)—$C_{3-5}$cycloalkyl, —(C=O)—$NR_{31}R_{32}$, —(C=S)—$NR_{31}R_{32}$, —(C=O)-$Het_5$, —(C=S)-$Het_5$, —(C=O)—$Ar_6$, —(C=S)—$Ar_6$, —(C=O)—$NR_{31}$—(C=O)—$R_{32}$; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{25}R_{26}$;

$R_8$ is selected from —$NR_{34}$—(C=O)—$R_{35}$, —$NR_{36}$—(C=O)—$NR_{34}R_{35}$, —$NR_{34}$—(SO2)-$R_{35}$, —$NR_{34}$—(C=O)—O—$R_{35}$, —O—(C=O)—$NR_{34}R_{35}$;

$R_9, R_{10}, R_{11}, R_{12}, R_{13}, R_{14}, R_{15}, R_{16}, R_{17}, R_{18}, R_{19}, R_{20}, R_{21}, R_{22}, R_{23}, R_{24}, R_{25}, R_{26}, R_{27}, R_{28}, R_{29}, R_{30}, R_{31}, R_{32}, R_{33}, R_{34}, R_{35}, R_{36}, R_{37}, R_{38}, R_{39}$ and $R_{40}$ are each independently selected from —H, -halo, —O, —OH, —O—$C_{1-6}$alkyl, —$C_{1-6}$alkyl, —$C_{3-6}$cycloalkyl or -$Het_1$; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_6$, —$Ar_5$;

$X_1$ is selected from —$C_{1-6}$alkyl-, —O—$C_{1-6}$alkyl-, —S—$C_{1-6}$alkyl-, —(C=O)—, —$NR_3$—(C=O)—, —$NR_3$—(C=O)—$C_{1-6}$alkyl, —(C=O)—$NR_3$—$C_{1-6}$alkyl-, —$NR_3$—$C_{1-6}$alkyl-, —$C_{1-6}$alkyl-$NR_3$—$C_{1-6}$alkyl-, —$SO_2$—$NR_3$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{37}R_{38}$; wherein when $X_1$ is —O—$CH_2$—, then $R_5$ is not —H;

$X_2$ is selected from —$C_{1-6}$alkyl-, —O—$C_{1-6}$alkyl-, —O—$C_{1-6}$alkyl-O—$C_{1-6}$alkyl-, —S—$C_{1-6}$alkyl-, —(C=O)—, —(C=O)—$NR_2$—, —$NR_2$—$C_{1-6}$alkyl-, —$NR_2$—, —$SO_2$—$NR_2$—; wherein each of said $C_{1-6}$alkyl $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{39}R_{40}$;

B is selected from —(C=O)—, —(C=N)$R_{39}$—, —($SO_2$)—, —(C=O)—$NR_5$—, —(C=S)—NRr, —$NR_5$—(C=O)—$NR_7$—, —$NR_5$—(C=S)—$NR_7$—, —$SO_2$—$NR_5$—, —$NR_6$—, —$NR_5$—(C=O)—O—, —$NR_5$—(C=S)—O—, —$CHR_8$—;

$Ar_1, Ar_2, Ar_3, Ar_4, Ar_5,$ and $Ar_6$ are each independently a 5- or 6-membered aromatic heterocycle optionally comprising 1 or 2 heteroatoms selected from O, N and S; each of said $Ar_1, Ar_2, Ar_3, Ar_4,$ and $Ar_5$ being optionally and independently substituted with from 1 to 3 substituents selected from —$NR_{19}R_{20}$, —$C_{1-6}$alkyl, —O—$C_{1-6}$alkyl, —S—$C_{1-6}$alkyl;

$Het_1, Het_2, Het_3, Het_4, Het_5,$ and $Het_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —$C_{1-6}$alkyl, —$OC_{1-6}$alkyl, —$SC_{1-6}$alkyl, —$NR_{21}R_{22}$; each of said —$C_{1-6}$alkyl being optionally substituted with from 1 to 3 -halo;

$Z_1, Z_2, Z_3, Z_4$ and $Z_5$ are each independently is selected from C and N

More in particular the present invention provides a compound of Formula I or a stereoisomer, tautomer, racemic, metabolite, pro- or predrug, salt, hydrate, N-oxide form, or solvate thereof, wherein, $A_1$ is N and $A_2$ is C;

$R_1$ is selected from —H, —OH, —$C_{1-6}$alkyl, —$C_{3-6}$cycloalkyl, —O—$C_{1-6}$alkyl, —S—$C_{1-6}$alkyl, —$NR_9R_{10}$, —$SO_2$—$R_4$, —CN, —$NR_9$—$SO_2$—$R_4$, -$Het_1$; wherein each of said $C_{1-6}$alkyl is optionally and independently substituted with from 1 to 3 substituents selected from -halo, —OH, —$NR_{11}R_{12}$, —O—$C_{1-6}$alkyl, —S—$C_{1-6}$alkyl;

$R_2$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, —(C=O)—$NR_{27}R_{28}$, -$Het_3$, —(C=O)-$Het_3$, —$SO_2$—$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, —$NR_{13}R_{14}$;

$R_3$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, -$Het_2$, —(C=O)-$Het_2$, —(C=O)—$NR_{29}R_{30}$, —$SO_2$—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, —$NR_{15}R_{16}$, -$Het_2$, —$Ar_4$;

$R_4$ is selected from -halo, —OH, —$C_{1-6}$alkyl, —O—$C_{1-6}$alkyl, —S—$C_{1-6}$alkyl, —$NR_{17}R_{18}$, -$Het_4$;

$R_5$ and $R_7$ are each independently selected from —H, -halo, —$C_{1-6}$alkyl, —$OC_{1-6}$alkyl, —S—$C_{1-6}$alkyl, —$Het_5$, —$Ar_1$, —$C_{3-6}$cycloalkyl, —$SO_2$—$Ar_3$, —$SO_2$, —$SO_2$—$C_{1-6}$alkyl, —(C=O), —(C=O)—$C_{1-6}$alkyl, —O—(C=O)—$C_{1-6}$alkyl, —(C=O)—O—$C_{1-6}$alkyl; wherein each of said $C_{1-6}$alkyl is optionally and independently substituted with from 1 to 3 substituents selected from —OH, —$OC_{1-4}$alkyl, —$SC_{1-6}$alkyl, -$Het_5$, —$NR_{23}R_{24}$;

$R_6$ is selected from —$SO_2$, —(C=O), —(C=S), —(C=O)—O—$C_{1-6}$alkyl, —(C=O)—$C_{2-6}$alkenyl, —(C=S)—O—$C_{1-6}$alkyl, —(C=O)—$C_{1-6}$alkyl, —(C=S)—$C_{1-6}$alkyl, —(C=S)—$C_{2-6}$alkenyl, —$C_{1-6}$alkyl-(C=S)—$NR_{31}R_{32}$, —$C_{1-6}$alkyl-$NR_{33}$(C=O)—$NR_{31}R_{32}$, —$C_{1-6}$alkyl-$NR_{33}$(C=S)—$NR_{31}R_{32}$, —(C=S)—$C_{3-5}$cycloalkyl, —(C=S)—$NR_{31}R_{32}$, —(C=O)-$Het_5$, —(C=S)-$Het_5$, —(C=O)—$NR_{31}$—(C=O)—$R_{32}$; wherein each of said $C_{1-6}$alkyl is optionally and independently substituted with from 1 to 3 substituents selected from —OH, —$OC_{1-6}$alkyl, —$SC_{1-6}$alkyl, -$Het_5$, —$NR_{25}R_{26}$;

$R_8$ is selected from —$NR_{36}$—(C=O)—$NR_{34}R_{35}$, —$NR_{34}$—(SO2)-$R_{35}$, —$NR_{34}$—(C=O)—O—$R_{35}$, —O—(C=O)—$NR_{34}R_{35}$;

$R_9, R_{10}, R_{11}, R_{12}, R_{13}, R_{14}, R_{15}, R_{16}, R_{17}, R_{18}, R_{19}, R_{20}, R_{21}, R_{22}, R_{23}, R_{24}, R_{25}, R_{26}, R_{27}, R_{28}, R_{29}, R_{30}, R_{31}, R_{32}, R_{33}, R_{34}, R_{35}, R_{36}, R_{37}, R_{38}, R_{39}$ and $R_{40}$ are each independently selected from —H; -halo, —O, —OH, —O—$C_{1-6}$alkyl, —$C_{1-6}$alkyl, —$C_{3-6}$cycloalkyl or -$Het_1$; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_6$, —$Ar_5$;

$X_1$ is selected from —$C_{1-6}$alkyl-, —O—$C_{1-6}$alkyl-, —S—$C_{1-6}$alkyl-, —(C=O)—, —$NR_3$—(C=O)—, —$NR_3$—(C=O)—$C_{1-6}$alkyl, —(C=O)—$NR_3$—$C_{1-6}$alkyl-, —$C_{1-6}$alkyl-$NR_3$—$C_{1-6}$alkyl-, —$SO_2$—$NR_3$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{37}R_{38}$;

$X_2$ is selected from —$C_{1-6}$alkyl-, —O—$C_{1-6}$alkyl-, —S—$C_{1-6}$alkyl-, —(C=O)—, —(C=O)—$NR_2$—, —$NR_2$—$C_{1-6}$alkyl-, —$NR_2$—, —$SO_2$—$NR_2$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{39}R_{40}$;

B is selected from —(C=O)—, —(C=N)$R_{39}$—, —(SO2)-, —(C=O)—$NR_5$—, —(C=S)—$NR_5$—, —$NR_5$—

(C=O)—NR$_7$—, —NR$_5$—(C=S)—NR$_7$—, —SO$_2$—NR$_5$—, —NR$_6$—, —NR$_5$—(C=S)—O—, —CHR$_8$—;

Ar$_1$, Ar$_2$, Ar$_3$, Ar$_4$, Ar$_5$, and Ar$_6$ are each independently a 5- or 6-membered aromatic heterocycle optionally comprising 1 or 2 heteroatoms selected from O, N and S; each of said Ar$_1$, Ar$_2$, Ar$_3$, Ar$_4$, and Ar$_5$ being optionally and independently substituted with from 1 to 3 substituents selected from —NR$_{19}$R$_{20}$, —C$_{1-6}$alkyl, —O—C$_{1-6}$alkyl, —S—C$_{1-6}$alkyl;

Het$_1$, Het$_2$, Het$_3$, Het$_4$, Het$_5$, and Het$_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —C$_{1-6}$alkyl, —OC$_{1-6}$alkyl, —SC$_{1-6}$alkyl, —NR$_{21}$R$_{22}$; each of said —C$_{1-6}$alkyl being optionally substituted with from 1 to 3 -halo;

Z$_1$, Z$_2$, Z$_3$, Z$_4$ and Z$_5$ are each C.

More in particular the present invention provides a compound of Formula I or a stereoisomer, tautomer, racemic, metabolite, pro- or predrug, salt, hydrate, N-oxide form, or solvate thereof, wherein, A$_1$ and A$_2$ are selected from C and N; wherein when A$_1$ is C, then A$_2$ is N; and wherein when A$_2$ is C, then A$_1$ is N;

R$_1$ is selected from —H, -halo, —C$_{1-6}$alkyl, —O—C$_{1-6}$alkyl, —(C=O)—R$_4$, and —CN; wherein each of said C$_{1-6}$alkyl is optionally and independently substituted with from 1 to 3 —OH;

R$_2$ is selected from —H and —C$_{1-6}$alkyl; wherein each of said C$_{1-6}$alkyl is optionally and independently substituted with from 1 to 3 substituents selected from —OH, —O—C$_{1-6}$alkyl, —NR$_{13}$R$_{14}$;

R$_3$ is selected from —H and —C$_{1-6}$alkyl;

R$_4$ is —NR$_{17}$R$_{18}$;

R$_5$ and R$_7$ are each independently selected from —H, —C$_{1-6}$alkyl; wherein each of said C$_{1-6}$alkyl is optionally and independently substituted with from 1 to 3 substituents selected from -halo, and —NR$_{23}$R$_{24}$;

R$_6$ is selected from —SO$_2$, —(C=O)—O—C$_{1-6}$alkyl, —(C=O)—C$_{1-6}$alkyl, —(CO)—C$_{2-6}$alkenyl, —C$_{1-6}$alkyl-(C=O)—NR$_{31}$R$_{32}$, —SO$_2$—C$_{3-5}$cycloalkyl, —(C=O)—C$_{3-5}$cycloalkyl, —(C=O)—NR$_{31}$R$_{32}$, —(C=O)-Het$_5$, —(C=O)—Ar$_6$; wherein each of said C$_{1-6}$alkyl is optionally and independently substituted with from 1 to 3 substituents selected from -halo, —OH, —OC$_{1-6}$alkyl, -Het$_5$, —NR$_{25}$R$_{26}$;

R$_8$ is —NR$_{34}$—(C=O)—R$_{35}$;

R$_{13}$, R$_{14}$, R$_{17}$, R$_{18}$, R$_{23}$, R$_{24}$, R$_{25}$, R$_{26}$, R$_{31}$, R$_{32}$, R$_{34}$, and R$_{35}$ are each independently selected from —H, —C$_{1-6}$alkyl, and —C$_{3-6}$cycloalkyl;

X$_1$ is selected from —O—C$_{1-6}$alkyl-, —NR$_3$—(C=O)—C$_{1-6}$alkyl, —(C=O)—NR—C$_{1-6}$alkyl-, —NR$_3$—C$_{1-6}$alkyl-, —C$_{1-6}$alkyl-NR$_3$—C$_{1-6}$alkyl-, —SO$_2$—NR$_3$—; wherein each of said C$_{1-6}$alkyl is optionally and independently substituted with from 1 to 3 —C$_{1-6}$alkyl;

X$_2$ is selected from —O—C$_{1-6}$alkyl-, —S—C$_{1-6}$alkyl-, —NR$_2$—C$_{1-6}$alkyl-;

B is selected from —(C=O)—NR$_5$—, —NR$_5$—(C=O)—NR$_7$—, —SO$_2$—NR$_5$—, —NR$_6$—, —NR$_5$—(C=O)—O—, —CHR$_8$—;

Ar$_6$ is a 5- or 6-membered aromatic heterocycle optionally comprising 1 or 2 heteroatoms selected from O, N and S;

Het$_5$ is a 5- or 6-membered monocyclic heterocycle having from 1 to 3 heteroatoms selected from O, N and S, wherein each heterocycle is being optionally and independently substituted with from 1 to 3 —C$_{1-6}$alkyl; each of said —C$_{1-6}$alkyl being optionally substituted with from 1 to 3 -halo;

Z$_1$, Z$_2$, Z$_3$, Z$_4$ and Z$_5$ are each independently selected from C and N More in particular the present invention provides a compound of Formula I or a stereoisomer, tautomer, racemic, metabolite, pro- or predrug, salt, hydrate, N-oxide form, or solvate thereof, wherein A$_1$ is N and A$_2$ is C;

R$_1$, R$_2$, R$_3$ and R$_5$ are each —H;

R$_6$ is selected from —(C=O)—C$_{1-6}$alkyl, —(C=O)—C$_{3-5}$cycloalkyl, and —(C=O)—NR$_{31}$R$_{32}$; wherein each of said C$_{1-6}$alkyl is optionally and independently substituted with from 1 to 3 —NR$_{25}$R$_{26}$;

R$_{25}$ and R$_{26}$, are each independently selected from —H, and —C$_{1-6}$alkyl;

R$_{31}$ and R$_{32}$ are each —H

X$_1$ is selected from —O—C$_{1-6}$alkyl and —NR$_3$—C$_{1-6}$alkyl-;

X$_2$ is —NR$_2$—C$_{1-6}$alkyl-;

B is selected from —(C=O)—NR$_5$—, and —NR$_6$—;

Z$_1$, Z$_2$, Z$_3$, Z$_4$ and Z$_5$ are each C

More in particular the present invention provides a compound selected from the list comprising

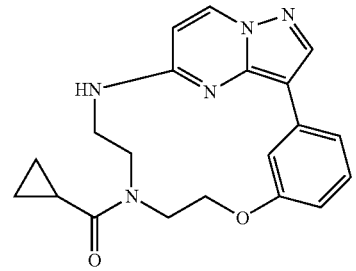

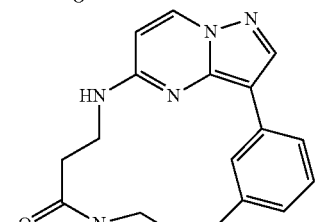

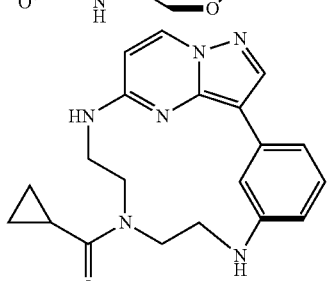

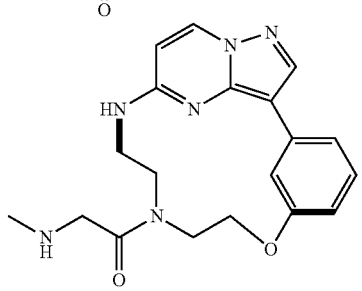

-continued

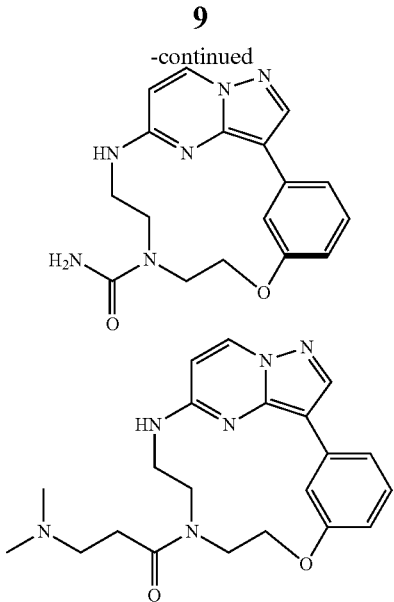

In particular for the compounds according to this invention, the pyrazolopyrimidine moiety is linked to the aryl or heteroaryl moiety at position $Z_1$ or $Z_2$, in accordance with the numbering as provided in Formula I, and/or $R_1$ is linked to the aryl or heteroaryl moiety at position $Z_3$, $Z_4$ or $Z_5$, in accordance with the numbering as provided in Formula I.

It is a further object of the present invention to provide (pharmaceutical) compositions comprising a compound according to this invention. In particular, the compounds and compositions according to this invention are suitable for use as a human or veterinary medicine. The compounds and compositions according to this invention are suitable for inhibiting the activity of a kinase, in particular LRRK2 kinase, and may be used for the treatment and/or prevention of neurological disorders such as Alzheimer's disease or Parkinson's disease.

In a final objective, the present invention provides a method for the prevention and/or treatment of a neurological disorder, such as Alzheimer's disease or Parkinson's disease; said method comprising administering to a subject in need thereof a compound or a composition according to this invention.

DETAILED DESCRIPTION OF THE INVENTION

Figure 1:
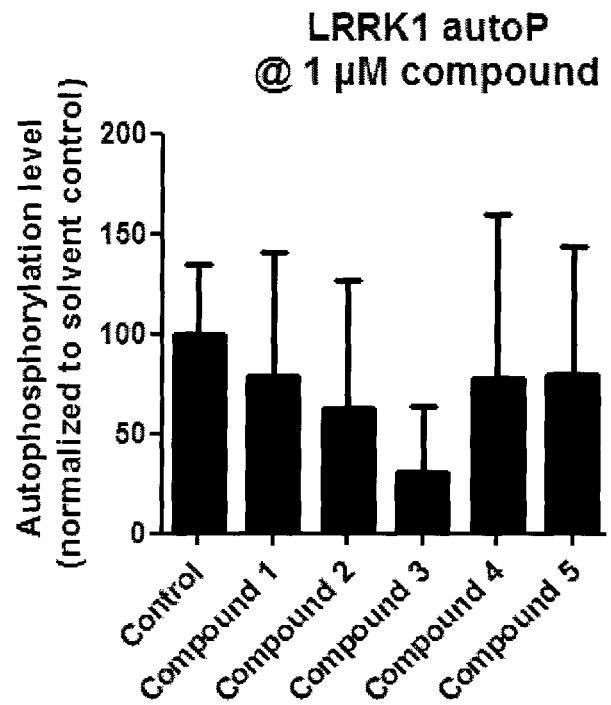
FIG. 1: Autophosphorylation of LRRK1 in the presence of 1 μM compound (mean+/−SD, N=3)

The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Unless a context dictates otherwise, asterisks are used herein to indicate the point at which a mono- or bivalent radical depicted is connected to the structure to which it relates and of which the radical forms part.

As already mentioned hereinbefore, in a first aspect the present invention provides compounds of Formula I or a stereoisomer, tautomer, racemic, metabolite, pro- or predrug, salt, hydrate, N-oxide form, or solvate thereof

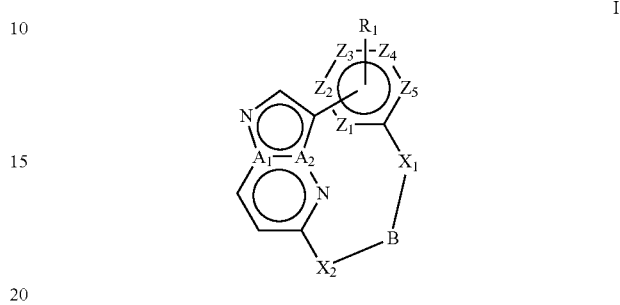

wherein $A_1$ and $A_2$ are selected from C and N; wherein when $A_1$ is C, then $A_2$ is N; and wherein when $A_2$ is C, then $A_1$ is N;

$R_1$ is selected from —H, -halo, —OH, —$C_{1-6}$alkyl, —$C_{3-6}$cycloalkyl, —O—$C_{1-6}$alkyl, —S—$C_{1-6}$alkyl, —$NR_9R_{10}$, —(C=O)—$R_4$, —$SO_2$—$R_4$, —CN, —$NR_9$—$SO_2$—$R_4$, -$Het_1$; wherein each of said $C_{1-6}$alkyl is optionally and independently substituted with from 1 to 3 substituents selected from -halo, —OH, —$NR_{11}R_{12}$, —O—$C_{1-6}$alkyl, —S—$C_{1-6}$alkyl;

$R_2$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, —(C=O)—$NR_{27}R_{28}$, -$Het_3$, —(C=O)-$Het_3$, —$SO_2$—$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, —$NR_{13}R_{14}$;

$R_3$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, -$Het_2$, —(C=O)-$Het_2$, —(C=O)—$NR_{29}R_{30}$, —$SO_2$—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, —$NR_{15}R_{16}$, -$Het_2$, —$Ar_4$;

$R_4$ is selected from -halo, —OH, —$C_{1-6}$alkyl, —O—$C_{1-6}$alkyl, —S—$C_{1-6}$alkyl, —$NR_{17}R_{18}$, -$Het_4$;

$R_5$ and $R_7$ are each independently selected from —H, -halo, —$C_{1-6}$alkyl, —$OC_{1-6}$alkyl, —$SC_{1-6}$alkyl, -$Het_5$, —$Ar_1$, —$C_{3-6}$cycloalkyl, —$SO_2$—$Ar_3$, —$SO_2$, —$SO_2$—$C_{1-6}$alkyl, —(C=O), —(C=O)—$C_{1-6}$alkyl, —O—(C=O)—$C_{1-6}$alkyl, —(C=O)—O—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{23}R_{24}$;

$R_6$ is selected from —$SO_2$, —$SO_2$—$C_{1-6}$alkyl, —(C=O), —(C=S), —(C=O)—O—$C_{1-6}$alkyl, —(C=S)—O—$C_{1-6}$alkyl, —(C=O)—$C_{1-6}$alkyl, —(C=O)—$C_{2-6}$alkenyl, —(C=S)—$C_{1-6}$alkyl, —(C=S)—$C_{2-6}$alkenyl, —$C_{1-6}$alkyl-(C=O)—$NR_{31}R_{32}$, —$C_{1-6}$alkyl-(C=S)—$NR_{31}R_{32}$, —$C_{1-6}$alkyl-$NR_{33}$(C=O)—$NR_{31}R_{32}$, —$C_{1-6}$alkyl-$NR_{33}$(C=S)—$NR_{31}R_{32}$, —$SO_2$—$C_{3-5}$cycloalkyl, —(C=O)—$C_{3-5}$cycloalkyl, —(C=S)—$C_{3-5}$cycloalkyl, —(C=O)—$NR_{31}R_{32}$, —(C=S)—$NR_{31}R_{32}$, —(C=O)-$Het_5$, —(C=S)-$Het_5$, —(C=O)—$Ar_6$, —(C=S)—Ar$_6$, —(C=O)—NR$_{31}$—(C=O)—R$_{32}$; wherein each of said C$_{1-6}$alkyl is optionally and independently substituted with from 1 to 3 substituents selected from -halo, —OH, —OC$_{1-6}$alkyl, —SC$_{1-6}$alkyl, -Het$_5$, —NR$_{25}$R$_{26}$;

R$_8$ is selected from —NR$_{34}$—(C=O)—R$_{35}$, —NR$_{36}$—(C=O)—NR$_{34}$R$_{35}$, —NR$_{34}$—(SO2)-R$_{35}$, —NR$_{34}$—(C=O)—O—R$_{35}$, —O—(C=O)—NR$_{34}$R$_{35}$;

R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, R$_{36}$, R$_{37}$, R$_{38}$, R$_{39}$ and R$_{40}$ are each independently selected from —H, -halo, =O, —OH, —O—C$_{1-6}$alkyl, —C$_{1-6}$alkyl, —C$_{3-6}$cycloalkyl or -Het$_1$; wherein each of said C$_{1-6}$alkyl is optionally and independently substituted with from 1 to 3 substituents selected from -halo, —OH, —O—C$_{1-6}$alkyl, —S—C$_{1-6}$alkyl, -Het$_6$, —Ar$_5$;

X$_1$ is selected from —C$_{1-6}$alkyl-, —O—C$_{1-6}$alkyl-, —S—C$_{1-6}$alkyl-, —(C=O)—, —NR$_3$—(C=O)—, —NR$_3$—(C=O)—C$_{1-6}$alkyl, —(C=O)—NR$_3$—C$_{1-6}$alkyl-, —NR$_3$—C$_{1-6}$alkyl-, —C$_{1-6}$alkyl-NR$_3$—C$_{1-6}$alkyl-, —SO$_2$—NR$_3$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, —NR$_{37}$R$_{38}$;

X$_2$ is selected from —C$_{1-6}$alkyl-, —O—C$_{1-6}$alkyl-, —O—C$_{1-6}$alkyl-O—C$_{1-6}$alkyl-, —S—C$_{1-6}$alkyl-, —(C=O)—, —(C=O)—NR$_2$—, —NR$_2$—C$_{1-6}$alkyl-, —NR$_2$—, —SO$_2$—NR$_2$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, —NR$_{39}$R$_{40}$;

B is selected from —(C=O)—, —(C=N)—R$_{39}$—, —(SO$_2$)—, —(C=O)—NR$_5$—, —(C=S)—NR$_5$—, —NR$_5$—(C=O)—NR$_7$—, —NR$_5$—(C=S)—NR$_7$—, —SO$_2$—NR$_5$—, —NR$_6$—, —NR$_5$—(C=O)—O—, —NR$_5$—(C=S)—O—, —CHR$_8$—;

Ar$_1$, Ar$_2$, Ar$_3$, Ar$_4$, Ar$_5$, and Ar$_6$ are each independently a 5- or 6-membered aromatic heterocycle optionally comprising 1 or 2 heteroatoms selected from O, N and S; each of said Ar$_1$, Ar$_2$, Ar$_3$, Ar$_4$, and Ar$_5$ being optionally and independently substituted with from 1 to 3 substituents selected from —NR$_{19}$R$_{20}$, —C$_{1-6}$alkyl, —O—C$_{1-6}$alkyl, —S—C$_{1-6}$alkyl;

Het$_1$, Het$_2$, Het$_3$, Het$_4$, Het$_5$, and Het$_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —C$_{1-6}$alkyl, —OC$_{1-6}$alkyl, —SC$_{1-6}$alkyl, —NR$_{21}$R$_{22}$; each of said —C$_{1-6}$alkyl being optionally substituted with from 1 to 3 -halo;

Z$_1$, Z$_2$, Z$_3$, Z$_4$ and Z$_5$ are each independently selected from C and N Unless indicated otherwise, all of the above radicals can be read both ways. For example, when B is —(C=O)—NR$_5$—, the —(C=O)— is attached to X$_2$ and —NR$_5$— is attached to X$_1$. Alternatively, the —(C=O)— is attached to X$_1$ and —NR$_5$— is attached to X$_1$.

What is called "left part" of a radical is for example when B is —(C=O)—NR$_5$—, —(C=O)—, and the "right part" is —NR$_5$—.

Preferably, B is such as the left part of the possible values of B (i.e. in particular —(C=N) from —(C=N)R$_{39}$, —(C=O) from —(C=O)—NR$_5$, —(C=S) from —(C=S)—NR$_5$, —CH from —CHR$_8$—, —NR$_5$ from —NR$_5$—(C=O)—NR$_7$, —NR$_5$—(C=S)—NR$_7$, NR$_5$—(C=O)—O— and NR$_5$—(C=S)—O—, —SO$_2$ from —SO$_2$—NR$_5$) is attached to X$_1$. Alternatively, B is such as the right part of the possible values of B (i.e. in particular (R$_{39}$)— from —(C=N)R$_{39}$, (NR$_5$)— from —(C=O)—NR$_5$, —SO$_2$—NR$_5$ and —(C=S)—NR$_5$, (NR$_7$)— from —NR$_5$—(C=O)—NR$_7$ and —NR$_5$—(C=S)—NR$_7$, O— from NR$_5$—(C=O)—O— and NR$_5$—(C=S)—O—, R$_8$— from —CHR$_8$— is attached to X$_1$.

Preferably, X$_1$ is such as the left part of the possible values of X$_1$ (i.e. in particular —O from —O—C$_{1-6}$alkyl, —S from —S—C$_{1-6}$alkyl, —NR$_3$ from —NR$_3$—(C=O) and —NR$_3$—C$_{1-6}$alkyl, —SO$_2$ from —SO$_2$—NR$_3$) is attached to the Z$_1$-Z$_5$ aryl or heteroaryl moiety. Alternatively, X$_1$ is such as the right part of the possible values of X$_1$ (i.e. in particular (C$_{1-6}$alkyl)- from —O—C$_{1-6}$alkyl, —S—C$_{1-6}$alkyl and —NR$_3$—C$_{1-6}$alkyl, —(C=O) from —NR$_3$—(C=O), (NR$_3$)— from —SO$_2$—NR$_3$) is attached to the Z$_1$-Z$_5$ aryl or heteroaryl moiety.

Preferably, X$_2$ is such as the left part of the possible values of X$_2$ (i.e. in particular —O from —O—C$_{1-6}$alkyl, —S from —S—C$_{1-6}$alkyl, —(C=O) from —(C=O)—NR$_2$, —NR$_2$ from —NR$_2$—C$_{1-6}$alkyl, —SO$_2$ from —SO$_2$—NR$_2$) is attached to the pyrazolopyrimidine moiety. Alternatively, X$_2$ is such as the right part of the possible values of X$_2$ (i.e. in particular (C$_{1-6}$alkyl)- from —O—C$_{1-6}$alkyl, —S—C$_{1-6}$alkyl and —NR$_2$—C$_{1-6}$alkyl, (NR$_2$)— from —(C=O)—NR$_2$ and —SO$_2$—NR$_2$) is attached to the pyrazolopyrimidine moiety.

The same principle applies to all the radicals of the invention unless specified otherwise.

When describing the compounds of the invention, the terms used are to be construed in accordance with the following definitions, unless a context dictates otherwise:

The term "alkyl" by itself or as part of another substituent refers to fully saturated hydrocarbon radicals. Generally, alkyl groups of this invention comprise from 1 to 6 carbon atoms. Alkyl groups may be linear or branched and may be substituted as indicated herein. When a subscript is used herein following a carbon atom, the subscript refers to the number of carbon atoms that the named group may contain. Thus, for example, C$_{1-6}$alkyl means an alkyl of one to six carbon atoms. Examples of alkyl groups are methyl, ethyl, n-propyl, i-propyl, butyl, and its isomers (e.g. n-butyl, i-butyl and t-butyl); pentyl and its isomers, hexyl and its isomers. C$_1$-C$_6$ alkyl includes all linear, branched, or cyclic alkyl groups with between 1 and 6 carbon atoms, and thus includes methyl, ethyl, n-propyl, i-propyl, butyl and its isomers (e.g. n-butyl, i-butyl and t-butyl); pentyl and its isomers, hexyl and its isomers, cyclopropyl, cyclobutyl, cyclopentyl, and cyclohexyl.

The term "optionally substituted alkyl" refers to an alkyl group optionally substituted with one or more substituents (for example 1 to 3 substituents, for example 1, 2 or 3 substituents or 1 to 2 substituents) at any available point of attachment. Non-limiting examples of such substituents include -halo, —OH, primary and secondary amides, —O—C$_{1-6}$alkyl, —S—C$_{1-6}$alkyl, heteroaryl, aryl, and the like.

The term "cycloalkyl" by itself or as part of another substituent is a cyclic alkyl group, that is to say, a monovalent, saturated, or unsaturated hydrocarbyl group having a cyclic structure. Cycloalkyl includes all saturated or partially saturated (containing 1 or 2 double bonds) hydrocarbon groups having a cyclic structure. Cycloalkyl groups may comprise 3 or more carbon atoms in the ring and generally, according to this invention comprise from 3 to 6 atoms. Examples of cycloalkyl groups include but are not limited to cyclopropyl, cyclobutyl, cyclopentyl, cyclohexyl.

Where alkyl groups as defined are divalent, i.e., with two single bonds for attachment to two other groups, they are termed "alkylene" groups. Non-limiting examples of alkylene groups includes methylene, ethylene, methylmethylene, trimethylene, propylene, tetramethylene, ethylethylene, 1,2-dimethylethylene, pentamethylene and hexamethylene.

Generally, alkylene groups of this invention preferably comprise the same number of carbon atoms as their alkyl counterparts. Where an alkylene or cycloalkylene biradical is present, connectivity to the molecular structure of which it forms part may be through a common carbon atom or different carbon atom. To illustrate this applying the asterisk nomenclature of this invention, a $C_3$ alkylene group may be for example *—$CH_2CH_2CH_2$—*, *—$CH(-CH_2CH_3)$—*, or *—$CH_2CH(-CH_3)$—*. Likewise a $C_3$ cycloalkylene group may be

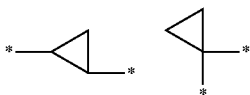

The terms "heterocycle" as used herein by itself or as part of another group refer to non-aromatic, fully saturated or partially unsaturated cyclic groups (for example, 3 to 6 membered monocyclic ring systems) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms. An optionally substituted heterocyclic refers to a heterocyclic having optionally one or more substituents (for example 1 to 4 substituents, or for example 1, 2, 3 or 4), selected from those defined above for substituted alkyl.

Exemplary heterocyclic groups include piperidinyl, azetidinyl, imidazolinyl, imidazolidinyl, isoxazolinyl, oxazolidinyl, isoxazolidinyl, thiazolidinyl, isothiazolidinyl, piperidyl, succinimidyl, 3H-indolyl, isoindolinyl, chromenyl, isochromanyl, xanthenyl, 2H-pyrrolyl, 1-pyrrolinyl, 2-pyrrolinyl, 3-pyrrolinyl, pyrrolidinyl, 4H-quinolizinyl, 4aH-carbazolyl, 2-oxopiperazinyl, piperazinyl, homopiperazinyl, 2-pyrazolinyl, 3-pyrazolinyl, pyranyl, dihydro-2H-pyranyl, 4H-pyranyl, 3,4-dihydro-2H-pyranyl, phthalazinyl, oxetanyl, thietanyl, 3-dioxanyl, 1,3-dioxanyl, 2,5-dioximidazolidinyl, 2,2,4-piperidonyl, 2-oxopiperidinyl, 2-oxopyrrolodinyl, 2-oxoazepinyl, indolinyl, tetrahydropyranyl, tetrahydrofuranyl, tetrehydrothienyl, tetrahydroquinolinyl, tetrahydroisoquinolinyl, thiomorpholinyl, thiomorpholinyl sulfoxide, thiomorpholinyl sulfone, 1,3-dioxolanyl, 1,4-oxathianyl, 1,4-dithianyl, 1,3,5-trioxanyl, 6H-1,2,5-thiadiazinyl, 2H-1,5,2-dithiazinyl, 2H-oxocinyl, 1H-pyrrolizinyl, tetrahydro-1,1-dioxothienyl, N-formylpiperazinyl, and morpholinyl; in particular pyrrolidinyl, imidazolidinyl, pyrazolidinyl, piperidinyl, dioxolanyl, dioxanyl, morpholinyl, thiomorpholinyl, piperazinyl, thiazolidinyl, tetrahydropyranyl, and tetrahydrofuranyl.

The term "aryl" as used herein refers to a polyunsaturated, aromatic hydrocarbyl group having a single ring (i.e. phenyl). Aryl is also intended to include the partially hydrogenated derivatives of the carbocyclic systems enumerated herein. Non-limiting examples of aryl comprise phenyl, biphenylyl, biphenylenyl, 5- or 6-tetralinyl, 1-, 2-, 3-, 4-, 5-, 6-, 7-, or 8-azulenyl, 1- or 2-naphthyl, 1-, 2-, or 3-indenyl, 1-, 2-, or 9-anthryl, 1- 2-, 3-, 4-, or 5-acenaphtylenyl, 3-, 4-, or 5-acenaphtenyl, 1-, 2-, 3-, 4-, or 10-phenanthryl, 1- or 2-pentalenyl, 1, 2-, 3-, or 4-fluorenyl, 4- or 5-indanyl, 5-, 6-, 7-, or 8-tetrahydronaphthyl, 1,2,3,4-tetrahydronaphthyl, 1,4-dihydronaphthyl, dibenzo[a,d]cylcoheptenyl, and 1-, 2-, 3-, 4-, or 5-pyrenyl; in particular phenyl.

The aryl ring can optionally be substituted by one or more substituents. An "optionally substituted aryl" refers to an aryl having optionally one or more substituents (for example 1 to 5 substituents, for example 1, 2, 3 or 4) at any available point of attachment, selected from those defined above for substituted alkyl.

Where a carbon atom in an aryl group is replaced with a heteroatom, the resultant ring is referred to herein as a heteroaryl ring.

The term "heteroaryl" as used herein by itself or as part of another group refers but is not limited to 5 to 6 carbon-atom aromatic rings in which one or more carbon atoms can be replaced by oxygen, nitrogen or sulfur atoms. Non-limiting examples of such heteroaryl, include: pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazoyl, oxatriazolyl, thiatriazolyl, pyridinyl, pyrimidyl, pyrazinyl, pyridazinyl, oxazinyl, dioxinyl, thiazinyl, triazinyl, imidazo[2,1-b][1,3]thiazolyl, thieno[3,2-b]furanyl, thieno[3,2-b]thiophenyl, thieno[2,3-d][1,3]thiazolyl, thieno[2,3-d]imidazolyl, tetrazolo[1,5-a]pyridinyl, indolyl, indolizinyl, isoindolyl, benzofuranyl, isobenzofuranyl, benzothiophenyl, isobenzothiophenyl, indazolyl, benzimidazolyl, 1,3-benzoxazolyl, 1,2-benzisoxazolyi, 2,1-benzisoxazolyl, 1,3-benzothiazolyl, 1,2-benzoisothiazolyl, 2,1-benzoisothiazolyl, benzotriazolyl, 1,2,3-benzoxadiazolyl, 2,1,3-benzoxadiazolyl, 1,2,3-benzothiadiazolyl, 2,1,3-benzothiadiazolyl, thienopyridinyl, purinyl, imidazo[1,2-a]pyridinyl, 6-oxo-pyridazin-1(6H)-yl, 2-oxopyridin-1(2H)-yl, 6-oxo-pyridazin-1(6H)-yl, 2-oxopyridin-1(2H)-yl, 1,3-benzodioxolyl, quinolinyl, isoquinolinyl, cinnolinyl, quinazolinyl, quinoxalinyl, 7-azaindolyl, 6-azaindolyl, 5-azaindolyl, 4-azaindolyl.

An "optionally substituted heteroaryl" refers to a heteroaryl having optionally one or more substituents (for example 1 to 4 substituents, for example 1, 2, 3 or 4), selected from those defined above for substituted alkyl.

The term "halo" or "halogen" as a group or part of a group is generic for fluoro, chloro, bromo, or iodo, as well as any suitable isotope thereof.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture, and formulation into a therapeutic and/or diagnostic agent.

Where groups may be optionally substituted, such groups may be substituted once or more, and preferably once, twice or thrice. Substituents may be selected from, those defined above for substituted alkyl.

As used herein the terms such as "alkyl, aryl, or cycloalkyl, each being optionally substituted with" or "alkyl, aryl, or cycloalkyl, optionally substituted with" refers to optionally substituted alkyl, optionally substituted aryl and optionally substituted cycloalkyl.

More generally, from the above, it will be clear to the skilled person that the compounds of the invention may exist in the form of different isomers and/or tautomers, including but not limited to geometrical isomers, conformational isomers, E/Z-isomers, stereochemical isomers (i.e. enantiomers and diastereoisomers) and isomers that correspond to the presence of the same substituents on different positions of the rings present in the compounds of the invention. All such possible isomers, tautomers and mixtures thereof are included within the scope of the invention.

In addition, the invention includes isotopically-labelled compounds and salts, which are identical to compounds of formula (I), but for the fact that one or more atoms are replaced by an atom having an atomic mass or mass number different from the atomic mass or mass number most commonly found in nature. Examples of isotopes that can be incorporated into compounds of formula (I) are isotopes of hydrogen, carbon, nitrogen, fluorine, such as $^3$H, $^{11}$C, $^{13}$N, $^{14}$C, $^{15}$O and $^{18}$F. Such isotopically-labelled compounds of formula (I) are useful in drug and/or substrate tissue distribution assays. For example $^{11}$C and $^{18}$F isotopes are particularly useful in PET (Positron Emission Tomography). PET is useful in brain imaging. Isotopically labeled compounds of formula (I) can generally be prepared by carrying out the procedures disclosed below, by substituting a readily available non-isotopically labeled reagent with an isotopically labeled reagent.

Whenever used in the present invention the term "compounds of the invention" or a similar term is meant to include the compounds of general Formula I and any subgroup thereof. This term also refers to the compounds as depicted in Table 1, their derivatives, N-oxides, salts, solvates, hydrates, stereoisomeric forms, racemic mixtures, tautomeric forms, optical isomers, analogues, pro-drugs, esters, and metabolites, as well as their quaternized nitrogen analogues. The N-oxide forms of said compounds are meant to comprise compounds wherein one or several nitrogen atoms are oxidized to the so-called N-oxide.

As used in the specification and the appended claims, the singular forms "a", "an", and "the" include plural referents unless the context clearly dictates otherwise. By way of example, "a compound" means one compound or more than one compound.

The terms described above and others used in the specification are well understood to those in the art.

Preferably, compounds of Formula I are defined above as such that $A_1$ and $A_2$ are selected from C and N; wherein when $A_1$ is C, then $A_2$ is N; and wherein when $A_2$ is C, then $A_1$ is N.

More preferably, $A_1$ is N and $A_2$ is C. Alternatively, $A_2$ is N and $A_1$ is C.

Preferably, $R_1$ is selected from —H, -halo, —OH, —$C_{1-6}$alkyl, —$C_{3-6}$cycloalkyl, —O—$C_{1-6}$alkyl, —S—$C_{1-6}$alkyl, —$NR_9R_{10}$, —(C=O)—$R_4$, —$SO_2$—$R_4$, —CN, —$NR_9$—$SO_2$—$R_4$, -$Het_1$; wherein each of said $C_{1-6}$alkyl is optionally and independently substituted with from 1 to 3 substituents selected from -halo, —OH, —$NR_{11}R_{12}$, —O—$C_{1-6}$alkyl, —S—$C_{1-6}$alkyl.

$R_1$ is selected from —H, -halo, —$C_{1-6}$alkyl, —O—$C_{1-6}$alkyl, —(C=O)—$R_4$, and —CN; wherein each of said $C_{1-6}$alkyl is optionally and independently substituted with from 1 to 3 —OH;

Even more preferably, $R_1$ is —H.

Preferably, $R_2$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, —(C=O)—$NR_{27}R_{28}$, -$Het_3$, —(C=O)-$Het_3$, —$SO_2$—$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, —$NR_{13}R_{14}$.

More preferably, $R_2$ is selected from —H and —$C_{1-6}$alkyl; wherein each of said $C_{1-6}$alkyl is optionally and independently substituted with from 1 to 3 substituents selected from —OH, —O—$C_{1-6}$alkyl, —$NR_{13}R_{14}$.

Even more preferably, $R_2$ is H.

Preferably, $R_3$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, -$Het_2$, —(C=O)-$Het_2$, —(C=O)—$NR_{29}R_{30}$, —$SO_2$—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, —$NR_{15}R_{16}$, -$Het_2$, —$Ar_4$.

More preferably, $R_3$ is selected from —H and —$C_{1-6}$alkyl;

Even more preferably, $R_3$ is H.

Preferably, $R_4$ is selected from -halo, —OH, —$C_{1-6}$alkyl, —O—$C_{1-6}$alkyl, —S—$C_{1-6}$alkyl, —$NR_{17}R_{18}$, -$Het_4$. More preferably, $R_4$ is —$NR_{17}R_{18}$;

Preferably, $R_5$ and $R_7$ are each independently selected from —H, -halo, —$C_{1-6}$alkyl, —$OC_{1-6}$alkyl, —S—$C_{1-6}$alkyl, -$Het_5$, —$Ar_1$, —$C_{3-6}$cycloalkyl, —$SO_2$—$Ar_3$, —$SO_2$, —$SO_2$—$C_{1-6}$alkyl, —(C=O), —(C=O)—$C_{1-6}$alkyl, —O—(C=O)—$C_{1-6}$alkyl, —(C=O)—O—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{23}R_{24}$.

More preferably, $R_5$ and $R_7$ are each independently selected from —H, —$C_{1-6}$alkyl; wherein each of said $C_{1-6}$alkyl is optionally and independently substituted with from 1 to 3 substituents selected from -halo, and —$NR_{23}R_{24}$;

Even more preferably, $R_5$ and $R_7$ are each —H.

Preferably, $R_6$ is selected from —$SO_2$, —$SO_2$—$C_{1-6}$alkyl, —(C=O), —(C=S), —(C=O)—O—$C_{1-6}$alkyl, —(C=S)—O—$C_{1-6}$alkyl, —(C=O)—$C_{1-6}$alkyl, —(C=O)—$C_{2-6}$alkenyl, —(C=S)—$C_{1-6}$alkyl, —(C=S)—$C_{2-6}$alkenyl, —$C_{1-6}$alkyl-(C=O)—$NR_{31}R_{32}$, —$C_{1-6}$alkyl-(C=S)—$NR_{31}R_{32}$, —$C_{1-6}$alkyl-$NR_{33}$(C=O)—$NR_{31}R_{32}$, —$C_{1-6}$alkyl-$NR_{33}$(C=S)—$NR_{31}R_{32}$, —$SO_2$—$C_{3-5}$cycloalkyl, —(C=O)—$C_{3-5}$cycloalkyl, —(C=S)—$C_{3-5}$cycloalkyl, —(C=O)—$NR_{31}R_{32}$, —(C=S)—$NR_{31}R_{32}$, —(C=O)-$Het_5$, —(C=S)-$Het_5$, —(C=O)—$Ar_6$, —(C=S)—$Ar_6$, —(C=O)—$NR_{31}$—(C=O)—$R_{32}$; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{25}R_{26}$.

More preferably, $R_6$ is selected from —$SO_2$, —(C=O)—O—$C_{1-6}$alkyl, —(C=O)—$C_{1-6}$alkyl, —(C=O)—$C_{2-6}$alkenyl, —$C_{1-6}$alkyl-(C=O)—$NR_{31}R_{32}$, —$SO_2$—$C_{3-5}$cycloalkyl, —(C=O)—$C_{3-5}$cycloalkyl, —(C=O)—$NR_{31}R_{32}$, —(C=O)-$Het_5$, —(C=O)—$Ar_6$; wherein each of said $C_{1-6}$alkyl is optionally and independently substituted with from 1 to 3 substituents selected from -halo, —OH, —$OC_{1-6}$alkyl, -$Het_5$, —$NR_{25}R_{26}$. Even more preferably, $R_6$ is selected from —(C=O)—$C_{1-6}$alkyl, —(C=O)—$C_{3-5}$cycloalkyl, and —(C=O)—$NR_{31}R_{32}$; wherein each of said $C_{1-6}$alkyl is optionally and independently substituted with from 1 to 3 —$NR_{25}R_{26}$.

Preferably, $R_8$ is selected from —$NR_{34}$—(C=O)—$R_{35}$, —$NR_{36}$—(C=O)—$NR_{34}R_{35}$, —$NR_{34}$—(SO2)-$R_{35}$, —$NR_{34}$—(C=O)—O—$R_{35}$, —O—(C=O)—$NR_{34}R_{35}$.

More preferably, $R_8$ is —$NR_{34}$—(C=O)—$R_{35}$.

Preferably $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$ and $R_{40}$ are each independently selected from —H, -halo, —O, —OH, —O—$C_{1-6}$alkyl, —$C_{1-6}$alkyl, —$C_{3-6}$cycloalkyl or -$Het_1$; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_6$, —$Ar_5$.

More preferably $R_{13}$, $R_{14}$, $R_{17}$, $R_{18}$, $R_{23}$, $R_{24}$, $R_{25}$, $R_{26}$, $R_{31}$, $R_{32}$, $R_{34}$, and $R_{35}$ are each independently selected from —H, —$C_{1-6}$alkyl, and —$C_{3-6}$cycloalkyl.

Even more preferably $R_{25}$ and $R_{26}$, are each independently selected from —H, and —$C_{1-6}$alkyl; and $R_{31}$ and $R_{32}$ are each —H Preferably, $X_1$ is selected from —$C_{1-6}$alkyl-, —O—$C_{1-6}$alkyl-, —S—$C_{1-6}$alkyl-, —(C=O)—, —$NR_3$—(C=O)—, —$NR_3$—(C=O)—$C_{1-6}$alkyl, —(C=O)—$NR_3$—$C_{1-6}$alkyl-, —$NR_3$—$C_{1-6}$alkyl-, —$C_{1-6}$alkyl-$NR_3$—$C_{1-6}$alkyl-, —$SO_2$—$NR_3$; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{37}R_{38}$.

More preferably, $X_1$ is selected from —O—$C_{1-6}$alkyl-, —$NR_3$—(C=O)—$C_{1-6}$alkyl, —(C=O)—$NR_3$—$C_{1-6}$alkyl-, —$NR_3$—$C_{1-6}$alkyl-, —$C_{1-6}$alkyl-$NR_3$—$C_{1-6}$alkyl-, —$SO_2$—$NR_3$—; wherein each of said $C_{1-6}$alkyl is optionally and independently substituted with from 1 to 3 —$C_{1-6}$alkyl.

Even more preferably, $X_1$ is selected from —O—$C_{1-6}$alkyl and —$NR_3$—$C_{1-6}$alkyl-.

Preferably, $X_2$ is selected from —$C_{1-6}$alkyl-, —O—$C_{1-6}$alkyl-, —O—$C_{1-6}$alkyl-O—$C_{1-6}$alkyl-, —S—$C_{1-6}$alkyl-, —(C=O)—, —(C=O)—$NR_2$—, —$NR_2$—$C_{1-6}$alkyl-, —$NR_2$—, —$SO_2$—$NR_2$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{39}R_{40}$.

More preferably, $X_2$ is selected from —O—$C_{1-6}$alkyl-, —S—$C_{1-6}$alkyl-, —$NR_2$—$C_{1-6}$alkyl-.

Even more preferably, $X_2$ is —$NR_2$—$C_{1-6}$alkyl-.

Preferably, B is selected from B is selected from —(C=O)—, —(C=N)—$R_{39}$—, —($SO_2$)—, —(C=O)—$NR_5$—, —(C=S)—$NR_5$—, —$NR_5$—(C=O)—$NR_7$—, —$NR_5$—(C=S)—$NR_7$—, —$SO_2$—$NR_5$—, —$NR_6$—, —$NR_5$—(C=O)—O—, —$NR_5$—(C=S)—O—, —$CHR_8$—.

More preferably, —(C=O)—$NR_5$—, —$NR_5$—(C=O)—$NR_7$—, —$SO_2$—$NR_5$—, —$NR_6$—, —$NR_5$—(C=O)—O—, —$CHR_8$—.

Even more preferably, B is selected from —(C=O)—$NR_5$—, and —$NR_6$—.

Preferably, $Ar_1$, $Ar_2$, $Ar_3$, $Ar_4$, $Ar_5$, and $Ar_6$ are each independently a 5- or 6-membered aromatic heterocycle optionally comprising 1 or 2 heteroatoms selected from O, N and S; each of said $Ar_1$, $Ar_2$, $Ar_3$, $Ar_4$, and $Ar_5$ being optionally and independently substituted with from 1 to 3 substituents selected from —$NR_{19}R_{20}$, —$C_{1-6}$alkyl, —O—$C_{1-6}$alkyl, —S—$C_{1-6}$alkyl.

More preferably, $Ar_6$ is a 5- or 6-membered aromatic heterocycle optionally comprising 1 or 2 heteroatoms selected from O, N and S.

Preferably, $Het_1$, $Het_2$, $Het_3$, $Het_4$, $Het_5$, and $Het_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —$C_{1-6}$alkyl, —$OC_{1-6}$alkyl, —$SC_{1-6}$alkyl, —$NR_{21}R_{22}$; each of said —$C_{1-6}$alkyl being optionally substituted with from 1 to 3 -halo.

More preferably, $Het_5$ is a 5- or 6-membered monocyclic heterocycle having from 1 to 3 heteroatoms selected from O, N and S, wherein each heterocycle is being optionally and independently substituted with from 1 to 3 —$C_{1-6}$alkyl; each of said —$C_{1-6}$alkyl being optionally substituted with from 1 to 3 -halo.

Preferably, $Z_1$, $Z_2$, $Z_3$, $Z_4$ and $Z_5$ are each independently selected from C and N.

More preferably, $Z_1$, $Z_2$, $Z_3$, $Z_4$ and $Z_5$ are each C.

In a particular embodiment, the present invention provides compounds of Formula I or a stereoisomer, tautomer, racemic, metabolite, pro- or predrug, salt, hydrate, N-oxide form, or solvate thereof

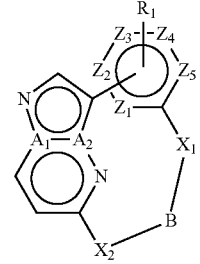

I

Wherein one or more of the following applies
$A_1$ and $A_2$ are selected from C and N; wherein when $A_1$ is C, then $A_2$ is N; and wherein when $A_2$ is C, then $A_1$ is N;
$R_1$ is selected from —H, -halo, —OH, —$C_{1-6}$alkyl, —$C_{3-6}$cycloalkyl, —O—$C_{1-6}$alkyl, —S—$C_{1-6}$alkyl, —$NR_9R_{10}$, —(C=O)—$R_4$, —$SO_2$—$R_4$, —CN, —$NR_9$—$SO_2$—$R_4$, -$Het_1$; wherein each of said $C_{1-6}$alkyl is optionally and independently substituted with from 1 to 3 substituents selected from -halo, —OH, —$NR_{11}R_{12}$, —O—$C_{1-6}$alkyl, —S—$C_{1-6}$alkyl;
$R_2$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, —(C=O)—$NR_{27}R_{28}$, -$Het_3$, —(C=O)-$Het_3$, —$SO_2$—$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_5$, —$Ar_2$, —$NR_{13}R_{14}$;
$R_3$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, -$Het_2$, —(C=O)-$Het_2$, —(C=O)—$NR_{29}R_{30}$, —$SO_2$—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, —$NR_{15}R_{16}$, -$Het_2$, —$Ar_4$;
$R_4$ is selected from -halo, —OH, —$C_{1-6}$alkyl, —O—$C_{1-6}$alkyl, —S—$C_{1-6}$alkyl, —$NR_{17}R_{18}$, -$Het_4$;
$R_5$ and $R_7$ are each independently selected from —H, -halo, —$C_{1-6}$alkyl, —$OC_{1-6}$alkyl, —S—$C_{1-6}$alkyl, -$Het_5$, —$Ar_1$, —$C_{3-6}$cycloalkyl, —$SO_2$—$Ar_3$, —$SO_2$, —$SO_2$—$C_{1-6}$alkyl, —(C=O), —(C=O)—$C_{1-6}$alkyl, —O—(C=O)—$C_{1-6}$alkyl, —(C=O)—O—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{23}R_{24}$;
$R_6$ is selected from —$SO_2$, —$SO_2$—$C_{1-6}$alkyl, —(C=O), —(C=S), —(C=O)—O—$C_{1-6}$alkyl, —(C=S)—O—$C_{1-6}$alkyl, —(C=O)—$C_{1-6}$alkyl, —(C=O)—$C_{2-6}$alkenyl, —(C=S)—$C_{1-6}$alkyl, —(C=S)—$C_{2-6}$alkenyl, —$C_{1-6}$alkyl-(C=O)—$NR_{31}R_{32}$, —$C_{1-6}$alkyl-(C=S)—$NR_{31}R_{32}$, —$C_{1-6}$alkyl-$NR_{33}$(C=O)—$NR_{31}R_{32}$, —$C_{1-6}$alkyl-$NR_{33}$(C=S)—$NR_{31}R_{32}$, —$SO_2$—$C_{3-5}$cycloalkyl, —(C=O)—$C_{3-5}$cycloalkyl, —(C=S)—$C_{3-5}$cycloalkyl, —(C=O)—$NR_{31}R_{32}$, —(C=S)—$NR_{31}R_{32}$, —(C=O)-$Het_5$, —(C=S)-$Het_5$, —(C=O)—$Ar_6$, —(C=S)—$Ar_6$, —(C=O)—$NR_{31}$—(C=O)—$R_{32}$; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{25}R_{26}$;

$R_8$ is selected from —$NR_{34}$—(C=O)—$R_{35}$, —$NR_{36}$—(C=O)—$NR_{34}R_{35}$, —$NR_{34}$—($SO2$)-$R_{35}$, —$NR_{34}$—(C=O)—O—$R_{35}$, —O—(C=O)—$NR_{34}R_{35}$;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$ and $R_{40}$ are each independently selected from —H, -halo, —O, —OH, —O—$C_{1-6}$alkyl, —$C_{1-6}$alkyl, —$C_{3-6}$cycloalkyl or -$Het_1$; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_6$, —$Ar_5$;

$X_1$ is selected from —$C_{1-6}$alkyl-, —O—$C_{1-6}$alkyl-, —S—$C_{1-6}$alkyl-, —(C=O)—, —$NR_3$—(C=O)—, —$NR_3$—(C=O)—$C_{1-6}$alkyl, —(C=O)—$NR_3$—$C_{1-6}$alkyl-, —$C_{1-6}$alkyl-$NR_3$—$C_{1-6}$alkyl-, —$NR_3$—$C_{1-6}$alkyl-, —$SO_2$—$NR_3$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{37}R_{38}$;

$X_2$ is selected from —$C_{1-6}$alkyl-, —O—$C_{1-6}$alkyl-, —O—$C_{1-6}$alkyl-O—$C_{1-6}$alkyl-, —S—$C_{1-6}$alkyl-, —(C=O)—, —(C=O)—$NR_2$—, —$NR_2$—$C_{1-6}$ alkyl-, —$NR_2$—, —$SO_2$—$NR_2$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{39}R_{40}$;

B is selected from —(C=O)—, —(C=N)—$R_{39}$—, —($SO_2$)—, —(C=O)—$NR_5$—, —(C=S)—$NR_5$—, —$NR_5$—(C=O)—$NR_7$—, —$NR_5$—(C=S)—$NR_7$—, —$SO_2$—$NR_5$—, —$NR_6$—, —$NR_5$—(C=O)—O—, —$NR_5$—(C=S)—O—, —$CHR_8$—;

$Ar_1$, $Ar_2$, $Ar_3$, $Ar_4$, $Ar_5$, and $Ar_6$ are each independently a 5- or 6-membered aromatic heterocycle optionally comprising 1 or 2 heteroatoms selected from O, N and S; each of said $Ar_1$, $Ar_2$, $Ar_3$, $Ar_4$, and $Ar_5$ being optionally and independently substituted with from 1 to 3 substituents selected from —$NR_{19}R_{20}$, —$C_{1-6}$alkyl, —O—$C_{1-6}$alkyl, —S—$C_{1-6}$alkyl;

$Het_1$, $Het_2$, $Het_3$, $Het_4$, $Het_5$, and $Het_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —$C_{1-6}$alkyl, —$OC_{1-6}$alkyl, —$SC_{1-6}$alkyl, —$NR_{21}R_{22}$; each of said —$C_{1-6}$alkyl being optionally substituted with from 1 to 3 -halo;

$Z_1$, $Z_2$, $Z_3$, $Z_4$ and $Z_5$ are each independently selected from C and N In another particular embodiment, the present invention provides compounds of Formula I wherein one or more of the following applies $A_1$ and $A_2$ are selected from C and N; wherein when $A_1$ is C, then $A_2$ is N; and wherein when $A_2$ is C, then $A_1$ is N;

$R_1$ is selected from —H, -halo, —$C_{1-6}$alkyl, —O—$C_{1-6}$alkyl, —(C=O)—$R_4$, and —CN; wherein each of said $C_{1-6}$alkyl is optionally and independently substituted with from 1 to 3 —OH;

$R_2$ is selected from —H and —$C_{1-6}$alkyl; wherein each of said $C_{1-6}$alkyl is optionally and independently substituted with from 1 to 3 substituents selected from —OH, —O—$C_{1-6}$alkyl, —$NR_{13}R_{14}$;

$R_3$ is selected from —H and —$C_{1-6}$alkyl;

$R_4$ is —$NR_{17}R_{18}$;

$R_5$ and $R_7$ are each independently selected from —H, —$C_{1-6}$alkyl; wherein each of said $C_{1-6}$alkyl is optionally and independently substituted with from 1 to 3 substituents selected from -halo, and —$NR_{23}R_{24}$;

$R_6$ is selected from —$SO_2$, —(C=O)—O—$C_{1-6}$alkyl, —(C=O)—$C_{1-6}$alkyl, —(C=O)—$C_{2-6}$alkenyl, —$C_{1-6}$alkyl-(C=O)—$NR_{31}R_{32}$, —$SO_2$—$C_{3-5}$cycloalkyl, —(C=O)—$C_{3-5}$cycloalkyl, —(C=O)—$NR_{31}R_{32}$, —(C=O)-$Het_5$, —(C=O)—$Ar_6$; wherein each of said $C_{1-6}$alkyl is optionally and independently substituted with from 1 to 3 substituents selected from -halo, —OH, —$OC_{1-6}$alkyl, -$Het_5$, —$NR_{25}R_{26}$;

$R_8$ is —$NR_{34}$—(C=O)—$R_{35}$;

$R_{13}$, $R_{14}$, $R_{17}$, $R_{18}$, $R_{23}$, $R_{24}$, $R_{25}$, $R_{26}$, $R_{31}$, $R_{32}$, $R_{34}$, and $R_{35}$ are each independently selected from —H, —$C_{1-6}$alkyl, and —$C_{3-6}$cycloalkyl;

$X_1$ is selected from —O—$C_{1-6}$alkyl-, —$NR_3$—(C=O)—$C_{1-6}$alkyl, —(C=O)—$NR_3$—$C_{1-6}$alkyl-, —$NR_3$—$C_{1-6}$alkyl-, —$C_{1-6}$alkyl-$NR_3$—$C_{1-6}$alkyl-, —$SO_2$—$NR_3$—; wherein each of said $C_{1-6}$alkyl is optionally and independently substituted with from 1 to 3 —$C_{1-6}$alkyl;

$X_2$ is selected from —O—$C_{1-6}$alkyl-, —S—$C_{1-6}$alkyl-, —$NR_2$—$C_{1-6}$alkyl-;

B is selected from —(C=O)—$NR_5$—, —$NR_5$—(C=O)—$NR_7$—, —$SO_2$—$NR_5$—, —$NR_6$—, —$NR_5$—(C=O)—O—, —$CHR_8$—;

$Ar_6$ is a 5- or 6-membered aromatic heterocycle optionally comprising 1 or 2 heteroatoms selected from O, N and S;

$Het_5$ is a 5- or 6-membered monocyclic heterocycle having from 1 to 3 heteroatoms selected from O, N and S, wherein each heterocycle is being optionally and independently substituted with from 1 to 3 —$C_{1-6}$alkyl; each of said —$C_{1-6}$alkyl being optionally substituted with from 1 to 3 -halo;

$Z_1$, $Z_2$, $Z_3$, $Z_4$ and $Z_5$ are each independently selected from C and N In yet another particular embodiment, the present invention provides compounds of Formula I wherein one or more of the following applies:

$A_1$ is N and $A_2$ is C;

$R_1$, $R_2$, $R_3$ and $R_5$ are each —H;

$R_6$ is selected from —(C=O)—$C_{1-6}$alkyl, —(C=O)—$C_{3-5}$cycioalkyl, and —(C=O)—$NR_{31}R_{32}$; wherein each of said $C_{1-6}$alkyl is optionally and independently substituted with from 1 to 3 —$NR_{25}R_{26}$;

$R_{25}$ and $R_{26}$, are each independently selected from —H, and —$C_{1-6}$alkyl;

$R_{31}$ and $R_{32}$ are each —H $X_1$ is selected from —O—$C_{1-6}$alkyl and —$NR_3$—$C_{1-6}$alkyl-;

$X_2$ is —$NR_2$—$C_{1-6}$alkyl-;

B is selected from —(C=O)—$NR_5$—, and —$NR_6$—;

$Z_1$, $Z_2$, $Z_3$, $Z_4$ and $Z_5$ are each C

In particular, $X_1$, and $X_2$ as used herein, represent biradikals, which taken together with the radicals to which they are attached form a macrocyclic pyrazolopyrimidine compound. Said biradicals may be present in either of both directions in the macrocyclic pyrazolopyrimidine, but are preferably present in the direction as described below:

Referring to formula I:

$X_1$ is selected from the list comprising *—$C_{1-6}$alkyl-, *—O—$C_{1-6}$alkyl-, *—S—$C_{1-6}$alkyl-, *—(C=O)—,

*—$NR_3$—(C=O)—, *—$NR_3$—(C=O)—$C_{1-6}$alkyl, *—(C=O)—$NR_3$—$C_{1-6}$alkyl-, *—$NR_3$—$C_{1-6}$alkyl-, *—$C_{1-6}$alkyl-$NR_3$—$C_{1-6}$alkyl-, —$SO_2$—$NR_3$—*, wherein said biradical is preferably attached to the aryl or heteroaryl moiety via *;

$X_2$ is selected from *—$C_{1-6}$ alkyl-, *—O—$C_{1-6}$alkyl-, *—S—$C_{1-6}$alkyl-, *—(C=O)—, —(C=O)—$NR_2$—*, *—$NR_2$—$C_{1-6}$alkyl-, *—$NR_2$—, —$SO_2$—$NR_2$—*; wherein said biradical is preferably attached to the pyrazolopyrimidine moiety via *;

In a preferred embodiment, the present invention provides compounds of formula I or a stereoisomer, tautomer, racemic, metabolite, pro- or predrug, salt, hydrate, N-oxide form, or solvate thereof, wherein $A_1$ and $A_2$ are selected from C and N; wherein when $A_1$ is C, then $A_2$ is N; and wherein when $A_2$ is C, then $A_1$ is N;

$R_1$ is selected from —H, -halo, —OH, —$C_{1-6}$alkyl, —$C_{3-6}$cycloalkyl, —O—$C_{1-6}$alkyl, —S—$C_{1-6}$alkyl, —$NR_9R_{10}$, —(C=O)—$R_4$, —$SO_2$—$R_4$, —CN, —$NR_9$—$SO_2$—$R_4$, -$Het_1$; wherein each of said $C_{1-6}$alkyl is optionally and independently substituted with from 1 to 3 substituents selected from -halo, —OH, —$NR_{11}R_{12}$, —O—$C_{1-6}$alkyl, —S—$C_{1-6}$alkyl;

$R_2$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, —(C=O)—$NR_{27}R_{28}$, -$Het_3$, —(C=O)-$Het_3$, —$SO_2$—$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, —$NR_{13}R_{14}$;

$R_3$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, -$Het_2$, —(C=O)-$Het_2$, —(C=O)—$NR_{29}R_{30}$, —$SO_2$—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, —$NR_{15}R_{16}$, -$Het_2$, —$Ar_4$;

$R_4$ is selected from -halo, —OH, —$C_{1-6}$alkyl, —O—$C_{1-6}$alkyl, —S—$C_{1-6}$alkyl, —$NR_{17}R_{18}$, -$Het_4$;

$R_5$ and $R_7$ are each independently selected from —H, -halo, —$C_{1-6}$alkyl, —$OC_{1-6}$alkyl, —S—$C_{1-6}$alkyl, -$Het_5$, —$Ar_1$, —$C_{3-6}$cycloalkyl, —$SO_2$—$Ar_3$, —$SO_2$, —$SO_2$—$C_{1-6}$alkyl, —(C=O), —(C=O)—$C_{1-6}$alkyl, —O—(C=O)—$C_{1-6}$alkyl, —(C=O)—O—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{23}R_{24}$;

$R_6$ is selected from —$SO_2$, —$SO_2$—$C_{1-6}$alkyl, —(C=O), —(C=S), —(C=O)—O—$C_{1-6}$alkyl, —(C=S)—O—$C_{1-6}$alkyl, —(C=O)—$C_{1-6}$alkyl, —(C=O)—$C_{2-6}$alkenyl, —(C=S)—$C_{1-6}$alkyl, —(C=S)—$C_{2-6}$alkenyl, —$C_{1-6}$alkyl-(C=O)—$NR_{31}R_{32}$, —$C_{1-6}$alkyl-(C=S)—$NR_{31}R_{32}$, —$C_{1-6}$alkyl-$NR_{33}$(C=O)—$NR_{31}R_{32}$, —$C_{1-6}$alkyl-$NR_{33}$(C=S)—$NR_{31}R_{32}$, —$SO_2$—$C_{3-5}$cycloalkyl, —(C=O)—$C_{3-5}$cycloalkyl, —(C=S)—$C_{3-5}$cycloalkyl, —(C=O)—$NR_{31}R_{32}$, —(C=S)—$NR_{31}R_{32}$, —(C=O)-$Het_5$, —(C=S)-$Het_5$, —(C=O)—$Ar_6$, —(C=S)—$Ar_6$, —(C=O)—$NR_{31}$—(C=O)—$R_{32}$; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{25}R_{26}$;

$R_8$ is selected from —$NR_{34}$—(C=O)—$R_{35}$, —$NR_{36}$—(C=O)—$NR_{34}R_{35}$, —$NR_{34}$—(SO2)-$R_{35}$, —$NR_{34}$—(C=O)—O—$R_{35}$, —O—(C=O)—$NR_{34}R_{35}$;

$R_9, R_{10}, R_{11}, R_{12}, R_{13}, R_{14}, R_{15}, R_{16}, R_{17}, R_{18}, R_{19}, R_{20}, R_{21}, R_{22}, R_{23}, R_{24}, R_{25}, R_{26}, R_{27}, R_{28}, R_{29}, R_{30}, R_{31}, R_{32}, R_{33}, R_{34}, R_{35}, R_{36}, R_{37}, R_{38}, R_{39}$ and $R_{40}$ are each independently selected from —H, -halo, —O, —OH, —O—$C_{1-6}$alkyl, —$C_{1-6}$alkyl, —$C_{3-6}$cycloalkyl or -$Het_1$; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_6$, —$Ar_5$;

$X_1$ is selected from —$C_{1-6}$alkyl-, —O—$C_{1-6}$alkyl-, —S—$C_{1-6}$alkyl-, —(C=O)—, —$NR_3$—(C=O)—, —$NR_3$—(C=O)—$C_{1-6}$alkyl, —(C=O)—$NR_3$—$C_{1-6}$alkyl-, —$NR_3$—$C_{1-6}$alkyl-, —$C_{1-6}$alkyl-$NR_3$—$C_{1-6}$alkyl-, —$SO_2$—$NR_3$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{37}R_{38}$; wherein when $X_1$ is —O—$CH_2$—, then $R_5$ is not —H;

$X_2$ is selected from —$C_{1-6}$alkyl-, —O—$C_{1-6}$alkyl-, —O—$C_{1-6}$alkyl-O—$C_{1-6}$alkyl-, —S—$C_{1-6}$alkyl-, —(C=O)—, —(C=O)—$NR_2$—, —$NR_2$—$C_{1-6}$alkyl-, —$NR_2$—, —$SO_2$—$NR_2$—; wherein each of said $C_{1-6}$alkyl $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{39}R_{40}$;

B is selected from —(C=O)—, —(C=N)$R_{39}$—, —($SO_2$)—, —(C=O)—$NR_5$—, —(C=S)—$NR_5$—, —$NR_5$—(C=O)—$NR_7$—, —$NR_5$—(C=S)—$NR_7$—, —$SO_2$—$NR_5$—, —$NR_6$—, —$NR_5$—(C=O)—O—, —$NR_5$—(C=S)—O—, —$CHR_8$—;

$Ar_1, Ar_2, Ar_3, Ar_4, Ar_5,$ and $Ar_6$ are each independently a 5- or 6-membered aromatic heterocycle optionally comprising 1 or 2 heteroatoms selected from O, N and S; each of said $Ar_1, Ar_2, Ar_3, Ar_4,$ and $Ar_5$ being optionally and independently substituted with from 1 to 3 substituents selected from —$NR_{19}R_{20}$, —$C_{1-6}$alkyl, —O—$C_{1-6}$alkyl, —S—$C_{1-6}$alkyl;

$Het_1, Het_2, Het_3, Het_4, Het_5,$ and $Het_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —$C_{1-6}$alkyl, —$OC_{1-6}$alkyl, —$SC_{1-6}$alkyl, —$NR_{21}R_{22}$; each of said —$C_{1-6}$alkyl being optionally substituted with from 1 to 3 -halo;

$Z_1, Z_2, Z_3, Z_4$ and $Z_5$ are each independently is selected from C and N

In a particular embodiment the present invention provides compounds of formula I or a stereoisomer, tautomer, racemic, metabolite, pro- or predrug, salt, hydrate, N-oxide form, or solvate thereof, wherein $A_1$ is N and $A_2$ is C;

$R_1$ is selected from —H, —OH, —$C_{1-6}$alkyl, —$C_{3-6}$cycloalkyl, —O—$C_{1-6}$alkyl, —S—$C_{1-6}$alkyl, —$NR_9R_{10}$, —$SO_2$—$R_4$, —CN, —$NR_9$—$SO_2$—$R_4$, -$Het_1$; wherein each of said $C_{1-6}$alkyl is optionally and independently substituted with from 1 to 3 substituents selected from -halo, —OH, —$NR_{11}R_{12}$, —O—$C_{1-6}$alkyl, —S—$C_{1-6}$alkyl;

$R_2$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, —(C=O)—$NR_{27}R_{28}$, -$Het_3$, —(C=O)-$Het_3$, —$SO_2$—$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, —$NR_{13}R_{14}$;

$R_3$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, -Het$_2$, —(C=O)-Het$_2$, —(C=O)—NR$_{29}$R$_{30}$, —SO$_2$—$C_{1-6}$alkyl; wherein each of said $C_{1-6}$alkyl is optionally and independently substituted with from 1 to 3 substituents selected from -halo, —OH, —O$C_{1-6}$alkyl, —S$C_{1-6}$alkyl, —NR$_{15}$R$_{16}$, -Het$_2$, —Ar$_4$;

$R_4$ is selected from -halo, —OH, —$C_{1-6}$alkyl, —O—$C_{1-6}$alkyl, —S—$C_{1-6}$alkyl, —NR$_{17}$R$_{18}$, -Het$_4$;

$R_5$ and $R_7$ are each independently selected from —H, -halo, —$C_{1-6}$alkyl, —O$C_{1-6}$alkyl, —S—$C_{1-6}$alkyl, -Het$_5$, —Ar$_1$, —$C_{3-6}$cycloalkyl, —SO$_2$—Ar$_3$, —SO$_2$, —SO$_2$—$C_{1-6}$alkyl, —(C=O), —(C=O)—$C_{1-6}$alkyl, —O—(C=O)—$C_{1-6}$alkyl, —(C=O)—O—$C_{1-6}$alkyl; wherein each of said $C_{1-6}$alkyl is optionally and independently substituted with from 1 to 3 substituents selected from —OH, —O$C_{1-6}$alkyl, —S$C_{1-6}$alkyl, -Het$_5$, —NR$_{23}$R$_{24}$;

$R_6$ is selected from —SO$_2$, —(C=O), —(C=S), —(C=O)—O—$C_{1-6}$alkyl, —(C=O)—$C_{2-6}$alkenyl, —(C=S)—O—$C_{1-6}$alkyl, —(C=O)—$C_{1-6}$alkyl, —(C=S)—$C_{1-6}$alkyl, —(C=S)—$C_{2-6}$alkenyl, —$C_{1-6}$alkyl-(C=S)—NR$_{31}$R$_{32}$, —$C_{1-6}$alkyl-NR$_{33}$(C=O)—NR$_{31}$R$_{32}$, —$C_{1-6}$alkyl-NR$_{33}$(C=S)—NR$_{31}$R$_{32}$, —SO$_2$—$C_{3-5}$cycloalkyl, —(C=S)—$C_{3-5}$cycloalkyl, —(C=S)—NR$_{31}$R$_{32}$, —(C=O)-Het$_5$, —(C=S)-Het$_5$, —(C=O)—NR$_{31}$—(C=O)—R$_{32}$; wherein each of said $C_{1-6}$alkyl is optionally and independently substituted with from 1 to 3 substituents selected from —OH, —O$C_{1-6}$alkyl, —S$C_{1-6}$alkyl, -Het$_5$, —NR$_{25}$R$_{26}$;

$R_8$ is selected from —NR$_{36}$—(C=O)—NR$_{34}$R$_{35}$, —NR$_{34}$—(SO2)-R$_{35}$, —NR$_{34}$—(C=O)—O—R$_{35}$, —O—(C=O)—NR$_{34}$R$_{35}$;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$ and $R_{40}$ are each independently selected from —H, -halo, —O, —OH, —O—$C_{1-6}$alkyl, —$C_{1-6}$alkyl, —$C_{3-6}$cycloalkyl or -Het$_1$; wherein each of said $C_{1-6}$alkyl is optionally and independently substituted with from 1 to 3 substituents selected from -halo, —OH, —O—$C_{1-6}$alkyl, —S—$C_{1-6}$alkyl, -Het$_6$, —Ar$_5$;

$X_1$ is selected from —$C_{1-6}$alkyl-, —O—$C_{1-6}$alkyl-, —S—$C_{1-6}$alkyl-, —(C=O)—, —NR$_3$—(C=O)—, —NR$_3$—(C=O)—$C_{1-6}$alkyl, —(C=O)—NR$_3$—$C_{1-6}$alkyl-, —$C_{1-6}$alkyl-NR$_3$—$C_{1-6}$alkyl-, —SO$_2$—NR$_3$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —NR$_{37}$R$_{38}$;

$X_2$ is selected from —$C_{1-6}$alkyl-, —O—$C_{1-6}$alkyl-, —S—$C_{1-6}$alkyl-, —(C=O)—, —(C=O)—NR$_2$—, —NR$_2$—$C_{1-6}$alkyl-, —NR$_2$—, —SO$_2$—NR$_2$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —NR$_{39}$R$_{40}$;

B is selected from —(C=O)—, —(C=N)R$_{39}$—, —(SO2)-, —(C=O)—NR$_5$—, —(C=S)—NR$_5$—, —NR$_5$—(C=O)—NR$_7$—, —NR$_5$—(C=S)—NR$_7$—, —SO$_2$—NR$_5$—, —NR$_6$—, —NR$_5$—(C=S)—O—, —CHR$_8$—;

Ar$_1$, Ar$_2$, Ar$_3$, Ar$_4$, Ar$_5$, and Ar$_6$ are each independently a 5- or 6-membered aromatic heterocycle optionally comprising 1 or 2 heteroatoms selected from O, N and S; each of said Ar$_1$, Ar$_2$, Ar$_3$, Ar$_4$, and Ar$_5$ being optionally and independently substituted with from 1 to 3 substituents selected from —NR$_{19}$R$_{20}$, —$C_{1-6}$alkyl, —O—$C_{1-6}$alkyl, —S—$C_{1-6}$alkyl;

Het$_1$, Het$_2$, Het$_3$, Het$_4$, Het$_5$, and Het$_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —$C_{1-6}$alkyl, —O$C_{1-6}$alkyl, —S$C_{1-6}$alkyl, —NR$_{21}$R$_{22}$; each of said —$C_{1-6}$alkyl being optionally substituted with from 1 to 3 -halo;

$Z_1$, $Z_2$, $Z_3$, $Z_4$ and $Z_5$ are each C

In a particular embodiment the present invention provides compounds of formula I or a stereoisomer, tautomer, racemic, metabolite, pro- or predrug, salt, hydrate, N-oxide form, or solvate thereof, wherein $A_1$ is N and $A_2$ is C;

$R_1$ is selected from —H, —OH, —$C_{1-6}$alkyl, —$C_{3-6}$cycloalkyl, —O—$C_{1-6}$alkyl, —S—$C_{1-6}$alkyl, —NR$_9$R$_{10}$, —SO$_2$—R$_4$, —CN, —NR$_9$—SO$_2$—R$_4$, -Het$_1$; wherein each of said $C_{1-6}$alkyl is optionally and independently substituted with from 1 to 3 substituents selected from -halo, —OH, —NR$_{11}$R$_{12}$, —O—$C_{1-6}$alkyl, —S—$C_{1-6}$alkyl;

$R_2$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, —(C=O)—NR$_{27}$R$_{28}$, -Het$_3$, —(C=O)-Het$_3$, —SO$_2$—$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -Het$_3$, —Ar$_2$, —NR$_{13}$R$_{14}$;

$R_3$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, -Het$_2$, —(C=O)-Het$_2$, —(C=O)—NR$_{29}$R$_{30}$, —SO$_2$$C_{1-6}$alkyl; wherein each of said $C_{1-6}$alkyl is optionally and independently substituted with from 1 to 3 substituents selected from -halo, —OH, —O$C_{1-6}$alkyl, —S$C_{1-6}$alkyl, —NR$_{15}$R$_{16}$, -Het$_2$, —Ar$_4$;

$R_4$ is selected from -halo, —OH, —$C_{1-6}$alkyl, —O—$C_{1-6}$alkyl, —S—$C_{1-6}$alkyl, —NR$_{17}$R$_{18}$, -Het$_4$;

$R_5$ and $R_7$ are each independently selected from —H, -halo, —$C_{1-6}$alkyl, —O$C_{1-6}$alkyl, —S—$C_{1-6}$alkyl, -Het$_5$, —Ar$_1$, —$C_{3-6}$cycloalkyl, —SO$_2$—Ar$_3$, —SO$_2$, —SO$_2$—$C_{1-6}$alkyl, —(C=O), —(C=O)—$C_{1-6}$alkyl, —O—(C=O)—$C_{1-6}$alkyl, —(C=O)—O—$C_{1-6}$alkyl; wherein each of said $C_{1-6}$alkyl is optionally and independently substituted with from 1 to 3 substituents selected from —OH, —O$C_{1-6}$alkyl, —S$C_{1-6}$alkyl, -Het$_5$, —NR$_{23}$R$_{24}$;

$R_6$ is selected from —SO$_2$, —(C=O), —(C=S), —(C=O)—O—$C_{1-6}$alkyl, —(C=O)—$C_{2-6}$alkenyl, —(C=S)—O—$C_{1-6}$alkyl, —(C=O)—$C_{1-6}$alkyl, —(C=S)—$C_{1-6}$alkyl, —(C=S)—$C_{2-6}$alkenyl, —$C_{1-6}$alkyl-(C=S)—NR$_{31}$R$_{32}$, —$C_{1-6}$alkyl-NR$_{33}$(C=O)—NR$_{31}$R$_{32}$, —$C_{1-6}$alkyl-NR$_{33}$(C=S)—NR$_{31}$R$_{32}$, —(C=S)—$C_{3-5}$cycloalkyl, —(C=S)—NR$_{31}$R$_{32}$, —(C=O)-Het$_5$, —(C=S)-Het$_5$, —(C=O)—NR$_{31}$—(C=O)—R$_{32}$; wherein each of said $C_{1-6}$alkyl is optionally and independently substituted with from 1 to 3 substituents selected from —OH, —O$C_{1-6}$alkyl, —S$C_{1-6}$alkyl, -Het$_5$, —NR$_{25}$R$_{26}$;

$R_8$ is selected from —NR$_{36}$—(C=O)—NR$_{34}$R$_{35}$, —NR$_{94}$—(SO2)-R$_{35}$, —NR$_{34}$—(C=O)—O—R$_{35}$, —O—(C=O)—NR$_{34}$R$_{35}$;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$ and $R_{40}$ are each independently selected from —H, -halo, —O, —OH, —O—$C_{1-6}$alkyl, —$C_{1-6}$alkyl, —$C_{3-6}$cycloalkyl or -Het$_1$; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_6$, —$Ar_5$;

$X_1$ is selected from —$C_{1-6}$alkyl-, —O—$C_{1-6}$alkyl-, —S—$C_{1-6}$alkyl-, —(C=O)—, —$NR_3$—(C=O)—, —$NR_3$—(C=O)—$C_{1-6}$alkyl, —(C=O)—$NR_3$—$C_{1-6}$alkyl-, —$C_{1-6}$alkyl-$NR_3$—$C_{1-6}$alkyl-, —$SO_2$—$NR_3$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{37}R_{38}$;

$X_2$ is selected from —$C_{1-6}$alkyl-, —O—$C_{1-6}$alkyl-, —S—$C_{1-6}$alkyl-, —(C=O)—, —(C=O)—$NR_2$—, —$NR_2$—$C_{1-6}$alkyl-, —$NR_2$—, —SO—$NR_2$—; wherein each of said $C_{1-6}$alkyl is optionally and independently substituted with from 1 to 3 substituents selected from -halo, —OH, —$C_{1-6}$alkyl, —O—$C_{1-6}$alkyl, —S—$C_{1-6}$alkyl, —$NR_{39}R_{40}$;

B is selected from —(C=O)—, —(C=N)$R_{39}$—, —(SO2)-, —(C=O)—$NR_5$—, —(C=S)—$NR_5$—, —$NR_5$—(C=O)—$NR_7$—, —$NR_5$—(C=S)—$NR_7$—, —$SO_2$—$NR_5$—, —$NR_6$—, —$NR_5$—(C=S)—O—, —$CHR_8$—;

$Ar_1$, $Ar_2$, $Ar_3$, $Ar_4$, $Ar_5$, and $Ar_6$ are each independently a 5- or 6-membered aromatic heterocycle optionally comprising 1 or 2 heteroatoms selected from O, N and S; each of said $Ar_1$, $Ar_2$, $Ar_3$, $Ar_4$, and $Ar_5$ being optionally and independently substituted with from 1 to 3 substituents selected from —$NR_{19}R_{20}$, —$C_{1-6}$alkyl, —O—$C_{1-6}$alkyl, —S—$C_{1-6}$alkyl;

$Het_1$, $Het_2$, $Het_3$, $Het_4$, $Het_5$, and $Het_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —$C_{1-6}$alkyl, —$OC_{1-6}$alkyl, —$SC_{1-6}$alkyl, —$NR_{21}R_{22}$; each of said —$C_{1-6}$alkyl being optionally substituted with from 1 to 3 -halo;

$Z_1$, $Z_2$, $Z_3$, $Z_4$ and $Z_5$ are each C.

In another particular embodiment the present invention provides compounds of formula I or a stereoisomer, tautomer, racemic, metabolite, pro- or predrug, salt, hydrate, N-oxide form, or solvate thereof, wherein $A_1$ and $A_2$ are selected from C and N; wherein when $A_1$ is C, then $A_2$ is N; and wherein when $A_2$ is C, then $A_1$ is N;

$R_1$ is selected from —H, -halo, —$C_{1-6}$alkyl, —O—$C_{1-6}$alkyl, —(C=O)—$R_4$, and —CN; wherein each of said $C_{1-6}$alkyl is optionally and independently substituted with from 1 to 3 —OH;

$R_2$ is selected from —H and —$C_{1-6}$alkyl; wherein each of said $C_{1-6}$alkyl is optionally and independently substituted with from 1 to 3 substituents selected from —OH, —O—$C_{1-6}$alkyl, —$NR_{13}R_{14}$;

$R_3$ is selected from —H and —$C_{1-6}$alkyl;

$R_4$ is —$NR_{17}R_{18}$;

$R_5$ and $R_7$ are each independently selected from —H, —$C_{1-6}$alkyl; wherein each of said $C_{1-6}$alkyl is optionally and independently substituted with from 1 to 3 substituents selected from -halo, and —$NR_{23}R_{24}$;

$R_6$ is selected from —$SO_2$, —(C=O)—O—C)—$C_{1-6}$alkyl, —(C=O)—$C_{1-6}$alkyl, —(C=O)—$C_{2-6}$alkenyl, —$C_{1-6}$alkyl-(C=O)—$NR_{31}R_{32}$, —$SO_2$—$C_{3-5}$cycloalkyl, —(C=O)—$C_{3-5}$cycloalkyl, —(C=O)—$NR_{31}R_{32}$, —(C=O)-$Het_5$, —(C=O)—$Ar_6$; wherein each of said $C_{1-6}$alkyl is optionally and independently substituted with from 1 to 3 substituents selected from -halo, —OH, —$OC_{1-6}$alkyl, -$Het_5$, —$NR_{25}R_{26}$;

$R_8$ is —$NR_{34}$—(C=O)—$R_{35}$;

$R_{13}$, $R_{14}$, $R_{17}$, $R_{18}$, $R_{23}$, $R_{24}$, $R_{25}$, $R_{26}$, $R_{31}$, $R_{32}$, $R_{34}$, and $R_{35}$ are each independently selected from —H, —$C_{1-6}$alkyl, and —$C_{3-6}$cycloalkyl;

$X_1$ is selected from —O—$C_{1-6}$alkyl-, —$NR_3$—(C=O)—$C_{1-6}$alkyl, —(C=O)—$NR_3$—$C_{1-6}$alkyl-, —$NR_3$—$C_{1-6}$alkyl-, —$C_{1-6}$alkyl-$NR_3$—$C_{1-6}$alkyl-, —$SO_2$—$NR_3$—; wherein each of said $C_{1-6}$alkyl is optionally and independently substituted with from 1 to 3 —$C_{1-6}$alkyl;

$X_2$ is selected from —O—$C_{1-6}$alkyl-, —S—$C_{1-6}$alkyl-, —$NR_2$—$C_{1-6}$alkyl-;

B is selected from —(C=O)—$NR_5$—, —$NR_5$—(C=O)—$NR_7$—, —$SO_2$—$NR_5$—, —$NR_6$—, —$NR_5$—(C=O)—O—, —$CHR_8$—;

$Ar_6$ is a 5- or 6-membered aromatic heterocycle optionally comprising 1 or 2 heteroatoms selected from O, N and S;

$Het_5$ is a 5- or 6-membered monocyclic heterocycle having from 1 to 3 heteroatoms selected from O, N and S, wherein each heterocycle is being optionally and independently substituted with from 1 to 3 —$C_{1-6}$alkyl; each of said —$C_{1-6}$alkyl being optionally substituted with from 1 to 3 -halo;

$Z_1$, $Z_2$, $Z_3$, $Z_4$ and $Z_5$ are each independently selected from C and N In another particular embodiment the present invention provides compounds of formula I or a stereoisomer, tautomer, racemic, metabolite, pro- or predrug, salt, hydrate, N-oxide form, or solvate thereof, wherein $A_1$ is N and $A_2$ is C;

$R_1$, $R_2$, $R_3$ and $R_5$ are each —H;

$R_6$ is selected from —(C=O)—$C_{1-6}$alkyl, —(C=O)—$C_{3-5}$cycloalkyl, and —(C=O)—$NR_{31}R_{32}$; wherein each of said $C_{1-6}$alkyl is optionally and independently substituted with from 1 to 3 —$NR_{25}R_{26}$;

$R_{25}$ and $R_{26}$, are each independently selected from —H, and —$C_{1-6}$alkyl;

$R_{31}$ and $R_{32}$ are each —H $X_1$ is selected from —O—$C_{1-6}$alkyl and —$NR_3$—$C_{1-6}$alkyl-;

$X_2$ is —$NR_2$—$C_{1-6}$alkyl-;

B is selected from —(C=O)—$NR_5$—, and —$NR_6$—;

$Z_1$, $Z_2$, $Z_3$, $Z_4$ and $Z_5$ are each C

In a specific embodiment the present invention provides a compound of formula II or a stereoisomer, tautomer, racemic, metabolite, pro- or predrug, salt, hydrate, N-oxide form, or solvate thereof, wherein Wherein B is selected from —(C=O)—$NR_5$—, —$NR_5$—(C=O)—$NR_7$—, —$SO_2$—$NR_5$—, —$NR_6$—, —$NR_5$—(C=O)—O—, —$CHR_8$—;

$R_5$ and $R_7$ are each independently selected from —H, and —$C_{1-6}$alkyl; wherein each of said $C_{1-6}$alkyl is optionally and independently substituted with from 1 to 3 substituents selected from -halo and, —$NR_{23}R_{24}$;

$R_6$ is selected from —$SO_2$—$C_{1-6}$alkyl, —(C=O)—O—$C_{1-6}$alkyl, —(C=O)—$C_{1-6}$alkyl, —(C=O)—$C_{2-6}$alkenyl, —$C_{1-6}$alkyl-(C=O)—$NR_{31}R_{32}$, —$SO_2$—$C_{3-5}$cycloalkyl, —(C=O)—$C_{3-5}$cycloalkyl, —(C=O)—$NR_{31}R_{32}$, —(C=O)-$Het_5$; wherein each of said $C_{1-6}$alkyl is optionally and independently substituted with from 1 to 3 substituents selected from -halo, —OH, —$OC_{1-6}$alkyl, -$Het_5$, —$NR_{25}R_{26}$;

$R_8$ is —$NR_{34}$—(C=O)—$R_{35}$;

$R_{23}$, $R_{24}$, $R_{25}$, $R_{26}$, $R_{31}$, and $R_{32}$, are each independently selected from —H, and —$C_{1-6}$alkyl $R_{35}$ is —$C_{3-6}$cycloalkyl $Het_5$ is a 5- or 6-membered monocyclic heterocycle having from 1 to 3 heteroatoms selected from O, N and S, wherein each heterocycle is being optionally and independently substituted with from 1 to 3 —$C_{1-6}$alkyl; each of said —$C_{1-6}$alkyl being optionally substituted with from 1 to 3 -halo;

In another specific embodiment the present invention provides a compound of formula III or a stereoisomer, tautomer, racemic, metabolite, pro- or predrug, salt, hydrate, N-oxide form, or solvate thereof, wherein

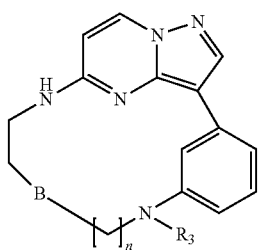

III

Wherein
$R_3$ is selected from —H, and —$C_{1-6}$alkyl;
$R_5$ is —H;
$R_6$ is selected from —(C=O)—$C_{1-6}$alkyl, —(C=O)—$C_{3-5}$cycloalkyl, and —$OC_{1-6}$alkyl; wherein each of said $C_{1-6}$alkyl is optionally and independently substituted with from 1 to 3 —$OC_{1-6}$alkyl B is selected from —(C=O)—$NR_5$—, and —$NR_6$—;

In another specific embodiment the present invention provides a compound of formula IV or a stereoisomer, tautomer, racemic, metabolite, pro- or predrug, salt, hydrate, N-oxide form, or solvate thereof, wherein

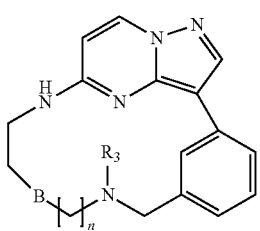

IV

Wherein
$R_3$ is selected from —H, and —$C_{1-6}$alkyl;
$R_5$ is —H;
$R_6$ is selected from —(C=O)—$C_{1-6}$alkyl, and —(C=O)—$C_{1-6}$cycloalkyl; wherein each of said $C_{1-6}$alkyl is optionally and independently substituted with from 1 to 3 substituents selected from —$OC_{1-6}$alkyl, and —$NR_{25}R_{26}$ $R_{25}$ and $R_{26}$, are each —$C_{1-6}$alkyl;
B is selected from —(C=O)—$NR_5$—, and —$NR_6$—;

In yet another particular embodiment, the present invention provides a compound or a stereoisomer, tautomer, racemic, metabolite, pro- or predrug, salt, hydrate, N-oxide form, or solvate thereof, selected from the list comprising:

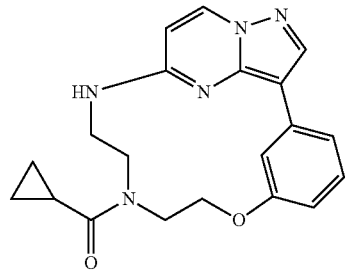

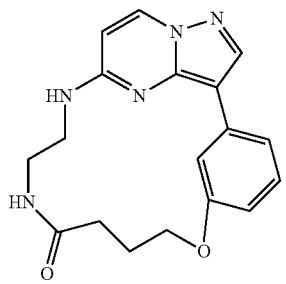

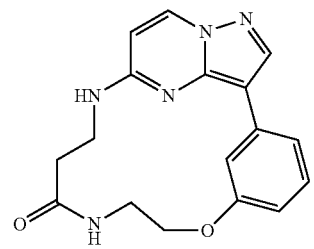

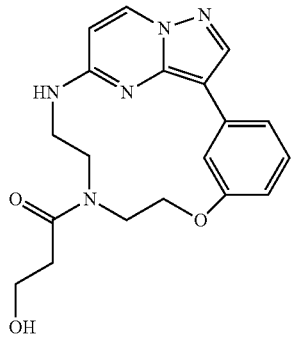

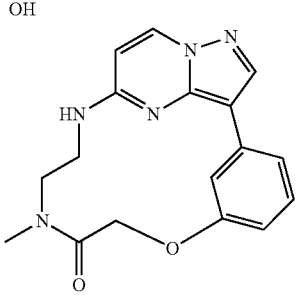

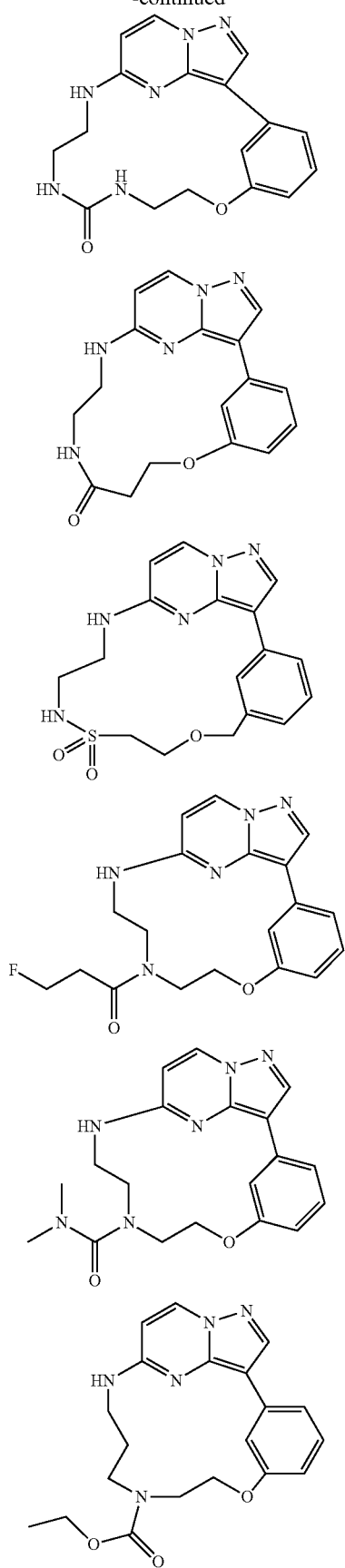
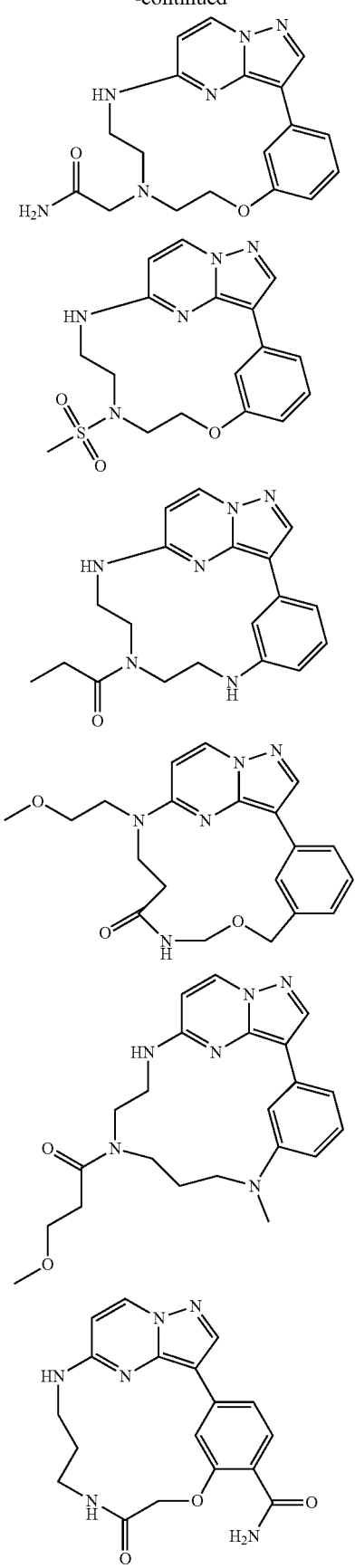

31
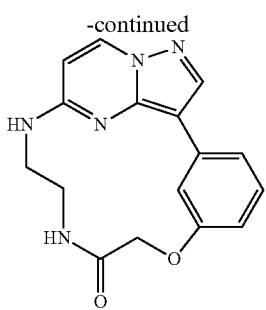
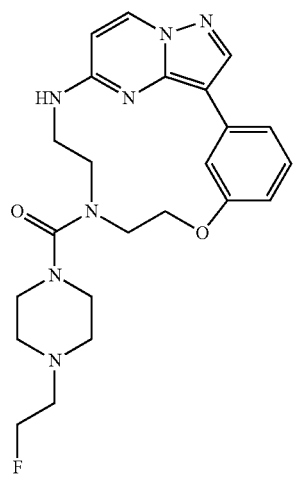
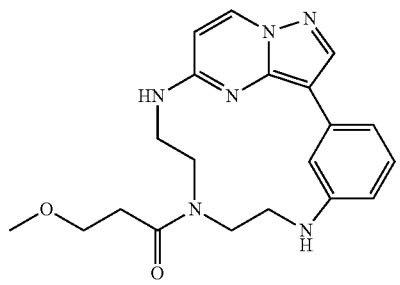
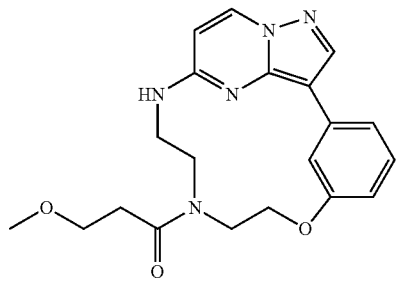
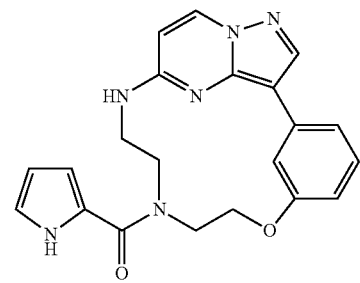
32
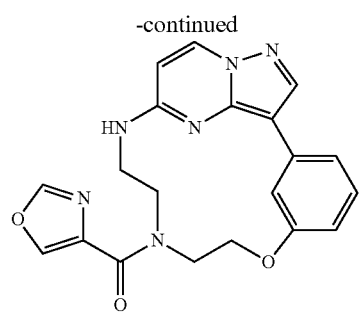
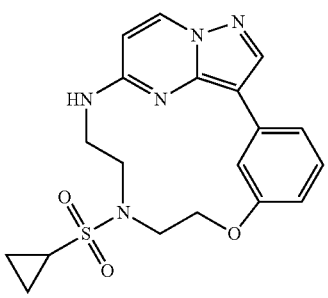
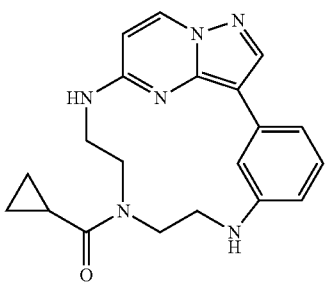
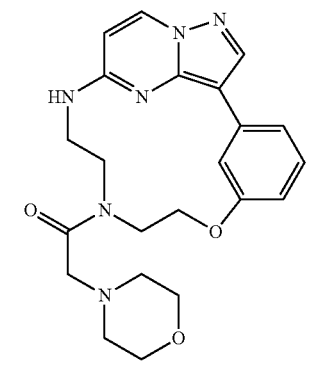
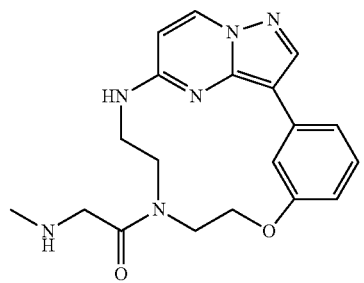

33
-continued
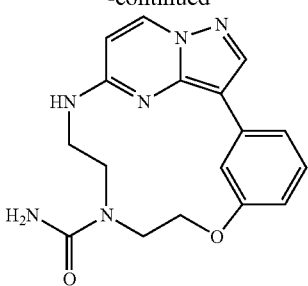
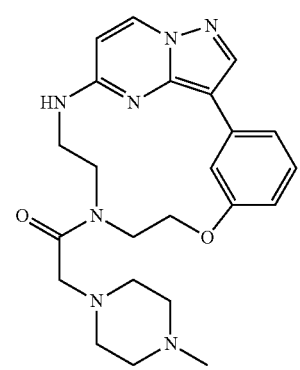
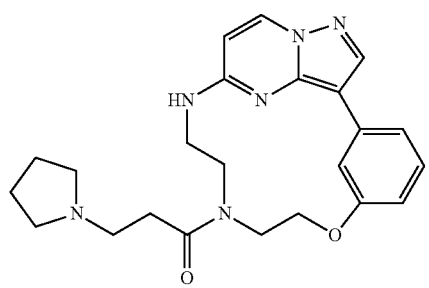
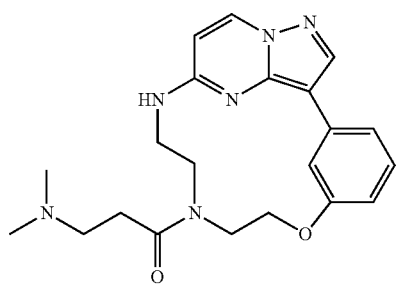
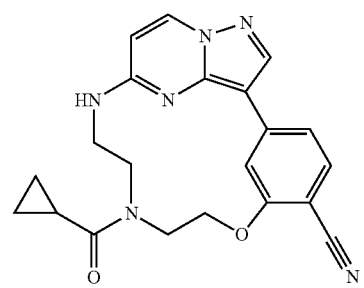
34
-continued
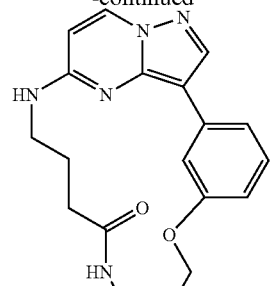
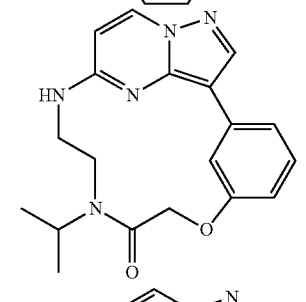
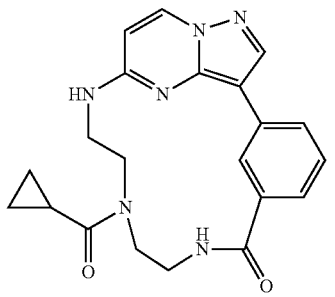
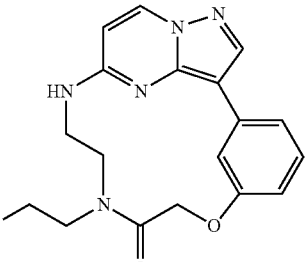
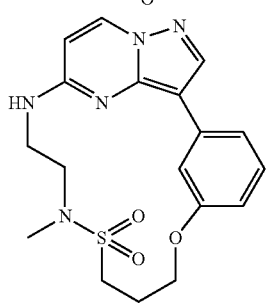
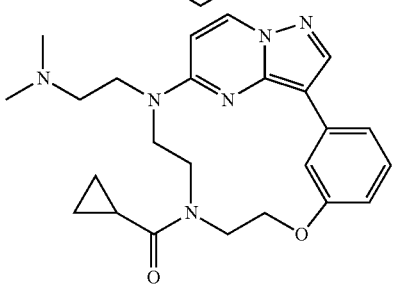

35
-continued
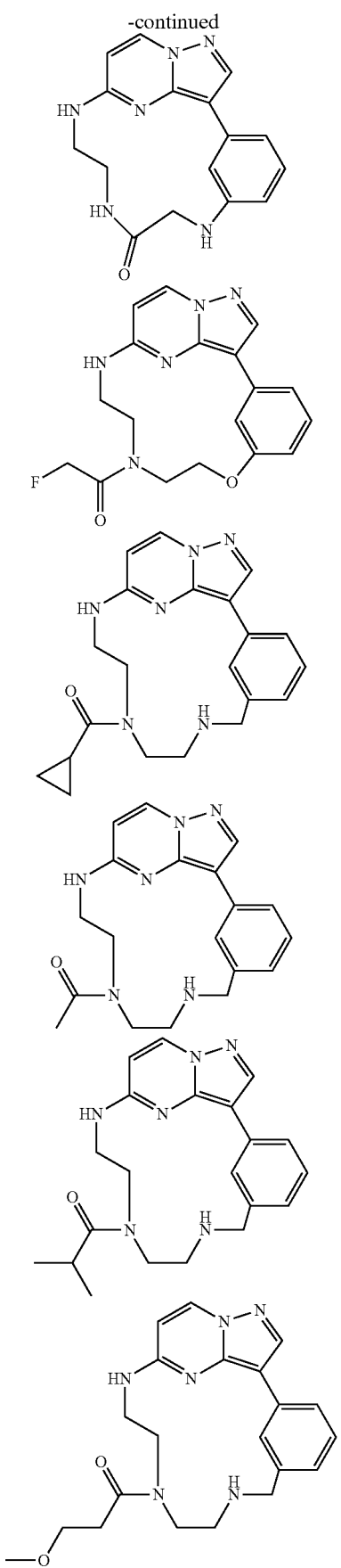
36
-continued
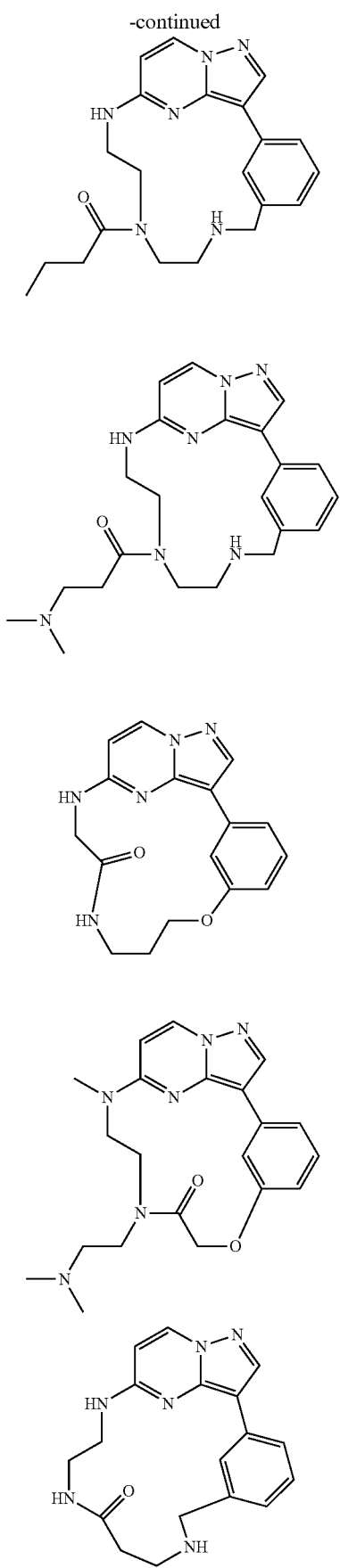

| 37 | 38 |
|---|---|
| -continued | -continued |
| 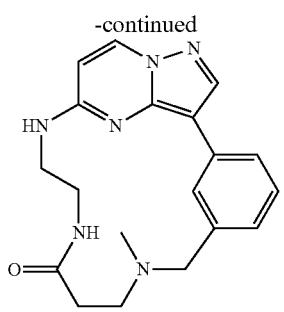 | 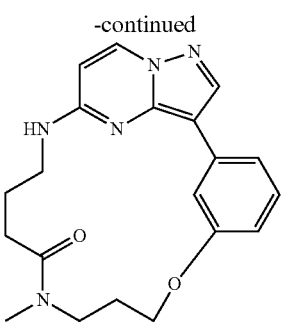 |
| 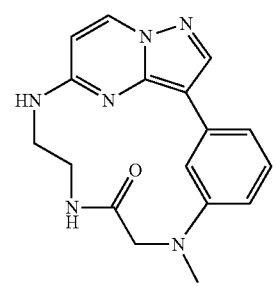 | 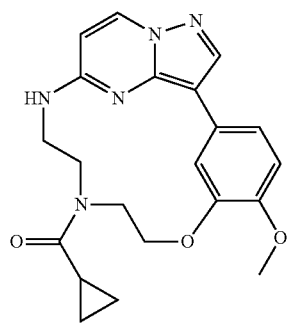 |
| 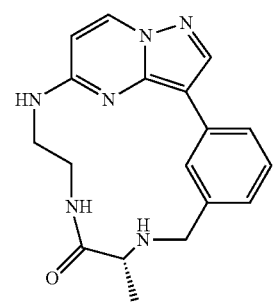 | 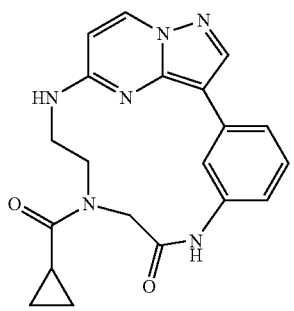 |
| 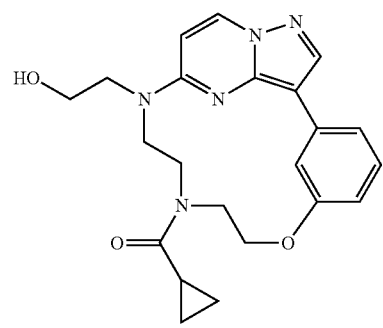 | 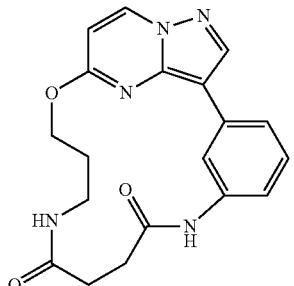 |
| 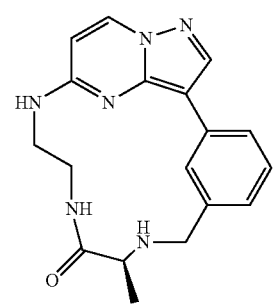 | 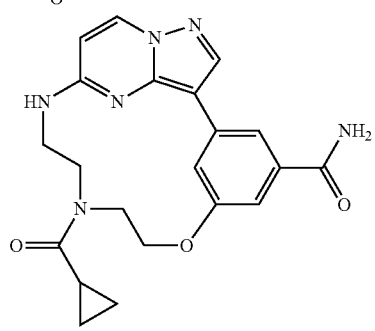 |

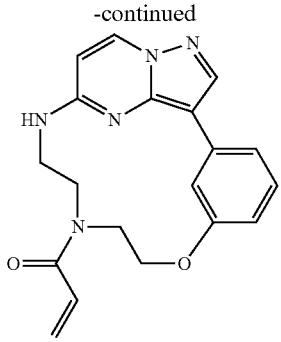
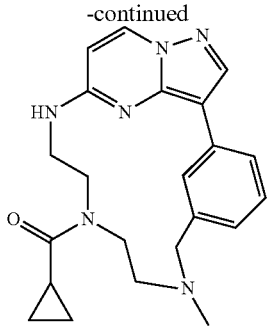
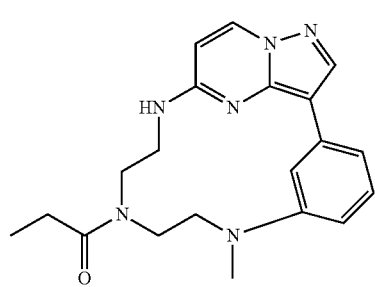
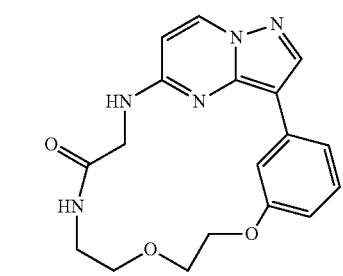
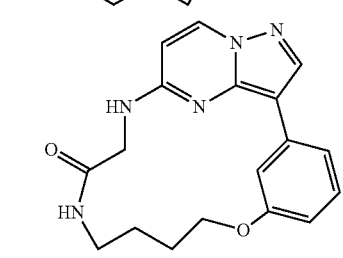
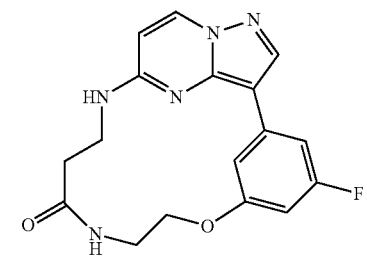
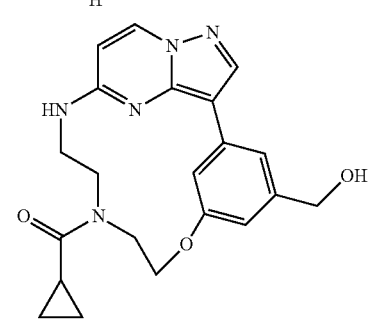
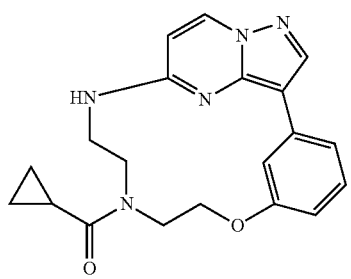
In particular the present invention provides a compound selected from the list comprising
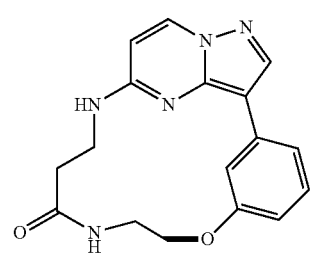
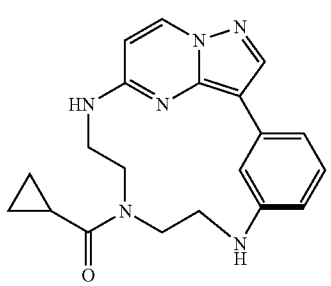

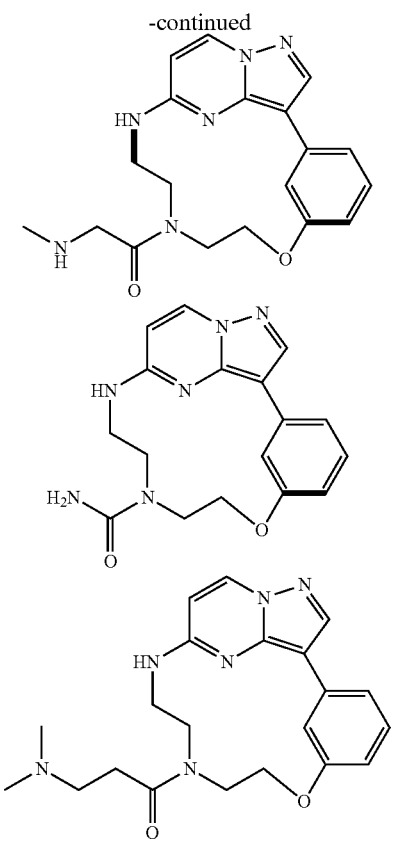

In particular in the compounds according to this invention, the pyrazolopyrimidine moiety is linked to the aryl or heteroaryl moiety at position $Z_1$ or $Z_2$, in accordance with the numbering as provided in Formula I. Furthermore, the $R_1$ of the compounds according to this invention is preferably linked to the aryl or heteroaryl moiety at position $Z_3$, $Z_4$ or $Z_5$, in accordance with the numbering as provided in Formula I.

The compounds of the present invention can be prepared according to the reaction schemes provided in the examples hereinafter, but those skilled in the art will appreciate that these are only illustrative for the invention and that the compounds of this invention can be prepared by any of several standard synthetic processes commonly used by those skilled in the art of organic chemistry.

In a preferred embodiment, the compounds of the present invention are useful in human or veterinary medicine, in particular for use as kinase inhibitors, more in particular for the inhibition of LRRK2 kinase.

The present invention further provides the use of a compound as defined hereinbefore or the use of a composition comprising said compound, as a human or veterinary medicine, in particular for the prevention and/or treatment of neurological disorders such as but not limited to Parkinson's disease and Alzheimer's disease.

In a preferred embodiment, the invention provides the use of a compound as defined hereinbefore or the use of a composition comprising said compound in the prevention and/or treatment of neurological disorders such as but not limited to Parkinson's disease and Alzheimer's disease.

The present invention further provides a compound as defined hereinbefore or a composition comprising said compound for use in the prevention and/or treatment of neurological disorders such as but not limited to Parkinson's disease and Alzheimer's disease.

Further embodiments of the present invention are detailed herein below in the form of numbered statements:

1. A compound of Formula I or a stereoisomer, tautomer, racemic, metabolite, pro- or predrug, salt, hydrate, N-oxide form, or solvate thereof,

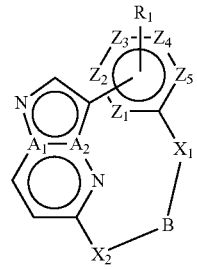

I wherein $A_1$ and $A_2$ are selected from C and N; wherein when $A_1$ is C, then $A_2$ is N; and wherein when $A_2$ is C, then $A_1$ is N;

$R_1$ is selected from —H, -halo, —OH, —$C_{1-6}$alkyl, —$C_{3-6}$cycloalkyl, —O—$C_{1-6}$alkyl, —S—$C_{1-6}$alkyl, —$NR_9R_{10}$, —(C=O)—$R_4$, —$SO_2$—$R_4$, —CN, —$NR_9$—$SO_2$—$R_4$, -$Het_1$; wherein each of said $C_{1-6}$ alkyl is optionally and independently substituted with from 1 to 3 substituents selected from -halo, —OH, —$NR_{11}R_{12}$, —O—$C_{1-6}$alkyl, —S—$C_{1-6}$alkyl;

$R_2$ is selected from —H, -halo, —OH, —$C_{1-6}$alkyl, —$C_{1-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, —(C=O)—$NR_{27}R_{28}$, -$Het_3$, —(C=O)-$Het_3$, —$SO_2$—$C_{1-6}$alkyl; wherein each of said $C_{1-6}$alkyl is optionally and independently substituted with from 1 to 3 substituents selected from -halo, —OH, —O—$C_{1-6}$alkyl, —S—$C_{1-6}$alkyl, -$Het_3$, —$Ar_2$, —$NR_{13}R_{14}$;

$R_3$ is selected from —H, -halo, —OH, —$C_{1-6}$alkyl, —$C_{3-6}$cycloalkyl, —O—$C_{1-6}$alkyl, —S—$C_{1-6}$alkyl, —(C=O)—$C_{1-6}$alkyl, —(C=O)—O—$C_{1-6}$alkyl, -$Het_2$, —(C=O)-$Het_2$, —(C=O)—$NR_{29}R_{30}$, —$SO_2$—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, —$NR_{15}R_{16}$, -$Het_2$, —$Ar_4$;

$R_4$ is selected from -halo, —OH, —$C_{1-6}$alkyl, —O—$C_{1-6}$alkyl, —S—$C_{1-6}$alkyl, —$NR_{17}R_{18}$, -$Het_4$;

$R_5$ and $R_7$ are each independently selected from —H, -halo, —$C_{1-6}$alkyl, —$OC_{1-6}$alkyl, —S—$C_{1-6}$ alkyl, -$Het_5$, —$Ar_1$, —$C_{3-6}$cycloalkyl, —$SO_2$—$Ar_3$, —$SO_2$, —$SO_2$—$C_{1-6}$alkyl, —(C=O), —(C=O)—$C_{1-6}$alkyl, —O—(C=O)—$C_{1-6}$alkyl, —(C=O)—O—$C_{1-6}$alkyl; wherein each of said $C_{1-6}$alkyl is optionally and independently substituted with from 1 to 3 substituents selected from -halo, —OH, —$OC_{1-6}$alkyl, —$SC_{1-6}$alkyl, -$Het_5$, —$NR_{23}R_{24}$;

$R_6$ is selected from —$SO_2$, —$SO_2$—$C_{1-6}$alkyl, —(C=O), —(C=S), —(C=O)—O—$C_{1-6}$alkyl, —(C=S)—O—$C_{1-6}$alkyl, —(C=O)—$C_{1-6}$alkyl, —(C=S)—$C_{1-6}$alkyl, —$C_{1-6}$alkyl-(C=O)—$NR_{31}R_{32}$, —$C_{1-6}$alkyl-(C=S)—$NR_{31}R_{32}$, —$C_{1-6}$alkyl-$NR_{33}$(C=O)—$NR_{31}R_{32}$, —$C_{1-6}$alkyl-$NR_{33}$(C=S)—$NR_{31}R_{32}$, —(C=O)—$C_{3-5}$cycloalkyl, —(C=S)—$C_{3-5}$cycloalkyl, —(C=O)—$NR_{31}R_{32}$, —(C=S)—$NR_{31}R_{32}$, —(C=O)-$Het_5$, —(C=S)-$Het_5$, —(C=O)—$Ar_6$, —(C=S)—$Ar_6$, —(C=O)—$NR_{31}$—(C=O)—$R_{32}$; wherein each of said $C_{1-6}$alkyl is optionally and independently substituted with from 1 to 3 substituents selected from -halo, —OH, —OC$_{1-6}$alkyl, —SC$_{1-6}$alkyl, -Het$_5$, —NR$_{25}$R$_{26}$;

R$_8$ is selected from —NR$_{34}$—(C=O)—R$_{35}$, —NR$_{36}$—(C=O)—NR$_{34}$R$_{35}$, —NR$_{34}$—(SO2)-R$_{35}$, —NR$_{34}$—(C=O)—O—R$_{35}$, —O—(C=O)—NR$_{34}$R$_{35}$;

R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, R$_{36}$, R$_{37}$, R$_{38}$, R$_{39}$ and R$_{40}$ are each independently selected from —H, -halo, —O, —OH, —O—C$_{1-6}$alkyl, —C$_{1-6}$alkyl, —C$_{3-6}$cycloalkyl or -Het$_1$; wherein each of said C$_{1-6}$alkyl is optionally and independently substituted with from 1 to 3 substituents selected from -halo, —OH, —O—C$_{1-6}$alkyl, —S—C$_{1-6}$alkyl, -Het$_6$, —Ar$_5$;

X$_1$ is selected from —C$_{1-6}$alkyl-, —O—C$_{1-6}$alkyl-, —S—C$_{1-6}$alkyl-, —(C=O)—, —NR$_3$—(C=O)—, —NR$_3$—C$_{1-6}$alkyl-, —SO$_2$—NR$_3$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, —NR$_{37}$R$_{38}$;

X$_2$ is selected from —C$_{1-6}$alkyl-, —O—C$_{1-6}$alkyl-, —S—C$_{1-6}$alkyl-, —(C=O)—, —(C=O)—NR$_2$—, —NR$_2$—C$_{1-6}$alkyl-, —NR$_2$—, —SO$_2$—NR$_2$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, —NR$_{39}$R$_{40}$;

B is selected from —(C=O)—, —(C=N)R$_{39}$—, —(SO2)-, —(C=O)—NR$_5$—, —(C=S)—NR$_5$—, —NR$_5$—(C=O)—NR$_7$—, —NR$_5$—(C=S)—NR$_7$—, —SO$_2$—NR$_5$—, —NR$_6$—, —NR$_5$—(C=O)—O—, —NR$_5$—(C=S)—O—, —CHR$_8$—;

Ar$_1$, Ar$_2$, Ar$_3$, Ar$_4$, Ar$_5$, and Ar$_6$ are each independently a 5- or 6-membered aromatic heterocycle optionally comprising 1 or 2 heteroatoms selected from O, N and S; each of said Ar$_1$, Ar$_2$, Ar$_3$, Ar$_4$, and Ar$_5$ being optionally and independently substituted with from 1 to 3 substituents selected from —NR$_{19}$R$_{20}$, —C$_{1-6}$alkyl, —O—C$_{1-6}$alkyl, —S—C$_4$alkyl;

Het$_1$, Het$_2$, Het$_3$, Het$_4$, Het$_5$, and Het$_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —C$_{1-6}$alkyl, —OC$_{1-6}$alkyl, —SC$_{1-6}$alkyl, —NR$_{21}$R$_{22}$; each of said —C$_{1-6}$alkyl being optionally substituted with from 1 to 3 -halo;

Z$_1$, Z$_2$, Z$_3$, Z$_4$ and Z$_5$ are each independently selected from C and N 2. A compound as defined in statement 1, wherein A$_1$ and A$_2$ are selected from C and N; wherein when A$_1$ is C, then A$_2$ is N; and wherein when A$_2$ is C, then A$_1$ is N;

R$_1$ is selected from —H, -halo, —OH, —C$_{1-6}$alkyl, —C$_{3-6}$cycloalkyl, —O—C$_{1-6}$alkyl, —S—C$_{1-6}$alkyl, —NR$_9$R$_{10}$, —(C=O)—R$_4$, —SO$_2$—R$_4$, —CN, —NR$_9$SO$_2$—R$_4$, -Het$_1$; wherein each of said C$_{1-6}$alkyl is optionally and independently substituted with from 1 to 3 substituents selected from -halo, —OH, —NR$_{11}$R$_{12}$, —O—C$_{1-6}$alkyl, —S—C$_{1-6}$alkyl;

R$_2$ is selected from —H, -halo, —OH, —C$_{1-6}$alkyl, —C$_{3-6}$cycloalkyl, —O—C$_{1-6}$alkyl, —S—C$_{1-6}$alkyl, —(C=O)—C$_{1-6}$alkyl, —(C=O)—O—C$_{1-6}$alkyl, —(C=O)—NR$_{27}$R$_{28}$, -Het$_3$, —(C=O)-Het$_3$, —SO$_2$—C$_{1-6}$alkyl; wherein each of said C$_{1-6}$alkyl is optionally and independently substituted with from 1 to 3 substituents selected from -halo, —OH, —O—C$_{1-6}$alkyl, —S—C$_{1-6}$alkyl, -Het$_3$, —Ar$_2$, —NR$_{13}$R$_{14}$;

R$_3$ is selected from —H, -halo, —OH, —C$_{1-6}$alkyl, —C$_{3-6}$cycloalkyl, —O—C$_{1-6}$alkyl, —S—C$_{1-6}$alkyl, —(C=O)—C$_{1-6}$alkyl, —(C=O)—O—C$_{1-6}$alkyl, -Het$_2$, —(C=O)-Het$_2$, —(C=O)—NR$_{29}$R$_{30}$, —SO$_2$—C$_{1-6}$alkyl; wherein each of said C$_{1-6}$alkyl is optionally and independently substituted with from 1 to 3 substituents selected from -halo, —OH, —OC$_{1-6}$alkyl, —SC$_{1-6}$alkyl, —NR$_{15}$R$_{16}$, -Het$_2$, —Ar$_4$;

R$_4$ is selected from -halo, —OH, —C$_{1-6}$alkyl, —O—C$_{1-6}$alkyl, —S—C$_{1-6}$alkyl, —NR$_{17}$R$_{18}$, -Het$_4$;

R$_5$ and R$_7$ are each independently selected from —H, -halo, —C$_{1-6}$alkyl, —OC$_{1-6}$alkyl, —S—C$_{1-6}$alkyl, -Het$_5$, —Ar$_1$, —C$_{3-6}$cycloalkyl, —SO$_2$—Ar$_3$, —SO$_2$—C$_{1-6}$alkyl, —(C=O), —(C=O)—C$_{1-6}$alkyl, —O—(C=O)—C$_{1-6}$alkyl, —(C=O)—O—C$_{1-6}$alkyl; wherein each of said C$_{1-6}$alkyl is optionally and independently substituted with from 1 to 3 substituents selected from -halo, —OH, —OC$_{1-6}$alkyl, —SC$_{1-6}$alkyl, -Het$_5$, —NR$_{23}$R$_{24}$;

R$_6$ is selected from —SO$_2$, —SO$_2$—C$_{1-6}$alkyl, —(C=O), —(C=S), —(C=O)—O—C$_{1-6}$alkyl, —(C=S)—O—C$_{1-6}$alkyl, —(C=O)—C$_{1-6}$alkyl, —(C=S)—C$_{1-6}$alkyl, —C$_{1-6}$alkyl-(C=O)—NR$_{31}$R$_{32}$, —C$_{1-6}$alkyl-(C=S)—NR$_{31}$R$_{32}$, —C$_{1-6}$alkyl-NR$_{33}$(C=O)—NR$_{31}$R$_{32}$, —C$_{1-6}$alkyl-NR$_{33}$(C=S)—NR$_{31}$R$_{32}$, —(C=O)—C$_{3-5}$cycloalkyl, —(C=S)—C$_{3-5}$cycloalkyl, —(C=O)—NR$_{31}$R$_{32}$, —(C=S)—NR$_{31}$R$_{32}$, —(C=O)-Het$_5$, —(C=S)-Het$_5$, —(C=O)—Ar$_6$, —(C=S)—Ar$_6$, —(C=O)—NR$_{31}$—(C=O)—R$_{32}$; wherein each of said C$_{1-6}$alkyl is optionally and independently substituted with from 1 to 3 substituents selected from -halo, —OH, —OC$_{1-6}$alkyl, —SC$_{1-6}$alkyl, -Het$_5$, —NR$_{25}$R$_{26}$;

R$_8$ is selected from —NR$_{34}$—(C=O)—R$_{35}$, —NR$_{36}$—(C=O)—NR$_{34}$R$_{35}$, —NR$_{34}$—(SO2)-R$_{35}$, —NR$_{34}$—(C=O)—O—R$_{35}$, —O—(C=O)—NR$_{34}$R$_{35}$;

R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, R$_{36}$, R$_{37}$, R$_{38}$, R$_{39}$ and R$_{40}$ are each independently selected from —H, -halo, —O, —OH, —O—C$_{1-6}$alkyl, —C$_{1-6}$alkyl, —C$_{3-6}$cycloalkyl or -Het$_1$; wherein each of said C$_{1-6}$alkyl is optionally and independently substituted with from 1 to 3 substituents selected from -halo, —OH, —O—C$_{1-6}$alkyl, —S—C$_{1-6}$alkyl, -Het$_6$, —Ar$_5$;

X$_1$ is selected from —C$_{1-6}$alkyl-, —O—C$_{1-6}$alkyl-, —S—C$_{1-6}$alkyl-, —(C=O)—, —NR$_3$—(C=O)—, —NR$_3$—C$_{1-6}$alkyl-, —SO$_2$—NR$_3$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, —NR$_{37}$R$_{38}$; wherein when X$_1$ is —O—CH$_3$—, then R$_5$ is not —H;

X$_2$ is selected from —C$_{1-6}$alkyl-, —O—C$_{1-6}$alkyl-, —S—C$_{1-6}$alkyl-, —(C=O)—, —(C=O)—NR$_2$—, —NR$_2$—C$_{1-6}$alkyl-, —NR$_2$—, —SO$_2$—NR$_2$—; wherein each of said C$_{1-6}$alkyl C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, —NR$_{39}$R$_{40}$;

B is selected from —(C=O)—, —(C=N)R$_{39}$—, —(SO2)-, —(C=O)—NR$_5$—, —(C=S)—NR$_5$—, —NR$_5$—(C=O)—NR$_7$—, —NR$_5$—(C=S)—NR$_7$—, —SO$_2$—NR$_5$—, —NR$_6$—, —NR$_5$—(C=O)—O—, —NR$_5$—(C=S)—O—, —CHR$_8$—;

Ar$_1$, Ar$_2$, Ar$_3$, Ar$_4$, Ar$_5$, and Ar$_6$ are each independently a 5- or 6-membered aromatic heterocycle optionally comprising 1 or 2 heteroatoms selected from O, N and S; each of said Ar$_1$, Ar$_2$, Ar$_3$, Ar$_4$, and Ar$_5$ being optionally and independently substituted with from 1 to 3 substituents selected from —NR$_{19}$R$_{20}$, —C$_{1-6}$alkyl, —O—C$_{1-6}$alkyl, —S—C$_{1-6}$alkyl;

Het$_1$, Het$_2$, Het$_3$, Het$_4$, Het$_5$, and Het$_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —C$_4$alkyl, —OC$_{1-6}$alkyl, —SC$_{1-6}$alkyl, —NR$_{21}$R$_{22}$; each of said —C$_{1-6}$alkyl being optionally substituted with from 1 to 3 -halo;

Z$_1$, Z$_2$, Z$_3$, Z$_4$ and Z$_5$ are each independently is selected from C and N 3. A compound as defined in statement 1, wherein A$_1$ is N and A$_2$ is C;

R$_1$ is selected from —H, —OH, —C$_{1-6}$alkyl, —C$_{3-6}$cycloalkyl, —O—C$_{1-6}$alkyl, —S—C$_{1-6}$alkyl, —NR$_9$R$_{10}$, —SO$_2$—R$_4$, —CN, —NR$_9$—SO$_2$—R$_4$, -Het$_1$; wherein each of said C$_{1-6}$alkyl is optionally and independently substituted with from 1 to 3 substituents selected from -halo, —OH, —NR$_{11}$R$_{12}$, —O—C$_{1-6}$alkyl, —S—C$_{1-6}$alkyl;

R$_2$ is selected from —H, -halo, —OH, —C$_{1-6}$alkyl, —C$_{3-6}$cycloalkyl, —O—C$_{1-6}$alkyl, —S—C$_{1-6}$alkyl, —(C=O)—C$_{1-6}$alkyl, —(C=O)—O—C$_{1-6}$alkyl, —(C=O)—NR$_{27}$R$_{28}$, -Het$_3$, —(C=O)-Het$_3$, —SO$_2$—C$_{1-6}$alkyl; wherein each of said C$_{1-6}$alkyl is optionally and independently substituted with from 1 to 3 substituents selected from -halo, —OH, —O—C$_{1-6}$alkyl, —S—C$_{1-6}$alkyl, -Het$_3$, —Ar$_2$, —NR$_{13}$R$_{14}$;

R$_3$ is selected from —H, -halo, —OH, —C$_{1-6}$alkyl, —C$_{3-6}$cycloalkyl, —O—C$_{1-6}$alkyl, —S—C$_{1-6}$alkyl, —(C=O)—C$_{1-6}$alkyl, —(C=O)—O—C$_{1-6}$alkyl, -Het$_2$, —(C=O)-Het$_2$, —(C=O)—NR$_{29}$R$_{30}$, —SO$_2$—C$_{1-6}$alkyl; wherein each of said C$_{1-6}$alkyl is optionally and independently substituted with from 1 to 3 substituents selected from -halo, —OH, —O—C$_{1-6}$alkyl, —SC$_{1-6}$alkyl, —NR$_{15}$R$_{16}$, -Het$_2$, —Ar$_4$;

R$_4$ is selected from -halo, —OH, —C$_{1-6}$alkyl, —O—C$_{1-6}$alkyl, —S—C$_{1-6}$alkyl, —NR$_{17}$R$_{18}$, -Het$_4$;

R$_5$ and R$_7$ are each independently selected from —H, -halo, —C$_{1-6}$alkyl, —OC$_{1-6}$alkyl, —S—C$_{1-6}$alkyl, -Het$_5$, —Ar$_1$, —C$_{3-6}$cycloalkyl, —SO$_2$—Ar$_3$, —SO$_2$, —SO$_2$—C$_{1-6}$alkyl, —(C=O), —(C=O)—C$_{1-6}$alkyl, —O—(C=O)—C$_{1-6}$alkyl, —(C=O)—O—C$_{1-6}$alkyl; wherein each of said C$_{1-6}$alkyl is optionally and independently substituted with from 1 to 3 substituents selected from —OH, —OC$_{1-6}$alkyl, —SC$_{1-6}$alkyl, -Het$_5$, —NR$_{23}$R$_{24}$;

R$_6$ is selected from —SO$_2$, —(C=O), —(C=S), —(C=O)—O—C$_{1-6}$alkyl, —(C=S)—O—C$_{1-6}$alkyl, —(C=O)—C$_{1-6}$alkyl, —(C=S)—C$_{1-6}$alkyl, —C$_{1-6}$alkyl-(C=S)—NR$_{31}$R$_{32}$, —C$_{1-6}$alkyl-NR$_{33}$(C=O)—NR$_{31}$R$_{32}$, —C$_{1-6}$alkyl-NR$_{33}$(C=S)—NR$_{31}$R$_{32}$, —(C=S)—C$_{3-5}$cycloalkyl, —(C=S)—NR$_{31}$R$_{32}$, —(C=O)-Het$_5$, —(C=S)-Het$_5$, —(C=O)—NR$_{31}$—(C=O)—R$_{32}$; wherein each of said C$_{1-6}$alkyl is optionally and independently substituted with from 1 to 3 substituents selected from —OH, —OC$_{1-6}$alkyl, —SC$_{1-6}$alkyl, -Het$_5$, —NR$_{25}$R$_{26}$;

R$_8$ is selected from —NR$_{36}$—(C=O)—NR$_{34}$R$_{35}$, —NR$_{34}$—(SO2)-R$_{35}$, —NR$_{34}$—(C=O)—O—R$_{35}$, —O—(C=O)—NR$_{34}$R$_{35}$;

R$_9$, R$_{10}$, R$_{11}$, R$_{12}$, R$_{13}$, R$_{14}$, R$_{15}$, R$_{16}$, R$_{17}$, R$_{18}$, R$_{19}$, R$_{20}$, R$_{21}$, R$_{22}$, R$_{23}$, R$_{24}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, R$_{36}$, R$_{37}$, R$_{38}$, R$_{39}$ and R$_{40}$ are each independently selected from —H, -halo, —O, —OH, —O—C$_{1-6}$alkyl, —C$_{1-6}$alkyl, —C$_{3-5}$cycloalkyl or -Het$_1$; wherein each of said C$_{1-6}$alkyl is optionally and independently substituted with from 1 to 3 substituents selected from -halo, —OH, —O—C$_{1-6}$alkyl, —S—C$_{1-6}$alkyl, -Het$_6$, —Ar$_5$;

X$_1$ is selected from —C$_{1-6}$alkyl-, —O—C$_{1-6}$alkyl-, —S—C$_{1-6}$alkyl-, —(C=O)—, —NR$_3$—(C=O)—, —SO$_2$—NR$_3$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, —NR$_{37}$R$_{38}$;

X$_2$ is selected from —C$_{1-6}$alkyl-, —O—C$_{1-6}$alkyl-, —S—C$_{1-6}$alkyl-, —(C=O)—, —(C=O)—NR$_2$—, —NR$_2$—C$_{1-6}$alkyl-, —NR$_2$—, —SO$_2$—NR$_2$—; wherein each of said C$_{1-6}$alkyl is optionally and independently substituted with from 1 to 3 substituents selected from -halo, —OH, —C$_{1-6}$alkyl, —O—C$_{1-6}$alkyl, —S—C$_{1-6}$alkyl, —NR$_{39}$R$_{40}$;

B is selected from —(C=O)—, —(C=N)R$_{39}$—, —(SO2)-, —(C=O)—NR$_5$—, —(C=S)—NR$_5$—, —NR$_5$—(C=O)—NR$_7$—, —NR$_5$—(C=S)—NR$_7$—, —SO$_2$—NR$_5$—, —NR$_6$—, —NR$_5$—(C=S)—O—, —CHR$_8$—;

Ar$_1$, Ar$_2$, Ar$_3$, Ar$_4$, Ar$_5$, and Ar$_6$ are each independently a 5- or 6-membered aromatic heterocycle optionally comprising 1 or 2 heteroatoms selected from O, N and S; each of said Ar$_1$, Ar$_2$, Ar$_3$, Ar$_4$, and Ar$_5$ being optionally and independently substituted with from 1 to 3 substituents selected from —NR$_{19}$R$_{20}$, —C$_{1-6}$alkyl, —O—C$_{1-6}$alkyl, —S—C$_{1-6}$alkyl;

Het$_1$, Het$_2$, Het$_3$, Het$_4$, Het$_5$, and Het$_6$ are each independently a 5- or 6-membered monocyclic heterocycle having from 1 to 3 heteroatoms selected from O, N and S, wherein each heterocycle is being optionally and independently substituted with from 1 to 3 substituents selected from -halo, —C$_{1-6}$alkyl, —OC$_{1-6}$alkyl, —SC$_{1-6}$alkyl, —NR$_{21}$R$_{22}$; each of said —C$_{1-6}$alkyl being optionally substituted with from 1 to 3 -halo;

Z$_1$, Z$_2$, Z$_3$, Z$_4$ and Z$_5$ are each C.

4. A compound according to statement 1, wherein

A$_1$ and A$_2$ are selected from C and N; wherein when A$_1$ is C, then A$_2$ is N; and wherein when A$_2$ is C, then A$_1$ is N;

R$_1$ is selected from —H, -halo, —(C=O)—R$_4$;

R$_2$ is selected from —H, —C$_{1-6}$alkyl; wherein each of said C$_{1-6}$alkyl is optionally and independently substituted with from 1 to 3 —O—C$_{1-6}$alkyl;

R$_3$ is selected from —H, —C$_{1-6}$alkyl;

R$_4$ is —NR$_{17}$R$_{18}$;

R$_5$ and R$_7$ are each independently selected from —H, —C$_{1-6}$alkyl; wherein each of said C$_{1-6}$alkyl is optionally and independently substituted with from 1 to 3 -halo;

R$_6$ is selected from —SO$_2$—C$_{1-6}$alkyl, —(C=O)—O—C$_{1-6}$alkyl, —(C=O)—C$_{1-6}$alkyl, —C$_{1-6}$alkyl-(C=O)—NR$_{31}$R$_{32}$, —(C=O)—C$_{3-5}$cycloalkyl, —(C=O)—NR$_{31}$R$_{32}$, —(C=O)-Het$_5$, —(C=O)—Ar$_6$; wherein each of said C$_{1-6}$alkyl is optionally and independently substituted with from 1 to 3 substituents selected from -halo, —OH, —OC$_{1-6}$alkyl R$_8$ is —NR$_{34}$—(C=O)—R$_{35}$;

R$_{17}$, R$_{18}$, R$_{31}$, R$_{32}$, R$_{34}$, R$_{35}$, are each independently selected from —H, —C$_{1-6}$alkyl, —C$_{3-6}$cycloalkyl;

X$_1$ is selected from —O—C$_{1-6}$alkyl-, —NR$_3$—C$_{1-6}$alkyl-;

X$_2$ is selected from —S—C$_{1-6}$alkyl-, —NR$_2$—C$_{1-6}$alkyl-;

B is selected from —(C=O)—NR$_5$—, —NR$_5$—(C=O)—NR$_7$—, —SO$_2$—NR$_5$—, —NR$_6$—, —NR$_5$—(C=O)—O—, —CHR$_8$—

Het$_5$ is a 5- or 6-membered monocyclic heterocycle having from 1 to 3 heteroatoms selected from O, N and S, wherein each heterocycle is being optionally substituted with from 1 to 3 —C$_{1-6}$alkyl; each of said —C$_{1-6}$alkyl being optionally substituted with from 1 to 3 -halo;

Ar$_6$ is a 5- or 6-membered aromatic heterocycle optionally comprising 1 or 2 heteroatoms selected from O, N and S;

$Z_1$, $Z_2$, $Z_3$, $Z_4$ and $Z_5$ are each independently is selected from C and N.

5. A compound as defined in statement 1, wherein
$A_1$ and $A_2$ are selected from C and N; wherein when $A_1$ is C, than $A_2$ is N; and wherein when $A_2$ is C, than $A_1$ is N;
$R_1$ and $R_2$ are —H;
$R_5$ and $R_7$ are each independently selected from —H and —$C_{1-6}$alkyl;
$R_6$ is selected from —(C=O)—$C_{3-5}$cycloalkyl, —(C=O)—(CH$_2$)$_2$—OH;
$X_1$ is —O—$C_{1-3}$alkyl-; wherein when $X_1$ is —O—CH$_3$—, then $R_5$ is not —H;
$X_2$ is —NR$_2$—$C_{1-6}$alkyl-;
B is selected from —(C=O)—NR$_5$—, —NR$_5$—(C=O)—NR$_7$, —SO$_2$—NR$_5$, —NR$_6$—;
$Z_1$, $Z_2$, $Z_3$, $Z_4$ and $Z_5$ are each C.

6. A compound as defined in any one of statements 1 to 5 wherein the pyrazolopyrimidine moiety is linked to the aryl or heteroaryl moiety at position $Z_1$ or $Z_2$, in accordance with the numbering as provided in Formula I.

7. A compound as defined in any one of statements 1 to 6 wherein $R_1$ is linked to the aryl or heteroaryl moiety at position $Z_3$, $Z_4$ or $Z_5$, in accordance with the numbering as provided in Formula I.

8. A compound as defined in any one of statements 1 to 7, for use as a human or veterinary medicine.

9. Use of a compound as defined in any one of statements 1 to 7 in the manufacture of a medicament for the prevention, treatment and/or diagnosis of neurological disorders, such as Parkinson's disease or Alzheimer's disease.

10. A pharmaceutical composition comprising a compound as defined in any one of statements 1 to 7, suitable for use as a human or veterinary medicine.

11. Use of a compound as defined in any one of statements 1 to 7, or a composition as defined in statement 10, suitable for inhibiting the activity of a kinase; in particular a LRRK2 kinase.

12. Use of a compound as defined in any one of statements 1 to 7, or a composition as defined in statement 10, for the prevention, treatment and/or diagnosis of neurological disorders, such as Parkinson's disease or Alzheimer's disease.

13. A method for the prevention and/or treatment of neurological disorders, such as Parkinson's disease or Alzheimer's disease; said method comprising administering to a subject in need thereof a compound according to any one of statements 1 to 7 or a composition as defined in statement 10.

Method of Treatment

Compounds of formula (I) a stereoisomer, tautomer, racemic, metabolite, pro- or predrug, salt, hydrate, N-oxide form, or solvate thereof, are inhibitors of LRRK2 kinase activity and are thus believed to be of potential use in the treatment of neurological disorders including Parkinson's disease, Alzheimer's disease, dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), withdrawal symptoms/relapse associated with drug addiction, L-Dopa induced dyskinesia, and renal, breast, lung, prostate cancers as well as acute myelogenous leukemia (AML).

In the context of the present invention, treatment of Parkinson's disease refers to the treatment of idiopathic Parkinson's disease and familial Parkinson's disease. In one embodiment, familial Parkinson's disease includes patients expressing LRRK2 kinase bearing the G2019S mutation or the R1441G mutation. Treatment of Parkinson's disease may be symptomatic or may be disease modifying. In one embodiment, treatment of Parkinson's disease refers to symptomatic treatment. Compounds of the present invention may also be useful in treating patients identified as susceptible to progression to severe Parkinsonism by means of one of more subtle features associated with disease progression such as family history, olfaction deficits, constipation, cognitive defects, gait or biological indicators of disease progression gained from molecular, biochemical, immunological or Imaging technologies. In this context, treatment may be symptomatic or disease modifying.

In the context of the present invention, treatment of Alzheimer's disease refers to the treatment of idiopathic Alzheimer's disease and familial Alzheimer's disease. Treatment of Alzheimer's disease may be symptomatic or may be disease modifying. In one embodiment, treatment of Alzheimer's disease refers to symptomatic treatment.

Similarly, treatment of dementia (including Lewy body dementia and vascular dementia), age related memory dysfunction, mild cognitive impairment argyrophilic grain disease, Pick's disease, corticobasal degeneration, progressive supranuclear palsy, inherited frontotemporal dementia and parkinsonism linked to chromosome 17 (FTDP-7) and renal, breast, lung, prostate cancers as well as acute myelogenous leukemia (AML) may be symptomatic or disease modifying. In one embodiment, treatment of dementia (including Lewy body dementia and vascular dementia), age related memory dysfunction, mild cognitive impairment, argyrophilic grain disease, Pick's disease, corticobasal degeneration, progressive supranuclear palsy, inherited frontotemporal dementia and parkinsonism linked to chromosome 17 (FTDP-17), and renal, breast, lung, prostate cancers as well as acute myelogenous leukemia (A L) refers to symptomatic treatment.

In the context of the present invention, treatment of withdrawal symptoms/relapse associated with drug addiction and L-Dopa induced dyskinesia refers to symptomatic treatment.

Accordingly, the present invention further provides a method for the prevention and/or treatment of neurological disorders such as but not limited to Parkinson's disease and Alzheimer's disease, said method comprising administering to a subject in need thereof a therapeutic effective amount of a compound or a composition as defined herein. The methods of the present invention can be utilized in a variety of settings, including, for example, in selecting the optimal treatment course for a patient, in predicting the likelihood of success when treating an individual patient with a particular treatment regimen, in assessing disease progression, in monitoring treatment efficacy, in determining prognosis for individual patients and in assessing predisposition of an individual to benefit from a particular therapy.

In the invention, particular preference is given to compounds of Formula I or any subgroup thereof that in the inhibition assay for LRRK2 described below inhibit kinase activity with an $IC_{50}$ value of less than 10 μM, preferably less than 1 μM, most preferably less than 100 nM.

Said inhibition may be effected in vitro and/or in vivo, and when effected in vivo, is preferably effected in a selective manner, as defined above.

The term "LRRK2 kinase-mediated condition" or "disease", as used herein, means any disease or other deleterious condition in which the LRKK2 kinase is known to play a role. The term "LRRK2 kinase-mediated condition" or "disease" also means those diseases or conditions that are alleviated by treatment with a LRRK2 kinase inhibitor. Accordingly, another embodiment of the present invention relates to treating or lessening the severity of one or more diseases in which the LRRK2 kinase is known to play a role.

For pharmaceutical use, the compounds of the invention may be used as a free acid or base, and/or in the form of a pharmaceutically acceptable acid-addition and/or base-addition salt (e.g. obtained with non-toxic organic or inorganic acid or base), in the form of a hydrate, solvate and/or complex, and/or in the form or a pro-drug or pre-drug, such as an ester. As used herein and unless otherwise stated, the term "solvate" includes any combination which may be formed by a compound of this invention with a suitable inorganic solvent (e.g. hydrates) or organic solvent, such as but not limited to alcohols, ketones, esters and the like. Such salts, hydrates, solvates, etc. and the preparation thereof will be clear to the skilled person; reference is for instance made to the salts, hydrates, solvates, etc. described in U.S. Pat. No. 6,372,778, U.S. Pat. No. 6,369,086, U.S. Pat. No. 6,369,087 and U.S. Pat. No. 6,372,733.

The pharmaceutically acceptable salts of the compounds according to the invention, i.e. in the form of water-, oil-soluble, or dispersible products, include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, palmoate, pectinate, persulfate, 3-phenylpropionate, picrate, pivalate, propionate, succinate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. In addition, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl-bromides and others. Other pharmaceutically acceptable salts include the sulfate salt ethanolate and sulfate salts.

Generally, for pharmaceutical use, the compounds of the inventions may be formulated as a pharmaceutical preparation or pharmaceutical composition comprising at least one compound of the invention and at least one pharmaceutically acceptable carrier, diluent or excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is again made to for instance U.S. Pat. No. 6,372,778, U.S. Pat. No. 6,369,086, U.S. Pat. No. 6,369,087 and U.S. Pat. No. 6,372,733, as well as to the standard handbooks, such as the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, creams, lotions, soft and hard gelatin capsules, suppositories, eye drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other pharmaceutically active substances (which may or may not lead to a synergistic effect with the compounds of the invention) and other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein, for example using liposomes or hydrophilic polymeric matrices based on natural gels or synthetic polymers. In order to enhance the solubility and/or the stability of the compounds of a pharmaceutical composition according to the invention, it can be advantageous to employ $\alpha$-, $\beta$- or $\gamma$-cyclodextrins or their derivatives. An interesting way of formulating the compounds in combination with a cyclodextrin or a derivative thereof has been described in EP-A-721, 331. In particular, the present invention encompasses a pharmaceutical composition comprising an effective amount of a compound according to the invention with a pharmaceutically acceptable cyclodextrin.

In addition, co-solvents such as alcohols may improve the solubility and/or the stability of the compounds. In the preparation of aqueous compositions, addition of salts of the compounds of the invention can be more suitable due to their increased water solubility.

For local administration, the compounds may advantageously be used in the form of a spray, ointment or transdermal patch or another suitable form for topical, transdermal and/or intradermal administration.

More in particular, the compositions may be formulated in a pharmaceutical formulation comprising a therapeutically effective amount of particles consisting of a solid dispersion of the compounds of the invention and one or more pharmaceutically acceptable water-soluble polymers.

The term "a solid dispersion" defines a system in a solid state (as opposed to a liquid or gaseous state) comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are preferred physical systems because the components therein are usually readily bioavailable to the organisms to which they are administered.

It may further be convenient to formulate the compounds in the form of nanoparticles which have a surface modifier adsorbed on the surface thereof in an amount sufficient to maintain an effective average particle size of less than 1000 nm. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

Yet another interesting way of formulating the compounds according to the invention involves a pharmaceutical composition whereby the compounds are incorporated in hydrophilic polymers and applying this mixture as a coat film over many small beads, thus yielding a composition with good bio-availability which can conveniently be manufactured and which is suitable for preparing pharmaceutical dosage forms for oral administration. Materials suitable for use as cores in the beads are manifold, provided that said materials are pharmaceutically acceptable and have appropriate dimensions and firmness. Examples of such materials are polymers, inorganic substances, organic substances, and saccharides and derivatives thereof.

The preparations may be prepared in a manner known per se, which usually involves mixing at least one compound according to the invention with the one or more pharmaceutically acceptable carriers, and, if desired, in combination with other pharmaceutical active compounds, when necessary under aseptic conditions. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

The pharmaceutical preparations of the invention are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use. Generally, such unit dosages will contain between 1 and 1000 mg, and usually between 5 and 500 mg, of the at least one compound of the invention, e.g. about 10, 25, 50, 100, 200, 300 or 400 mg per unit dosage.

The compounds can be administered by a variety of routes including the oral, rectal, ocular, transdermal, subcutaneous, intravenous, intramuscular or intranasal routes, depending mainly on the specific preparation used and the condition to be treated or prevented, and with oral and intravenous administration usually being preferred. The at least one compound of the invention will generally be administered in an "effective amount", by which is meant any amount of a compound of Formula or any subgroup thereof that, upon suitable administration, is sufficient to achieve the desired therapeutic or prophylactic effect in the individual to which it is administered. Usually, depending on the condition to be prevented or treated and the route of administration, such an effective amount will usually be between 0.01 to 1000 mg per kilogram body weight day of the patient per day, more often between 0.1 and 500 mg, such as between 1 and 250 mg, for example about 5, 10, 20, 50, 100, 150, 200 or 250 mg, per kilogram body weight day of the patient per day, which may be administered as a single daily dose, divided over one or more daily doses, or essentially continuously, e.g. using a drip infusion. The amount(s) to be administered, the route of administration and the further treatment regimen may be determined by the treating clinician, depending on factors such as the age, gender and general condition of the patient and the nature and severity of the disease/symptoms to be treated. Reference is again made to U.S. Pat. No. 6,372,778, U.S. Pat. No. 6,369,086, U.S. Pat. No. 6,369,087 and U.S. Pat. No. 6,372,733 and the further prior art mentioned above, as well as to the standard handbooks, such as the latest edition of Remington's Pharmaceutical Sciences.

In accordance with the method of the present invention, said pharmaceutical composition can be administered separately at different times during the course of therapy or concurrently in divided or single combination forms. The present invention is therefore to be understood as embracing all such regimes of simultaneous or alternating treatment and the term "administering" is to be interpreted accordingly.

For an oral administration form, the compositions of the present invention can be mixed with suitable additives, such as excipients, stabilizers, or inert diluents, and brought by means of the customary methods into the suitable administration forms, such as tablets, coated tablets, hard capsules, aqueous, alcoholic, or oily solutions. Examples of suitable inert carriers are gum arabic, magnesia, magnesium carbonate, potassium phosphate, lactose, glucose, or starch, in particular, corn starch. In this case, the preparation can be carried out both as dry and as moist granules. Suitable oily excipients or solvents are vegetable or animal oils, such as sunflower oil or cod liver oil. Suitable solvents for aqueous or alcoholic solutions are water, ethanol, sugar solutions, or mixtures thereof. Polyethylene glycols and polypropylene glycols are also useful as further auxiliaries for other administration forms. As immediate release tablets, these compositions may contain microcrystalline cellulose, dicalcium phosphate, starch, magnesium stearate and lactose and/or other excipients, binders, extenders, disintegrants, diluents and lubricants known in the art.

When administered by nasal aerosol or inhalation, these compositions may be prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Suitable pharmaceutical formulations for administration in the form of aerosols or sprays are, for example, solutions, suspensions or emulsions of the compounds of the invention or their physiologically tolerable salts in a pharmaceutically acceptable solvent, such as ethanol or water, or a mixture of such solvents. If required, the formulation can also additionally contain other pharmaceutical auxiliaries such as surfactants, emulsifiers and stabilizers as well as a propellant.

For subcutaneous administration, the compound according to the invention, if desired with the substances customary therefore such as solubilizers, emulsifiers or further auxiliaries are brought into solution, suspension, or emulsion. The compounds of the invention can also be lyophilized and the lyophilizates obtained used, for example, for the production of injection or infusion preparations. Suitable solvents are, for example, water, physiological saline solution or alcohols, e.g. ethanol, propanol, glycerol, in addition also sugar solutions such as glucose or mannitol solutions, or alternatively mixtures of the various solvents mentioned. The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

When rectally administered in the form of suppositories, these formulations may be prepared by mixing the compounds according to the invention with a suitable non-irritating excipient, such as cocoa butter, synthetic glyceride esters or polyethylene glycols, which are solid at ordinary temperatures, but liquefy and/or dissolve in the rectal cavity to release the drug.

In preferred embodiments, the compounds and compositions of the invention are used orally or parenterally.

The invention will now be illustrated by means of the following synthetic and biological examples, which do not limit the scope of the invention in any way.

EXAMPLES

A. Compound Synthesis and Physicochemical Properties

The compounds of this invention can be prepared by any of several standard synthetic processes commonly used by those skilled in the art of organic chemistry. The compounds are generally prepared from starting materials which are either commercially available or prepared by standard means obvious to those skilled in the art.

General Schemes:

In general the compounds of formula (I) can be prepared as shown in scheme 1 below wherein a pyrazolo[1,5-a]pyrimidine or a imidazo[2,1-f]pyridazine of formula (II) is converted by reaction with a compound of formula (III) into a compound of formula (IV), which is then reacted with a (hetero-) aryl of formula (V) to form a compound of formula (VI). The compound of formula (VI) can then be optionally deprotected if desired before cyclisation to form a compound of formula (VII). The compound of formula (VII) can be optionally converted into a compound of general formula (I).

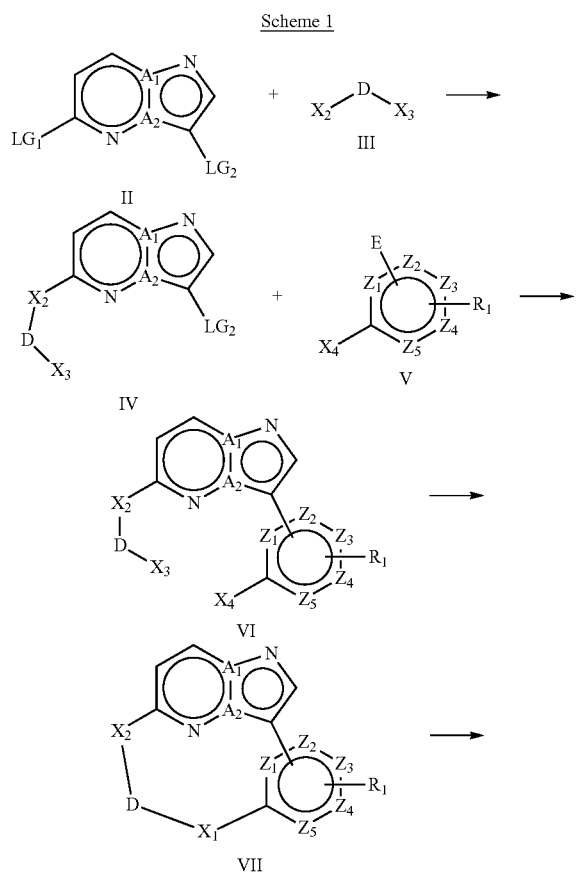

Scheme 1

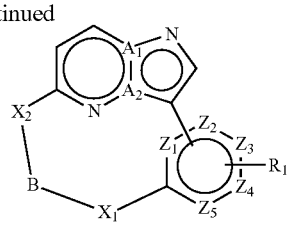

I

In the above scheme:

$LG_1$ and $LG_2$ each independently represent suitable leaving or functional groups;

$X_3$ and $X_4$ together with the functional moiety to which they are attached represent an unprotected or a protected functional group which upon reaction (after deprotection) produce together $X_1$ as defined in formula I;

E represents a suitable functional group that can be used to form a direct bond between the (hetero-)aryl group and the scaffold.

D represents a functional group such as B or a protected functional group, which upon further reaction and/or deprotection produces a functional group such as B as defined in formula I;

In the above reaction of the compound of formula (II) with the compound of formula (III) the leaving groups $LG_1$ and $LG_2$ are advantageously a halo group such as a chlorine or a bromine group. The reaction can be affected by a substitution for example by treating the compound of formula (II) with the compound of formula (III) in an organic solvent such as acetonitrile with an appropriate base such as for example diisopropylethylamine at an elevated temperature for example under reflux.

Compounds of formula (III) can be obtained through various selective protection and deprotection steps. The protection reactions can be effected using for example isoindoline-1,3-dione in a solvent such as toluene at an elevated temperature for example reflux or it can be effected by using for example tert-butoxycarbonyl anhydride in the presence of a base for example triethylamine in a solvent such as tetrahydrofuran at room temperature or it can be effected using for example tert-butyldimethylsilyl chloride and triethylamine in a solvent such as N,N-dimethylformamide at room temperature. The deprotection reaction can be effected in a conventional manner using for example hydrazine in a solvent such as ethanol at an elevated temperature for example under reflux.

The compound of formula (IV) can optionally be protected with a suitable protecting group such as a tert-butyloxycarbonylamino group in a conventional manner for example by treatment with tert-butoxycarbonyl anhydride in basic conditions using for example triethylamine and 4-(dimethylamino) pyridine in a solvent such as tetrahydrofuran at an elevated temperature such as under reflux.

The reaction of the resulting compound (IV) with a (hetero-)aryl compound of formula (V) is advantageously effected through the coupling of a boronic acid E or boronic ester E derivative of the (hetero-)aryl compound under Suzuki conditions using for example tetrakis(triphenylphosphine) palladium(0), 2-dicyclohexylphosphino-2',4',6'-triisopropyl-biphenyl (Xphos) and potassium phosphate tribasic in a solvent mixture such as 1,4-dioxane/water at an elevated temperature for example 80° C.

The resulting compound of formula (VI) can optionally be treated to remove any desired protecting groups for example silyl ether groups such as tert-butyldimethylsilyl groups can be converted to the parent free hydroxy group. Such deprotection can be effected in a conventional manner for example using tetrabutylammonium fluoride in 1,4-dioxane at room temperature.

The cyclisation of the compound of formula (VI) can be effected for example under Mitsunobu conditions using for example diisopropyl azodicarboxylate and triphenylphosphine in a solvent mixture such as 2-methyl-1,4-dioxane and toluene at an elevated temperature such as 90° C.

The resulting compound of formula (VII) can optionally be treated to remove any desired protecting groups for example tert-butyloxycarbonylamino groups can be converted to the parent free amino group. Such deprotection can be effected in a conventional manner for example by treatment under acidic conditions for example using a 4N hydrochloric acid solution in methanol at room temperature.

The deprotected compound can optionally be treated to form an amide compound of formula (I). The reaction can advantageously be affected by treatment with an acyichloride and a base such as triethylamine in a solvent such as tetrahydrofuran at room temperature. The reaction can also be affected using for example O-(benzotriazol-1-yl)-N,N,N',N'-tetramethyluronium hexafluorophosphate (HBTU) and diisopropylethylamine in a solvent such as N,N-dimethylformamide at for example room temperature.

Compounds 1, 4, 10, 11, 12, 13, 14, 15, 16, 20, 25 and 29 may be prepared according to the synthesis described in Scheme 1.

The compounds of formula (I) can also be prepared as shown in general scheme 2 below wherein a pyrazolo[1,5-a]pyrimidine or a imidazo[2,1-f]pyridazine of formula (II) is converted by reaction with a compound of formula (VIII) into a compound of formula (IX), which is then reacted with a (hetero-)aryl of formula (V) to form a compound of formula (X). The compound of formula (X) can be reacted with a compound of formula (XI) to yield a compound of formula (XII). The compound of formula (XII) can then be deprotected if desired before cyclisation to form a compound of formula (VII). The compound of formula (VII) can be optionally converted into a compound of general formula (I).

In the below scheme 2:

$LG_1$ and $LG_2$ each independently represent suitable leaving or functional groups;

$X_4$ and $X_5$ together with the functional moiety to which they are attached represent an unprotected or a protected functional group which upon reaction (after deprotection) produce together $X_1$ as defined in formula I;

E represents a suitable functional group that can be used to form a direct bond between the (hetero-)aryl group and the scaffold.

G and J represent functional groups or protected functional groups, which upon further reaction and/or deprotection produce a functional group such as D;

D represents a functional group such as B or a protected functional group, which upon further reaction and/or deprotection produces a functional group such as B as defined in formula I;

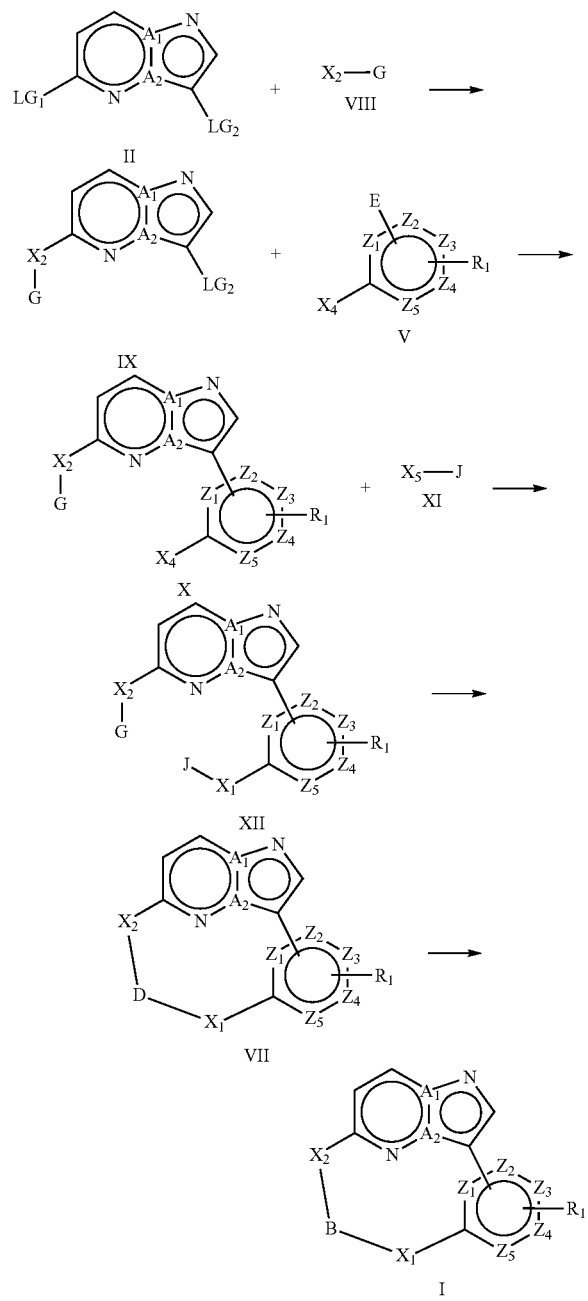

Scheme 2

In the above reaction of the compound of formula (II) with the compound of formula (VIII) the leaving groups $LG_1$ and $LG_2$ are advantageously a halo group such as a chlorine or a bromine group. The reaction can be affected by a substitution for example by treating the compound of formula (II) with the compound of formula (VIII) in an organic solvent such as acetonitrile with an appropriate base such as for example diisopropylethylamine at an elevated temperature for example under reflux.

Compounds of formula (VIII) and (XI) can be either commercially acquired or obtained through various selective protection and deprotection steps.

The resulting compound of formula (IX) can optionally be protected with a suitable protecting group such as a tert-butyloxycarbonylamino group in a conventional manner for example by treatment with tert-butoxycarbonyl anhydride in basic conditions using for example triethylamine and 4-(dimethylamino)pyridine in a solvent such as tetrahydrofuran at an elevated temperature such as under reflux.

The reaction of the resulting compound (IX) with a (hetero-)aryl compound of formula (V) is advantageously effected through the coupling of a boronic acid E or boronic ester E derivative of the (hetero-)aryl compound under Suzuki conditions using for example tetrakis(triphenylphosphine)palladium(0), 2-dicyclohexylphosphino-2',4',6'-triisopropylbiphenyl (Xphos) and potassium phosphate tribasic in a solvent mixture such as 1,4-dioxane/water at an elevated temperature for example 80° C.

The reaction of the resulting compound of formula (X) with a compound of formula (XI) which can be advantageously effected under Williamson conditions using a base such as potassium carbonate in a solvent such as acetonitrile at an elevated temperature such as under reflux. This reaction can also be effected under Mitsunobu conditions using for example diisopropyl azodicarboxylate and triphenylphosphine in a solvent such as tetrahydrofuran at an elevated temperature such as 90° C.

The resulting compound of formula (XII) can optionally be treated to remove any desired protecting groups for example tert-butyloxycarbonylamino groups can be converted to the parent free amino group and for example ester groups can be converted to the parent free carboxylic acid groups. Such deprotection can be effected in a conventional manner for example by treatment under acidic conditions for example using an aqueous 6N hydrochloric acid solution in a solvent such as acetonitrile at an elevated temperature for example 60C or using an acid such as trifluoroacetic acid in a solvent such as dichloromethane at for example room temperature.

The cyclisation of the compound of formula (XII) can be effected for example by treatment with O-(benzotriazol-1-yl)-N,N,N',N'-tetramethyluronium hexafluorophosphate (HBTU) and N,N-diisopropylethylamine in a solvent such as N,N-dimethylformamide at for example room temperature.

The resulting compound of formula (VII) can optionally be treated to form a compound of formula (I).

Compounds 2, 3, 9, 18 and 27 may be prepared according to the synthesis described in Scheme 2.

The compounds of formula (I) can also be prepared as shown in general scheme 3 below wherein a pyrazolo[1,5-a]pyrimidine or a imidazo[2,1-f]pyridazine of formula (II) is converted by reaction with a compound of formula (VIII) into a compound of formula (IX). The compound of formula (IX) can be optionally be converted into a compound of formula (XIII) which is then reacted with a (hetero-)aryl of formula (XIV) to form a compound of formula (XV). The compound of formula (XV) can then be optionally deprotected if desired before cyclisation to form a compound of formula (VII). The compound of formula (VII) can be optionally converted into a compound of general formula (I).

Scheme 3

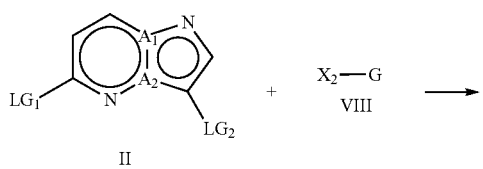

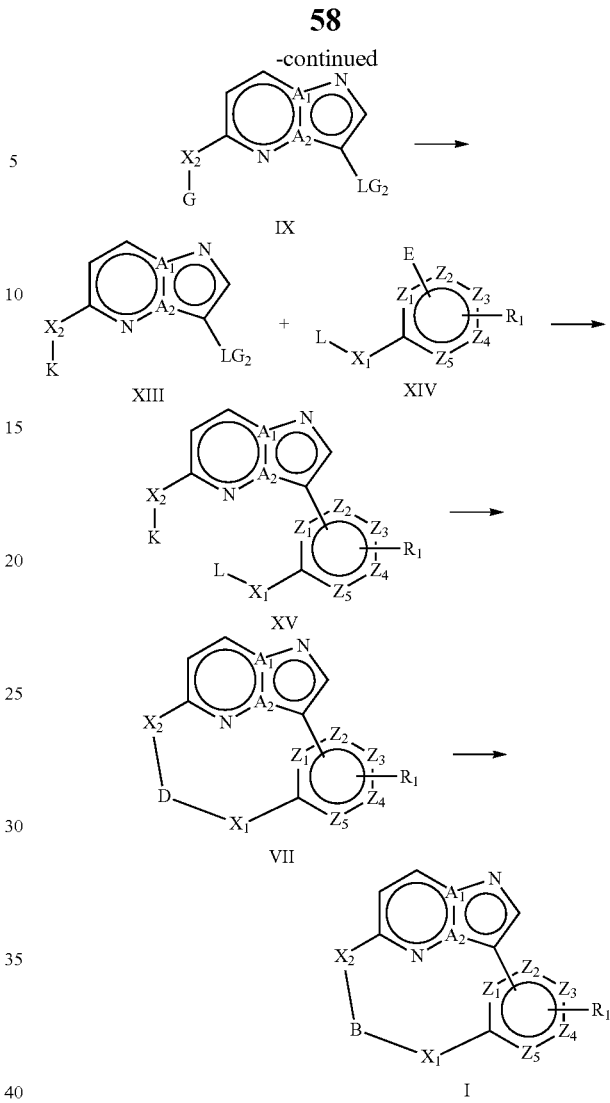

In the above scheme:

$LG_1$ and $LG_2$ each independently represent suitable leaving or functional groups;

E represents a suitable functional group that can be used to form a direct bond between the (hetero-)aryl group and the scaffold.

G represents a suitable functional group or protected functional group, which upon further reaction and/or deprotection produces a functional group such as K;

K and L represent functional groups or protected functional groups, which upon further reaction and/or deprotection produce a functional group such as D;

D represents a functional group such as B or a protected functional group, which upon further reaction and/or deprotection produces a functional group such as B as defined in formula I;

In the above reaction of the compound of formula (II) with the compound of formula (VIII) the leaving groups $LG_1$ and $LG_2$ are advantageously a halo group such as a chlorine or a bromine group. The reaction can be affected by a substitution for example by treating the compound of formula (II) with the compound of formula (VIII) in an organic solvent such as acetonitrile with an appropriate base such as for example diisopropylethylamine at an elevated temperature for example under reflux.

Compounds of formula (VIII) can be either commercially acquired or obtained through various selective protection and deprotection steps.

The compounds of formula (IX) can be deprotected using for example acidic conditions such as a 4N hydrochloric acid solution in methanol at room temperature.

The resulting deprotected compound can be reacted with for example 2-nitrobenzenesulfonyl chloride and triethylamine in a solvent such as dichloromethane at a temperature going from 0° C. to room temperature.

The resulting compound can optionally be protected with a suitable protecting group such as a tert-butyloxycarbonylamino group in a conventional manner for example by treatment with tert-butoxycarbonyl anhydride in basic conditions using for example triethylamine and 4-(dimethylamino)pyridine in a solvent such as tetrahydrofuran at an elevated temperature such as under reflux.

The compound of formula (IX) can optionally be alkylated using for example iodomethane and cesium carbonate in a solvent such as N,N-dimethylformamide at a temperature such as room temperature.

The nitrobenzenesulfonyl can optionally be removed by treatment with for example thiophenol and cesium carbonate in a solvent such as N,N-dimethylformamide at for example room temperature.

The resulting compound can optionally be protected with a suitable protecting group such as a tert-butyloxycarbonylamino group in a conventional manner for example by treatment with tert-butoxycarbonyl anhydride in basic conditions using for example triethylamine and 4-(dimethylamino)pyridine in a solvent such as tetrahydrofuran at an elevated temperature such as under reflux.

The boronic ester of formula (XIV) can be obtained through for example Williamson reaction using for example potassium carbonate in a solvent such as acetonitrile at for example room temperature, followed by boronation through for example treatment with bis(pinacolato)diboron, [1,1-bis(diphenylphosphino)ferrocene]dichloropalladium(II) and potassium acetate in a solvent such as 1,4-dioxane at for example an elevated temperature such as 80° C. Some intermediate steps can be required to obtain the desired boronic esters.

The reaction of the compound with formula (XIII) with a (hetero-)aryl compound of formula (XIV) is advantageously effected under Suzuki conditions using for example tetrakis(triphenylphosphine)palladium(0), 2-dicyclohexylphosphino-2',4',6'-triisopropylbiphenyl (Xphos) and potassium phosphate tribasic in a solvent mixture such as 1,4-dioxane/water at an elevated temperature for example 80° C.

The resulting compound of formula (XV) can optionally be treated to remove any desired protecting groups for example tert-butyloxycarbonylamino groups can be converted to the parent free amino group and for example ester groups can be converted to the parent free carboxylic acid groups. Such deprotection can be effected in a conventional manner for example by treatment under acidic conditions for example using an aqueous 6N hydrochloric acid solution in a solvent such as acetonitrile at an elevated temperature for example 60° C.

The cyclisation of the compound of formula (XV) can be effected for example by treatment with O-(benzotriazol-1-yl)-N,N,N',N'-tetramethyluronium hexafluorophosphate (HBTU) and N,N-diisopropylethylamine in a solvent such as N,N-dimethylformamide at for example room temperature.

The resulting compound of formula (VII) can optionally be treated to form a compound of formula (I).

Compounds 5 and 7 may be prepared according to the synthesis described in Scheme 3. The compounds of formula (I) can also be prepared as shown in general scheme 4 below wherein a pyrazolo[1,5-a]pyrimidine or a imidazo[2,1-f]pyridazine of formula (II) is converted by reaction with a compound of formula (VIII) into a compound of formula (IX), which is then reacted with a (hetero-)aryl of formula (V) to form a compound of formula (X). The compound of formula (X) can be reacted with a compound of formula (XI) to yield a compound of formula (XVI). The compound of formula (XVI) can then be deprotected if desired before cyclisation to form a compound of formula (VII). The compound of formula (VII) can be optionally converted into a compound of general formula (I).

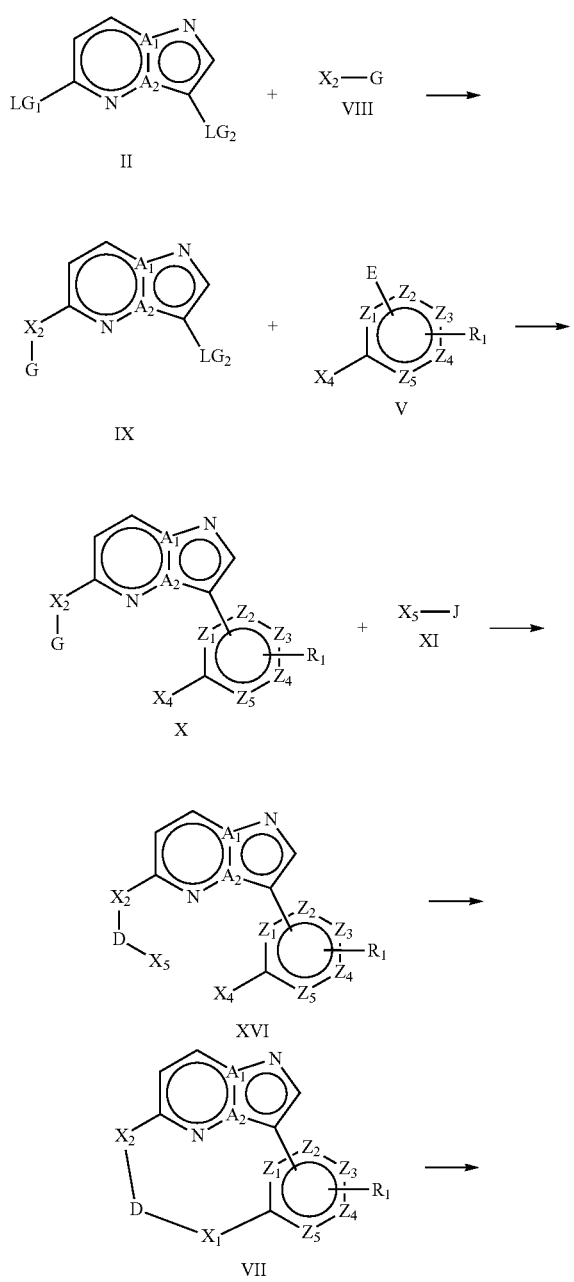

Scheme 4

-continued

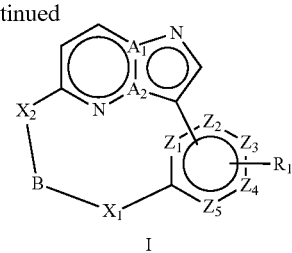

In the above scheme:

LG$_1$ and LG$_2$ each independently represent suitable leaving or functional groups;

X$_4$ and X$_5$ together with the functional moiety to which they are attached represent an unprotected or a protected functional group which upon reaction (after deprotection) produce together X$_1$ as defined in formula I;

E represents a suitable functional group that can be used to form a direct bond between the (hetero-)aryl group and the scaffold.

G and J represent functional groups or protected functional groups, which upon further reaction and/or deprotection produce a functional group such as D;

D represents a functional group such as B or a protected functional group, which upon further reaction and/or deprotection produces a functional group such as B as defined in formula I;

In the above reaction of the compound of formula (II) with the compound of formula (VIII) the leaving groups LG$_1$ and LG$_2$ are advantageously a halo group such as a chlorine or a bromine group. The reaction can be affected by a substitution for example by treating the compound of formula (II) with the compound of formula (VIII) in an organic solvent such as acetonitrle with an appropriate base such as for example diisopropyl ethylamine at an elevated temperature for example under reflux.

Compounds of formula (VIII) and (XI) can be either commercially acquired or obtained through various selective protection and deprotection steps.

The resulting compound of formula (IX) can optionally be protected with a suitable protecting group such as a tert-butyloxycarbonylamino group in a conventional manner for example by treatment with tert-butoxycarbonyl anhydride in basic conditions using for example triethylamine and 4-(dimethylamino)pyridine in a solvent such as tetrahydrofuran at an elevated temperature such as under reflux.

The reaction of the resulting compound (IX) with a (hetero-)aryl compound of formula (V) is advantageously effected through the coupling of a boronic acid E or boronic ester E derivative of the (hetero-)aryl compound under Suzuki conditions using for example tetrakis(triphenylphosphine) palladium(0), 2-dicyclohexylphosphino-2',4',6'-triisopropylbiphenyl (Xphos) and potassium phosphate tribasic in a solvent mixture such as 1,4-dioxane/water at an elevated temperature for example 80° C.

The resulting compound of formula (X) can optionally be protected with a suitable protecting group such as a benzyl group in a conventional manner for example by treatment with benzylbromide in a solvent such as acetonitrile at an elevated temperature such as 80° C.

The compounds of formula (IX) can be deprotected using for example acidic conditions such as a 4N hydrochloric acid solution in methanol at room temperature.

The reaction of the resulting compound of formula (X) with a compound of formula (XI) which can be advantageously effected using a reagent such as 1,1'-carbonyl diimidazole in a solvent such as tetrahydrofuran at a temperature such as room temperature.

The reaction of the resulting compound of formula (X) with a compound of formula (XI) which can also be advantageously effected using a reagent such as sulfonylchloride and a base such as triethylamine in a solvent such as dichloromethane at a temperature such as room temperature.

The resulting compound of formula (XVI) can optionally be protected with a suitable protecting group such as a tert-butyloxycarbonylamino group in a conventional manner for example by treatment with tert-butoxycarbonyl anhydride in basic conditions using for example triethylamine and 4-(dimethylamino)pyridine in a solvent such as tetrahydrofuran at an elevated temperature such as under reflux.

The resulting compound of formula (XVI) can optionally be treated to remove any desired protecting groups such as benzyl groups which can be removed using a 1N boron tribromide solution in a solvent such as dichloromethane at for example room temperature or by using palladium on activated charcoal under hydrogen atmosphere in a solvent mixture such as tetrahydrofuran/methanol at for example room temperature.

The cyclisation of the compound of formula (VXI) can be effected for example by treatment with cesium carbonate, potassium iodide and tetrabutylammonium iodide at for example an elevated temperature such as 50° C. or 90° C. in a solvent such as N,N-dimethylacetamide or tetrahydrofuran.

The resulting compound of formula (VII) can optionally be treated to form a compound of formula (I).

Compounds 6, 8, 17, 19, 21, 22, 23, 24, 26 and 28 may be prepared according to the synthesis described in Scheme 4.

The above general processes are illustrated by the following specific processes which describe the preparation of the compounds of formula (I).

Experimental Part

In obtaining the compounds described in the examples, the following experimental protocols were followed unless otherwise indicated.

Unless otherwise stated, reaction mixtures were magnetically stirred at room temperature.

Where solutions were "dried", they were generally dried over a drying agent such as sodium sulfate or magnesium sulfate. Where mixtures, solutions and extracts were "concentrated", they were typically concentrated on a rotary evaporator under reduced pressure.

For some compounds that were purified by reversed phase high-performance liquid chromatography (HPLC) the used method is described below (indicated in the compound procedure with HPLC method A). When necessary, these methods can be slightly adjusted by a person skilled in the art to obtain a more optimal result for the separation.

HPLC Method A

The crude product was purified by reverse phase HPLC, using a Gilson semi-preparative HPLC system operated by Gilson UNIPOINT software.

The purification was carried out on a Phenomenex Luna column (100 mm long×21.2 mm i.d.; 5 μm particles) at room temperature, with a constant flow rate of 20.0 mL/min. A gradient elution was performed from 32% (25 mM NH4HCO3 aqueous solution)/68% (Acetonitrile-Methanol 1:1) to 4% (25 mM NH4HCO3 aqueous solution)/96% (Acetonitrle-Methanol 1:1) in 20 minutes. The UV detector was set to 226 nm, which corresponds to the wavelength of maximum absorbance observed for the compound.

Preparation of the Compounds

Example 1

Example 1 is prepared following general scheme 1.

Preparation of Intermediate 1

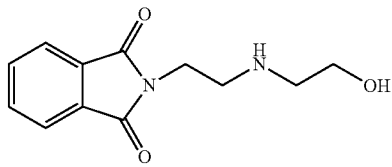 [SMILES: O=C1c2ccccc2C(=O)N1CCNCCO]

A mixture of 2-(2-aminoethylamino)ethanol (14.56 g, 139.80 mmol) and isoindoline-1,3-dione (20.16 g, 137.00 mmol) in toluene (420 ml) was refluxed for 3 hours. The solvent was removed under reduced pressure and the residue was used in the next step without further purification.

LCMS method 1: MH$^+$=235, RT=0.181 min

Preparation of Intermediate 2

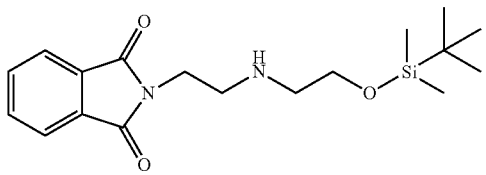 [SMILES: CC(C)(C)[Si](C)(C)OCCNCCN1C(=O)c2ccccc2C1=O]

Tert-butyldimethylsilyl chloride (31.0 g, 205.5 mmol) was added to a suspension of intermediate 1 (32.0 g, 137.0 mmol) and triethylamine (38.0 ml, 274.0 mmol) in N,N-dimethylformamide (411 ml). The mixture was stirred overnight at room temperature. The reaction mixture was diluted with ethyl acetate and washed with water and brine (3×). The organic layer was dried, filtered and the solvent was removed under reduced pressure. The residue was purified by flash column chromatography using heptane and ethyl acetate as eluents. The product fractions were collected and the solvent was evaporated.

Yield: 16.6 g of intermediate 2 (35%)
LCMS method 1: MH$^+$=349, RT=0.728 min

Preparation of Intermediate 3

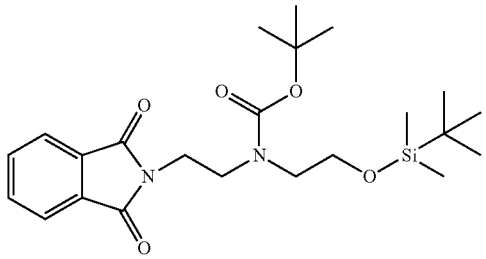 [SMILES: CC(C)(C)OC(=O)N(CCO[Si](C)(C)C(C)(C)C)CCN1C(=O)c2ccccc2C1=O]

Tert-butoxycarbonyl anhydride (4.3 g, 19.6 mmol) was added to a mixture of intermediate 2 (6.5 g, 18.6 mmol) and triethylamine (3.1 ml, 22.4 mmol) in tetrahydrofuran (56 ml). The reaction mixture was stirred for 1 hour and the solvent was removed under reduced pressure. The residue was dissolved in ethyl acetate and washed with water and brine (3×). The organic layer was dried, filtered and the solvent was removed under reduced pressure. Intermediate 3 was used in the next step without further purification.

Yield: 6.0 g of intermediate 3 (72%)
LCMS method 1: MH$^+$=349 (MW-Boc), RT=2.185 min Preparation of Intermediate 4

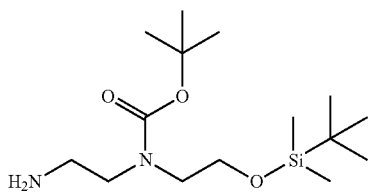 [SMILES: CC(C)(C)OC(=O)N(CCN)CCO[Si](C)(C)C(C)(C)C]

A mixture of intermediate 3 (6.0 g, 13.4 mmol) and hydrazine (1.2 ml, 40.1 mmol) was stirred overnight at 60° C. The reaction mixture was cooled, filtered and the solvent was removed under reduced pressure. The residue was dissolved in ethyl acetate and washed with 1N sodium hydroxide and water. The organic layer was dried, filtered and the solvent was removed under reduced pressure. Intermediate 4 was used in the next step without further purification.

Yield: 3.8 g of intermediate 4 (89%)
LCMS method 1: MH$^+$=319, RT=0.948 min

7-Oxa-10,13,17,18,21-pentaazatetracyclo[12.5.2.1^{2,6}.0^{17,20}]docosa-1(20),2,4,6(22),14(21),-15,18-heptaene was prepared according to similar synthetic procedures as described to obtain intermediate 7 using intermediate 4 for the coupling to the scaffold and (3-hydroxyphenyl)boronic acid for the Suzuki coupling. The ring closure was effected after TBDMS deprotection using Mitsunobu conditions. The unprotected 7-Oxa-10,13,17,18,21-pentaazatetracyclo-[12.5.2.1^{2,6}.0^{17,20}]docosa-1 (20),2,4,6(22),14(21),-15,18-heptaene was obtained after Boc deprotection under acidic conditions.

Preparation of Example 1

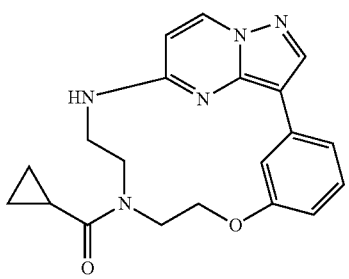 [SMILES: O=C(C1CC1)N1CCNc2ccn3ncc(c3n2)-c2cccc(c2)OCC1]

A mixture of 7-oxa-10,13,17,18,21-pentaazatetracyclo[12.5.2.1^{2,6}.0^{17,20}]docosa-1(20),2,4,6(22),14(21),-15,18-heptaene (0.2 g, 0.6 mmol) and triethylamine (208 μl, 1.5 mmol) in dry tetrahydrofuran (5 ml) was stirred for 5 minutes and then cyclopropanecarbonyl chloride (60 μl, 0.66 mmol) was added. The mixture was stirred at room temperature for 1 hour. The solvent was removed under reduced pressure and the residue was triturated in methanol to give the desired product.

Yield: 156 mg of example 1 (72%)
LCMS method 1: MH$^+$=364, RT=1.059 min

Example 2

Example 2 is prepared following general scheme 2.

Preparation of Intermediate 5

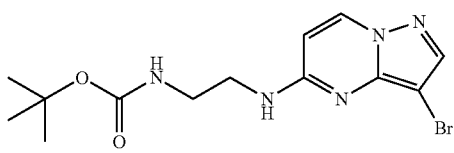 [SMILES: CC(C)(C)OC(=O)NCCNc1ccn2ncc(Br)c2n1]

A mixture of 3-bromo-5-chloro-pyrazolo[1,5-a]pyrimidine (5.0 g, 21.5 mmol), tert-butyl N-(2-aminoethyl)carbamate (4.22 ml, 26.89 mmol) and N,N-diisopropylethylamine (4.5 ml, 25.81 mmol) in acetonitrile (65 ml) was refluxed overnight. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 4.91 g of intermediate 5 (64%)
LCMS method 1: MH$^+$=356, RT=1.035 min

Preparation of Intermediate 6

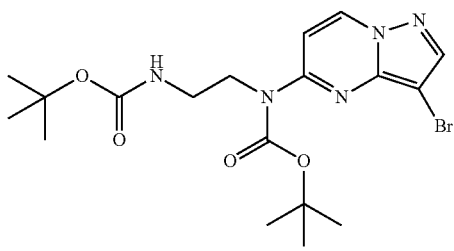 [SMILES: CC(C)(C)OC(=O)NCCN(C(=O)OC(C)(C)C)c1ccn2ncc(Br)c2n1]

A mixture of intermediate 5 (4.91 g, 13.79 mmol), tert-butoxycarbonyl anhydride (3.31 g, 15.17 mmol), triethylamine (2.9 ml, 20.68 mmol) and 4-(dimethylamino)pyridine (0.084 g, 0.69 mmol) in tetrahydrofuran (41 ml) was refluxed for 2 hours. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 4.37 g of intermediate 6 (69%)
LCMS method 1: MH$^+$=456, RT=1.602 min

Preparation of Intermediate 7

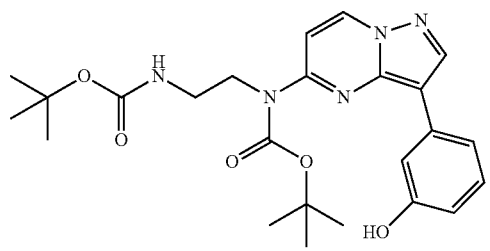 [SMILES: CC(C)(C)OC(=O)NCCN(C(=O)OC(C)(C)C)c1ccn2ncc(-c3cccc(O)c3)c2n1]

A mixture of 1,4-dioxane and water (3:1, 26 ml) was degassed by bubbling nitrogen gas through the mixture. Intermediate 6 (4.0 g, 8.77 mmol), (3-hydroxyphenyl)boronic acid (1.57 g, 11.40 mmol), tetrakis(triphenylphosphine)palladium (0) (104 mg, 0.09 mmol), 2-dicyclohexylphosphino-2',4',6'-triisopropylbiphenyl (Xphos) (167 mg, 0.35 mmol) and potassium phosphate tribasic (9.31 g, 5 eq.) were added and the mixture was stirred under nitrogen gas at 80° C. for 2 hours. The reaction mixture was cooled, diluted with ethyl acetate and the organic layer was washed with brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 3.98 g of intermediate 7 (97%)
LCMS method 2: MH$^+$=470, RT=1.060 min

Preparation of Intermediate 8

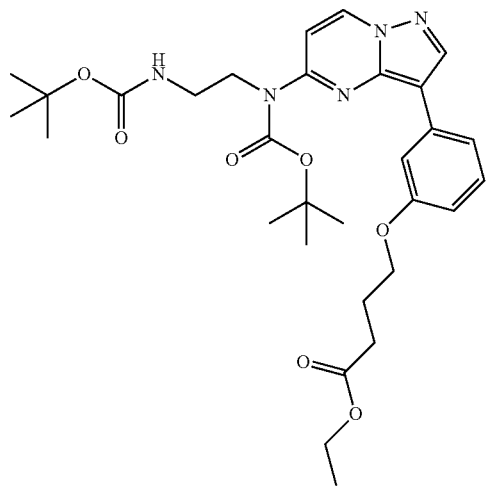 [SMILES: CCOC(=O)CCCOc1cccc(-c2cnn3ccc(N(CCNC(=O)OC(C)(C)C)C(=O)OC(C)(C)C)nc23)c1]

Ethyl 4-bromobutanoate (0.8 ml, 5.6 mmol) was added to a suspension of intermediate 7 (1.75 g, 3.7 mmol) and potassium carbonate (1.0 g, 7.5 mmol) in acetonitrile (11 ml). The mixture was reluxed overnight, cooled and ethyl acetate was added. The organic layer was washed with brine, dried, filtered and the solvent was removed under reduced pressure. The residue was purified by flash column chromatography over silica gel using heptane and ethyl acetate as eluents. The product fractions were collected and the solvent was evaporated.

Yield: 2.1 g of intermediate 8 (97%)
LCMS method 1: MH$^+$=584, RT=1.986 min

Preparation of Intermediate 9

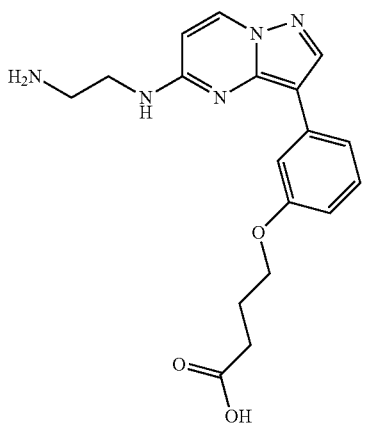 [SMILES: NCCNc1ccn2ncc(-c3cccc(OCCCC(=O)O)c3)c2n1]

Intermediate 8 (2.0 g, 3.4 mmol) was dissolved in acetonitrile (42 ml) and 6N hydrochloric acid (12 ml/mmol) was added. The mixture was stirred at 60° C. for 2 hours. After cooling, the resulting solid was filtered, washed with dichloromethane and dried under high vacuum. Intermediate 5 was used in the next step without further purification.

Yield: 1.3 g of intermediate 9 (86%)
LCMS method 1: MH$^+$=356, RT=0.515 min

Preparation of Example 2

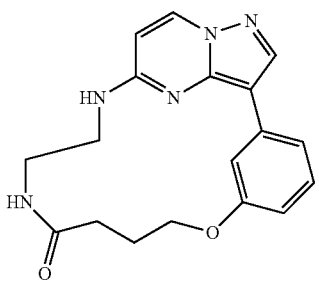 [SMILES: O=C1CCCOc2cccc(c2)-c2cnn3ccc(nc23)NCCN1]

A solution of intermediate 8 (0.6 g, 1.4 mmol) and N,N-diisopropylethylamine (0.7 ml, 4.2 mmol) in N,N-dimethylformamide (66 ml) was added slowly over a period of 1 hour using a Marlow peristaltic pump to a solution O-(benzotriazol-1-yl)-N,N,N',N'-tetramethyluronium hexafluorophosphate (HBTU) (1.2 g, 3.1 mmol) and N,N-diisopropylethylamine (1.6 ml, 9.8 mmol) in N,N-dimethylformamide (33 ml). The reaction mixture was stirred at room temperature for 1 more hour after the addition was completed. The mixture was quenched with 7N ammonia in methanol. The solvent was removed under reduced pressure. The residue was dissolved in dichloromethane and washed with a saturated sodium bicarbonate solution. The aqueous layer was extracted with dichloromethane. The combined organic layers were washed with brine, dried, filtered and the solvent was removed under reduced pressure. The residue was purified by flash column chromatography over silica gel using dichloromethane and methanol as eluents. The product fractions were collected and the solvent was evaporated.

Yield: 212 mg of example 2 (45%)
LCMS method 2: MH$^+$=338, RT=2.266 min

Example 3

Example 3 is prepared following general scheme 2.

Preparation of Intermediate 10

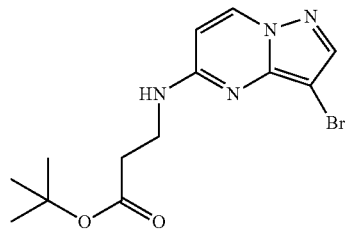 [SMILES: CC(C)(C)OC(=O)CCNc1ccn2ncc(Br)c2n1]

A mixture of 3-bromo-5-chloro-pyrazolo[1,5-a]pyrimidine (3.0 g, 12.9 mmol), tert-butyl 3-aminopropanoate (2.6 g, 14.2 mmol) and N,N-diisopropylethylamine (6.7 ml, 38.7 mmol) in acetonitrile (39 ml) was stirred overnight at 85° C. The reaction mixture was cooled and the solvent was removed under reduced pressure. The residue was dissolved in ethyl acetate and washed with water. The organic layer was dried, filtered and the solvent was removed under reduced pressure. The residue was purified by flash column chromatography over silica gel using heptane and ethyl acetate as eluents (gradient elution from 0% to 50% ethyl acetate). The product fractions were collected and the solvent was evaporated.

Yield: 4.0 g of intermediate 10 (91%)
LCMS method 2: MH$^+$=341, RT=0.918 min

Preparation of Intermediate 11

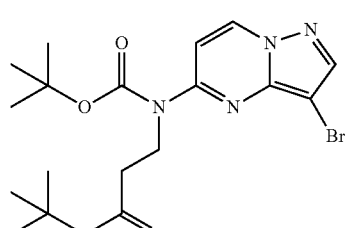

A mixture of intermediate 10 (4.0 g, 11.8 mmol), tert-butoxycarbonyl anhydride (3.2 g, 14.1 mmol), triethylamine (2.1 ml, 15.3 mmol) and 4-(dimethylamino)pyridine (0.07 g, 0.59 mmol) in tetrahydrofuran (35 ml) was refluxed overnight. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using heptane and ethyl acetate as eluents (gradient elution from 0% to 50% ethyl acetate). The product fractions were collected and the solvent was evaporated.

Yield: 4.9 g of intermediate 11 (95%)
LCMS method 1: MH$^+$=441, RT=1.863 min

Preparation of Intermediate 12

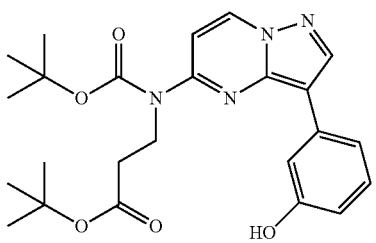 [SMILES: CC(C)(C)OC(=O)CCN(C(=O)OC(C)(C)C)c1ccn2ncc(-c3cccc(O)c3)c2n1]

A mixture of 1,4-dioxane and water (3:1, 7 ml) was degassed by bubbling nitrogen gas through the mixture. Intermediate 11 (1.0 g, 2.3 mmol), (3-hydroxyphenyl)boronic acid (0.4 g, 2.9 mmol), tetrakis(triphenylphosphine)palladium(0) (23 mg, 0.02 mmol), 2-dicyclohexylphosphino-2',4',6'-triisopropylbiphenyl (Xphos) (43 mg, 0.09 mmol) and potassium phosphate tribasic (2.6 g, 5 eq.) were added and the mixture was stirred under nitrogen gas at 80° C. for 2 hours. The reaction mixture was cooled, diluted with ethyl acetate and the organic layer was washed with brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 1.0 g of intermediate 12 (100%)
LCMS method 2: MH$^+$=455, RT=1.149 min

Preparation of Intermediate 13

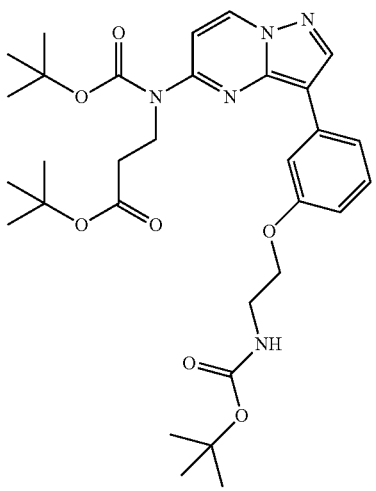 [SMILES: CC(C)(C)OC(=O)CCN(C(=O)OC(C)(C)C)c1ccn2ncc(-c3cccc(OCCNC(=O)OC(C)(C)C)c3)c2n1]

Diisopropyl azodicarboxylate (857 mg, 4.24 mmol) was added to a mixture of intermediate 12 (0.9 g, 2.0 mmol), tert-butyl N-(2-hydroxyethyl)carbamate (0.6 g, 3.8 mmol)) and triphenylphosphine (1.0 g, 3.8 mmol) in dry tetrahydrofuran (10 mil). The mixture was stirred at 90° C. for 1 hour. The reaction mixture was cooled and the solvent was removed under reduced pressure. The residue was purified by flash column chromatography over silica gel using hexane and ethyl acetate as eluents (gradient elution from 0% to 50% ethyl acetate). The product fractions were collected and the solvent was evaporated.

Yield: 1.2 g of intermediate 13 (100%)
LCMS method 1: MH$^+$=498 (MW-Boc), RT=2.144 min

Preparation of Intermediate 14

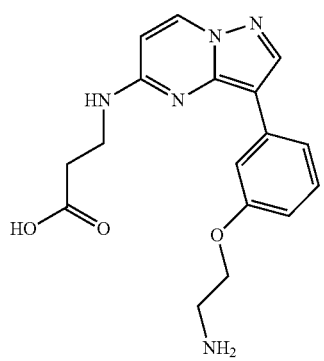 [SMILES: NCCOc1cccc(-c2cnn3ccc(NCCC(=O)O)nc23)c1]

Intermediate 13 (1.2 g, 2.0 mmol) was dissolved in dichloromethane (3 ml) and trifluoro acetic acid (3 ml) was added. The mixture was stirred at room temperature for 1 hour. The solvent was removed under reduced pressure. The residue was treated with toluene and the solvent was removed under reduced pressure (3×). Intermediate 20 was used in the next step without further purification.

LCMS method 1: MH$^+$=342, RT=0.416 min

Preparation of Example 3

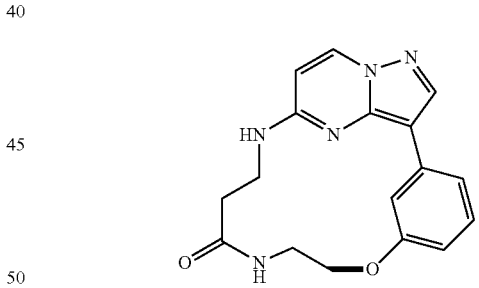

A solution of intermediate 14 (0.6 g, 2.0 mmol) in N,N-dimethylformamide (140 ml) was added slowly over a period of 3 hours to a solution of O-(benzotriazol-1-yl)-N,N,N',N'-tetramethyluronium hexafluorophosphate (HBTU) (2.3 g, 6.1 mmol) and N,N-diisopropylethylamine (10.6 ml, 60.6 mmol) in N,N-dimethylformamide (60 ml). The reaction mixture was stirred at room temperature for 1 more hour after the addition was completed. The mixture was quenched with an aqueous solution of ammonia (25%) and stirred for 30 minutes. The solvent was removed under reduced pressure and dichloromethane was added. The resulting solid was filtered and washed with diethyl ether and methanol.

Yield: 150 mg of example 3 (23%)
LCMS method 2: MH$^+$=324, RT=2.285 min

Example 4

Example 4 is prepared following general scheme 1.

Preparation of Intermediate 15

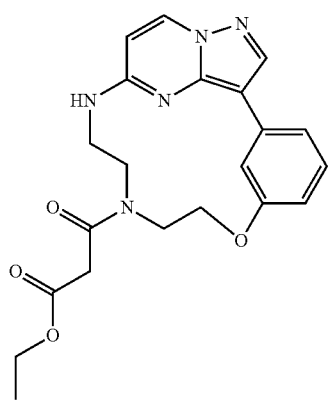 [SMILES: CCOC(=O)CC(=O)N1CCNc2ccn3ncc(c3n2)-c2cccc(c2)OCC1]

O-(Benzotriazol-1-yl)-N,N,N',N'-tetramethyluronium hexafluorophosphate (HBTU) (576 mg, 1.52 mmol) was added to a mixture of 7-oxa-10,13,17,18,21-pentaazatetracyclo[12.5.2.1^{2,6}.0^{17,20}]docosa-1(20),2,4,6(22),14(21),-15,18-heptaene (420 mg, 1.27 mmol), 3-ethoxy-3-oxo-propanoic acid (170 μl, 1.4 mmol) and N,N-diisopropylethylamine (887 μl, 1.52 mmol) in N,N-dimethylformamide (4 ml). The reaction mixture was stirred at room temperature for 1 hour. The crude reaction mixture was poured into ethyl acetate and washed with a saturated sodium bicarbonate solution, water and brine. The organic layer was dried, filtered and the solvent was removed under reduced pressure. The residue was purified by flash column chromatography over silica gel using dichloromethane and methanol as eluents. The product fractions were collected and the solvent was evaporated.

Yield: 270 mg of intermediate 15 (52%)
LCMS method 2: MH$^+$=410, RT=1.051 min

Preparation of Intermediate 16

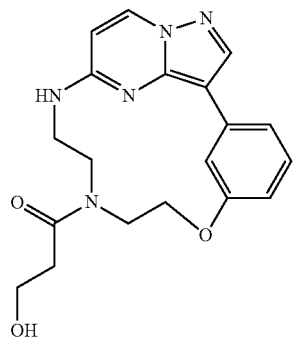 [SMILES: O=C(CCO)N1CCNc2ccn3ncc(c3n2)-c2cccc(c2)OCC1]

Sodium borohydride (150 mg, 3.96 mmol) was added to a suspension of intermediate 15 (270 mg, 0.66 mmol) in tetrahydrofuran (1 ml). The mixture was refluxed for 30 minutes and methanol (1 ml) was carefully added. The mixture was refluxed for 1 hour. After the reaction was completed, the mixture was quenched with a saturated aqueous ammonium chloride solution and stirred at room temperature for 1.5 hours. The mixture was extracted with ethyl acetate and the organic layer was washed with water and brine. The organic layer was dried, filtered and the solvent was removed under reduced pressure. The residue was purified by flash column chromatography over silica gel using dichloromethane and methanol as eluents. The product fractions were collected and the solvent was evaporated.

Yield: 163 mg of intermediate 16 (67%)
LCMS method 2: MH$^+$=368, RT=0.681 min

Preparation of Intermediate 17

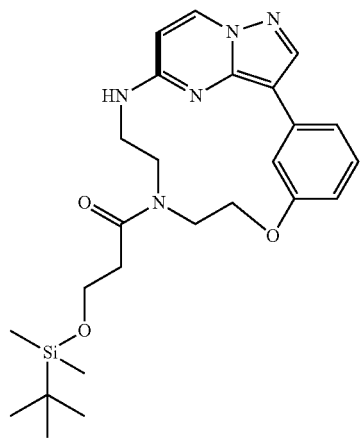

In order to increase the purity, intermediate 16 was protected as a tert-butyldimethylsilyl chloride which was purified by HPLC. A mixture of intermediate 16 (163 mg, 0.44 mmol), tert-butyldimethylsilyl chloride (100 mg, 0.66 mmol) and triethylamine (122 μl, 0.88 mmol) in N,N-dimethylformamide (1.3 ml) was stirred at room temperature for 30 minutes. The reaction mixture was diluted with ethyl acetate and washed with brine (3×). The organic layer was dried, filtered and the solvent was removed under reduced pressure. The residue was purified by reversed phase HPLC (HPLC method A). The product fractions were collected and the solvent was evaporated.

Yield: 75 mg of intermediate 17 (35%)
LCMS method 1: MH$^+$=482, RT=1.785 min

Preparation of Example 4

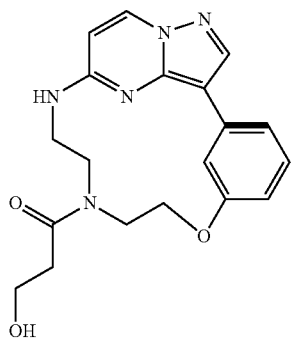 [SMILES: O=C(CCO)N1CCNc2ccn3ncc(c3n2)-c2cccc(c2)OCC1]

Intermediate 17 (75 mg, 0.15 mmol) was suspended in acetic acid/tetrahydrofuran/water (3:1:1, 0.5 ml) and the mixture was stirred at room temperature for 6 hours. Toluene was added and the solvents were removed under reduced pressure.

Yield: 63 mg of example 4 (95%)
LCMS method 2: MH$^+$=368, RT=2,433 min

Example 5

Example 5 is prepared following general scheme 3.

Preparation of Intermediate 18

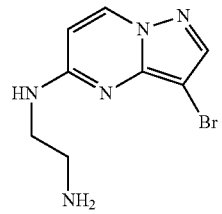

Intermediate 6 (2.45 g, 6.88 mmol) was dissolved in 4N hydrochloric acid in methanol (21 ml).

The mixture was stirred at room temperature for 2 hours. The resulting solid was filtered, washed with methanol and dried under high vacuum. Intermediate 18 was used in the next step without further purification.

Yield: 2.12 g of intermediate 18 (94%)
LCMS method 1: MH$^+$=256, RT=0.255 min

Preparation of Intermediate 19

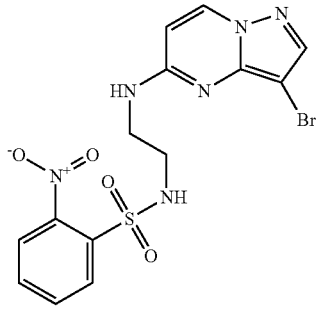

2-Nitrobenzenesulfonyl chloride (1.57 g, 7.08) mmol was added portionwise at 0° C. and under nitrogen atmosphere to a solution of intermediate 18 (2.12 g, 6.44 mmol) and triethylamine (3.12 ml, 22.54 mmol) in dichloromethane (19 ml). The reaction mixture was stirred for 1 hour allowing it to reach room temperature. The crude reaction mixture was poured into brine and the aqueous layer was extracted with ethyl acetate. The organic layer was dried, filtered and the solvent was removed under reduced pressure. Intermediate 19 was used in the next step without further purification.

Yield: 2.67 g of intermediate 19 (94%)
LCMS method 1: MH$^+$=443, RT=0.979 min

Preparation of Intermediate 20

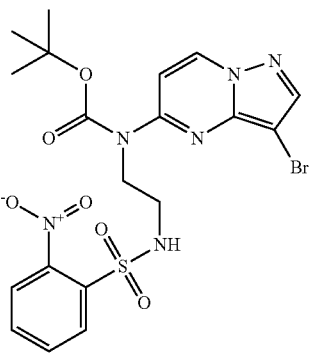

A mixture of intermediate 19 (2.6 g, 5.89 mmol), tert-butoxycarbonyl anhydride (1.35 g, 6.18 mmol), triethylamine (980 µl, 7.07 mmol) and 4-(dimethylamino)pyridine (7 mg, 0.06 mmol) in tetrahydrofuran (18 ml) was refluxed overnight. The reaction mixture was cooled and the solvent was removed under reduced pressure. The residue was purified by flash column chromatography over silica gel using dichloromethane and methanol as eluents. The product fractions were collected and the solvent was evaporated.

Yield: 3.06 g of intermediate 20 (96%)
LCMS method 1: MH$^+$=543, RT=1.407 min

Preparation of Intermediate 21

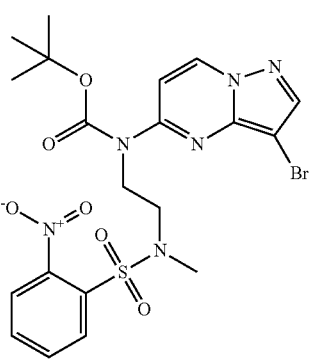

A mixture of intermediate 20 (3.0 g, 5.54 mmol) and cesium carbonate (3.61 g, 11.08 mmol) in N,N-dimethylformamide (17 ml) was stirred at room temperature for 15 minutes. Iodomethane (520 µl, 8.31 mmol) was added and the mixture was stirred at room temperature for 3 hours. The reaction mixture was diluted with ethyl acetate, washed with water and brine, dried, filtered and the solvent was removed under reduced pressure. Intermediate 21 was used in the next step without further purification.

Yield: 3.0 g of intermediate 21 (97%)
LCMS method 1: MH$^+$=555, RT=1.650 min

Preparation of Intermediate 22

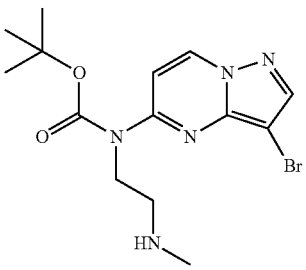 [SMILES: CNCCN(C(=O)OC(C)(C)C)c1ccn2ncc(Br)c2n1]

Intermediate 21 (3.0 g, 5.4 mmol) and cesium carbonate (3.52 g, 10.80 mmol) were suspended in N,N-dimethylformamide (16 ml). Thiophenol (660 μl, 6.48 mmol) was added and the mixture was stirred at room temperature for 2 hours. The reaction mixture was filtered and the solvent was removed under reduced pressure. The residue was purified by flash column chromatography over silica gel using dichloromethane and methanol as eluents. The product fractions were collected and the solvent was evaporated.

LCMS method 1: $MH^+$=372, RT=0.667 min

Preparation of Intermediate 23

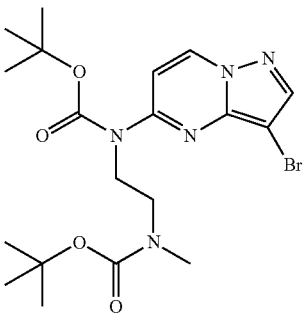 [SMILES: CN(CCN(C(=O)OC(C)(C)C)c1ccn2ncc(Br)c2n1)C(=O)OC(C)(C)C]

A mixture of intermediate 22 (2.0 g, 5.4 mmol), tert-butoxycarbonyl anhydride (1.77 g, 8.1 mmol) and triethylamine (1.5 ml, 10.8 mmol) in tetrahydrofuran (16 ml) was stirred at room temperature overnight. The solvent was removed under reduced pressure. The residue was purified by flash column chromatography over silica gel using heptane and ethyl acetate as eluents. The product fractions were collected and the solvent was evaporated.

Yield: 1.82 g of intermediate 23 (71% over 2 steps)
LCMS method 1: $MH^+$=472, RT=1.812 min

Preparation of Intermediate 24

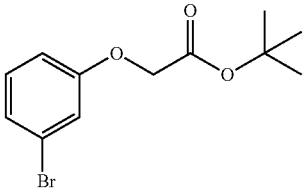 [SMILES: CC(C)(C)OC(=O)COc1cccc(Br)c1]

Tert-butyl 2-bromoacetate (1.28 ml, 8.67 mmol) was added to a suspension of 3-bromophenol (1.0 g, 5.78 mmol) and potassium carbonate (1.6 g, 11.56 mmol) in acetonitrile (17 ml). The mixture was refluxed for 1 hour, cooled and ethyl acetate was added. The organic layer was washed with brine, dried, filtered and the solvent was removed under reduced pressure. Intermediate 24 was used in the next step without further purification.

LCMS method 1: $MH^+$=309 (MW+Na), RT=1.577 min

Preparation of Intermediate 25

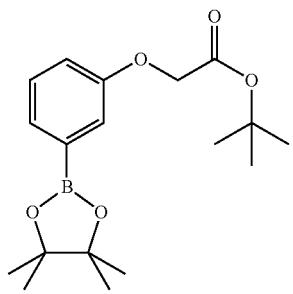 [SMILES: CC(C)(C)OC(=O)COc1cccc(B2OC(C)(C)C(C)(C)O2)c1]

1,4-Dioxane (17 ml) was degassed by bubbling nitrogen gas through it. Intermediate 24 (1.66 g, 5.78 mmol), bis(pinacolato)diboron (1.47 g, 5.78 mmol), [1,1'-bis(diphenylphosphino)ferrocene]dichloropalladium(II) (139 mg, 0.17 mmol) and potassium acetate (1.135 g, 11.56 mmol) were added. The suspension was stirred under nitrogen atmosphere at 80° C. for 2 hours. The reaction mixture was cooled, diluted with ethyl acetate and washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 1.32 g of intermediate 25 (68% over 2 steps)
LCMS method 1: $MH^+$=357 (MW+Na), RT=1.806 min

Preparation of Intermediate 26

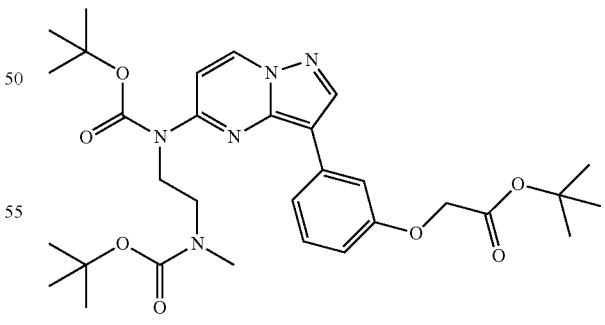

A mixture of 1,4-dioxane and water (3:1, 7 ml) was degassed by bubbling nitrogen gas through the mixture. Intermediate 22 (1.72 g, 3.66 mmol), intermediate 25 (1.2 g, 4.39 mmol), tetrakis(triphenylphosphine)palladium(0) (46 mg, 0.04 mmol), 2-dicyclohexylphosphino-2',4',6'-triisopropylbiphenyl (Xphos) (72 mg, 0.15 mmol) and potassium phosphate tribasic (3.88 g, 5 eq.) were added and the mixture was stirred under nitrogen gas at 80° C. for 2 hours. The reaction mixture was cooled, diluted with ethyl acetate and the organic layer was washed with brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 1.78 g of intermediate 26 (81%)
LCMS method 1: MH$^+$=598, RT=2.131 min

Preparation of Intermediate 27

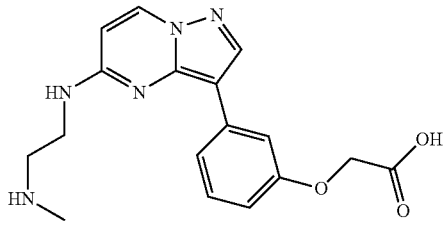 [SMILES: CNCCNc1ccn2ncc(-c3cccc(OCC(=O)O)c3)c2n1]

Intermediate 26 (1.78 g, 2.98 mmol) was dissolved in acetonitrile (12 ml/mmol) and 6N aqueous hydrochloric acid (12 mV/mmol) was added. The mixture was stirred at 60° C. for 2 hours. The solvent was removed under reduced pressure. Intermediate 27 was used in the next step without further purification.

LCMS method 1: MH$^+$=342, RT=0.442 min

Preparation of Example 5

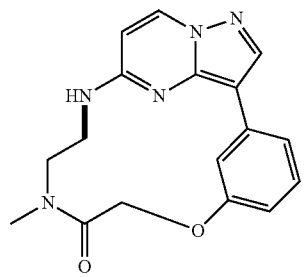

A solution of intermediate 27 (1.125 g, 2.98 mmol) and N,N-diisopropylethylamine (1.56 ml, 8.94 mmol) in N,N-dimethylformamide (150 ml) was added slowly using a Marlow peristaltic pump over a period of 1 hour to a solution of O-(benzotriazol-1-yl)-N,N,N',N'-tetramethyluronium hexafluorophosphate (HBTU) (2.49 g, 6.56 mmol) and N,N-diisopropylethylamine (3.64 ml, 20.86 mmol) in N,N-dimethylformamide (75 ml). The reaction mixture was stirred at room temperature for 1 more hour after the addition was completed. The mixture was quenched with an aqueous solution of ammonia (25%). The solvent was removed under reduced pressure and dichloromethane was added. The organic layer was washed with a saturated sodium bicarbonate solution and the aqueous layer was extracted with dichloromethane. The combined organic layers were washed with brine, dried, filtered and the solvent was removed under reduced pressure. The residue was purified by flash column chromatography over silica gel using dichloromethane and methanol as eluents. The product fractions were collected and the solvent was evaporated.

Yield: 512 mg of example 5 (53%)
LCMS method 2: MH$^+$=324, RT=2.097 min

Example 6

Example 6 is prepared following general scheme 4.

Preparation of Intermediate 28

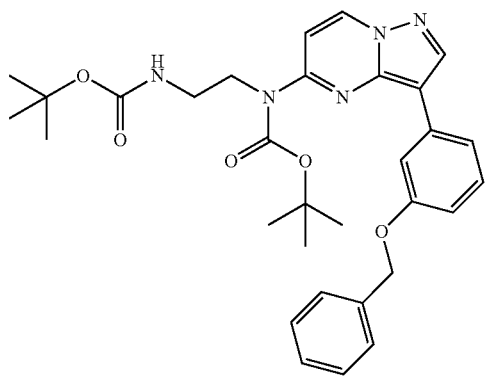 [SMILES: CC(C)(C)OC(=O)NCCN(C(=O)OC(C)(C)C)c1ccn2ncc(-c3cccc(OCc4ccccc4)c3)c2n1]

Benzylbromide (0.53 ml, 4.47 mmol) was added to a suspension of intermediate 7 (2.0 g, 4.26 mmol) in acetonitrile (13 ml). The mixture was stirred at 80° C. for 3 hours. Ethyl acetate was added and the organic layer was washed with brine. The organic layer was dried, filtered and the solvent was removed under reduced pressure. Intermediate 28 was used in the next step without further purification.

Yield: 2.4 g of intermediate 28 (100%)
LCMS method 1: MH$^+$=560, RT=2.125 min

Preparation of Intermediate 29

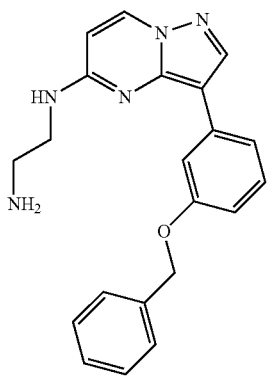 [SMILES: NCCNc1ccn2ncc(-c3cccc(OCc4ccccc4)c3)c2n1]

Intermediate 28 (2.4 g, 4.29 mmol) was dissolved in 4N hydrochloric acid in methanol (13 ml). The mixture was stirred at room temperature for 2 hours. Ethyl acetate was added and the organic layer was washed with water. The organic layer was dried, filtered and the solvent was removed under reduced pressure. Intermediate 29 was used in the next step without further purification.

LCMS method 1: MH$^+$=360, RT=0.729 min

Preparation of Intermediate 30

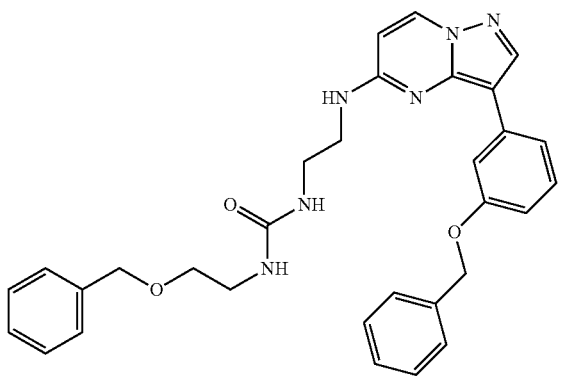 [SMILES: O=C(NCCNc1ccn2ncc(-c3cccc(OCc4ccccc4)c3)c2n1)NCCOCc1ccccc1]

A solution of N,N-diisopropylethylamine (2.31 ml, 13.2 mmol) and intermediate 29 (0.79 mg, 2.2 mmol) in dry tetrahydrofuran (6.6 ml) (+few drop of N,N-dimethylformamide) was added drop wise to a solution of 1,1'-carbonyl diimidazole (0.61 g, 3.74 mmol) in dry tetrahydrofuran (6 ml). The mixture was stirred at room temperature for 1 hour and 2-benzyloxyethanamine (0.998 g, 6.6 mmol) was added. The mixture was stirred at room temperature. When the reaction is completed, ethyl acetate was added and the organic layer was washed with water. The organic layer was dried, filtered and the solvent was removed under reduced pressure. The residue was purified by flash column chromatography over silica gel using dichloromethane and methanol as eluents. The product fractions were collected and the solvent was evaporated.

Yield: 1.065 g of intermediate 30 (90%)
LCMS method 1: MH$^+$=537, RT=1.035 min

Preparation of Intermediate 31

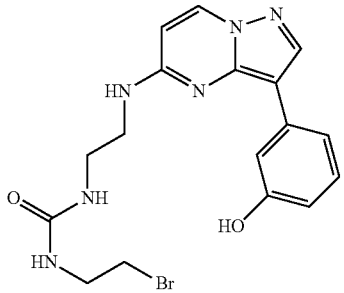 [SMILES: O=C(NCCBr)NCCNc1ccn2ncc(-c3cccc(O)c3)c2n1]

Intermediate 30 (1 g, 1.86 mmol) was suspended in dichloromethane (5.6 ml) and cooled on an ice bath. Boron tribromide (1M solution in dichloromethane, 3.72 ml, 3.72 mmol) was added and the reaction mixture was stirred at room temperature for 18 hours. A mixture of the hydroxyl and the bromo derivative was obtained. The reaction mixture was cooled on an ice bath and methanol was added. Dichloromethane was added until the product was completely solubilized and the mixture was used without further purification in the next step.

Preparation of Example 6

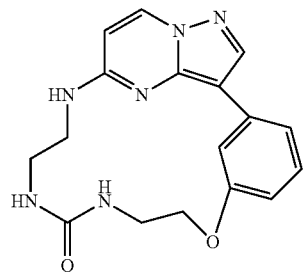 [SMILES: O=C1NCCNc2ccn3ncc(c3n2)-c2cccc(c2)OCCN1]

Cesium carbonate (3.03 g, 9.30 mmol) was suspended in N,N-dimethylacetamide (120 ml) and heated to 50° C. A solution of intermediate 31 (780 mg, 1.86 mmol) in dichloromethane was added drop wise over a period of 3 hours. The reaction mixture was filtered and concentrated under reduced pressure. The residue was suspended in ethyl acetate and washed with water. The organic layer was dried, filtered and the solvent was removed under reduced pressure. The residue was purified by reversed phase HPLC (HPLC method A). The product fractions were collected and the solvent was removed under reduced pressure while cooling.

Yield: 7 mg of example 5 (1%)
LCMS method 2: MH$^+$=339, RT=1.528 min

Example 7

Example 7 is prepared following general scheme 3.

Preparation of Intermediate 32

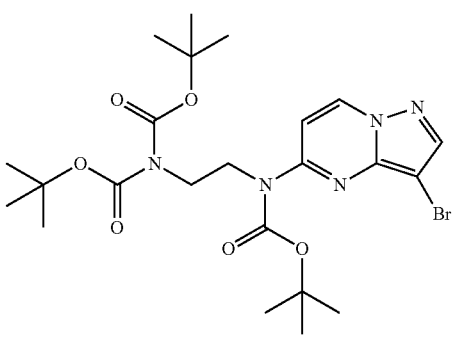 [SMILES: CC(C)(C)OC(=O)N(CCN(C(=O)OC(C)(C)C)c1ccn2ncc(Br)c2n1)C(=O)OC(C)(C)C]

Tert-butoxycarbonyl anhydride (2.82 g, 12.90 mmol) was added to a mixture of intermediate 6 (2.3 g, 6.45 mmol), triethylamine (1.63 ml, 16.13 mmol) and 4-(dimethylamino)pyridine (16 mg, 0.13 mmol) in tetrahydrofuran (19 ml). The mixture was refluxed for 3 hours. The reaction mixture was cooled and ethyl acetate was added. The organic layer was washed with water and brine, dried, filtered and the solvent was removed under reduced pressure. The residue was purified by flash column chromatography over silica gel using heptane and ethyl acetate as eluents. The product fractions were collected and the solvent was evaporated.

Yield: 1.65 g of intermediate 32 (46%)
LCMS method 1: MH$^+$=556-558, RT=2.094 min

Preparation of Intermediate 33

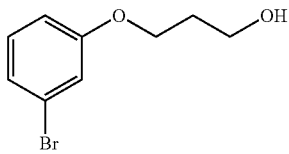 [SMILES: OCCCOc1cccc(Br)c1]

A mixture of 3-bromophenol (5.26 g, 30.4 mmol), 3-bromopropan-1-ol (6.60 ml, 67 mmol) and potassium carbonate (14.71 g, 106.4 mmol) in acetonitrile (91 ml) was reluxed overnight. The reaction mixture was cooled and ethyl acetate was added. The organic layer was washed with brine, dried, filtered and the solvent was removed under reduced pressure. Intermediate 33 was used in the next step without further purification.

LCMS method 1: $MH^+$=231-233, RT=0.967 min

Preparation of Intermediate 34

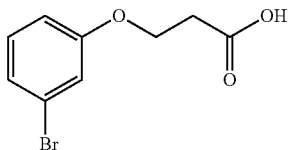 [SMILES: O=C(O)CCOc1cccc(Br)c1]

To a solution of intermediate 33 (7.02 g, 30.4 mmol) in acetone (91 ml) was added a mixture of water and sulfuric acid (14.9 ml; 2:1) at 0° C. and the mixture was stirred for several minutes. Then chromium (VI) oxide (12.16 ml, 121.60 mmol) was added drop wise and the mixture was stirred at 0° C. for 5 hours. The reaction mixture was quenched with 2-propanol (5 ml) and the solvent was removed under reduced pressure.

LCMS method 1: $MH^+$=no ionization, RT=0.208 min

Preparation of Intermediate 35

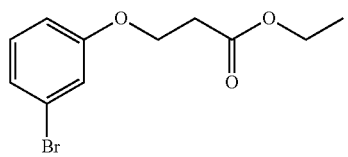

To a stirred solution of intermediate 34 (7.45 g, 30.4 mmol) in ethanol was added drop wise at 0° C. a solution of sulfuric acid (1.62 ml, 30.4 mmol) in ethanol. The mixture was refluxed overnight. The reaction mixture was cooled, concentrated and ethyl acetate was added. The organic layer was washed with sodium bicarbonate, dried, filtered and the solvent was removed under reduced pressure. Intermediate 35 was used in the next step without further purification.

Yield: 8.28 g of intermediate 35 (100%)

LCMS method 1: $MH^+$=273-275, RT=1.362 min

Preparation of Intermediate 36

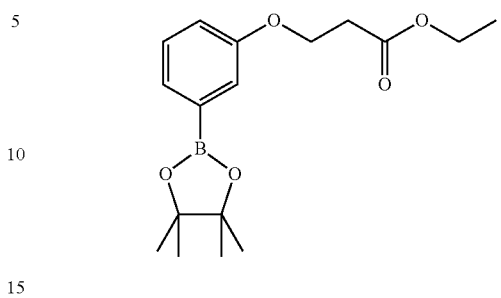

1,4-Dioxane (44 ml) was degassed by bubbling nitrogen gas through it. Intermediate 35 (4.0 g, 14.65 mmol), bis(pinacolato)diboron (4.46 g, 17.58 mmol), [1,1-bis(diphenylphosphino)ferrocene]dichloropalladium(II) (122 mg, 0.15 mmol) and potassium acetate (4.31 g, 43.95 mmol) were added. The suspension was stirred under nitrogen atmosphere at 80° C. for 3 hours. The reaction mixture was cooled, diluted with ethyl acetate and washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 3.03 g of intermediate 36 (65%)

LCMS method 1: $MH^+$=321, RT=1.591 min

Preparation of Intermediate 37

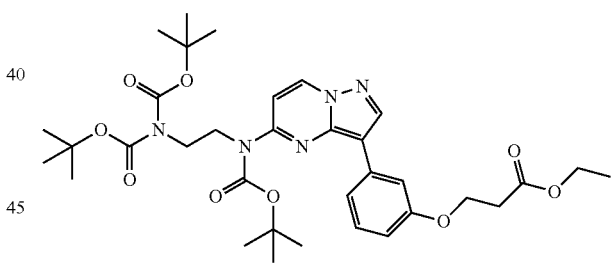

A mixture of 1,4-dioxane and water (3:1, 7 ml) was degassed by bubbling nitrogen gas through the mixture. Intermediate 32 (1.55 g, 2.79 mmol), intermediate 36 (1.16 g, 3.63 mmol), tetrakis(triphenylphosphine)palladium(0) (35 mg, 0.03 mmol), 2-dicyclohexylphosphino-2',4',6'-triisopropylbiphenyl (Xphos) (52 mg, 0.11 mmol) and potassium phosphate tribasic (2.95 g, 5 eq.) were added and the mixture was stirred under nitrogen gas at 80° C. overnight. The reaction mixture was cooled, diluted with ethyl acetate and the organic layer was washed with brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 1.78 g of intermediate 37 (95%)

LCMS method 1: $MH^+$=670, RT=2.247 min

Preparation of Intermediate 38

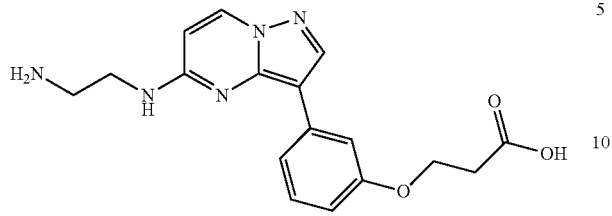

Intermediate 37 (1.78 g, 2.66 mmol) was dissolved in acetonitrile (8 ml) and 6N aqueous hydrochloric acid (12 ml/mmol) was added. The mixture was stirred at 60° C. for 2 hours. The solvent was removed under reduced pressure. Intermediate 38 was used in the next step without further purification.

LCMS method 1: MH$^+$=342, RT=0.470 min

Preparation of Example 7

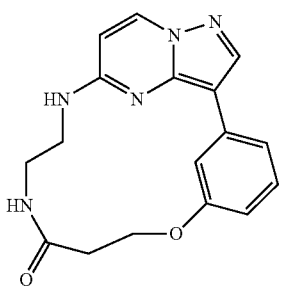 [SMILES: O=C1CCOc2cccc(c2)-c2cnn3ccc(nc23)NCCN1]

A solution of intermediate 38 (1.005 g, 2.66 mmol) and N,N-diisopropylethylamine (2.0 ml, 7.98 mmol) in N,N-dimethylformamide (167 ml) was added slowly using a Marlow peristaltic pump over a period of 1 hour to a solution of O-(benzotriazol-1-yl)-N,N,N',N'-tetramethyluronium hexafluorophosphate (HBTU) (2.22 g, 5.85 mmol) and N,N-diisopropylethylamine (3.25 ml, 18.62 mmol) in N,N-dimethylformamide (83 ml). The reaction mixture was stirred at room temperature for 1 more hour after the addition was completed. The mixture was quenched with an aqueous solution of ammonia (25%). The solvent was removed under reduced pressure and ethyl acetate was added. The organic layer was washed with a saturated sodium bicarbonate solution and brine. The organic layer was dried, filtered and the solvent was removed under reduced pressure. The residue was purified by flash column chromatography over silica gel using dichloromethane and methanol as eluents. The product fractions were collected and the solvent was evaporated.

Yield: 120 mg of example 7 (14% over 2 steps)
LCMS method 2: MH$^+$=339, RT=2.275 min

Example 8

Example 8 is prepared following general scheme 4.

Preparation of Intermediate 39

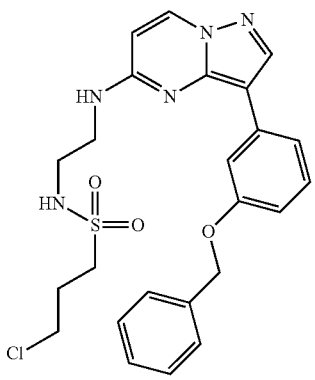 [SMILES: O=S(=O)(CCCCl)NCCNc1ccn2ncc(-c3cccc(OCc4ccccc4)c3)c2n1]

Triethylamine (1.78 ml, 12.87 mmol) and 3-chloropropane-1-sulfonyl chloride (0.79 ml, 6.44 mmol) were added to a solution of intermediate 38 (1.7 g, 4.29 mmol) in dichloromethane (13 ml). The reaction mixture was stirred at room temperature overnight. More 3-chloropropane-1-sulfonyl chloride (0.26 ml, 2.14 mmol) was added and the reaction mixture was stirred at room temperature until completion. The solvent was removed under reduced pressure and ethyl acetate was added. The organic layer was washed with water, dried, filtered and the solvent was removed under reduced pressure. The residue was purified by flash column chromatography over silica gel using hexane and ethylacetate as eluents. The product fractions were collected and the solvent was evaporated.

LCMS method 2: MH$^+$=500, RT=1.003 min

Preparation of Intermediate 40

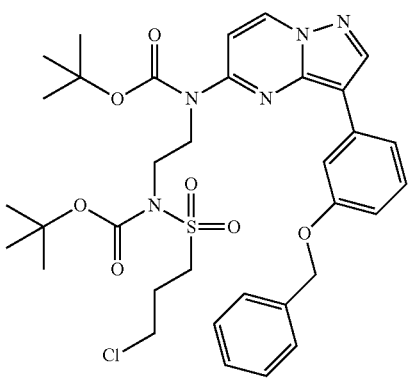 [SMILES: CC(C)(C)OC(=O)N(CCN(C(=O)OC(C)(C)C)S(=O)(=O)CCCCl)c1ccn2ncc(-c3cccc(OCc4ccccc4)c3)c2n1]

Intermediate 39 (2.145 g, 4.29 mmol), tert-butoxycarbonyl anhydride (2.06 g, 9.44 mmol), triethylamine (1.78 ml, 12.87 mmol) and 4-(dimethylamino)pyridine (53 mg, 0.43 mmol) were dissolved in tetrahydrofuran (13 ml). The mixture was refluxed in a sealed tube for 6 hours. The reaction mixture was cooled, the solvent was removed under reduced pressure and ethyl acetate was added. The organic layer was washed with water and brine, dried, filtered and the solvent was removed under reduced pressure. The residue was purified by flash column chromatography over silica gel using heptane and ethyl acetate as eluents. The product fractions were collected and the solvent was evaporated.

Yield: 1.27 g of intermediate 40 (42% over 2 steps)
LCMS method 1: MH$^+$=700, RT=2.252 min Preparation of Intermediate 41

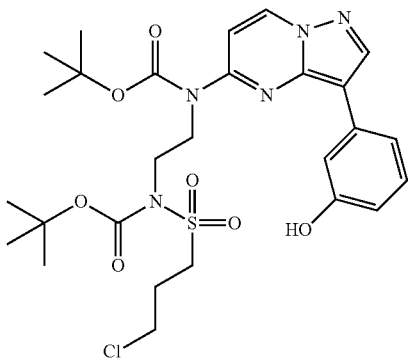 [SMILES: CC(C)(C)OC(=O)N(CCN(C(=O)OC(C)(C)C)S(=O)(=O)CCCCl)c1ccn2ncc(-c3cccc(O)c3)c2n1]

Intermediate 40 (0.720 g, 1.03 mmol) was dissolved in tetrahydrofuran (10 ml) and Pd/C (0.1 g) was added. The mixture was stirred at room temperature under hydrogen atmosphere for 20 hours. More Pd/C (0.1 g) and methanol (5 ml) were added and the mixture was stirred at room temperature under hydrogen atmosphere for 66 hours. The reaction mixture was filtered over celite and the residue was washed with dichloromethane and methanol. The solvent was removed under reduced pressure and the residue was purified by column chromatography over silica gel using dichloromethane and methanol as eluents. The product fractions were collected and the solvent was evaporated.

Yield: 100 mg of intermediate 41 (16%)
LCMS method 1: MH$^+$=610, RT=1.034 min

Preparation of Example 8

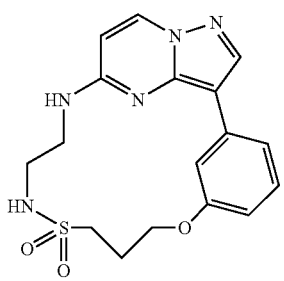 [SMILES: O=S1(=O)CCCOc2cccc(c2)-c2cnn3ccc(nc23)NCCN1]

Intermediate 41 (0.21 g, 0.34 mmol) in N,N-dimethylacetamide (15 ml) was added drop wise to a solution of cesium carbonate (0.55 g, 1.70 mmol), potassium iodide (113 mg, 0.68 mmol) and tetrabutylammonium iodide (11 mg, 0.03 mmol) in tetrahydrofuran (30 ml). The mixture was stirred at 90° C. for 2 hours. The solvent was removed under reduced pressure and ethyl acetate was added. The organic layer was washed with water and brine. The organic layer was separated and the solvent was removed under reduced pressure. The residue was purified by column chromatography over silica gel using dichloromethane and methanol as eluents. The product fractions were collected and the solvent was evaporated. Another purification was performed using reversed phase HPLC (HPLC method A). The product fractions were collected and the solvent was evaporated.

Yield: 35 mg of example 8 (28%)
LCMS method 2: MH$^+$=374, RT=2.590 min

Example 9

Preparation of Example 9

Example 9 is prepared following general scheme 1.

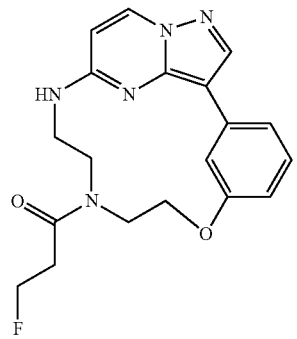 [SMILES: O=C(CCF)N1CCNc2ccn3ncc(c3n2)-c2cccc(c2)OCC1]

7-Oxa-10,13,17,18,21-pentaazatetracyclo[12.5.2.1^{2,6}.0^{17,20}]docosa-1(20),2,4,6(22),14(21),-15,18-heptaene hydrochloride (0.15 g, 0.452 mmol), 3-fluoropropanoic acid (50 mg, 0.50 mmol) and N,N-diisopropylethylamine (0.269 ml, 1.58 mmol) were dissolved in N,N-dimethylformamide (1.36 ml). O-(Benzotriazol-1-yl)-N,N,N',N'-tetramethyluronium hexafluorophosphate (HBTU) (0.205 g, 0.54 mmol) was added and the mixture was stirred at room temperature for 2 hours. The solvent was removed under reduced pressure and the residue was purified by reversed phase HPLC (HPLC method A). The product fractions were collected and the solvent was removed under reduced pressure.

Yield: 20 mg of example 9 (12%)
LCMS method 2: MH$^+$=370, RT=2.917 min

Preparation of Example 10

Example 10

Example 10 is prepared following general scheme 1.

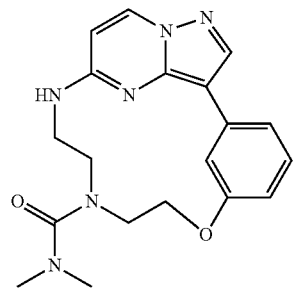 [SMILES: CN(C)C(=O)N1CCNc2ccn3ncc(c3n2)-c2cccc(c2)OCC1]

To a solution of 7-oxa-10,13,17,18,21-pentaazatetracyclo[12.5.2.1^{2,6}.0^{17,20}]docosa-1(20),2,4,6(22),14(21),-15,18-heptaene hydrochloride (0.15 g, 0.452 mmol) and N,N-diisopropylethylamine (0.230 ml, 1.35 mmol) in N,N-dimethylformamide (1.35 ml) was added N,N-dimethylcarbamoyl chloride (57 mg, 0.557 mmol). The reaction mixture was stirred at room temperature for 4 hours. The solvent was removed under reduced pressure and methanol was added. The mixture was stirred at room temperature for 1 hour, the precipitate was filtered and dried under reduced pressure.

Yield: 123 mg of example 10 (74%)

LCMS method 2: MH$^+$=367, RT=2.939 min

Example 11

Preparation of Example 11

Example 11 is prepared following general scheme 1.

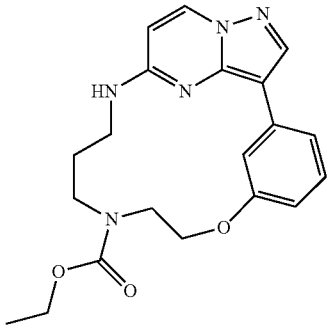 [SMILES: CCOC(=O)N1CCCNc2ccn3ncc(c3n2)-c2cccc(c2)OCC1]

7-oxa-10,14,18,19,22-pentaazatetracyclo[13.5.2.1^{2,6}.0^{18,21}]tricosa-1(21),2(23),3,5,15(22),16,19-heptaene hydrochloride was prepared according to similar synthetic procedures as described to obtain intermediate 7 using tert-butyl N-(3-aminopropyl)-N—[2-(tert-butyl(dimethyl)silyl)oxyethyl]carbamate for the coupling to the scaffold and (3-hydroxyphenyl)boronic acid for the Suzuki coupling. The ring closure was effected after TBDMS deprotection using Mitsunobu conditions. The unprotected 7-oxa-10,14,18,19,22-pentaazatetracyclo[13.5.2.1^{2,6}.0^{18,21}]tricosa-1(21),2(23),3,5,15(22),16,19-heptaene hydrochloride was obtained after Boc deprotection under acidic conditions.

Ethyl carbonochloridate (100 µl, 1.01 mmol) was added at 0° C. to a solution of 7-oxa-10,14,18,19,22-pentaazatetracyclo[13.5.2.1^{2,6}.0^{18,21}]tricosa-1(21),2(23),3,5,15(22),16,19-heptaene hydrochloride (350 mg, 1.01 mmol) and triethylamine (349 µl, 2.52 mmol) in dichloromethane (10 ml). The reaction mixture was stirred at room temperature for 1 hour. Water was added and the product was extracted with ethyl acetate. The organic layer was washed with brine, dried, filtered and the solvent was removed under reduced pressure. The residue was purified by flash chromatography over silica gel using dichloromethane and methanol as eluents. The product fractions were collected and the solvent was evaporated.

Yield: 212 mg of example 11 (55%)

LCMS method 2: MH$^+$=382, RT=3.414 min

Example 12

Preparation of Example 12

Example 12 is prepared following general scheme 1.

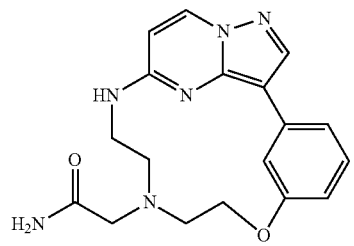 [SMILES: NC(=O)CN1CCNc2ccn3ncc(c3n2)-c2cccc(c2)OCC1]

2-Bromoacetamide (80 mg, 0.58 mmol) was added to a suspension of 7-oxa-10,13,17,18,21-pentaazatetracyclo[12.5.2.1^{2,6}.0^{17,20}]docosa-1(20),2,4,6(22),14(21),-15,18-heptaene hydrochloride (175 mg, 0.527 mmol) and potassium bicarbonate (158 mg, 1.58 mmol) in acetonitrile (1.58 ml). The suspension was stirred under reflux for 2 hours. 2-Bromoacetamide (65 mg, 0.474 mmol) and potassium bicarbonate (32 mg, 0.316 mmol) were added and the mixture was stirred under reflux for 6 hours. The solvent was removed under reduced pressure and the crude was stirred in methanol/H2O (1:1). The precipitate was filtered, washed with methanol and ether and recrystallized from hot methanol/dichloromethane (4:1). The product was taken up in dichloromethane/methanol (4:1, 225 ml) and 4N HCl in 1,4-dioxane (15 µl, 0.4 mmol) was added. The reaction mixture was stirred at room temperature for 1 hour. The solvent was removed under reduced pressure and the compound was triturated with diethyl ether, filtered and dried under vacuum.

Yield: 146 mg of example 12 (71%)

LCMS method 2: MH$^+$=353, RT=1.889 min

Example 13

Preparation of Example 13

Example 13 is prepared following general scheme 1.

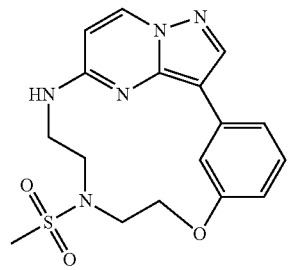 [SMILES: CS(=O)(=O)N1CCNc2ccn3ncc(c3n2)-c2cccc(c2)OCC1]

Methanesulfonyl chloride (45 µl, 0.58 mmol) was added to a solution of 7-oxa-10,13,17,18,21-pentaazatetracyclo[12.5.2.1^{2,6}.0^{17,20}]docosa-1 (20),2,4,6(22),14(21),-15,18-heptaene hydrochloride (175 mg, 0.527 mmol) and diisopropylethylamine (269 µl, 1.58 mmol) in N,N-dimethylformamide (1.58 ml). The mixture was stirred at room temperature for 3 hours. Methanesulfonyl chloride (12 µl, 0.16 mmol) was added and stirred at room temperature overnight. The solvent was removed under reduced pressure. Methanol was added. The precipitate was filtered and dried under reduced pressure.

Yield: 155 mg of example 13 (79%)

LCMS method 2: MH$^+$=374, RT=3.011 min

Example 14

Preparation of Example 14

Example 14 is prepared following general scheme 1.

7-[(2-nitrobenzene)sulfonyl]-7,10,13,17,18,21-hexaaza-tetracyclo[12.5.2.1^{2,6}.0^{17,20}]docosa-1(20),2,4,6(22),14(21),15,18-heptaene was prepared according to similar synthetic procedures as described to obtain intermediate 7 using intermediate 4 for the coupling to the scaffold and ((3-aminophenyl)boronic acid for the Suzuki coupling. After the Suzuki coupling the anilinic NH was protected with nosyl chloride under classic conditions. The ring closure was effected after TBDMS deprotection using Mitsunobu conditions. The Boc-unprotected 7-[(2-nitrobenzene)sulfonyl]-7,10,13,17,18,21-hexaazatetracyclo[12.5.2.1^{2,6}.0^{17,20}]docosa-1(20),2,4,6(22), 14(21),15,18-heptaene was obtained after Boc deprotection under acidic conditions.

Preparation of Intermediate 42

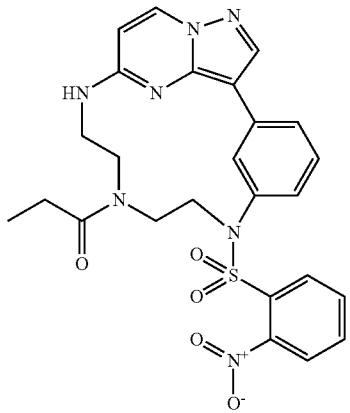 [SMILES: CCC(=O)N1CCNc2ccn3ncc(c3n2)-c2cccc(c2)N(S(=O)(=O)c2ccccc2[N+](=O)[O-])CC1]

7-[(2-nitrobenzene)sulfonyl]-7,10,13,17,18,21-hexaaza-tetracyclo[12.5.2.1^{2,6}.0^{17,20}]docosa-1(20),2,4,6(22),14(21),15,18-heptaene hydrochloride (495 mg, 0.96 mmol) and triethylamine (334 µl, 2.40 mmol) were stirred in dry tetrahydrofuran (2.88 ml). Propanoyl chloride (90 µl, 1.06 mmol) was added and the mixture was stirred at room temperature for 1 hour. Another amount of propanoyl chloride (9 µl, 0.106 mmol) was added and the mixture was stirred at room temperature for 1 more hour. The solvent was removed under reduced pressure and the precipitate was triturated in methanol.

The solid was filtered, washed with diethyl ether and dried under vacuum.

Yield: 417 mg of intermediate 42 (81%)

LCMS method 1: MH$^+$=536, RT=0.877 min

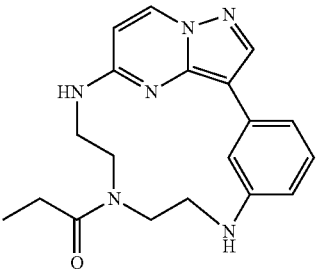 [SMILES: CCC(=O)N1CCNc2cccc(c2)-c2cnn3ccc(nc23)NCC1]

To a solution of intermediate 42 (417 mg, 0.78 mmol) in N,N-dimethylformamide (2.34 ml) were added cesium carbonate (508 mg, 1.56 mmol) and thiophenol (100 µl, 0.94 mmol). The mixture was stirred at room temperature for 4 hours. Ethyl acetate was added and the organic layer was washed with water, dried, filtered and the solvent was removed under reduce pressure. The product was purified by flash chromatography over silica gel using dichloromethane and methanol as eluents. The product fractions were collected and the solvent was removed under reduced pressure.

Yield: 197 mg of example 14 (72%)

LCMS method 2: MH$^+$=351, RT=2.700 min

Example 15

Preparation of Example 15

Example 15 is prepared following general scheme 1.

Preparation of Intermediate 43

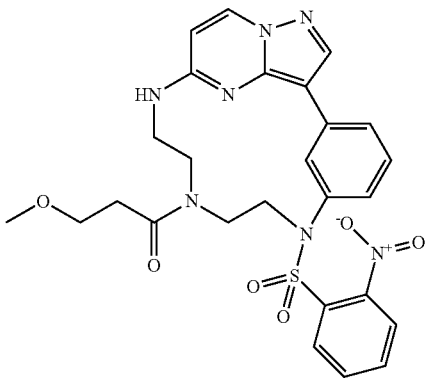

7-[(2-nitrobenzene)sulfonyl]-7,10,13,17,18,21-hexaaza-tetracyclo[12.5.2.1^{2,6}.0^{17,20}]docosa-1 (20),2,4,6(22),14(21),15,18-heptaene hydrochloride (600 mg, 1.13 mmol), 3-methoxypropanoic acid (120 µl, 1.24 mmol) and N,N-diisopropylethylamine (494 µl, 2.83 mmol) were dissolved in N,N-dimethylformamide (5 ml). O-(Benzotriazol-1-yl)-N,N,N',N'-tetramethyluronium hexafluorophosphate (HBTU) (516 mg, 1.36 mmol) was added and the mixture was stirred at room temperature for 1 hour. Diethyl ether was added and the organic layer was washed with a saturated aqueous sodium bicarbonate solution, water and brine. The organic layer was dried, filtered and the solvent was removed under reduced pressure. The product was purified by flash chromatography over silica gel using dichloromethane and methanol as eluents. The product fractions were collected and the solvent was removed under reduced pressure.

Yield: 558 mg of intermediate 43 (85%)
LCMS method 1: MH$^+$=580, RT=0.858 min

Preparation of Example 15

Example 15 is prepared following general scheme 1.

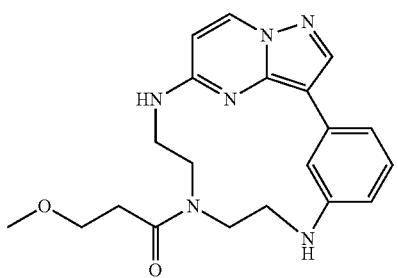

Cesium carbonate (626 mg, 1.92 mmol) and thiophenol (120 μl, 1.15 mmol) were dissolved in N,N-dimethylformamide (5 ml) and the mixture was stirred at room temperature for 10 minutes. A solution of intermediate 43 (558 mg, 0.96 mmol) in N,N-dimethylformamide (5 ml) was added. The mixture was stirred at room temperature overnight. Ethyl acetate was added and the organic layer was washed with a 1M aqueous sodium hydroxide solution and water. The organic layer was dried, filtered and the solvent was removed under reduce pressure. The product was purified by flash chromatography over silica gel using dichloromethane and methanol as eluents. The product fractions were collected and the solvent was removed under reduced pressure.

Yield: 258 mg of example 15 (68%)
LCMS method 2: MH$^+$=395, RT=1.910 min

Example 16

Preparation of Example 16

Example 16 is prepared following general scheme 1.

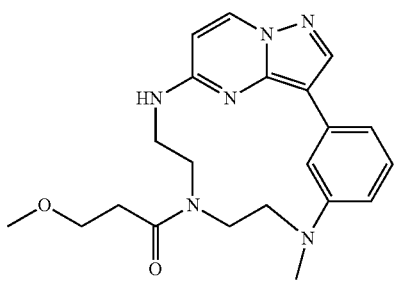 [SMILES: COCCC(=O)N1CCNc2ccn3ncc(c3n2)-c2cccc(c2)N(C)CC1]

A mixture of example 15 (220 mg, 0.56 mmol), formaldehyde (70 mg, 0.84 mmol) and glacial acetic acid (32 μl, 0.56 mmol) was stirred at room temperature for 30 minutes. Sodium triacetoxyborohydride (237 mg, 1.12 mmol) was added and the mixture was stirred at room temperature for 1 hour. Ethyl acetate was added and the organic layer was washed with a saturated aqueous sodium bicarbonate solution, water and brine. The organic layer was dried, filtered and the solvent was removed under reduce pressure. The residue was purified by flash column chromatography over silica gel using dichloromethane and methanol as eluents. The product fractions were collected and the solvent was removed under reduced pressure.

Yield: 176 mg of example 16 (77%)
LCMS method 2: MH$^+$=409, RT=2.224 min

Example 17

Preparation of Example 17

Example 17 is prepared following general scheme 1.

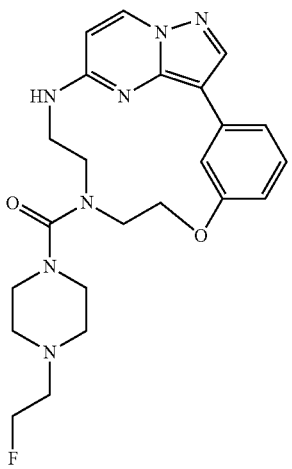 [SMILES: O=C(N1CCNc2ccn3ncc(c3n2)-c2cccc(c2)OCC1)N1CCN(CCF)CC1]

A mixture of 7-oxa-10,13,17,18,21-pentaazatetracyclo[12.5.2.1^{2,6}.0^{17,20}]docosa-1(20),2,4,6(22),14(21),-15,18-heptaene hydrochloride (300 mg, 0.904 mmol) and diisopropylethylamine (616 μl, 3.62 mmol) in tetrahydrofuran (2.5 ml) and N,N-dimethylformamide (2.5 ml) was added drop wise to a solution of di(imidazol-1-yl)methanone (220 mg, 1.356 mmol) in tetrahydrofuran (1.5 ml). The mixture was stirred at room temperature for 2 hours. 1-(2-Fluoroethyl)piperazine hydrochloride (229 mg, 1.36 mmol) was added and the reaction mixture was stirred at 80° C. for 63 hours and at 110° C. for 24 hours. Di(imidazol-1-yl)methanone (150 mg, 0.904 mmol) was added and the mixture was stirred at 110° C. for 18 hours. The solvent was removed under reduced pressure and the residue was purified by reversed phase HPLC (HPLC method A). The product fractions were collected and the solvent was removed under reduced pressure. The product was taken up in dichloromethane/methanol (4:1, 520 μl) and 4N HCl in 1,4-dioxane (48 μl, 0.191 mmol) was added. The reaction mixture was stirred at room temperature for 2 hours. The solvent was removed under reduced pressure and the compound was triturated with diethyl ether, filtered and dried under vacuum.

Yield: 84 mg of example 17 (19%)
LCMS method 2: MH$^+$=454, RT=2.032 min

Example 18

Preparation of Example 18

Example 18 is prepared following general scheme 1.

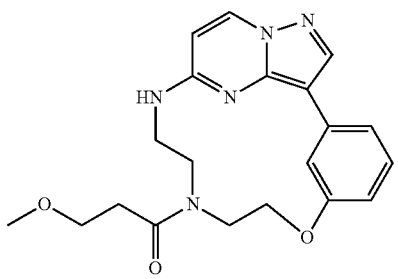 [SMILES: COCCC(=O)N1CCNc2ccn3ncc(c3n2)-c2cccc(c2)OCC1]

7-Oxa-10,13,17,18,21-pentaazatetracyclo[12.5.2.1^{2,6}.0^{17,20}]docosa-1(20),2,4,6(22),14(21),-15,18-heptaene hydrochloride (175 mg, 0.527 mmol), 3-methoxypropanoic acid (54 mg, 0.58 mmol) and N,N-diisopropylethylamine (313 µl, 1.84 mmol) were dissolved in N,N-dimethylformamide (2.10 ml). O-(Benzotriazol-1-yl)-N,N,N',N'-tetramethyluronium hexafluorophosphate (HBTU) (239 mg, 0.63 mmol) was added and the mixture was stirred at room temperature for 2 hours. The solvent was removed under reduced pressure and methanol was added. The precipitate was filtered and dried under reduced pressure.

Yield: 167 mg of example 18 (83%)
LCMS method 2: MH$^+$=382, RT=2.813 min

Example 19

Preparation of Example 19

Example 19 is prepared following general scheme 1.

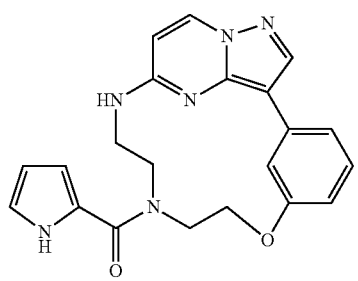 [SMILES: O=C(c1ccc[nH]1)N1CCNc2ccn3ncc(c3n2)-c2cccc(c2)OCC1]

7-Oxa-10,13,17,18,21-pentaazatetracyclo[12.5.2.1^{2,6}.0^{17,20}]docosa-1(20),2,4,6(22),14(21),-15,18-heptaene hydrochloride (175 mg, 0.527 mmol), 1H-pyrrole-2-carboxylic acid (64 mg, 0.58 mmol) and N,N-diisopropylethylamine (313 µl, 1.84 mmol) were dissolved in N,N-dimethylformamide (2.10 ml). O-(Benzotriazol-1-yl)-N,N,N',N'-tetramethyluronium hexafluorophosphate (HBTU) (239 mg, 0.63 mmol) was added and the mixture was stirred at room temperature for 2 hours. The reaction mixture was poured into ethyl acetate and the organic layer was washed with a saturated aqueous sodium bicarbonate solution, water and brine. The organic layer was dried, filtered and the solvent was removed under reduce pressure. Methanol was added and the precipitate was filtered. The residue was purified by reversed phase HPLC (HPLC method A). The product fractions were collected and the solvent was removed under reduced pressure.

Yield: 64 mg of example 19 (31%)
LCMS method 2: MH$^+$=389, RT=3.208 min

Example 20

Preparation of Example 20

Example 20 is prepared following general scheme 1.

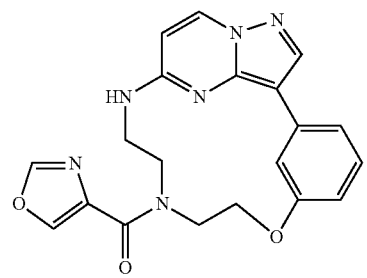 [SMILES: O=C(c1cocn1)N1CCNc2ccn3ncc(c3n2)-c2cccc(c2)OCC1]

7-Oxa-10,13,17,18,21-pentaazatetracyclo[12.5.2.1^{2,6}.0^{17,20}]docosa-1(20),2,4,6(22),14(21),-15,18-heptaene hydrochloride (128 mg, 0.386 mmol), oxazole-4-carboxylic acid (48 mg, 0.425 mmol) and N,N-diisopropylethylamine (230 µl, 1.35 mmol) were dissolved in N,N-dimethylformamide (1.16 ml). O-(Benzotriazol-1-yl)-N,N,N',N'-tetramethyluronium hexafluorophosphate (HBTU) (174 mg, 0.46 mmol) was added and the mixture was stirred at room temperature for 2 hours. The solvent was removed under reduced pressure and methanol was added. The precipitate was filtered and dried under reduced pressure.

Yield: 125 mg of example 20 (83%)
LCMS method 2: MH$^+$=391, RT=2.988 min

Example 21

Preparation of Example 21

Example 21 is prepared following general scheme 1.

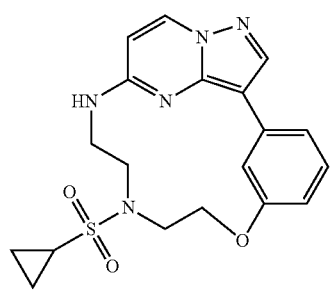 [SMILES: O=S(=O)(C1CC1)N1CCNc2ccn3ncc(c3n2)-c2cccc(c2)OCC1]

Cyclopropanesulfonyl chloride (81 mg, 0.58 mmol) was added to a solution of 7-oxa-10,13,17,18,21-pentaazatetracyclo[12.5.2.1^{2,6}.0^{17,20}]docosa-1(20),2,4,6(22),14(21),-15,18-heptaene hydrochloride (175 mg, 0.527 mmol) and diisopropylethylamine (269 µl, 1.58 mmol) in N,N-dimethylformamide (1.58 ml). The mixture was stirred at room temperature for 4 hours. Cyclopropanesulfonyl chloride (22 mg, 0.16 mmol) was added and stirred at room temperature for 2 hours. The solvent was removed under reduced pressure. Methanol was added. The precipitate was filtered and dried under reduced pressure.

Yield: 125 mg of example 21 (59%)
LCMS method 2: MH$^+$=400, RT=3.288 min

Example 22

Preparation of Example 22

Example 22 is prepared following general scheme 1.

Preparation of Intermediate 44

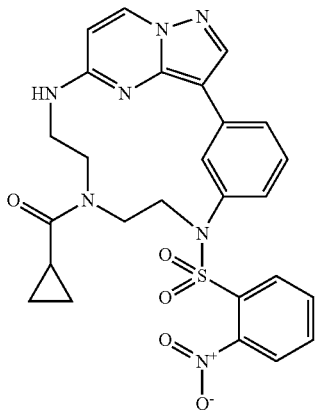 [SMILES: O=C(C1CC1)N1CCNc2ccn3ncc(c3n2)-c2cccc(c2)N(S(=O)(=O)c2ccccc2[N+](=O)[O-])CC1]

7-[(2-nitrobenzene)sulfonyl]-7,10,13,17,18,21-hexaazatetracyclo[12.5.2.1^{2,6}.0^{17,20}]docosa-1(20),2,4,6(22),14(21),15,18-heptaene hydrochloride (315 mg, 0.61 mmol) and triethylamine (211 µl, 1.52 mmol) were stirred in dry tetrahydrofuran (5.00 ml) for 5 minutes. Cyclopropanecarbonyl chloride (60 µl, 0.67 mmol) was added and the mixture was stirred at room temperature for 1 hour. The solvent was removed under reduced pressure. The product was purified by flash chromatography over silica gel using dichloromethane and methanol as eluents. The product fractions were collected and the solvent was removed under reduced pressure.

Yield: 190 mg of intermediate 44 (57%)
LCMS method 1: $MH^+$=548, RT=0.921 min

Preparation of Example 22

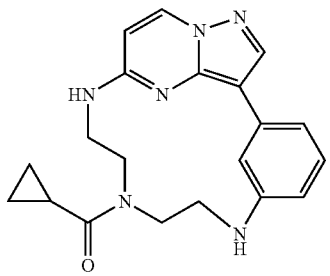 [SMILES: O=C(C1CC1)N1CCNc2cccc(c2)-c2cnn3ccc(nc23)NCC1]

Thiophenol (40 µl, 0.42 mmol) and cesium carbonate (228 mg, 0.70 mmol) were suspended in N,N-dimethylformamide (0.5 ml) and stirred at room temperature for 15 minutes. A solution of intermediate 43 (190 mg, 0.35 mmol) in N,N-dimethylformamide (0.5 ml) was added and the mixture was stirred at room temperature for 3 hours. Ethyl acetate was added and the organic layer was washed with brine, dried, filtered and the solvent was removed under reduce pressure. The product was purified by flash chromatography over silica gel using dichloromethane and methanol as eluents. The product fractions were collected and the solvent was removed under reduced pressure.

Yield: 82 mg of example 22 (65%)
LCMS method 2: $MH^+$=363, RT=2.740 min

Example 23

Preparation of Example 23

Example 23 is prepared following general scheme 1.

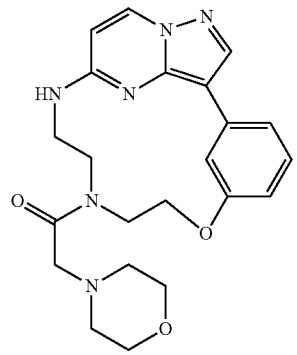 [SMILES: O=C(CN1CCOCC1)N1CCNc2ccn3ncc(c3n2)-c2cccc(c2)OCC1]

7-Oxa-10,13,17,18,21-pentaazatetracyclo[12.5.2.1^{2,6}.0^{17,20}]docosa-1(20),2,4,6(22),14(21),-15,18-heptaene hydrochloride (150 mg, 0.452 mmol), 2-morpholinoacetic acid hydrochloride (90 mg, 0.497 mmol) and N,N-diisopropylethylamine (384 µl, 2.26 mmol) were dissolved in N,N-dimethylformamide (1.80 ml). O-(Benzotriazol-1-yl)-N,N,N',N'-tetramethyluronium hexafluorophosphate (HBTU) (205 mg, 0.54 mmol) was added and the mixture was stirred at room temperature for 2 hours. The solvent was removed under reduced pressure and methanol was added. The precipitate was filtered and dried under reduced pressure. The product was taken up in dichloromethane/methanol (4:1, 100 ml) and 4N HCl in 1,4-dioxane (90 µl, 0.36 mmol) was added. The reaction mixture was stirred at room temperature for 90 minutes. The solvent was removed under reduced pressure and the compound was triturated with diethyl ether, filtered and dried under reduced pressure.

Yield: 155 mg of example 23 (75%)
LCMS method 2: $MH^+$=423, RT=1.942 min

Example 24

Preparation of Example 24

Example 24 is prepared following general scheme 1.

Preparation of Intermediate 45

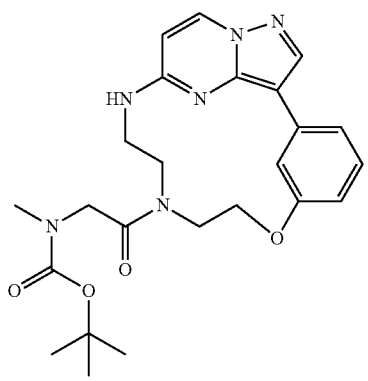 [SMILES: CN(CC(=O)N1CCNc2ccn3ncc(c3n2)-c2cccc(c2)OCC1)C(=O)OC(C)(C)C]

7-Oxa-10,13,17,18,21-pentaazatetracyclo[12.5.2.1^{2,6}.0^{17,20}]docosa-1(20),2,4,6(22),14(21),-15,18-heptaene hydrochloride (125 mg, 0.377 mmol), 2-(tert-butoxycarbonyl(methyl)amino)acetic acid (79 mg, 0.415 mmol) and N,N-diisopropylethylamine (224 µl, 1.32 mmol) were dissolved in N,N-dimethylformamide (1.13 ml). O-(Benzotriazol-1-yl)-N,N,N',N'-tetramethyluronium hexafluorophosphate (HBTU) (171 mg, 0.45 mmol) was added and the mixture was stirred at room temperature for 2 hours. The solvent was removed under reduced pressure, methanol was added and the mixture was stirred at room temperature for 1 hour. The precipitate was filtered and recrystallized from hot methanol/dichloromethane (4:1).
Yield: 122 mg of intermediate 45 (69%)
LCMS method 2: MH+=427, RT=3.412 min Preparation of Example 24

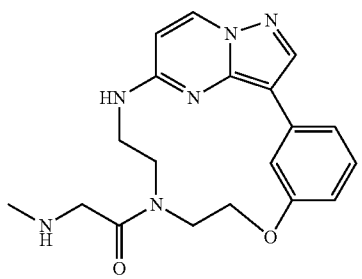 [SMILES: CNCC(=O)N1CCNc2ccn3ncc(c3n2)-c2cccc(c2)OCC1]

Intermediate 44 (119 mg, 0.255 mmol) was stirred in 4N HCl in 1,4-dioxane (1.02 ml, 0.255 mmol) for 3 hours. The solvent was removed under reduced pressure and the compound was triturated with diethyl ether, filtered and dried under vacuum.
Yield: 101 mg of example 24 (98%)
LCMS method 2: MH+=367, RT=1.875 min Example 25

Preparation of Example 25

Example 25 is prepared following general scheme 1.

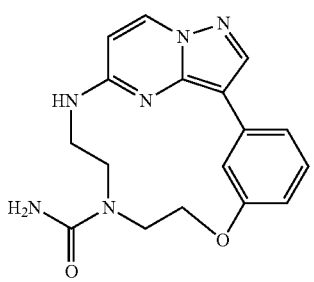 [SMILES: NC(=O)N1CCNc2ccn3ncc(c3n2)-c2cccc(c2)OCC1]

Urea (29 mg, 0.490 mmol) was added to a solution of 7-oxa-10,13,17,18,21-pentaazatetracyclo[12.5.2.1^{2,6}.0^{17,20}]docosa-1 (20),2,4,6(22),14(21),-15,18-heptaene hydrochloride (125 mg, 0.377 mmol) and N,N-diisopropylethylamine (74 µl, 0.57 mmol) in N,N-dimethylacetamide (1.13 ml). The mixture was stirred at 110° C. for 18 hours. The solvent was removed under reduced pressure, methanol was added and the mixture was stirred at room temperature for 1 hour. The precipitate was filtered and recrystallized from hot methanol/dichloromethane (4:1).
Yield: 98 mg of example 25 (77%)
LCMS method 2: MH+=339, RT=2.412 min Example 26

Preparation of Example 26

Example 26 is prepared following general scheme 1.

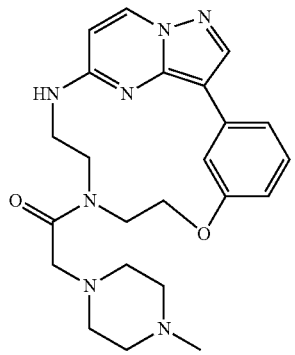 [SMILES: CN1CCN(CC(=O)N2CCNc3ccn4ncc(c4n3)-c3cccc(c3)OCC2)CC1]

7-Oxa-10,13,17,18,21-pentaazatetracyclo[12.5.2.1^{2,6}.0^{17,20}]docosa-1(20),2,4,6(22),14(21),-15,18-heptaene hydrochloride (150 mg, 0.452 mmol), 2-morpholinoacetic acid hydrochloride (90 mg, 0.497 mmol) and N,N-diisopropylethylamine (384 µl, 2.26 mmol) were dissolved in N,N-dimethylformamide (1.80 ml). O-(Benzotriazol-1-yl)-N,N,N',N'-tetramethyluronium hexafluorophosphate (HBTU) (205 mg, 0.54 mmol) was added and the mixture was stirred at room temperature for 2 hours. The solvent was removed under reduced pressure and methanol was added. The mixture was stirred at room temperature for 1 hour. The precipitate was filtered and dried under reduced pressure. The product was taken up in dichloromethane/methanol (4:1, 200 ml) and 4N HCl in 1,4-dioxane (84 µl, 0.368 mmol) was added. The reaction mixture was stirred at room temperature for 2 hours. The solvent was removed under reduced pressure and the compound was triturated with diethyl ether, filtered and dried under reduced pressure.
Yield: 142 mg of example 26 (67%)
LCMS method 2: MH+=436, RT=1.930 min Example 27

Preparation of Example 27

Example 27 is prepared following general scheme 1.

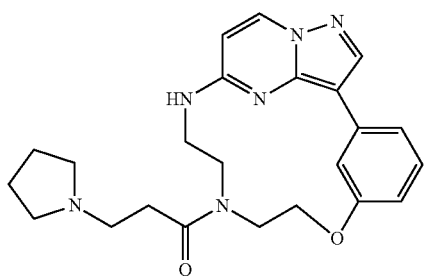 [SMILES: O=C(CCN1CCCC1)N1CCNc2ccn3ncc(c3n2)-c2cccc(c2)OCC1]

7-Oxa-10,13,17,18,21-pentaazatetracyclo[12.5.2.1ˆ{2,6}.0ˆ{17,20}]docosa-1(20),2,4,6(22),14(21),-15,18-heptaene hydrochloride (125 mg, 0.377 mmol), 3-pyrrolidin-1-ylpropanoic acid hydrochloride (75 mg, 0.415 mmol) and N,N-diisopropylethylamine (321 μl, 1.89 mmol) were dissolved in N,N-dimethylformamide (1.50 ml). O-(Benzotriazol-1-yl)-N,N,N',N'-tetramethyluronium hexafluorophosphate (HBTU) (171 mg, 0.45 mmol) was added and the mixture was stirred at room temperature for 2 hours. The solvent was removed under reduced pressure and methanol was added. The mixture was stirred at room temperature for 1 hour. The precipitate was filtered and dried under reduced pressure. The product was taken up in dichloromethane/methanol (4:1, 200 ml) and 4N HCl in 1,4-dioxane (65 μl, 0.259 mmol) was added. The reaction mixture was stirred at room temperature for 2 hours. The solvent was removed under reduced pressure and the compound was triturated with diethyl ether, filtered and dried under reduced pressure.

Yield: 91 mg of example 27 (53%)

LCMS method 2: MH$^+$=421, RT=2.050 min

Example 28

Preparation of Example 28

Example 28 is prepared following general scheme 1.

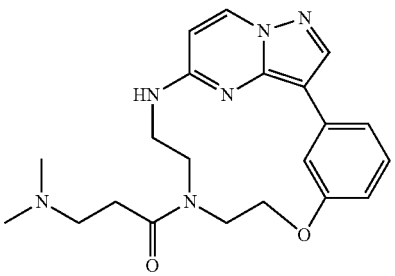 [SMILES: CN(C)CCC(=O)N1CCNc2ccn3ncc(c3n2)-c2cccc(c2)OCC1]

7-Oxa-10,13,17,18,21-pentaazatetracyclo[12.5.2.1ˆ{2,6}.0ˆ{17,20}]docosa-1(20),2,4,6(22),14(21),-15,18-heptaene hydrochloride (100 mg, 0.301 mmol), 3-dimethylaminopropanoic acid hydrochloride (51 mg, 0.331 mmol) and N,N-diisopropylethylamine (255 μl, 1.50 mmol) were dissolved in N,N-dimethylformamide (1.20 ml). O-(Benzotriazol-1-yl)-N,N,N',N'-tetramethyluronium hexafluorophosphate (HBTU) (137 mg, 0.36 mmol) was added and the mixture was stirred at room temperature for 2 hours. The solvent was removed under reduced pressure and methanol was added. The mixture was stirred at room temperature for 1 hour. The precipitate was filtered and recrystallized from hot methanol/dichloromethane (4:1). The compound was purified by reversed phase HPLC (HPLC method A). The product fractions were collected and the solvent was removed under reduced pressure. The product was taken up in dichloromethane/methanol (4:1, 40 ml) and 4N HCl in 1,4-dioxane (69 μl, 0.276 mmol) was added. The reaction mixture was stirred at room temperature for 2 hours. The solvent was removed under reduced pressure and the compound was triturated with diethyl ether, filtered and dried under reduced pressure.

Yield: 102 mg of example 28 (79%)

LCMS method 2: MH$^+$=395, RT=1.977 min

Preparation of Example 29

Example 29 is prepared following general scheme 1.

7-oxa-10,13,17,18,21-pentaazatetracyclo[12.5.2.1ˆ{2,6}.0ˆ{17,20}]docosa-1(20),2,4,6(22),14(21),15,18-heptaene-5-carbonitrile was prepared according to similar synthetic procedures as described to obtain intermediate 7 using intermediate 4 for the coupling to the scaffold and 2-hydroxy-4-(4,4,5,5-tetramethyl-1,3,2-dioxaborolan-2-yl)benzonitrile for the Suzuki coupling. The ring closure was effected after TBDMS deprotection using Mitsunobu conditions.

The Boc-unprotected 7-oxa-10,13,17,18,21-pentaazatetracyclo[12.5.2.1ˆ{2,6}.0ˆ{17,20}]docosa-1 (20),2,4,6(22),14(21),15,18-heptaene-5-carbonitrile was obtained after Boc deprotection under acidic conditions.

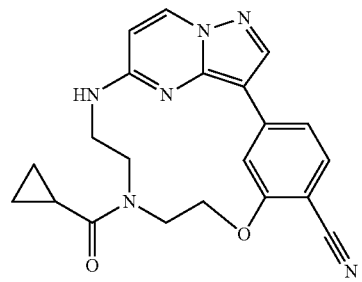 [SMILES: N#Cc1ccc2cc1OCCN(C(=O)C1CC1)CCNc1ccn3ncc-2c3n1]

7-oxa-10,13,17,18,21-pentaazatetracyclo[12.5.2.1ˆ{2,6}.0ˆ{17,20}]docosa-1(20),2,4,6(22),14(21),15,18-heptaene-5-carbonitrile hydrochloride (580 mg, 1.63 mmol) and triethylamine (498 μl, 3.59 mmol) were stirred in dry tetrahydrofuran (4.89 ml) for 5 minutes. Cyclopropanecarbonyl chloride (160 μl, 1.79 mmol) was added and the mixture was stirred at room temperature for 1 hour. The solvent was removed under reduced pressure. The product was purified by flash chromatography over silica gel using dichloromethane and methanol as eluents. The product fractions were collected and the solvent was removed under reduced pressure.

Yield: 220 mg of example 29 (35%)

LCMS method 2: MH$^+$=389, RT=3.056 min

Example 30

Preparation of Example 30

Example 30 is prepared following general scheme 1.

Preparation of Intermediate 46

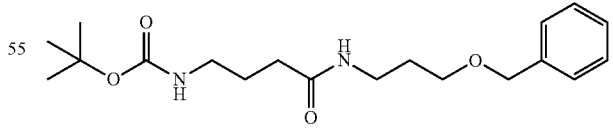

4-(tert-butoxycarbonylamino)butanoic acid (12.0 g, 59.04 mmol) and 3-benzyloxypropan-1-amine (11.91 g, 59.04 mmol) were dissolved in dichloromethane (360 ml). N,N-diisopropylethylamine (27.47 ml, 212.54 mmol) was added and the mixture was stirred at room temperature for 2 minutes. O-(Benzotriazol-1-yl)-N,N,N',N'-tetramethyluronium hexafluorophosphate (HBTU) (26.87 g, 70.85 mmol) was added and the mixture was stirred at room temperature overnight. A saturated aqueous sodium bicarbonate solution was added and the two layers were separated. The organic layer was washed with water, dried, filtered and the solvent was removed under reduced pressure. The product was purified by flash chromatography over silica gel. The product fractions were collected and the solvent was removed under reduced pressure.

LCMS method 2: MH$^+$=351, RT=2.930 min

Preparation of Intermediate 47

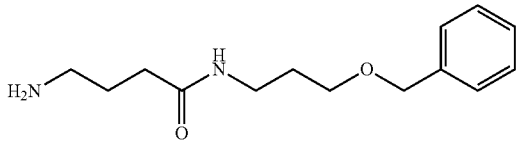 [SMILES: NCCCC(=O)NCCCOCc1ccccc1]

Intermediate 46 (4.0 g, 11.41 mmol) was dissolved in 4N HCl in MeOH (34 ml) and the reaction mixture was stirred at room temperature for 1 hour. The reaction mixture was concentrated and washed with toluene. The precipitate was washed with diethyl ether and dried under reduced pressure.

Yield: 3.2 g of intermediate 47 (98%)

LCMS method 1: MH$^+$=251, RT=0.241 min

Preparation of Intermediate 48

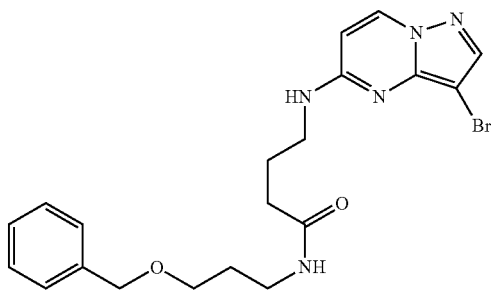 [SMILES: O=C(CCCNc1ccn2ncc(Br)c2n1)NCCCOCc1ccccc1]

A mixture of 3-bromo-5-chloro-pyrazolo[1,5-a]pyrimidine (2.00 g, 8.60 mmol), intermediate 47 (2.37 g, 9.46 mmol) and N,N-diisopropylethylamine (5.85 ml, 34.4 mmol) in acetonitrile (25.8 ml) was stirred under reflux overnight. Another amount of intermediate 46 (646 mg, 2.58 mmol) was added and the mixture was stirred under reflux for 3 more hours. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using heptane and ethyl acetate as eluents (gradient elution from 20% to 100% ethyl acetate). The product fractions were collected and the solvent was evaporated.

Yield: 2.3 g of intermediate 48 (60%)

LCMS method 1: MH$^+$=446, RT=0.825 min

Preparation of Intermediate 49

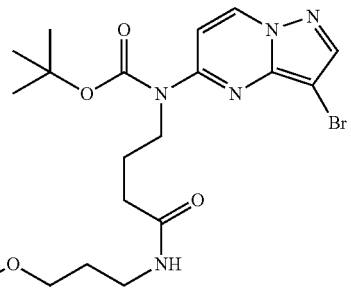

Tert-butoxycarbonyl anhydride (1.18 g, 5.41 mmol) was added to a mixture of intermediate 48 (2.3 g, 5.15 mmol), triethylamine (786 µl, 5.67 mmol) and 4-(dimethylamino)pyridine (32 mg, 0.26 mmol) in tetrahydrofuran (15 ml). The mixture was refluxed overnight. The reaction mixture was cooled and the solvent was removed under reduced pressure. Ethyl acetate was added and the organic layer was washed with water and brine, dried; filtered and the solvent was removed under reduced pressure. The residue was purified by flash column chromatography over silica gel using heptane and ethyl acetate as eluents (gradient elution from 0% to 33% ethyl acetate). The product fractions were collected and the solvent was evaporated.

Yield: 2.43 g of intermediate 49 (86%)

LCMS method 1: MH$^+$=447 (-Boc), RT=1.117 min

Preparation of Intermediate 50

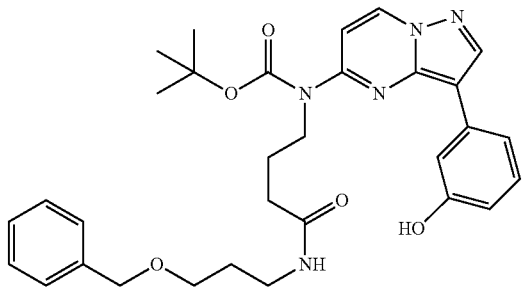 [SMILES: CC(C)(C)OC(=O)N(CCCC(=O)NCCCOCc1ccccc1)c1ccn2ncc(-c3cccc(O)c3)c2n1]

A mixture of 1,4-dioxane and water (3:1, 13.35 ml) was degassed by bubbling nitrogen gas through the mixture. Intermediate 49 (2.43 g, 4.45 mmol), (3-hydroxyphenyl)boronic acid (0.64 g, 4.67 mmol), tetrakis(triphenylphosphine)palladium(0) (104 mg, 0.09 mmol), 2-dicyclohexylphosphino-2', 4',6'-triisopropylbiphenyl (Xphos) (172 mg, 0.36 mmol) and potassium phosphate tribasic (4.717 g, 5 eq.) were added and the mixture was stirred under nitrogen gas at 80° C. for 18 hours. The reaction mixture was cooled, diluted with ethyl acetate and the organic layer was washed with water. The organic layer was dried, filtered and the solvent was removed under reduced pressure. The residue was purified by flash column chromatography over silica gel using heptane and ethyl acetate as eluents (gradient elution from 0% to 50% ethyl acetate). The product fractions were collected and the solvent was evaporated.

Yield: 1.91 g of intermediate 50 (77%)

LCMS method 1: MH$^+$=560, RT=1.141 min

Preparation of Intermediate 51

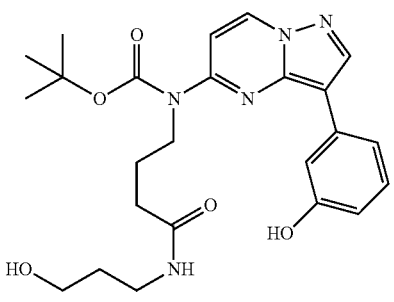 [SMILES: CC(C)(C)OC(=O)N(CCCC(=O)NCCCO)c1ccn2ncc(-c3cccc(O)c3)c2n1]

Intermediate 50 (1.91 g, 3.41 mmol) was dissolved in methanol (65 ml) and palladium (36 mg, 0.34 mmol) was added. The mixture was stirred at room temperature under hydrogen atmosphere for 24 hours. The reaction mixture was filtered over celite and the residue was washed with methanol. The solvent was removed under reduced pressure and the residue was purified by column chromatography over silica gel using heptane and ethyl acetate as eluents (gradient elution from 0% to 100% ethyl acetate). The product fractions were collected and the solvent was evaporated.

Yield: 641 mg of intermediate 51 (40%)

LCMS method 1: MH$^+$=470, RT=0.803 min

Preparation of Intermediate 52

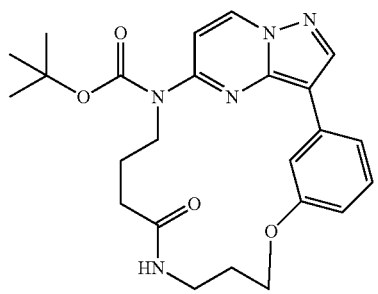 [SMILES: CC(C)(C)OC(=O)N1CCCC(=O)NCCCOc2cccc(c2)-c2cnn3ccc1nc23]

A solution of intermediate 51 (441 mg, 0.94 mmol) in 2-methyltetrahydrofuran (20 ml/mmol) and a solution of diisopropyl azodicarboxylate (560 µl, 2.82 mmol) in toluene (20 ml/mmol) were added simultaneously over a period of 3 hours to a solution of triphenylphosphine (740 mg, 2.82 mmol) in toluene (75 ml/mmol of intermediate 50) at 90° C. The mixture was stirred at 90° C. for 30 minutes. The reaction mixture was cooled and the solvent was removed under reduced pressure. The residue was purified by flash column chromatography over silica gel using heptane and ethyl acetate as eluents (gradient elution from 20% to 80% ethyl acetate). The product fractions were collected and the solvent was evaporated.

Yield: 240 mg of intermediate 52 (57%)

Preparation of Example 30

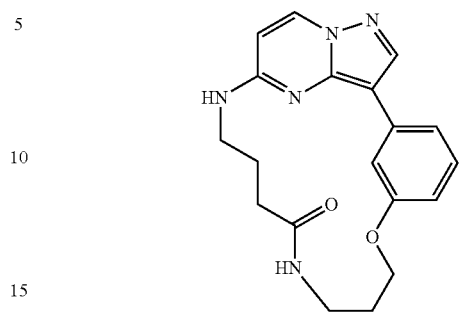

Intermediate 52 (240 mg, 0.53 mmol) was dissolved in 4N HCl in MeOH (1.59 ml) and the reaction mixture was stirred at room temperature for 2 hours. The reaction mixture was concentrated and diethyl ether was added. The precipitate was filtered and dried under reduced pressure.

Yield: 182 mg of example 30 (98%)

LCMS method 2: MH$^+$=352, RT=2.612 min

Example 31

Preparation of Example 31

Example 31 is prepared following general scheme 2.

Preparation of Intermediate 53

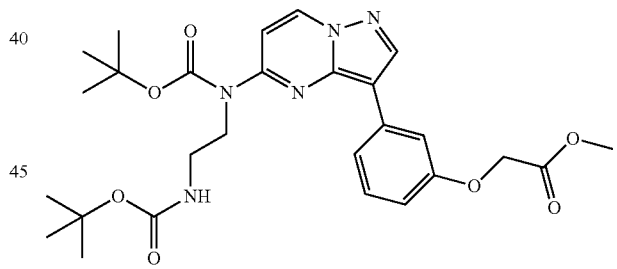

Intermediate 7 (1.62 g, 3.45 mmol), methyl 2-bromoacetate (490 mg, 5.17 mmol) and potassium carbonate (954 mg, 6.90 mmol) were dissolved N,N-dimethylformamide (10.35 ml). The reaction mixture was stirred at 80° C. for 3 hours. The reaction mixture was cooled, water was added and the product was extracted with ethyl acetate. The organic layer was dried, filtered and the solvent was removed under reduced pressure. The residue was purified by flash column chromatography over silica gel using heptane and ethyl acetate as eluents (gradient elution from 0% to 33% ethyl acetate). The product fractions were collected and the solvent was evaporated.

Yield: 1.317 g of intermediate 53 (70%)

LCMS method 1: MH$^+$=442 (-Boc), RT=1.166 min

Preparation of Intermediate 54

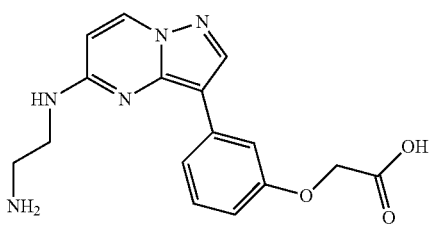

Intermediate 53 (1.317 g, 2.43 mmol) was dissolved in 4N HCl in 1,4-dioxane (7.29 ml) and the reaction mixture was stirred at room temperature overnight. The reaction mixture was concentrated and diethyl ether was added. The precipitate was filtered and dried under reduced pressure. The carboxylic acid was obtained.

LCMS method 1: MH$^+$=328 (carboxylic acid)

Preparation of Intermediate 55

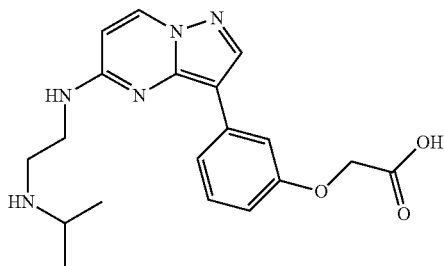 [SMILES: CC(C)NCCNc1ccn2ncc(-c3cccc(OCC(=O)O)c3)c2n1]

Acetone (260 µl, 3.52 mmol) was added to a solution of intermediate 54 (1.00, 2.93 mmol) and triethylamine (812 µl, 5.86 mmol) in 1,2-dichloroethane:methanol (1:1, 8.79 ml). The mixture was stirred at room temperature for 2 hours. Sodium borohydride (812 mg, 5.86 mmol) was added portion wise and the reaction mixture was stirred at room temperature for 30 minutes. Water was added and the compound was extracted with dichloromethane. The organic layer was dried, filtered and the solvent was removed under reduced pressure. The residue was purified by flash column chromatography over silica gel using heptane and ethyl acetate as eluents (gradient elution from 20% to 100% ethyl acetate). The product fractions were collected and the solvent was evaporated.

Yield: 127 mg of intermediate 55 (11%)
LCMS method 1: MH$^+$=370, RT=0.402 min

Preparation of Example 31

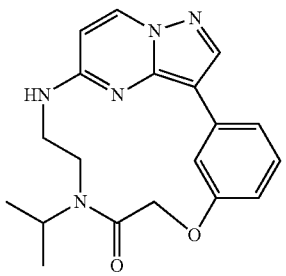 [SMILES: CC(C)N1CCNc2ccn3ncc(c3n2)-c2cccc(c2)OCC1=O]

A suspension of intermediate 55 (127 mg, 0.34 mmol) in N,N-dimethylformamide (12 ml) was added drop wise to a solution of O-(benzotriazol-1-yl)-N,N,N',N'-tetramethyluronium hexafluorophosphate (HBTU) (390 mg, 1.02 mmol) and N,N-diisopropylethylamine (347 lpl, 2.04 mmol) in N,N-dimethylformamide (24 ml). The reaction mixture was stirred at room temperature for 1 hour. The solvent was removed under reduced pressure. The residue was purified by flash column chromatography over silica gel using heptane and ethyl acetate as eluents (gradient elution from 0% to 50% ethyl acetate). The product fractions were collected and the solvent was evaporated.

Yield: 31 mg of example 31 (26%)
LCMS method 2: MH$^+$=353, RT=2.507 min

Example 32

Preparation of Example 32

Example 32 is prepared following general scheme 1.
8,11,14,18,19,22-hexaazatetracyclo[13.5.2.1ˆ{2,6}.0ˆ{18,21}]tricosa-1(21),2,4,6(23),15(22),16,19-heptaen-7-one was prepared according to similar synthetic procedures as described to obtain intermediate 7 using tert-butyl N-[2-(2-aminoethyl(tert-butoxycarbonyl)amino)ethyl]carbamate for the coupling to the scaffold and 3-boronobenzoic acid for the Suzuki coupling. The ring closure was effected after Boc deprotection using HBTU conditions.

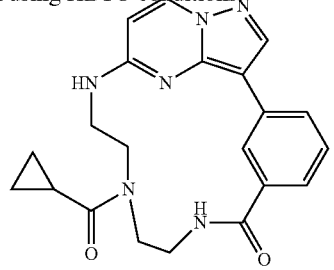

8,11,14,18,19,22-hexaazatetracyclo[13.5.2.1ˆ{2,6}.0ˆ{18,21}]tricosa-1(21),2,4,6(23),15(22),16,19-heptaen-7-one (120 mg, 0.372 mmol) and triethylamine (63 µl, 0.45 mmol) were stirred in dry tetrahydrofuran (1.12 ml) for 5 minutes. Cyclopropanecarbonyl chloride (40 µl, 0.41 mmol) was added and the mixture was stirred at room temperature for 1 hour. The solvent was removed under reduced pressure and methanol was added. The precipitate was filtered, washed with diethyl ether and dried under reduced pressure.

Yield: 102 mg of example 32 (70%)
LCMS method 2: MH$^+$=391, RT=2.410 min

Example 33

Preparation of Example 33

Example 33 is prepared following general scheme 2.

Preparation of Intermediate 56

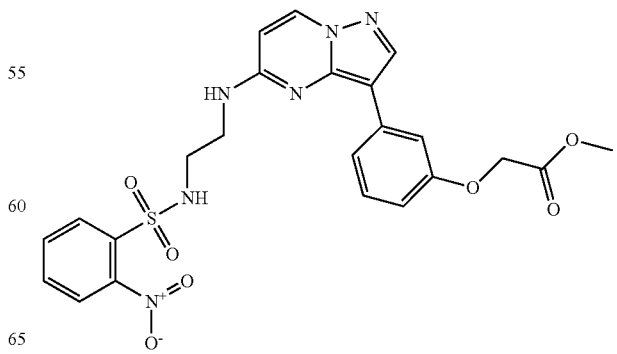

2-Nitrobenzenesulfonyl chloride (1.124 g, 5.073 mmol) was added portion wise at 0° C. and under nitrogen atmosphere to a solution of intermediate 54 (1.277 g, 3.382 mmol) and triethylamine (1.646 ml, 11.84 mmol) in dichloromethane (10.15 ml). The reaction mixture was stirred for 1 hour allowing it to reach room temperature. Ethyl acetate was added and the organic layer was washed with water and brine. The organic layer was dried, filtered and the solvent was removed under reduced pressure. The residue was purified by flash column chromatography over silica gel using dichloromethane and methanol as eluents (gradient elution from 0% to 20% methanol). The product fractions were collected and the solvent was evaporated.

Yield: 1.568 g of intermediate 56 (88%)
LCMS method 1: $MH^+$=527, RT=0.837 min

Preparation of Intermediate 57

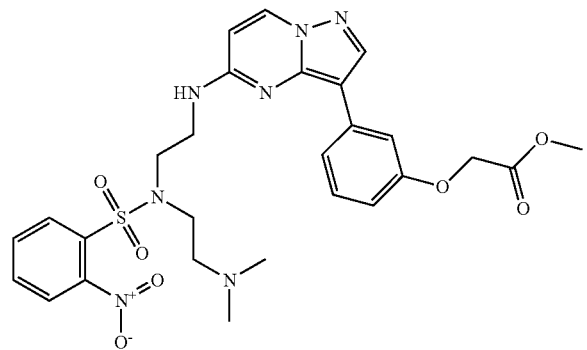 [SMILES: COC(=O)COc1cccc(-c2cnn3ccc(NCCN(CCN(C)C)S(=O)(=O)c4ccccc4[N+](=O)[O-])nc23)c1]

To a solution of intermediate 56 (1.468 g, 2.788 mmol), 2-dimethylaminoethanol (838 µl, 8.364 mmol) and triphenylphosphine (1.828 g, 6.97 mmol) in tetrahydrofuran (8.36 ml) and N,N-dimethylformamide (3 ml) was added diisopropyl azodicarboxylate (1,382 ml, 6.97 mmol). The mixture was stirred at 70° C. for 90 minutes. More 2-dimethylaminoethanol (83.8 µl, 0.836 mmol), diisopropyl azodicarboxylate (138.2 µl, 0.697 mmol) and triphenylphosphine (182.8 mg, 0.697 mmol) were added and the mixture was stirred at 70° C. for 30 minutes. The reaction mixture was cooled and the solvent was removed under reduced pressure. Ethyl acetate was added and the organic layer was washed with water, dried, filtered and the solvent was removed under reduced pressure. The residue was purified by flash column chromatography over silica gel using dichloromethane and methanol as eluents (gradient elution from 0% to 10% methanol). The product fractions were collected and the solvent was evaporated. The product was washed with diethyl ether.

Yield: 1.078 g of intermediate 57 (65%)
LCMS method 1: $MH^+$=598, RT=0.283 min

Preparation of Intermediate 58

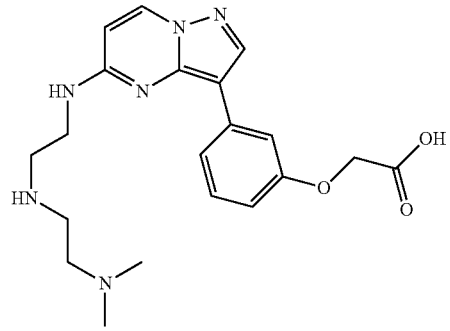 [SMILES: CN(C)CCNCCNc1ccn2ncc(-c3cccc(OCC(=O)O)c3)c2n1]

To a solution of intermediate 57 (1.028 g, 1.72 mmol) in N,N-dimethylformamide (5.16 ml) were added cesium carbonate (1.121 g, 3.44 mmol) and thiophenol (211 µl, 2.064 mmol). The mixture was stirred at room temperature for 2 hours. Sodium hydroxide (206 mg, 5.16 mmol) and water (0.86 ml) were added and the mixture was stirred at room temperature for 17 hours. The solvent was removed under reduce pressure. The product was purified by flash chromatography over silica gel using dichloromethane and methanol as eluents. The product fractions were collected and the solvent was removed under reduced pressure. The residue was purified by reversed phase HPLC (HPLC method A). The product fractions were collected and the solvent was removed under reduced pressure.

Yield: 632 mg of intermediate 58 (92%)
LCMS method 2: $MH^+$=399, RT=1.410 min

Preparation of Example 33

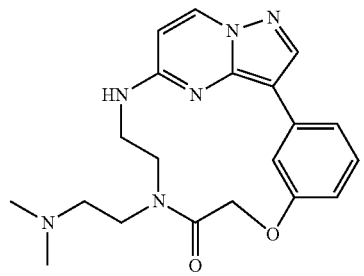 [SMILES: CN(C)CCN1CCNc2ccn3ncc(c3n2)-c2cccc(c2)OCC1=O]

A solution of intermediate 58 (583 mg, 1.461 mmol) in N,N-dimethylformamide (44 ml) was added drop wise to a solution of O-(benzotriazol-1-yl)-N,N,N',N'-tetramethyluronium hexafluorophosphate (HBTU) (1.66 g, 4.38 mmol) and N,N-diisopropylethylamine (1.491 ml, 8.77 mmol) in N,N-dimethylformamide (102 ml). The mixture was stirred at room temperature for 2 hours. The solvent was removed under reduced pressure and methanol was added. The precipitate was filtered and dried under reduced pressure. The residue was purified by reversed phase HPLC (HPLC method A). The product fractions were collected and the solvent was removed under reduced pressure. The product (120 mg, 0.315 mmol) was taken up in dichloromethane/methanol (4:1, 50 ml) and 4N HCl in 1,4-dioxane (90 µl, 0.35 mmol) was added.

The reaction mixture was stirred at room temperature for 2 hours. The solvent was removed under reduced pressure and the compound was triturated with diethyl ether, filtered and dried under reduced pressure.

Yield: 122 mg of example 33 (77%)
LCMS method 2: MH$^+$=381, RT=1.603 min

Example 34

Preparation of Example 34

Example 34 is prepared following general scheme 4.

Preparation of Intermediate 59

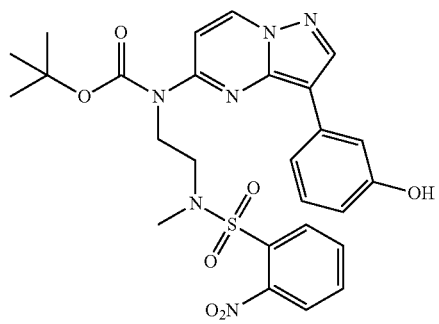 [SMILES: CN(CCN(C(=O)OC(C)(C)C)c1ccn2ncc(-c3cccc(O)c3)c2n1)S(=O)(=O)c1ccccc1[N+](=O)[O-]]

A mixture of 1,4-dioxane and water (3:1, 20 ml) was degassed by bubbling nitrogen gas through the mixture. Intermediate 21 (1.38 g, 2.48 mmol), (3-hydroxyphenyl)boronic acid (440 mg, 3.22 mmol), tetrakis(triphenylphosphine)palladium(0) (58 mg, 0.05 mmol), 2-dicyclohexylphosphino-2',4',6'-triisopropylbiphenyl (Xphos) (95 mg, 0.20 mmol) and potassium phosphate tribasic (2.63 g, 5 eq.) were added and the mixture was stirred under nitrogen gas at 80° C. overnight. The reaction mixture was cooled, diluted with ethyl acetate and the organic layer was washed with water and brine. The organic layer was dried, filtered and the solvent was removed under reduced pressure. The residue was purified by flash column chromatography over silica gel using heptane and ethyl acetate as eluents. The product fractions were collected and the solvent was evaporated.

Yield: 1.21 g of intermediate 59 (86%)
LCMS method 1: MH$^+$=569, RT=1.046 min

Preparation of Intermediate 60

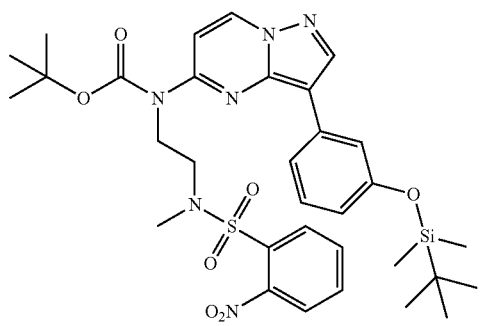 [SMILES: CN(CCN(C(=O)OC(C)(C)C)c1ccn2ncc(-c3cccc(O[Si](C)(C)C(C)(C)C)c3)c2n1)S(=O)(=O)c1ccccc1[N+](=O)[O-]]

Tert-butyldimethylsilyl chloride (390 mg, 2.56 mmol) was added to a suspension of intermediate 59 (1.21 g, 2.13 mmol) and triethylamine (442 µl, 3.19 mmol) in N,N-dimethylformamide (20 ml). The mixture was stirred at room temperature for 48 hours. The reaction mixture was diluted with ethyl acetate and washed with water and brine (3×). The organic layer was dried, filtered and the solvent was removed under reduced pressure. The residue was purified by flash column chromatography using heptane and ethyl acetate as eluents. The product fractions were collected and the solvent was evaporated.

Yield: 1.10 g of intermediate 60 (76%)
LCMS method 1: MH$^+$=583 (-Boc), RT=1.527 min Preparation of Intermediate 61

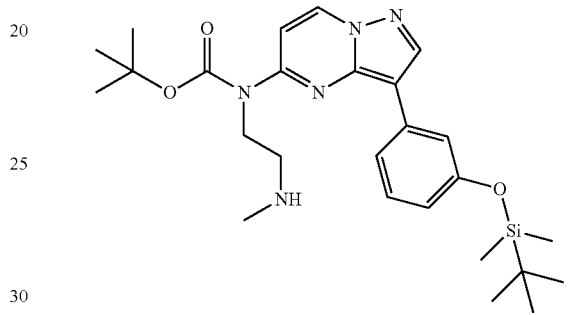

Cesium carbonate (1.049 g, 3.22 mmol) and thiophenol (200 µl, 1.93 mmol) were suspended in N,N-dimethylformamide (2.42 ml) and the mixture was stirred at room temperature for 15 minutes. A solution of intermediate 60 (1.10 g, 1.61 mmol) in N,N-dimethylformamide (2.42 ml) was added and the reaction mixture was stirred at room temperature for 3 hours. Ethyl acetate was added and the organic layer was washed with 1M aqueous sodium hydroxide solution, dried, filtered and the solvent was removed under reduce pressure. The product was purified by flash chromatography over silica gel using dichloromethane and methanol as eluents. The product fractions were collected and the solvent was removed under reduced pressure.

Yield: 310 mg of intermediate 61 (39%)
LCMS method 1: MH$^+$=498, RT=1.038 min

Preparation of Intermediate 62

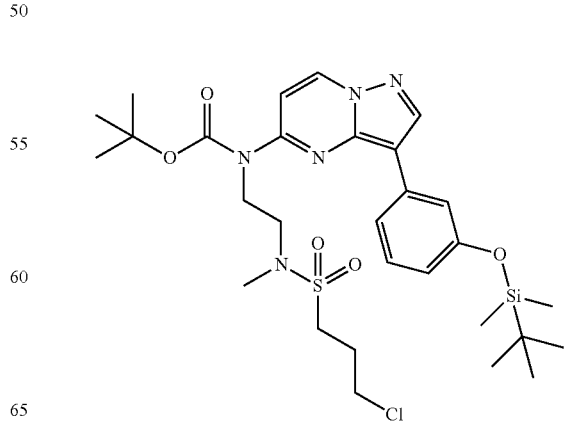

3-Chloropropane-1-sulfonyl chloride (80 µl, 0.68 mmol) was added to a solution of intermediate 61 (310 mg, 0.62 mmol) and triethylamine (112 µl, 0.81 mmol) in dichloromethane (2 ml) and the reaction mixture was stirred at room temperature for 2 hours. Water was added and the product was extracted with ethyl acetate. The organic layer was washed with brine, dried, filtered and the solvent was removed under reduced pressure. The residue was used in the next step without further purification.

LCMS method 1: $MH^+=639$, RT=1.523 min

Preparation of Intermediate 63

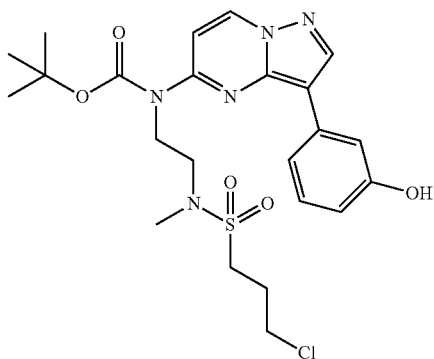 [SMILES: CN(CCN(C(=O)OC(C)(C)C)c1ccn2ncc(-c3cccc(O)c3)c2n1)S(=O)(=O)CCCCl]

Tetrabutyl ammonium fluoride (1M solution in tetrahydrofuran, 1 ml, 0.93 mmol) was added to a solution of intermediate 62 (396 mg, 0.62 mmol) in tetrahydrofuran (1.86 ml) and the mixture was stirred at room temperature for 2 hours. The solvent was removed under reduced pressure. The residue was diluted with ethyl acetate and washed with water (3×) and brine. The organic layer was dried, filtered and the solvent was removed under reduced pressure. The residue was used in the next step without further purification.

LCMS method 1: $MH^+=525$, RT=1.022 min

Preparation of Intermediate 64

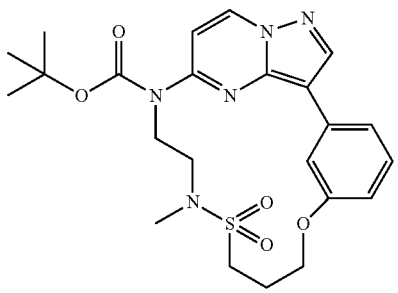 [SMILES: CN1CCN(C(=O)OC(C)(C)C)c2ccn3ncc(c3n2)-c2cccc(c2)OCCCS1(=O)=O]

A solution of intermediate 63 (325 mg, 0.62 mmol) in N,N-dimethylformamide (40 ml) was added drop wise to a suspension of cesium carbonate (1.01 g, 3.10 mmol) in N,N-dimethylformamide (20 ml) at 90° C. over a period of 1 hour. The solids were filtered and the filtrate was evaporated under reduced pressure. The residue was diluted with ethyl acetate and washed with water and brine (2×). The organic layer was dried, filtered and the solvent was removed under reduced pressure. The residue was purified by flash chromatography using heptane and ethyl acetate as eluents. The product fractions were collected and the solvent was removed under reduced pressure.

Yield: 122 mg of intermediate 64 (40% over 3 steps)

LCMS method 1: $MH^+=488$, RT=1.061 min

Preparation of Example 34

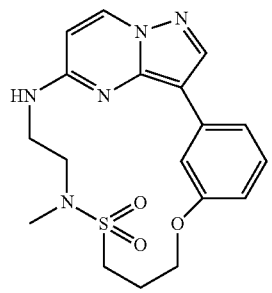 [SMILES: CN1CCNc2ccn3ncc(c3n2)-c2cccc(c2)OCCCS1(=O)=O]

Intermediate 64 (120 mg, 0.25 mmol) was dissolved in 2N HCl in methanol (10 ml) and the mixture was stirred at room temperature overnight. The solvent was removed under reduced pressure. The residue was suspended in dichloromethane and 7N ammonia in methanol (0.5 ml) was added. The solvent was removed under reduced pressure and the residue was purified by flash chromatography using dichloromethane and methanol as eluents. The product fractions were collected and the solvent was removed under reduced pressure. The residue was triturated with diethyl ether and the product was dried under reduced pressure.

Yield: 74 mg of example 34 (76%)

LCMS method 1: $MH^+=388$, RT=2.887 min

Example 35

Preparation of Example 35

Example 35 is prepared following general scheme 1.

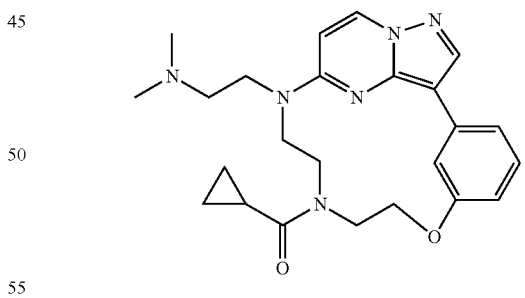

Dimethyl(2-{7-oxa-10,13,17,18,21-pentaazatetracyclo[12.5.2.1^{2,6}.0^{17,20}]docosa-1(20),2,4,6(22),14(21),15,18-heptaen-13-yl}ethyl)amine was prepared according to similar synthetic procedures as described to obtain intermediate 7 using tert-butyl N-[2-(tert-butyl(dimethyl)silyl)oxyethyl]-N-[2-(2-dimethylaminoethylamino)ethyl]carbamate for the coupling to the scaffold and (3-hydroxyphenyl)boronic acid for the Suzuki coupling. The ring closure was effected after TBDMS deprotection using Mitsunobu conditions. The unprotected dimethyl(2-{7-oxa-10,13,17,18,21-pentaazatetracyclo[12.5.2.1^{2,6}.0^{17,20}]docosa-1(20), 2,4,6(22),14(21),15,18-heptaen-13-yl}ethyl)amine was obtained after Boc deprotection under acidic conditions.

Dimethyl(2-{7-oxa-10,13,17,18,21-pentaazatetracyclo[12.5.2.1^{2,6}.0^{17,20}]docosa-1(20),2,4,6(22),14(21),15,18-heptaen-13-yl}ethyl)amine (197 mg, 0.49 mmol) and triethylamine (340 µl, 2.45 mmol) were dissolved in dichloromethane (2 ml) and cooled to 0° C. Cyclopropanecarbonyl chloride (50 µl, 0.59 mmol) was added at 0° C. and the mixture was stirred at room temperature for 1 hour. Ethyl acetate was added and the organic layer was washed with water and brine. The organic layer was dried, filtered and the solvent was removed under reduced pressure. The residue was purified by flash chromatography using dichloromethane and methanol as eluents. The product fractions were collected and the solvent was removed under reduced pressure. The residue was triturated with diethyl ether and the product was dried under reduced pressure.

Yield: 70 mg of example 35 (33%)
LCMS method 2: MH$^+$=435, RT=2.265 min

Example 36

Preparation of Example 36

Example 36 is prepared following general scheme 2.

Preparation of Intermediate 65

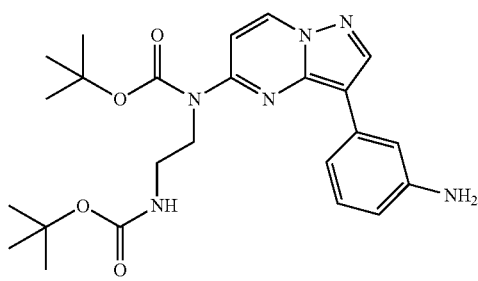 [SMILES: CC(C)(C)OC(=O)NCCN(C(=O)OC(C)(C)C)c1ccn2ncc(-c3cccc(N)c3)c2n1]

A mixture of 1,4-dioxane and water (3:1, 30 ml) was degassed by bubbling nitrogen gas through the mixture. Intermediate 6 (2.277 g, 4.99 mmol), (3-hydroxyphenyl)boronic acid (1.05 g, 6.487 mmol), tetrakis(triphenylphosphine)palladium(0) (116 mg, 0.10 mmol), 2-dicyclohexylphosphino-2',4',6'-triisopropylbiphenyl (Xphos) (191 mg, 0.40 mmol) and potassium phosphate tribasic (5.296 g, 5 eq.) were added and the mixture was stirred under nitrogen gas at 80° C. for 2 hours. The reaction mixture was cooled, diluted with ethyl acetate and the organic layer was washed with water. The organic layer was dried, filtered and the solvent was removed under reduced pressure. The residue was purified by flash column chromatography over silica gel using heptane and ethyl acetate as eluents (gradient elution from 20% to 100% ethyl acetate). The product fractions were collected and the solvent was evaporated.

LCMS method 1: MH$^+$=469, RT=0.945 min

Preparation of Intermediate 66

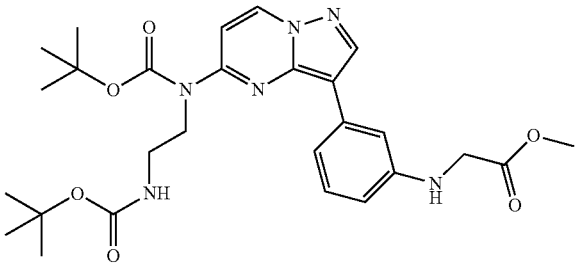 [SMILES: COC(=O)CNc1cccc(-c2cnn3ccc(N(CCNC(=O)OC(C)(C)C)C(=O)OC(C)(C)C)nc23)c1]

Intermediate 65 (1.209 g, 2.58 mmol), methyl 2-bromoacetate (240 mg, 2.58 mmol) and potassium carbonate (535 mg, 3.87 mmol) were dissolved N,N-dimethylformamide (7.74 ml). The reaction mixture was stirred at 60° C. for 2.5 hours. The reaction mixture was cooled and diluted with ethyl acetate. The organic layer was washed with water, dried, filtered and the solvent was removed under reduced pressure. The residue was purified by flash column chromatography over silica gel using heptane and ethyl acetate as eluents (gradient elution from 0% to 50% ethyl acetate). The product fractions were collected and the solvent was evaporated.

Yield: 1.281 g of intermediate 66 (92%)
LCMS method 1: MH$^+$=541, RT=1.122 min

Preparation of Intermediate 67

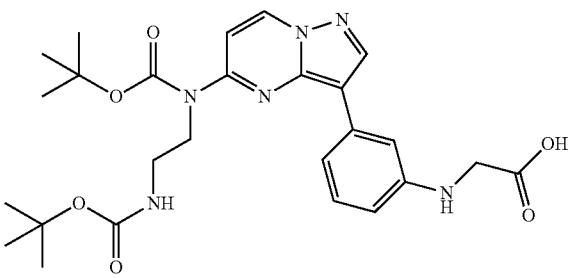 [SMILES: CC(C)(C)OC(=O)NCCN(C(=O)OC(C)(C)C)c1ccn2ncc(-c3cccc(NCC(=O)O)c3)c2n1]

Intermediate 66 (1.278 g, 2.364 mmol) and lithium hydroxide monohydrate (110 mg, 2.60 mmol) in a mixture tetrahydrofuran/methanol/water (2:2:1, 14.2 ml) were stirred at room temperature for 3 hours. The solvent was removed under reduced pressure. Toluene was added and evaporated twice. The residue was used in the next step without further purification.

LCMS method 1: MH$^+$=527, RT=0.983 min

Preparation of Intermediate 68

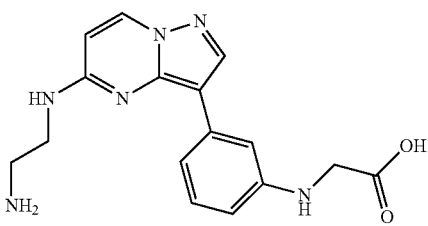 [SMILES: NCCNc1ccn2ncc(-c3cccc(NCC(=O)O)c3)c2n1]

Intermediate 67 (771 mg, 2.364 mmol) was dissolved in 4N HCl in 1,4-dioxane (7.09 ml) and the reaction mixture was stirred at room temperature for 5 hours. The solvent was removed under reduced pressure. Toluene was added and evaporated twice. The residue was used in the next step without further purification.

LCMS method 1: MH$^+$=327, RT=0.275 min

Preparation of Example 36

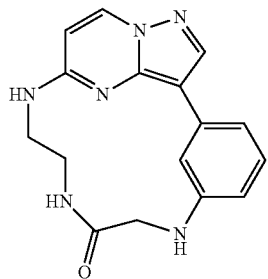 [SMILES: O=C1CNc2cccc(c2)-c2cnn3ccc(nc23)NCCN1]

A solution of intermediate 68 (773 mg, 2.37 mmol) in N,N-dimethylformamide (71 ml) was added drop wise to a solution of O-(benzotriazol-1-yl)-N,N,N',N'-tetramethyluronium hexafluorophosphate (HBTU) (2.70 g, 7.11 mmol) and N,N-diisopropylethylamine (12.092 ml, 71.10 mmol) in N,N-dimethylformamide (166 ml). The reaction mixture was stirred at room temperature for 3 hours. A 25% aqueous ammonia solution (2.5 ml) was added and the mixture was stirred at room temperature for 30 minutes. The solvent was removed under reduced pressure. The residue was purified by reversed phase HPLC (HPLC method A). The product fractions were collected and the solvent was evaporated.

Yield: 31 mg of example 36 (26%)
LCMS method 2: MH$^+$=309, RT=1.757 min

Example 37

Example 37 is prepared following general scheme 1.

Preparation of Example 37

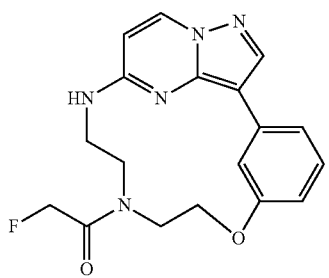 [SMILES: O=C(CF)N1CCNc2ccn3ncc(c3n2)-c2cccc(c2)OCC1]

7-Oxa-10,13,17,18,21-pentaazatetracyclo[12.5.2.1ˆ{2, 6}.0ˆ{17,20}]docosa-1(20),2,4,6(22),14(21),-15,18-heptaene hydrochloride (150 mg, 0.452 mmol) and triethylamine (189 µl, 1.36 mmol) were dissolved in dry tetrahydrofuran (1.36 ml) and the mixture was stirred at room temperature for 5 minutes. 2-Fluoroacetyl chloride (40 µl, 0.50 mmol) was added and the mixture was stirred at room temperature for 1.5 hours. More 2-fluoroacetyl chloride (7 µl, 0.09 mmol) and triethylamine (32 µl, 0.23 mmol) were added and the mixture was stirred at room temperature for 15 hours. The solvent was removed under reduced pressure and methanol was added. The precipitate was filtered, washed with diethyl ether and dried under reduced pressure. The residue was purified by reversed phase HPLC (HPLC method A). The product fractions were collected and the solvent was evaporated.

Yield: 83 mg of example 37 (52%)
LCMS method 2: MH$^+$=356, RT=2.790 min

Example 38

Preparation of Example 38

Example 38 is prepared following general scheme 1.

Preparation of Intermediate 69

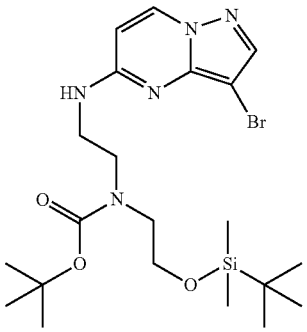 [SMILES: CC(C)(C)OC(=O)N(CCNc1ccn2ncc(Br)c2n1)CCO[Si](C)(C)C(C)(C)C]

A mixture of 3-bromo-5-chloro-pyrazolo[1,5-a]pyrimidine (1.5 g, 6.45 mmol), intermediate 4 (2.26 g, 7.10 mmol) and N,N-diisopropylethylamine (3.29 ml, 19.35 mmol) in acetonitrile (19.3 ml) was refluxed overnight. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using heptane and ethyl acetate as eluents (gradient elution from 10% to 55% ethyl acetate). The product fractions were collected and the solvent was evaporated.

Yield: 2.7 g of intermediate 69 (81%)
LCMS method 1: MH$^+$=415 (-Boc), RT=1.395 min Preparation of Intermediate 70

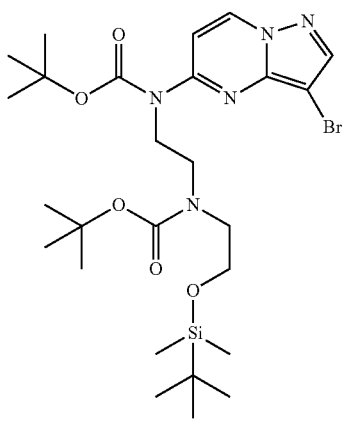 [SMILES: CC(C)(C)OC(=O)N(CCO[Si](C)(C)C(C)(C)C)CCN(C(=O)OC(C)(C)C)c1ccn2ncc(Br)c2n1]

Intermediate 69 (2.7 g, 5.25 mmol), tert-butoxycarbonyl anhydride (1.26 g, 5.78 mmol) and triethylamine (885 µl, 6.3 mmol) were dissolved in tetrahydrofuran (15.75 ml). The reaction mixture was stirred at 70° C. for 3 hours. An additional amount of tert-butoxycarbonyl anhydride (115 mg, 0.53 mmol) was added and the reaction mixture was stirred at 70° C. for 1 hour. The solvent was removed under reduced pressure. The residue was dissolved in ethyl acetate and washed with water and brine. The organic layer was dried, filtered and the solvent was removed under reduced pressure. Intermediate 3 was used in the next step without further purification. The residue was purified by flash column chromatography over silica gel using heptane and ethyl acetate as eluents (gradient elution from 0% to 25% ethyl acetate). The product fractions were collected and the solvent was evaporated.

Yield: 3.2 g of intermediate 70 (99%)

LCMS method 1: MH$^+$=515 (-Boc), RT=1.625 min

Preparation of Intermediate 71

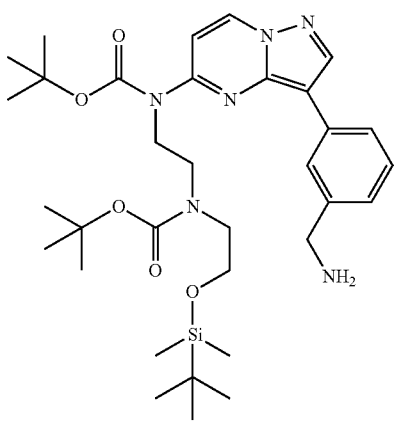 [SMILES: CC(C)(C)OC(=O)N(CCO[Si](C)(C)C(C)(C)C)CCN(C(=O)OC(C)(C)C)c1ccn2ncc(-c3cccc(CN)c3)c2n1]

A mixture of 1,4-dioxane and water (3:1, 30 ml) was degassed by bubbling nitrogen gas through the mixture. Intermediate 70 (3.10 g, 5.04 mmol), [3-(aminomethyl)phenyl]boronic acid hydrochloride (1.42 g, 7.56 mmol), tetrakis(triphenylphosphine)palladium(0) (232 mg, 0.20 mmol), 2-dicyclohexylphosphino-2',4',6'-triisopropylbiphenyl (Xphos) (191 mg, 0.40 mmol) and potassium phosphate tribasic (5.34 g, 5 eq.) were added and the mixture was stirred under nitrogen gas at 85° C. for 7 hours. The reaction mixture was cooled, diluted with ethyl acetate and the organic layer was washed with water and brine. The organic layer was dried, filtered and the solvent was removed under reduced pressure. The residue was purified by flash column chromatography over silica gel using dichloromethane and methanol as eluents. The product fractions were collected and the solvent was evaporated.

Yield: 2.53 g of intermediate 71 (78%)

LCMS method 1: MH$^+$=641, RT=0.928 min

Preparation of Intermediate 72

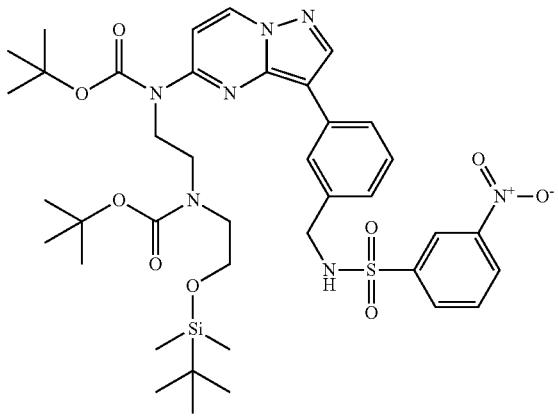 [SMILES: CC(C)(C)OC(=O)N(CCO[Si](C)(C)C(C)(C)C)CCN(C(=O)OC(C)(C)C)c1ccn2ncc(-c3cccc(CNS(=O)(=O)c4cccc([N+](=O)[O-])c4)c3)c2n1]

3-Nitrobenzenesulfonyl chloride (140 mg, 0.64) mmol was added portion wise at 0° C. and under nitrogen atmosphere to a solution of intermediate 71 (370 g, 0.58 mmol) and triethylamine (242 µl, 1.74 mmol) in anhydrous dichloromethane (1.74 ml). The reaction mixture was stirred for 2 hours allowing it to reach room temperature. The reaction mixture was diluted with dichloromethane and washed with an aqueous 1N sodium bicarbonate solution. The organic layer was dried, filtered and the solvent was removed under reduced pressure. The residue was purified by flash column chromatography over silica gel using dichloromethane and methanol as eluents. The product fractions were collected and the solvent was evaporated.

Yield: 380 mg of intermediate 72 (79%)

LCMS method 1: MH$^+$=726 (MW-Boc), RT=1.549 min

Preparation of Intermediate 73

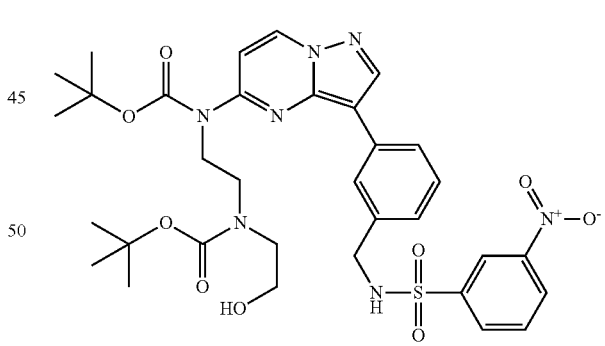

Intermediate 72 (380 mg, 0.46 mmol) was stirred at room temperature for 2 hours in tetrabutyl ammonium fluoride (1M solution in tetrahydrofuran, 1.38 ml). The solvent was removed under reduced pressure. The residue was diluted with ethyl acetate and washed with water and brine.

The organic layer was dried, filtered and the solvent was removed under reduced pressure. The residue was purified by flash column chromatography over silica gel using dichloromethane and methanol as eluents. The product fractions were collected and the solvent was evaporated.

LCMS method 1: MH$^+$=612 (MW-Boc), RT=1.121 min

Preparation of Intermediate 74

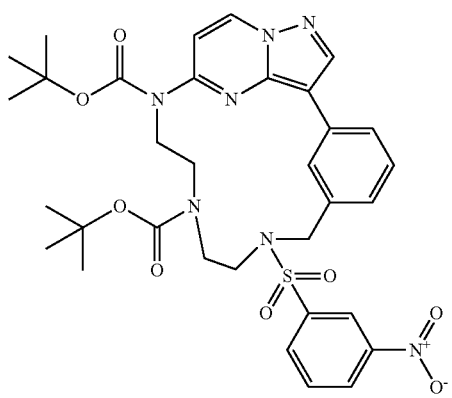 [SMILES: CC(C)(C)OC(=O)N1CCN(C(=O)OC(C)(C)C)c2ccn3ncc(c3n2)-c2cccc(c2)CN(S(=O)(=O)c2cccc([N+](=O)[O-])c2)CC1]

A solution of intermediate 73 (200 mg, 0.28 mmol) in 2-methyltetrahydrofuran (5.7 ml) and a solution of diisopropyl azodicarboxylate (0.17 g, 0.84 mmol) in toluene (16 ml) were added simultaneously to a solution of triphenylphosphine (220 mg, 0.84 mmol) in toluene (21 ml) at 90° C. The mixture was stirred at 90° C. for 30 minutes. The reaction mixture was cooled and the solvent was removed under reduced pressure. The residue was purified by flash column chromatography over silica gel using dichloromethane and methanol as eluents (gradient elution from 0% to 2% methanol). The product fractions were collected and the solvent was evaporated.

LCMS method 1: MH$^+$=694, RT=1.374 min

Preparation of Intermediate 75

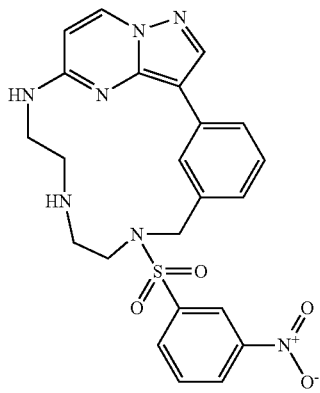 [SMILES: O=[N+]([O-])c1cccc(S(=O)(=O)N2CCNCCNc3ccn4ncc(c4n3)-c3cccc(c3)C2)c1]

To a solution of intermediate 74 (340 mg, 0.49 mmol) in 1,4-dioxane (1.47 ml) was added 4N HCl in 1,4-dioxane (3 ml) and the reaction mixture was stirred at room temperature for 18 hours. The solvent was removed under reduced pressure and the residue was used in the next step without further purification.

Yield: 206 mg of intermediate 75 (80%)

Preparation of Intermediate 76

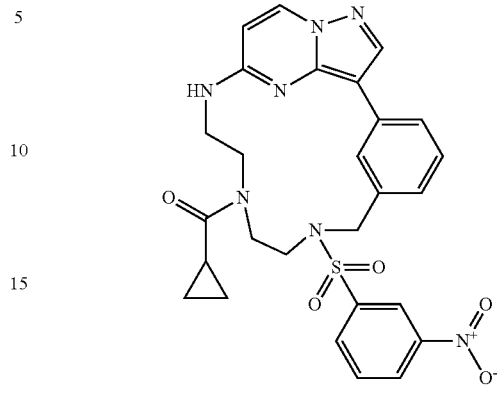

Cyclopropanecarbonyl chloride (40 µl, 0.47 mmol) was added drop wise under nitrogen atmosphere at 0° C. to a solution of intermediate 75 (206 mg, 0.39 mmol) and triethylamine (271 µl, 1.95 mmol) in anhydrous dichloromethane (1.17 ml). The mixture was stirred for 1 hour allowing it to reach room temperature. The solvent was removed under reduced pressure and dichloromethane was added. The organic layer was washed with water, dried, filtered and the solvent was removed under reduced pressure. The residue was used in the next step without further purification.

Yield: 220 mg of example 76 (100%)

Preparation of Example 38

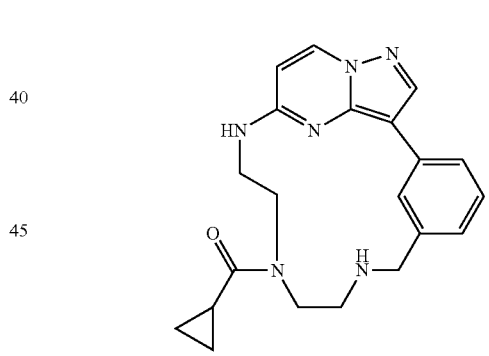

Thiophenol (50 µl, 0.47 mmol) and cesium carbonate (508 mg, 1.56 mmol) were suspended in N,N-dimethylformamide (1 ml) and the mixture was stirred at room temperature for 15 minutes. A solution of intermediate 76 (220 mg, 0.39 mmol) in N,N-dimethylformamide (2 ml) was added and the reaction mixture was stirred at room temperature for 3 hours. Ethyl acetate was added and the organic layer was washed with water and a 1N aqueous sodium hydroxide solution, dried, filtered and the solvent was removed under reduce pressure. The product was purified by flash chromatography over silica gel using dichloromethane and methanol as eluents (gradient elution from 0% to 3% methanol). The product fractions were collected and the solvent was removed under reduced pressure. The product was taken up in dichloromethane/methanol (4:1, 10 ml) and 4N HCl in 1,4-dioxane (20 µl, 0.08 mmol) was added. The reaction mixture was stirred at room temperature for 2 hours. The solvent was removed under reduced pressure and the compound was triturated with diethyl ether, filtered and dried under reduced pressure.

Yield: 18 mg of example 38 as HCl salt (11%)
LCMS method 2: MH⁺=377, RT=1.685 min Example 39

Preparation of Example 39

Example 39 is prepared following general scheme 1.

Preparation of Intermediate 77

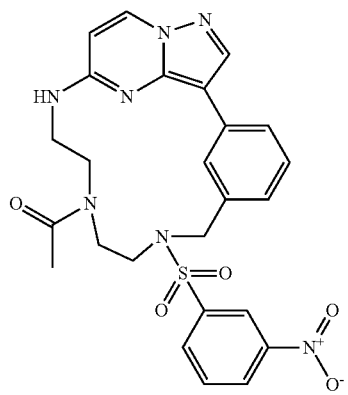 [SMILES: CC(=O)N1CCNc2ccn3ncc(c3n2)-c2cccc(c2)CN(S(=O)(=O)c2cccc([N+](=O)[O-])c2)CC1]

Acetyl chloride (30 μl, 0.46 mmol) was added drop wise under nitrogen atmosphere at 0° C. to a solution of intermediate 75 (200 mg, 0.38 mmol) and triethylamine (264 μl, 1.90 mmol) in anhydrous dichloromethane (2 ml). The mixture was stirred for 1 hour allowing it to reach room temperature. The solvent was removed under reduced pressure and the residue was used in the next step without further purification.

Yield: 205 mg of intermediate 77 (100%)
LCMS method 1: MH⁺=536, RT=0.976 min

Preparation of Example 39

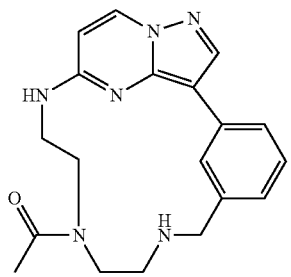 [SMILES: CC(=O)N1CCNCc2cccc(c2)-c2cnn3ccc(nc23)NCC1]

Thiophenol (50 μl, 0.47 mmol) and cesium carbonate (495 mg, 1.52 mmol) were suspended in N,N-dimethylformamide (2 ml) and the mixture was stirred at room temperature for 10 minutes. Intermediate 77 (205 mg, 0.38 mmol) was added and the reaction mixture was stirred at room temperature for 2 hours. Dichloromethane was added and the organic layer was washed with water and a 1N aqueous sodium hydroxide solution, dried, filtered and the solvent was removed under reduce pressure. The product was triturated with dichloromethane, filtered and dried under reduced pressure. The product was taken up in dichloromethane/methanol (4:1, 25 ml) and 4N HCl in 1,4-dioxane (1 ml) was added. The reaction mixture was stirred at room temperature for 2 hours. The reaction mixture was concentrated and the precipitate was filtered and washed with diethyl ether. The product was dried under reduced pressure.

Yield: 42 mg of example 39 as HCl salt (29%)
LCMS method 2: MH⁺=351, RT=1.073 min Example 40

Preparation of Example 40

Example 40 is prepared following general scheme 1.

Preparation of Intermediate 78

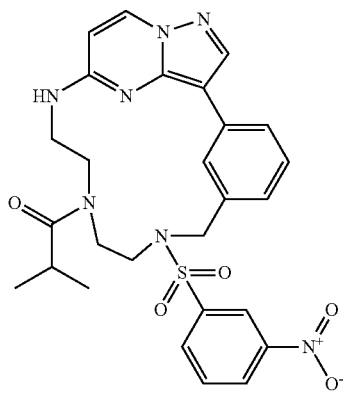 [SMILES: CC(C)C(=O)N1CCNc2ccn3ncc(c3n2)-c2cccc(c2)CN(S(=O)(=O)c2cccc([N+](=O)[O-])c2)CC1]

2-Methylpropanoyl chloride (50 μl, 0.46 mmol) was added drop wise under nitrogen atmosphere at 0° C. to a solution of intermediate 75 (200 mg, 0.38 mmol) and triethylamine (264 μl, 1.90 mmol) in anhydrous dichloromethane (2 ml). The mixture was stirred for 1 hour allowing it to reach room temperature. The solvent was removed under reduced pressure and the residue was used in the next step without further purification.

Yield: 215 mg of intermediate 78 (100%)
LCMS method 1: MH⁺=564, RT=0.977 min

Preparation of Example 40

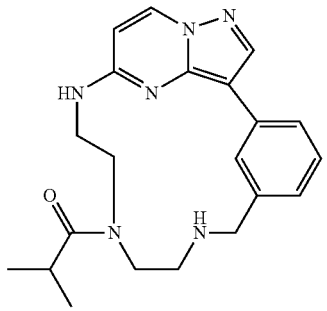 [SMILES: CC(C)C(=O)N1CCNCc2cccc(c2)-c2cnn3ccc(nc23)NCC1]

Thiophenol (50 μl, 0.47 mmol) and cesium carbonate (495 mg, 1.52 mmol) were suspended in N,N-dimethylformamide (2 ml) and the mixture was stirred at room temperature for 10

123 minutes. Intermediate 78 (215 mg, 0.38 mmol) was added and the reaction mixture was stirred at room temperature for 2 hours. Dichloromethane was added and the organic layer was washed with water and a 1N aqueous sodium hydroxide solution, dried, filtered and the solvent was removed under reduce pressure. The product was triturated with dichloromethane, filtered and dried under reduced pressure. The product was taken up in dichloromethane/methanol (4:1, 25 ml) and 4N HCl in 1,4-dioxane (1 ml) was added. The reaction mixture was stirred at room temperature for 2 hours. The reaction mixture was concentrated and the precipitate was filtered and washed with diethyl ether. The product was dried under reduced pressure.

Yield: 37 mg of example 40 as HCl salt (23%)
LCMS method 2: MH$^+$=379, RT=1.911 min Example 41

Preparation of Example 41

Example 41 is prepared following general scheme 1.

Preparation of Intermediate 79

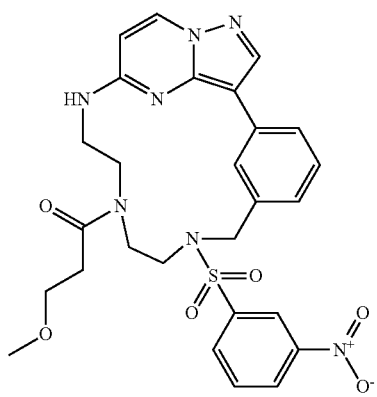 [SMILES: COCCC(=O)N1CCNc2ccn3ncc(c3n2)-c2cccc(c2)CN(S(=O)(=O)c2cccc([N+](=O)[O-])c2)CC1]

A mixture of intermediate 75 (204 mg, 0.38 mmol), 3-methoxypropanoic acid (40 µl, 0.42 mmol) and N,N-diisopropylethylamine (323 µl, 1.90 mmol) in N,N-dimethylformamide (2 ml) was stirred at room temperature for 10 minutes. O-(Benzotriazol-1-yl)-N,N,N',N'-tetramethyluronium hexafluorophosphate (HBTU) (174 mg, 0.46 mmol) was added. The reaction mixture was stirred at room temperature for 1 hour. The solvent was removed under reduced pressure and dichloromethane was added. The organic layer was washed with water, a 1N aqueous sodium bicarbonate solution and brine. The organic layer was dried, filtered and the solvent was removed under reduced pressure. The product was purified by flash chromatography over silica gel using dichloromethane and methanol as eluents (gradient elution from 0% to 6% methanol). The product fractions were collected and the solvent was removed under reduced pressure.

Yield: 210 mg of intermediate 79 (95%)
LCMS method 1: MH$^+$=580, RT=0.897 min

124

Preparation of Example 41

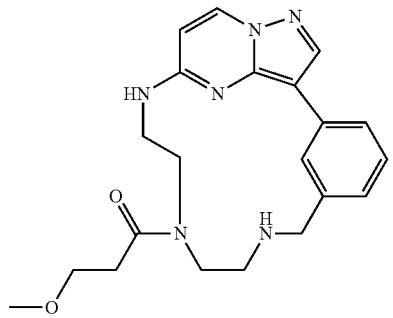 [SMILES: COCCC(=O)N1CCNCc2cccc(c2)-c2cnn3ccc(nc23)NCC1]

Thiophenol (40 µl, 0.43 mmol) and cesium carbonate (235 mg, 0.72 mmol) were suspended in N,N-dimethylformamide (2 ml). Intermediate 79 (210 mg, 0.36 mmol) was added and the reaction mixture was stirred at room temperature for 18 hours. Dichloromethane was added and the organic layer was washed with water and a 1N aqueous sodium hydroxide solution, dried, filtered and the solvent was removed under reduce pressure. The product was purified by flash chromatography over silica gel using dichloromethane and methanol as eluents (gradient elution from 0% to 10% methanol). The product fractions were collected and the solvent was removed under reduced pressure. The product was taken up in methanol (0.57 ml) and 4N HCl in 1,4-dioxane (1 ml) was added. The reaction mixture was stirred at room temperature for 18 hours. The precipitate was filtered and washed with methanol. The product was dried under reduced pressure.

Yield: 28 mg of example 41 as HCl salt (18%)
LCMS method 2: MH$^+$=395, RT=1.138 min Example 42

Preparation of Example 42

Example 42 is prepared following general scheme 1.

Preparation of Intermediate 80

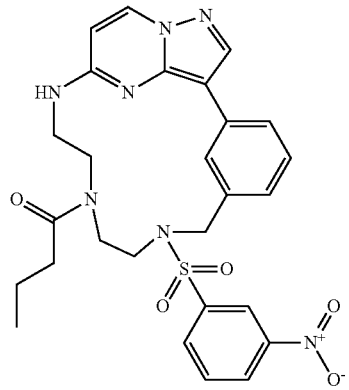 [SMILES: CCCC(=O)N1CCNc2ccn3ncc(c3n2)-c2cccc(c2)CN(S(=O)(=O)c2cccc([N+](=O)[O-])c2)CC1]

Butanoyl chloride (50 µl, 0.46 mmol) was added drop wise under nitrogen atmosphere at 0° C. to a solution of intermediate 75 (200 mg, 0.38 mmol) and triethylamine (264 µl, 1.90 mmol) in anhydrous dichloromethane (2 ml). The mixture was stirred for 1 hour allowing it to reach room temperature.

The solvent was removed under reduced pressure. The product was triturated with methanol, filtered and dried under reduced pressure.

Yield: 215 mg of example 80 (100%)
LCMS method 1: MH⁺=564, RT=0.980 min

Preparation of Example 42

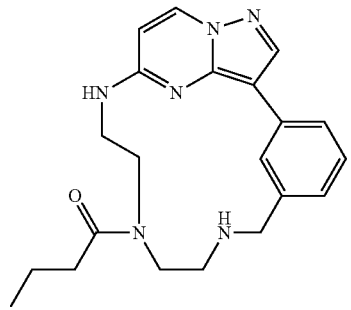 [SMILES: CCCC(=O)N1CCNCc2cccc(c2)-c2cnn3ccc(nc23)NCC1]

Thiophenol (390 µl, 0.47 mmol) and potassium carbonate (630 mg, 4.56 mmol) were suspended in acetonitrile (4 ml) and the mixture was stirred at 70° C. for 30 minutes. Intermediate 80 (215 mg, 0.38 mmol) was added and the reaction mixture was stirred at 90° C. for 48 hours. The reaction mixture was cooled to room temperature and sodium hydroxide (456 mg, 11.4 mmol) was added. The solvent was removed under reduced pressure and the residue was dissolved in dichloromethane. The organic layer was washed with a 1N aqueous sodium hydroxide solution and brine, dried, filtered and the solvent was removed under reduce pressure. The product was purified by flash chromatography over silica gel using dichloromethane and methanol as eluents (gradient elution from 0% to 10% methanol). The product fractions were collected and the solvent was removed under reduced pressure. The product was taken up in dichloromethane (20 ml) and 4N HCl in 1,4-dioxane (1 ml) was added. The reaction mixture was stirred at room temperature for 2 hours. The reaction mixture was concentrated and the resulting oil was co-evaporated with diethyl ether (3×). The product was dried under reduced pressure.

Yield: 8 mg of example 42 as HCl salt (5%)
LCMS method 2: MH⁺=379, RT=1.307 min

Example 43

Preparation of Example 43

Example 43 is prepared following general scheme 1.

Preparation of Intermediate 81

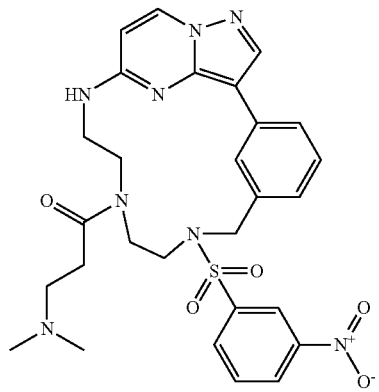 [SMILES: CN(C)CCC(=O)N1CCNc2ccn3ncc(c3n2)-c2cccc(c2)CN(S(=O)(=O)c2cccc([N+](=O)[O-])c2)CC1]

A mixture of intermediate 75 (203 mg, 0.38 mmol), 3-dimethylaminopropanoic acid (50 µl, 0.42 mmol) and N,N-diisopropylethylamine (323 µl, 1.90 mmol) in N,N-dimethylformamide (2 ml) was stirred at room temperature for 10 minutes. O-(Benzotriazol-1-yl)-N,N,N',N'-tetramethyluronium hexafluorophosphate (HBTU) (174 mg, 0.46 mmol) was added. The reaction mixture was stirred at room temperature for 1 hour. The solvent was removed under reduced pressure and dichloromethane was added. The organic layer was washed with water, a 1N aqueous sodium bicarbonate solution and brine. The organic layer was dried, filtered and the solvent was removed under reduced pressure. The product was purified by flash chromatography over silica gel using dichloromethane and methanol as eluents (gradient elution from 0% to 6% methanol). The product fractions were collected and the solvent was removed under reduced pressure.

Yield: 196 mg of intermediate 81 (87%)
LCMS method 1: MH⁺=593, RT=0.696 min

Preparation of Example 43

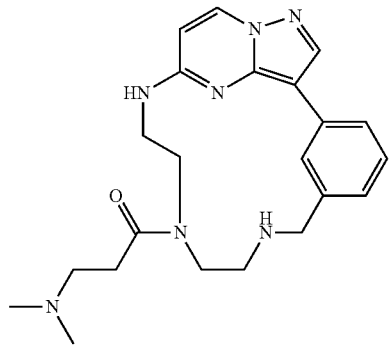 [SMILES: CN(C)CCC(=O)N1CCNCc2cccc(c2)-c2cnn3ccc(nc23)NCC1]

Thiophenol (40 µl, 0.40 mmol) and cesium carbonate (215 mg, 0.66 mmol) were suspended in N,N-dimethylformamide (2 ml). Intermediate 81 (196 mg, 0.33 mmol) was added and the reaction mixture was stirred at room temperature for 3 hours. Ethyl acetate was added and the organic layer was washed with water and a 1N aqueous sodium hydroxide solution, dried, filtered and the solvent was removed under reduce pressure. The product was purified by flash chromatography over silica gel using dichloromethane and methanol as eluents (gradient elution from 0% to 10% methanol). The product fractions were collected and the solvent was removed under reduced pressure.

Yield: 30 mg of example 43 (22%)
LCMS method 2: MH⁺=408, RT=0.733 min

Example 44

Preparation of Example 44

Example 44 is prepared following general scheme 2.

Preparation of Intermediate 82

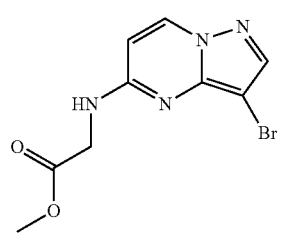 [SMILES: COC(=O)CNc1ccn2ncc(Br)c2n1]

A mixture of 3-bromo-5-chloro-pyrazolo[1,5-a]pyrimidine (2.0 g, 8.60 mmol), methyl 2-aminoacetate hydrochloride (2.16 g, 17.2 mmol) and N,N-diisopropylethylamine (7.51 ml, 43.0 mmol) in acetonitrile (25.8 ml) was refluxed overnight. The reaction mixture was cooled and the solvent was removed under reduced pressure. The residue was dissolved in ethyl acetate and washed with water. The organic layer was dried, filtered and the solvent was removed under reduced pressure. The residue was purified by flash column chromatography over silica gel using heptane and ethyl acetate as eluents (gradient elution from 0% to 67% ethyl acetate). The product fractions were collected and the solvent was removed under reduced pressure.

Yield: 1.72 g of intermediate 82 (70%)
LCMS method 2: MH$^+$=286, RT=2.402 min

Preparation of Intermediate 83

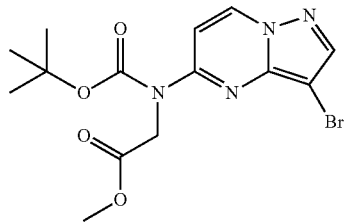 [SMILES: COC(=O)CN(C(=O)OC(C)(C)C)c1ccn2ncc(Br)c2n1]

A mixture of intermediate 82 (1.72 g, 6.03 mmol), tert-butoxycarbonyl anhydride (1.38 g, 6.33 mmol), triethylamine (922 µl, 6.63 mmol) and 4-(dimethylamino)pyridine (37 mg, 0.30 mmol) in tetrahydrofuran (18 ml) was refluxed overnight. The reaction mixture was cooled and the solvent was removed under reduced pressure. The residue was dissolved in ethyl acetate and washed with water and brine. The organic layer was dried, filtered and the solvent was removed under reduced pressure. The residue was purified by flash column chromatography over silica gel using heptane and ethyl acetate as eluents. The product fractions were collected and the solvent was removed under reduced pressure.

Yield: 1.9 g of intermediate 83 (82%)
LCMS method 1: MH$^+$=386, RT=0.998 min

Preparation of Intermediate 84

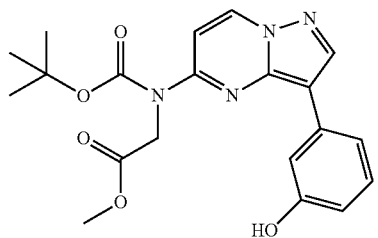 [SMILES: COC(=O)CN(C(=O)OC(C)(C)C)c1ccn2ncc(-c3cccc(O)c3)c2n1]

A mixture of 1,4-dioxane and water (3:1, 30 ml) was degassed by bubbling nitrogen gas through the mixture. Intermediate 83 (1.90 g, 4.93 mmol), (3-hydroxyphenyl)boronic acid (1.02 g, 7.40 mmol), tetrakis(triphenylphosphine)palladium(0) (116 mg, 0.10 mmol), 2-dicyclohexylphosphino-2',4',6'-triisopropylbiphenyl (Xphos) (186 mg, 0.39 mmol) and potassium phosphate tribasic (5.23 g, 5 eq.) were added and the mixture was stirred under nitrogen gas at 80° C. for 16 hours. More (3-hydroxyphenyl)boronic acid (0.51 g, 3.70 mmol), tetrakis(triphenylphosphine)palladium(0) (58 mg, 0.05 mmol), 2-dicyclohexylphosphino-2',4',6'-triisopropylbiphenyl (Xphos) (93 mg, 0.195 mmol) were added and the mixture was stirred under nitrogen gas at 80° C. for 3 hours. The reaction mixture was cooled and the solvent was removed under reduced pressure. Ethyl acetate was added and the organic layer was washed with water. The organic layer was dried, filtered and the solvent was removed under reduced pressure. The residue was triturated with diethyl ether, filtered and dried under reduced pressure.

Yield: 1.48 g of intermediate 84 (75%)
LCMS method 2: MH$^+$=399, RT=3.462 min

Preparation of Intermediate 85

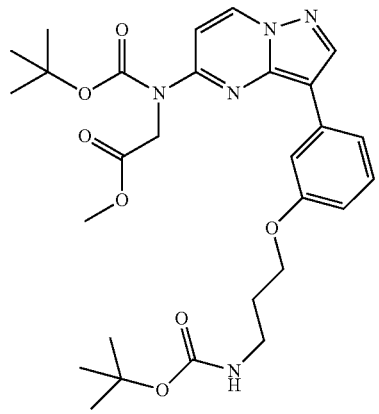 [SMILES: COC(=O)CN(C(=O)OC(C)(C)C)c1ccn2ncc(-c3cccc(OCCCNC(=O)OC(C)(C)C)c3)c2n1]

Intermediate 84 (800 mg, 2.01 mmol), tert-butyl N-(3-hydroxypropyl)carbamate (490 mg, 2.81 mmol) and triphenylphosphine (949 mg, 3.62 mmol) were suspended in dry tetrahydrofuran (12 ml/mmol). Diisopropyl azodicarboxylate (713 µl, 3.62 mmol) was added and the mixture was stirred at room temperature for 4 hours. The solvent was removed under reduced pressure. The residue was purified by flash column chromatography over silica gel using heptane and ethyl acetate as eluents. The product fractions were collected and the solvent was removed under reduced pressure.

Yield: 900 mg of intermediate 85 (81%)
LCMS method 2: MH$^+$=578 (MW+Na), RT=4.384 min Preparation of Intermediate 86

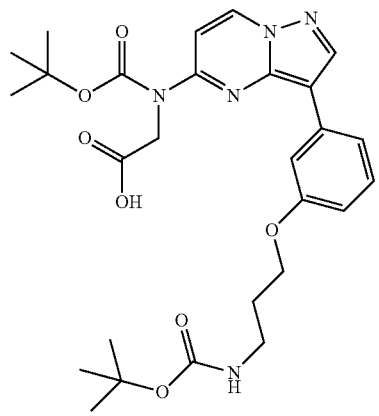 [SMILES: CC(C)(C)OC(=O)NCCCOc1cccc(-c2cnn3ccc(N(CC(=O)O)C(=O)OC(C)(C)C)nc23)c1]

Intermediate 85 (0.900 g, 1.62 mmol) and lithium hydroxide monohydrate (70 mg, 1.78 mmol) in a mixture tetrahydrofuran/methanol/water (2:2:1, 4.86 ml) were stirred at room temperature for 3 hours. More lithium hydroxide monohydrate (30 mg, 0.76 mmol) was added and the reaction mixture was stirred at room temperature for 18 hours. The solvent was removed under reduced pressure. The residue was used in the next step without further purification.

LCMS method 1: MH$^+$=442 (MW-Boc), RT=1.100 min

Preparation of Intermediate 87

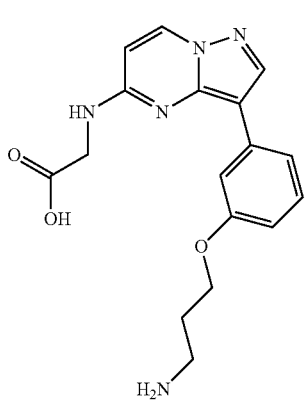 [SMILES: NCCCOc1cccc(-c2cnn3ccc(NCC(=O)O)nc23)c1]

Intermediate 86 (877 mg, 1.62 mmol) was stirred in a mixture of trifluoro acetic acid (5 ml) in dichloromethane (5 ml) and the reaction mixture was stirred at room temperature for 1 hour. The solvent was removed under reduced pressure. The residue was treated with toluene and the solvent was removed under reduced pressure. Intermediate 87 was used in the next step without further purification.

LCMS method 2: MH$^+$=342, RT=1.573 min

Preparation of Example 44

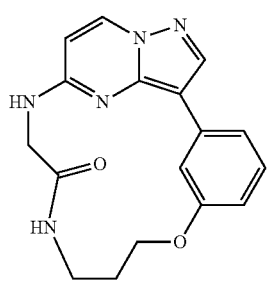 [SMILES: O=C1CNc2ccn3ncc(c3n2)-c2cccc(c2)OCCCN1]

A suspension of intermediate 87 (553 mg, 1.62 mmol) in N,N-dimethylformamide (55 ml) was added drop wise to a solution of O-(benzotriazol-1-yl)-N,N,N',N'-tetramethyluronium hexafluorophosphate (HBTU) (1.84 g, 4.86 mmol) and N,N-diisopropylethylamine (4.244 ml, 24.30 mmol) in N,N-dimethylformamide (110 ml). The reaction mixture was stirred at room temperature for 1 hour. A solution of ammonia in water was added and the solvent was removed under reduced pressure. Ethyl acetate was added and the organic layer was washed with a saturated aqueous sodium carbonate solution, water and brine. The organic layer was dried, filtered and the solvent was removed under reduced pressure. The residue was purified by reversed phase HPLC (HPLC method A). The product fractions were collected and the solvent was removed under reduced pressure.

Yield: 115 mg of example 44 (22%)

LCMS method 2: MH$^+$=324, RT=1.071 min

Example 45

Preparation of Example 45

Example 45 is prepared following general scheme 2.

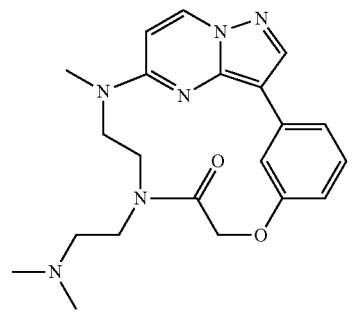 [SMILES: CN(C)CCN1CCN(C)c2ccn3ncc(c3n2)-c2cccc(c2)OCC1=O]

Sodium hydride (60% in mineral oil, 30 mg, 0.85 mmol) was added to a solution of example 33 (293 mg, 0.77 mmol) in N,N-dimethylformamide (2.31 ml). The mixture was stirred at 60° C. for 30 minutes and iodomethane (57 µl, 0.92 mmol) was added. The reaction was stirred at 60° C. for 90 minutes. Water was added and the mixture was stirred at room temperature for 5 minutes. The solvent was removed under reduced pressure and the residue was purified by reversed phase HPLC (HPLC method A). The product fractions were collected and the solvent was removed under reduced pressure. The product was taken up in dichloromethane/methanol (4:1, 45 ml) and 4N HCl in 1,4-dioxane (80 µl, 0.31 mmol) was added. The reaction mixture was stirred at room temperature for 2 hours. The solvent was removed under reduced pressure. The product was triturated with diethyl ether, filtered and dried under reduced pressure.

Yield: 101 mg of example 45 as HCl salt (30%)

LCMS method 2: MH$^+$=395, RT=1.225 min

Example 46

Preparation of Example 46

Example 46 is prepared following general scheme 2.

Preparation of Intermediate 88

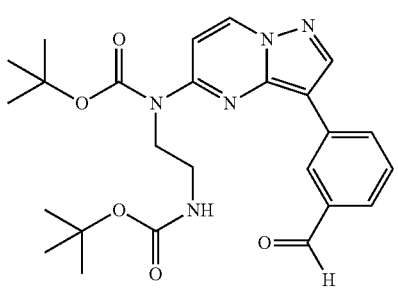 [SMILES: CC(C)(C)OC(=O)NCCN(C(=O)OC(C)(C)C)c1ccn2ncc(-c3cccc(C=O)c3)c2n1]

A mixture of 1,4-dioxane and water (3:1, 16.55 ml) was degassed by bubbling nitrogen gas through the mixture. Intermediate 6 (2.518 g, 5.518 mmol), (3-formylphenyl)boronic acid (1.076 g, 7.173 mmol), tetrakis(triphenylphosphine)palladium(0) (128 mg, 0.11 mmol), 2-dicyclohexylphosphino-2',4',6'-triisopropylbiphenyl (Xphos) (210 mg, 0.44 mmol) and potassium phosphate tribasic (5.856 g, 5 eq.) were added and the mixture was stirred under nitrogen gas at 80° C. for 15 hours. The reaction mixture was cooled and the solvent was removed under reduced pressure. Ethyl acetate was added and the organic layer was washed with water and brine. The organic layer was dried, filtered and the solvent was removed under reduced pressure. The residue was triturated with diethyl ether, filtered and dried under reduced pressure. The residue was purified by flash column chromatography over silica gel using heptane and ethyl acetate as eluents (gradient elution from 0% to 50% ethyl acetate). The product fractions were collected and the solvent was removed under reduced pressure.

Yield: 2.366 g of intermediate 88 (89%)
LCMS method 2: MH$^+$=482, RT=1.186 min

Preparation of Intermediate 89

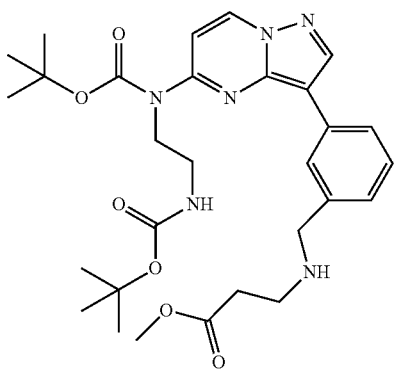 [SMILES: COC(=O)CCNCc1cccc(-c2cnn3ccc(N(CCNC(=O)OC(C)(C)C)C(=O)OC(C)(C)C)nc23)c1]

A mixture of intermediate 88 (2.170 g, 4.797 mmol), methyl 3-aminopropanoate hydrochloride (1.67 g, 11.99 mmol) and N,N-diisopropylethylamine (2.039 ml, 11.99 mmol) was stirred in a mixture of 1,2-dichloroethane/methanol (1:1, 14.39 ml) at room temperature for 1 hour. Sodium triacetoxyborohydride (2.541 g, 11.99 mmol) was added portion wise and the mixture was stirred at room temperature for 15 hours. More methyl 3-aminopropanoate hydrochloride (670 mg, 4.797 mmol), N,N-diisopropylethylamine (1.63 ml, 9.594 mmol) and sodium triacetoxyborohydride (1.016 g, 4.797 mmol) were added and the mixture was stirred at room temperature for 5 hours. The solvent was removed under reduced pressure and the residue was dissolved in ethyl acetate. The organic layer was washed with a saturated aqueous sodium bicarbonate solution. The organic layer was dried, filtered and the solvent was removed under reduce pressure. The residue was purified by flash column chromatography over silica gel using heptane and ethyl acetate as eluents (gradient elution from 0% to 100% ethyl acetate) and then dichloromethane and methanol as eluents (gradient elution from 50:1 to 9:1 methanol). The product fractions were collected and the solvent was removed under reduced pressure.

Yield: 2.170 g of intermediate 89 (80%)
LCMS method 1: MH$^+$=569, RT=0.743 min

Preparation of Intermediate 90

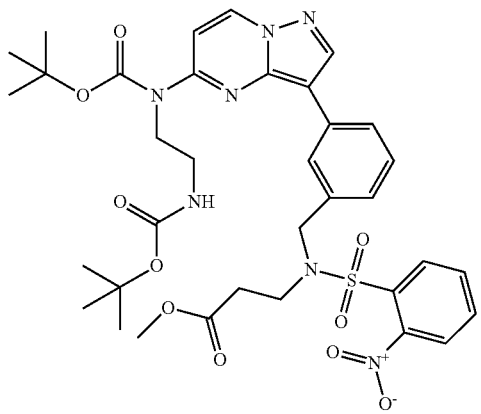 [SMILES: COC(=O)CCN(Cc1cccc(-c2cnn3ccc(N(CCNC(=O)OC(C)(C)C)C(=O)OC(C)(C)C)nc23)c1)S(=O)(=O)c1ccccc1[N+](=O)[O-]]

2-Nitrobenzenesulfonyl chloride (600 mg, 2.70) mmol was added portion wise at 0° C. and under nitrogen atmosphere to a solution of intermediate 89 (1.022 g, 1.797 mmol) and triethylamine (624 μl, 4.49 mmol) in anhydrous dichloromethane (5.39 ml). The reaction mixture was stirred for 2 hours allowing it to reach room temperature. The reaction mixture was diluted with dichloromethane and washed with water. The organic layer was dried, filtered and the solvent was removed under reduced pressure. The residue was purified by flash column chromatography over silica gel using heptane and ethyl acetate as eluents (gradient elution from 0% to 80% ethyl acetate). The product fractions were collected and the solvent was evaporated.

LCMS method 1: MH$^+$=775 (MW+Na), RT=1.240 min

Preparation of Intermediate 91

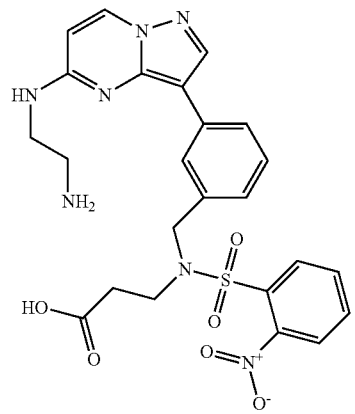 [SMILES: NCCNc1ccn2ncc(-c3cccc(CN(CCC(=O)O)S(=O)(=O)c4ccccc4[N+](=O)[O-])c3)c2n1]

A 6N HCl solution (12 ml/mmol, 22 ml) was added to a solution of intermediate 89 (1.373 g, 1.821 mmol) in tetrahydrofuran (12 ml/mmol, 22 ml). The mixture was stirred in a sealed tube at room temperature overnight. The solvent was removed under reduced pressure. Toluene was added and evaporated twice. The residue was used in the next step without further purification.

Preparation of Intermediate 92

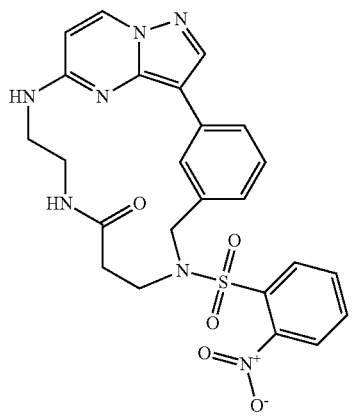 [SMILES: O=C1CCN(S(=O)(=O)c2ccccc2[N+](=O)[O-])Cc2cccc(c2)-c2cnn3ccc(nc23)NCCN1]

A solution of intermediate 91 (1.048 g, 1.82 mmol) in N,N-dimethylformamide (55 ml) was added drop wise to a solution of O-(benzotriazol-1-yl)-N,N,N',N'-tetramethyluronium hexafluorophosphate (HBTU) (2.07 g, 5.46 mmol) and N,N-diisopropylethylamine (9.286 ml, 54.60 mmol) in N,N-dimethylformamide (127 ml). The reaction mixture was stirred at room temperature for 2 hours. A The solvent was removed under reduced pressure. Ethyl acetate was added and the organic layer was washed with a saturated aqueous sodium bicarbonate solution. The organic layer was dried, filtered and the solvent was removed under reduced pressure. The residue was purified by flash column chromatography over silica gel using dichloromethane and methanol as eluents (gradient elution from 50:1 to 9:1 methanol). The product fractions were collected and the solvent was removed under reduced pressure.

LCMS method 1: MH$^+$=522, RT=0.793 min

Preparation of Example 46

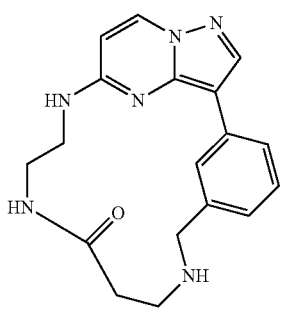 [SMILES: O=C1CCNCc2cccc(c2)-c2cnn3ccc(nc23)NCCN1]

Thiophenol (220 μl, 2.12 mmol) and cesium carbonate (577 mg, 1.77 mmol) were added to a solution of intermediate 92 (923 mg, 1.77 mmol) in N,N-dimethylformamide (3.5 ml) and the reaction mixture was stirred at room temperature for 5 hours. Ethyl acetate was added and the precipitate was filtered and dried under reduce pressure. The product was taken up in dichloromethane/methanol (4:1, 20 ml) and 4N HCl in 1,4-dioxane (80 μl) was added. The reaction mixture was stirred at room temperature for 2 hours. The solvent was removed under reduced pressure. The product was triturated with diethyl ether, filtered and dried under reduced pressure.

Yield: 96 mg of example 46 as HCl salt (15%)
LCMS method 2: MH$^+$=337, RT=0.998 min

Example 47

Preparation of Example 47

Example 47 is prepared following general scheme 2.

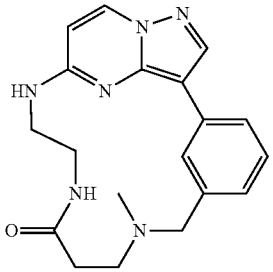 [SMILES: CN1CCC(=O)NCCNc2ccn3ncc(c3n2)-c2cccc(c2)C1]

Example 46 (100 mg, 0.297 mmol) and formaldehyde (37%, 10 μl, 0.36 mmol) were stirred in 1,2-dichloroethane at room temperature for 1 hour. Sodium triacetoxyborohydride (125 mg, 0.59 mmol) was added and the mixture was stirred at room temperature for 3 hours. The solvent was removed under reduced pressure and the residue was purified by reversed phase HPLC (HPLC method A). The product fractions were collected and the solvent was removed under reduced pressure. The product was taken up in dichloromethane/methanol (4:1, 30 ml) and 4N HCl in 1,4-dioxane (60 μl) was added. The reaction mixture was stirred at room temperature for 2 hours. The solvent was removed under reduced pressure. The product was triturated with diethyl ether, filtered and dried under reduced pressure.

Yield: 80 mg of example 47 as HCl salt (70%)
LCMS method 2: MH$^+$=351, RT=1.036 min

Example 48

Preparation of Example 48

Example 48 is prepared following general scheme 2.

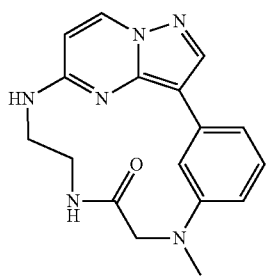 [SMILES: CN1CC(=O)NCCNc2ccn3ncc(c3n2)-c2cccc1c2]

A mixture of example 36 (170 mg, 0.551 mmol) and potassium carbonate (115 mg, 0.83 mmol) in N,N-dimethylformamide (1.65 ml) was stirred at room temperature for 15 minutes. Iodomethane (30 μl, 0.55 mmol) was added and the mixture was stirred at 60° C. for 2 hours. The solvent was removed under reduced pressure. The residue was purified by reversed phase HPLC (HPLC method A). The product fractions were collected and the solvent was removed under reduced pressure. The product was taken up in dichloromethane/methanol (4:1, 40 ml) and 4N HCl in 1,4-dioxane (60 μl) was added. The reaction mixture was stirred at room temperature for 2 hours. The solvent was removed under reduced pressure. The product was triturated with diethyl ether, filtered and dried under reduced pressure.

Yield: 69 mg of example 48 as HCl salt (35%)
LCMS method 1: MH⁺=323, RT=1.605 min Example 49

Preparation of Example 49

Example 49 is prepared following general scheme 2.

Preparation of Intermediate 93

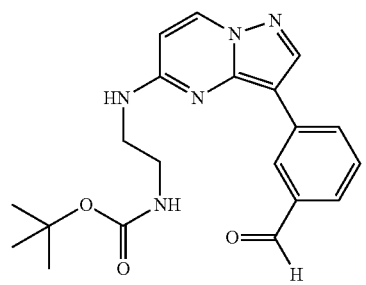 [SMILES: CC(C)(C)OC(=O)NCCNc1ccn2ncc(-c3cccc(C=O)c3)c2n1]

A mixture of 1,4-dioxane and water (3:1, 200 ml) was degassed by bubbling nitrogen gas through the mixture. Intermediate 5 (7.50 g, 21.05 mmol), (3-formylphenyl)boronic acid (6.35 g, 27.37 mmol), tetrakis(triphenylphosphine)palladium(0) (128 mg, 0.11 mmol), 2-dicyclohexylphosphino-2',4',6'-triisopropylbiphenyl (Xphos) (487 mg, 0.42 mmol) and potassium phosphate tribasic (22 g, 5 eq.) were added and the mixture was stirred under nitrogen gas at 80° C. for 2 hours. The reaction mixture was cooled and ethyl acetate was added. The organic layer was washed with water and brine. The organic layer was dried, filtered and the solvent was removed under reduced pressure. The residue was triturated with diethyl ether, filtered and dried under reduced pressure. The residue was purified by flash column chromatography over silica gel using dichloromethane and methanol as eluents. The product fractions were collected and the solvent was removed under reduced pressure. The product was triturated with diethyl ether, filtered and dried under reduced pressure.

Yield: 5.53 g of intermediate 93 (69%)
LCMS method 2: MH⁺=382, RT=0.882 min

Preparation of Intermediate 94

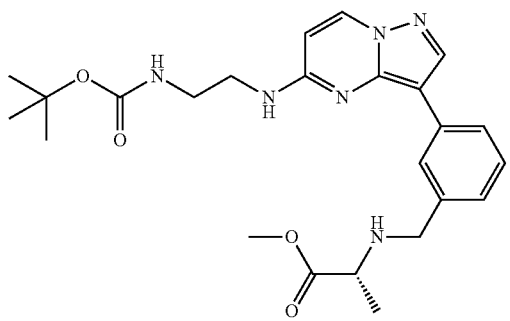 [SMILES: COC(=O)[C@@H](C)NCc1cccc(-c2cnn3ccc(NCCNC(=O)OC(C)(C)C)nc23)c1]

Sodium triacetoxyborohydride (3.00 g, 14.16 mmol) was added to a mixture of intermediate 93 (2.70 g, 7.08 mmol), methyl (2R)-2-aminopropanoate hydrochloride (0.99 g, 7.08 mmol) and N,N-diisopropylethylamine (0.981 ml, 7.08 mmol) in 1,2-dichloroethane (105 ml). The reaction mixture was stirred at room temperature overnight. A saturated aqueous sodium bicarbonate solution was added and the organic layer was washed with water and brine. The organic layer was dried, filtered and the solvent was removed under reduce pressure. The residue was purified by flash column chromatography over silica gel using heptane and ethyl acetate as eluents. The product fractions were collected and the solvent was removed under reduced pressure.

Yield: 3.01 g of intermediate 94 (71%)
LCMS method 1: MH⁺=469, RT=0.532 min

Preparation of intermediate 95

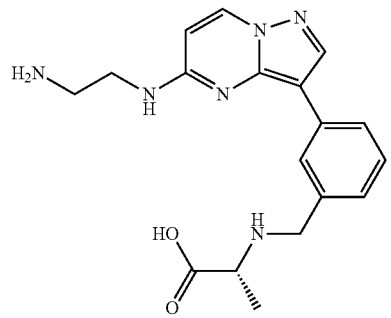 [SMILES: C[C@@H](NCc1cccc(-c2cnn3ccc(NCCN)nc23)c1)C(=O)O]

A 6N HCl solution (12 ml/mmol, 35 ml) was added to a solution of intermediate 94 (2.70 g, 5.76 mmol) in tetrahydrofuran (12 ml/mmol, 35 ml). The mixture was stirred in at 70° C. overnight. The solvent was removed under reduced pressure. The residue was triturated with diethyl ether, filtered and dried under reduced pressure. The product was used in the next step without further purification.

LCMS method 1: MH⁺=355, RT=0.204 min

Preparation of Example 49

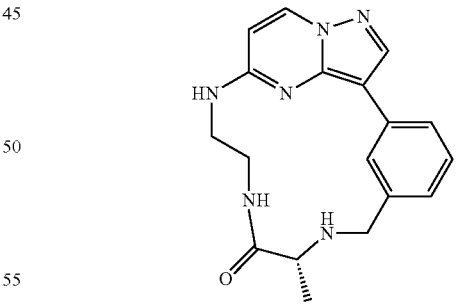

A solution of intermediate 95 (2.25 g, 5.76 mmol) and N,N-diisopropylethylamine (10.06 ml, 57.6 mmol) in N,N-dimethylformamide (40 ml) was added drop wise to a solution of O-(benzotriazol-1-yl)-N,N,N',N'-tetramethyluronium hexafluorophosphate (HBTU) (2.07 g, 5.46 mmol) and N,N-diisopropylethylamine (10.06 ml, 57.6 mmol) in N,N-dimethylformamide (20 ml). The reaction mixture was stirred at room temperature for 1 hour after the addition was completed. A 7N ammonia solution in methanol was added. The solvent was removed under reduced pressure. Ethyl acetate was added and the organic layer was washed with a saturated aqueous sodium bicarbonate solution and water. The organic layer was dried, filtered and the solvent was removed under reduced pressure. The residue was purified by flash column chromatography over silica gel using dichloromethane and methanol as eluents. The product fractions were collected and the solvent was removed under reduced pressure. The product was triturated with acetonitrile, filtered and dried under reduced pressure.

Yield: 292 mg of example 49 (15%)
LCMS method 2: MH⁺=337, RT=1.090 min

Example 50

Preparation of Example 50

Preparation of Intermediate 96

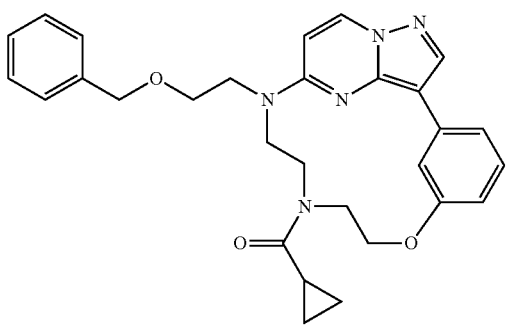 [SMILES: O=C(C1CC1)N1CCOc2cccc(c2)-c2cnn3ccc(nc23)N(CCOCc2ccccc2)CC1]

13-[2-(benzyloxy)ethyl]-7-oxa-10,13,17,18,21-pentaaza-tetracyclo[12.5.2.1^{2,6}.0^{17,20}]docosa-1(20),2,4,6(22),14(21),15,18-heptaene was prepared according to similar synthetic procedures as described to obtain intermediate 7 using tert-butyl N-[2-(2-benzyloxyethylamino)ethyl]-N-[2-(tert-butyl(dimethyl)silyl)oxyethyl]carbamate for the coupling to the scaffold and (3-hydroxyphenyl)boronic acid for the Suzuki coupling. The ring closure was effected after TBDMS deprotection using Mitsunobu conditions. The unprotected 13-[2-(benzyoxy)ethyl]-7-oxa-10,13,17,18,21-pentaazatetracyclo[12.5.2.1^{2,6}.0^{17,20}]docosa-1(20),2,4,6(22),14(21),15,18-heptaene was obtained after Boc deprotection under acidic conditions.

Cyclopropanecarbonyl chloride (10 µl, 0.08 mmol) was added to a solution of 13-[2-(benzyloxy)ethyl]-7-oxa-10,13,17,18,21-pentaazatetracyclo[12.5.2.1^{2,6}.0^{17,20}]docosa-1(20),2,4,6(22),14(21),15,18-heptaene (30 mg, 0.07 mmol) and triethylamine (11 µl, 0.08 mmol) in dichloromethane (2 ml). The mixture was stirred at room temperature under nitrogen atmosphere for 1 hour. Ethyl acetate was added and the organic layer was washed with water and brine.

The organic layer was dried, filtered and the solvent was removed under reduced pressure. The residue was used in the next step without further purification.

LCMS method 1: MH⁺=498, RT=1.109 min

Preparation of Example 50

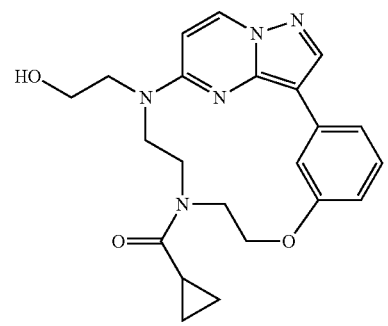 [SMILES: O=C(C1CC1)N1CCOc2cccc(c2)-c2cnn3ccc(nc23)N(CCO)CC1]

A suspension of intermediate 96 (35 mg, 0.07 mmol) and palladium (0.07 mmol) in tetrahydrofurane/methanol (1:1, 10 ml)) was stirred under hydrogen atmosphere for 2 days. The solid was removed by filtration over celite. The solvent of the filtrate was removed under reduced pressure and the residue was purified by flash column chromatography over silica gel using dichloromethane and methanol as eluents. The product fractions were collected and the solvent was removed under reduced pressure.

Yield: 12 mg of example 50 (42%)
LCMS method 2: MH⁺=408, RT=2.247 min

Example 51

Preparation of Example 51

Example 51 is prepared following general scheme 2.

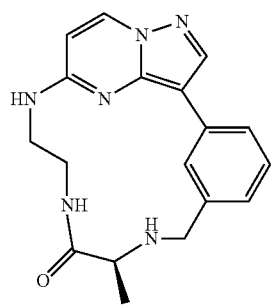 [SMILES: C[C@@H]1NCc2cccc(c2)-c2cnn3ccc(nc23)NCCNC1=O]

Example 51 was prepared according to the procedures used to obtain example 49 except that methyl (2S)-2-aminopropanoate hydrochloride is used instead of methyl (2R)-2-aminopropanoate hydrochloride in the reductive amination step.

LCMS method 2 example 51: MH⁺=337, RT=1.074 min

Example 52

Preparation of Example 52

Example 52 is prepared following general scheme 1.

Preparation of Intermediate 97

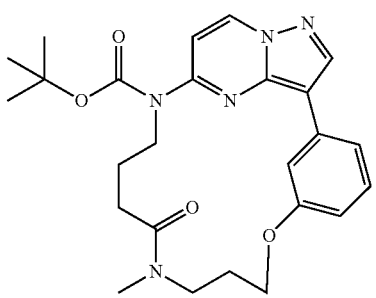 [SMILES: CN1CCCOc2cccc(c2)-c2cnn3ccc(nc23)N(C(=O)OC(C)(C)C)CCCC1=O]

Intermediate 52 (350 mg, 0.78 mmol) and sodium hydride (60% in mineral oil, 90 mg, 1.17 mmol) were dissolved in N,N-dimethylformamide (2.34 ml). The mixture was stirred at room temperature for 15 minutes and iodomethane (60 μl, 0.94 mmol) was added drop wise. The reaction was stirred at room temperature for 2 hours. The solvent was removed under reduced pressure and the residue was purified by flash column chromatography over silica gel using heptane, ethyl acetate, dichloromethane and dichloromethane:methanol (9:1) (from 20% 15 to 100% of ethyl acetate and from 50% to 100% of dichloromethane:methanol 9:1). The product fractions were collected and the solvent was removed under reduced pressure.

Yield: 147 mg of intermediate 97 (40%)

LCMS method 1: MH$^+$=366 (MW-Boc), RT=0.739 min

Preparation of Example 52

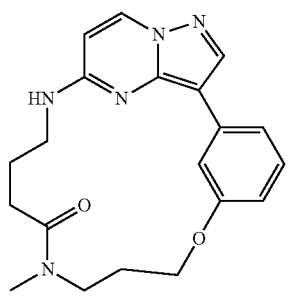 [SMILES: CN1CCCOc2cccc(c2)-c2cnn3ccc(nc23)NCCCC1=O]

Intermediate 92 (147 mg, 0.32 mmol) was dissolved in a 4N HCl solution in methanol (6 ml). The reaction mixture was stirred at room temperature for 2 hours. The solvent was removed under reduced pressure. The product was triturated with diethyl ether, filtered and dried under reduced pressure.

Yield: 25 mg of example 52 (21%)

LCMS method 2: MH$^+$=366, RT=2.210 min

Example 53

Preparation of Example 53

Example 53 is prepared following general scheme 1.

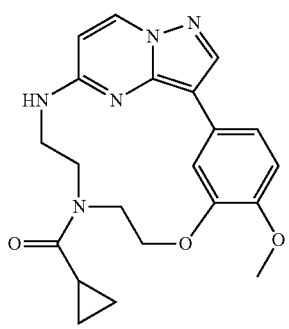 [SMILES: COc1ccc2cc1OCCN(C(=O)C1CC1)CCNc1ccn3ncc-2c3n1]

5-methoxy-7-oxa-10,13,17,18,21-pentaazatetracyclo[12.5.2.1^{2,6}.0^{17,20}]docosa-1(20),2,4,6(22),14(21),15,18-heptaene was prepared according to similar synthetic procedures as described to obtain intermediate 7 using intermediate 4 for the coupling to the scaffold and (3-hydroxy-4-methoxy-phenyl)boronic acid for the Suzuki coupling. The ring closure was effected after TBDMS deprotection using Mitsunobu conditions. The unprotected 5-methoxy-7-oxa-10,13,17,18,21-pentaazatetracyclo[12.5.2.1^{2,6}.0^{17,20}]docosa-1(20),2,4,6(22),14(21),15,18-heptaene was obtained after Boc deprotection under acidic conditions.

5-methoxy-7-oxa-10,13,17,18,21-pentaazatetracyclo[12.5.2.1^{2,6}.0^{17,20}]docosa-1(20),2,4,6(22),14(21),15,18-heptaene hydrochloride (105 mg, 0.32 mmol) and triethylamine (67 μl, 0.48 mmol) were stirred in dry tetrahydrofuran (0.96 ml). Cyclopropanecarbonyl chloride (40 μl, 0.35 mmol) was added and the mixture was stirred at room temperature for 1 hour. The solvent was removed under reduced pressure. The product was triturated with methanol, filtered and dried under reduced pressure.

Yield: 44 mg of example 53 (35%)

LCMS method 2: MH$^+$=394, RT=2.908 min

Example 54

Preparation of Example 54

Example 54 is prepared following general scheme 4.

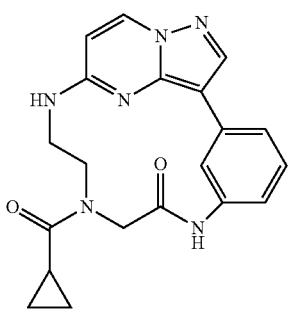 [SMILES: O=C1CN(C(=O)C2CC2)CCNc2ccn3ncc(c3n2)-c2cccc(c2)N1]

7,10,13,17,18,21-hexaazatetracyclo[12.5.2.1^{2,6}.0^{17,20}]docosa-1(20),2,4,6(22),14(21),15,18-heptaen-8-one was prepared according to similar synthetic procedures as described to obtain example 54 using intermediate 95 and

[3-(tert-butoxycarbonylamino)phenyl]boronic acid for the Suzuki coupling. The ring closure was effected after Boc deprotection and reaction with methyl 2-bromoacetate using HBTU conditions. The unprotected 7,10,13,17,18,21-hexaazatetracyclo[12.5.2.1^{2,6}.0^{17,20}]docosa-1(20), 2,4,6(22),14(21),15,18-heptaen-8-one was obtained after nosyl deprotection using thiophenol. 7,10,13,17,18,21-hexaazatetracyclo[12.5.2.1^{2,6}.0^{17,20}]docosa-1(20), 2,4,6(22),14(21),15,18-heptaen-8-one (25 mg, 0.08 mmol) and triethylamine (14 µl, 0.10 mmol) were stirred in dry tetrahydrofuran (240 µl). Cyclopropanecarbonyl chloride (10 µl, 0.09 mmol) was added and the mixture was stirred at room temperature for 1 hour. The solvent was removed under reduced pressure. The product was triturated with methanol, filtered and dried under reduced pressure. The residue was purified by flash column chromatography over silica gel. The product fractions were collected and the solvent was removed under reduced pressure. The product was recrystallized in hot methanol/dichloromethane (4:1).

Yield: 12 mg of example 54 (40%)
LCMS method 2: MH$^+$=377, RT=2.331 min

Example 55

Preparation of Example 55

Example 55 is prepared following general scheme 2.

Preparation of Intermediate 98

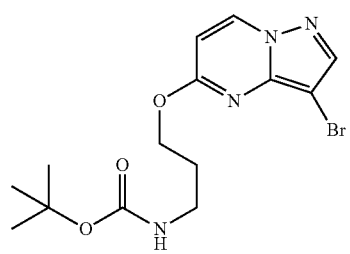 [SMILES: CC(C)(C)OC(=O)NCCCOc1ccn2ncc(Br)c2n1]

Sodium hydride (60% in mineral oil, 1.032 g, 25.81 mmol) was added to a solution of 3-bromo-5-chloro-pyrazolo[1,5-a]pyrimidine (1.50 g, 6.452 mmol) in dry N,N-dimethylformamide (19.36 ml). Tert-butyl N-(2-hydroxyethyl)carbamate (4.52 g, 25.81 mmol) was added and the mixture was stirred at room temperature for 30 minutes. The reaction mixture was cooled on an ice bath and water was added. The mixture was stirred for 5 minutes. The solvent was removed under reduced pressure and the residue was purified by flash column chromatography over silica gel using dichloromethane and methanol as eluents (gradient elution from 0% to 20% methanol). The product fractions were collected and the solvent was removed under reduced pressure.

Yield: 1.376 mg of intermediate 98(57%)
LCMS method 1: MH$^+$=372, RT=0.928 min

Preparation of Intermediate 99

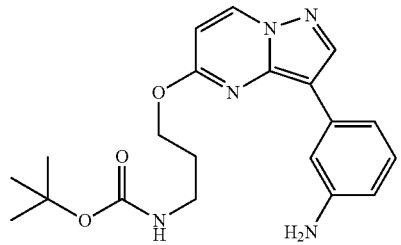 [SMILES: CC(C)(C)OC(=O)NCCCOc1ccn2ncc(-c3cccc(N)c3)c2n1]

A mixture of 1,4-dioxane and water (3:1, 21 ml) was degassed by bubbling nitrogen gas through the mixture. Intermediate 98 (1.32 g, 3.556 mmol), (3-aminophenyl)boronic acid (610 mg, 3.91 mmol), tetrakis(triphenylphosphine)palladium(0) (81 mg, 0.07 mmol), 2-dicyclohexylphosphino-2',4',6'-triisopropylbiphenyl (Xphos) (133 mg, 0.28 mmol) and potassium phosphate tribasic (3.778 g, 5 eq.) were added and the mixture was stirred under nitrogen gas at 85° C. for 15 hours. The reaction mixture was cooled and the solvent was removed under reduced pressure. Ethyl acetate was added and the organic layer was washed with water. The organic layer was dried, filtered and the solvent was removed under reduced pressure. The residue was purified by flash column chromatography over silica gel using heptane and ethyl acetate as eluents (gradient elution from 25% to 66% ethyl acetate). The product fractions were collected and the solvent was removed under reduced pressure.

Yield: 1.115 g of intermediate 99 (82%)
LCMS method 1: MH$^+$=384, RT=0.729 min

Preparation of Intermediate 100

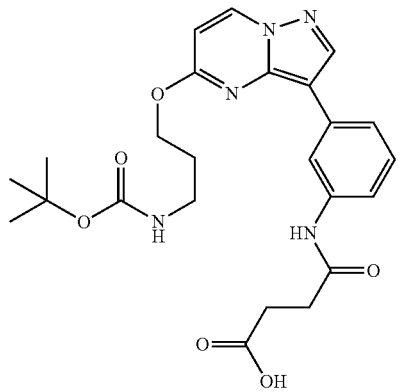 [SMILES: CC(C)(C)OC(=O)NCCCOc1ccn2ncc(-c3cccc(NC(=O)CCC(=O)O)c3)c2n1]

Pyridine (219 µl, 2.71 mmol) was added to a suspension of intermediate 99 (1.04 g, 2.712 mmol) and tetrahydrofuran-2,5-dione (540 mg, 5.42 mmol) in tetrahydrofuran (8.14 ml). The mixture was stirred at 80° C. for 3 hours. The solvent was removed under reduced pressure. Ethyl acetate was added and the organic layer was washed with a 1N aqueous HCl solution. The organic layer was dried, filtered and the solvent

Preparation of Intermediate 101

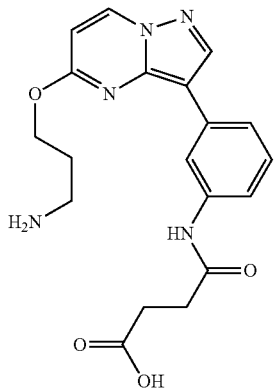 [SMILES: NCCCOc1ccn2ncc(-c3cccc(NC(=O)CCC(=O)O)c3)c2n1]

Intermediate 100 (1.311 g, 2.712 mmol) was stirred at room temperature in 4N HCl in 1,4-dioxane (8.14 ml) for 3 hours. The solvent was removed under reduced pressure. Toluene was added and evaporated (2×).

LCMS method 1: MH$^+$=384, RT=0.352 min

Preparation of Example 55

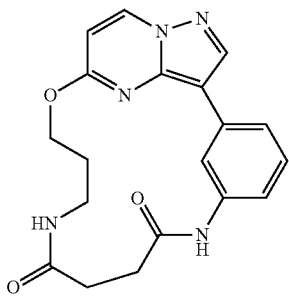 [SMILES: O=C1CCC(=O)Nc2cccc(c2)-c2cnn3ccc(nc23)OCCCN1]

A solution of intermediate 101 (1.062 g, 2.53 mmol) and N,N-diisopropylethylamine (1.291 ml, 7.59 mmol) in N,N-dimethylformamide (8 ml) was added drop wise over a period of 1 hour to a solution of 1-hydroxybenzotriazole hydrate (1.03 g, 7.59 mmol) and N,N'-diisopropylcarbodiimide (1.183 g, 7.59 mmol) in N,N-dimethylformamide (18 ml). The reaction mixture was stirred at room temperature for 15 hours. The solvent was removed under reduced pressure.

Yield: 76 mg of example 56 (8%)

LCMS method 2: MH$^+$=366, RT=2.158 min

Example 56

Preparation of Example 56

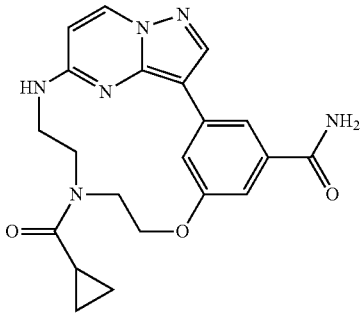 [SMILES: NC(=O)c1cc2cc(c1)-c1cnn3ccc(nc13)NCCN(C(=O)C1CC1)CCO2]

7-oxa-10,13,17,18,21-pentaazatetracyclo[12.5.2.1^{2,6}.0^{17,20}]docosa-1(20),2,4,6(22),14(21),15,18-heptaene-4-carboxamide hydrochloride was prepared according to similar synthetic procedures as described to obtain intermediate 7 using intermediate 4 for the coupling to the scaffold and (3-hydroxy-5-methoxycarbonyl-phenyl)boronic acid for the Suzuki coupling. The ring closure was effected after TBDMS deprotection using Mitsunobu conditions. The methyl ester on the phenyl ring was transformed into the carboxamide by saponification and subsequent amide formation using ammoniumchloride under HBTU coupling conditions. The unprotected 7-oxa-10,13,17,18,21-pentaazatetracyclo[12.5.2.1^{2,6}.0^{17,20}]docosa-1(20),2,4,6(22),14(21),15,18-heptaene-4-carboxamide hydrochloride was obtained after Boc deprotection under acidic conditions.

7-oxa-10,13,17,18,21-pentaazatetracyclo[12.5.2.1^{2,6}.0^{17,20}]docosa-1(20),2,4,6(22),14(21),15,18-heptaene-4-carboxamide hydrochloride (120 mg, 0.32 mmol) and triethylamine (111 µl, 0.80 mmol) were stirred in dry tetrahydrofuran (0.96 ml). Cyclopropanecarbonyl chloride (40 µl, 0.35 mmol) was added and the mixture was stirred at room temperature for 2 hours. More cyclopropanecarbonyl chloride (15 µl, 0.13 mmol) was added and the mixture was stirred at room temperature for 15 hours. The solvent was removed under reduced pressure. The residue was purified by reversed phase HPLC (HPLC method A). The product fractions were collected and the solvent was removed under reduced pressure.

Yield: 31 mg of example 56 (24%)

LCMS method 2: MH$^+$=407, RT=2.276 min

Example 57

Preparation of Example 57

Example 57 is prepared following general scheme 1.

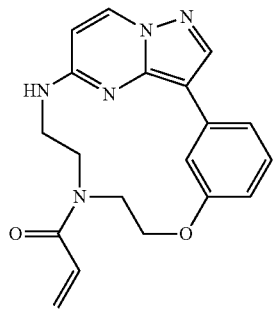 [SMILES: C=CC(=O)N1CCNc2ccn3ncc(c3n2)-c2cccc(c2)OCC1]

Example 57 was obtained as a side-product during the amide bond formation performed to obtain example 9.
Yield: 125 mg of example 57
LCMS method 2: MH+=350, RT=2.915 min Example 58

Preparation of Example 58

Example 58 is prepared following general scheme 1.

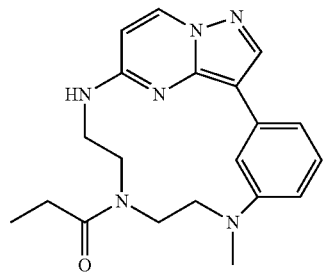 [SMILES: CCC(=O)N1CCNc2ccn3ncc(c3n2)-c2cccc(c2)N(C)CC1]

A mixture of example 14 (117 mg, 0.33 mmol) and potassium carbonate (68 mg, 0.49 mmol) in N,N-dimethylformamide (1 ml) was stirred at room temperature. Iodomethane (20 µl, 0.40 mmol) was added and the mixture was stirred at 60° C. for 19 hours. More potassium carbonate (68 mg, 0.49 mmol) and iodomethane (20 µl, 0.40 mmol) were added and the mixture was stirred at 60° C. for another 10 hours. The solvent was removed under reduced pressure and the product was purified by reversed phase HPLC (HPLC method A). The product fractions were collected and the solvent was evaporated.
Yield: 14 mg of example 58 (12%)
LCMS method 1: MH+=365, RT=3.060 min Example 59

Preparation of Example 59

Example 59 is prepared following general scheme 2.

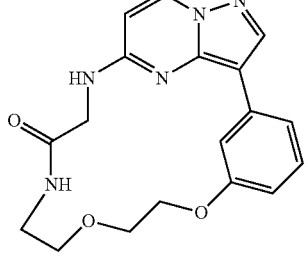

Example 59 was prepared according to the procedures applied to obtain example 44 except that for the Mitsunobu reaction tert-butyl N-[2-(2-hydroxyethoxy)ethyl]carbamate was being used. The ring closure was effected according to following procedure. A solution of 2-[[3-[3-[2-(2-aminoethoxy)ethoxy]phenyl]pyrazolo[1,5-a]pyrimidin-5-yl]amino] acetic acid (152 mg, 0.41 mmol) in N,N-dimethylformamide (28 ml) was added to a solution of O-(benzotriazol-1-yl)-N,N,N',N'-tetramethyluronium hexafluorophosphate (HBTU) (470 mg, 1.23 mmol) and N,N-diisopropylethylamine (795 µl, 6.015 mmol) in N,N-dimethylformamide (13 ml). The reaction mixture was stirred at room temperature for 2 hours. The solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.
Yield: 44 mg of example 59 (30%)
LCMS method 2: MH+=354, RT=2.218 min Example 60

Preparation of Example 60

Example 60 is prepared following general scheme 2.

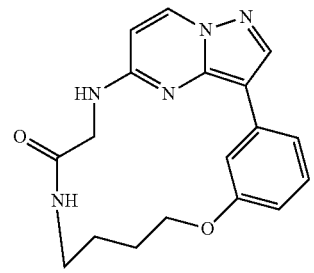 [SMILES: O=C1CNc2ccn3ncc(c3n2)-c2cccc(c2)OCCCCN1]

Example 60 was prepared according to similar procedures as the ones applied to obtain example 44 except that for the Mitsunobu reaction tert-butyl N-(4-hydroxybutyl)carbamate was being used. The ring closure was effected according to following procedure. A solution of 2-[[3-[3-(4-aminobutoxy)phenyl]pyrazolo[1,5-a]pyrimidin-5-yl]amino]acetic acid (131 mg, 0.37 mmol) in N,N-dimethylformamide (24 ml) was added to a solution of O-(benzotriazol-1-yl)-N,N,N',N'-tetramethyluronium hexafluorophosphate (HBTU) (420 mg, 1.11 mmol) and N,N-diisopropylethylamine (717 µl, 5.55 mmol) in N,N-dimethylformamide (13 ml). The reaction mixture was stirred at room temperature for 2 hours. The solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.
Yield: 24 mg of example 60 (19%)
LCMS method 2: MH+=338, RT=2.425 min Example 61

Preparation of Example 61

Example 61 is prepared following general scheme 3.

Preparation of Intermediate 102

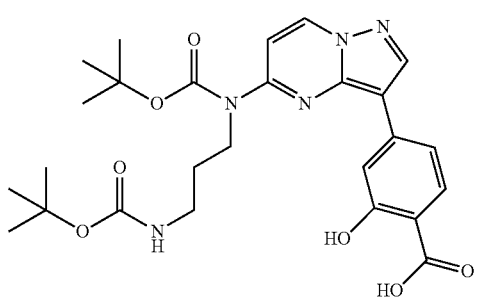 [SMILES: CC(C)(C)OC(=O)NCCCN(C(=O)OC(C)(C)C)c1ccn2ncc(-c3ccc(C(=O)O)c(O)c3)c2n1]

A mixture of 1,4-dioxane and water (3:1, 6.39 ml) was degassed by bubbling nitrogen gas through the mixture. Tert-butyl N-[3-[(3-bromopyrazolo[1,5-a]pyrimidin-5-yl)-tert-butoxycarbonyl-amino]propyl]carbamate (1.00 g, 2.13 mmol), (3-hydroxy-4-methoxycarbonyl-phenyl)boronic acid (710 mg, 2.56 mmol), tetrakis(triphenylphosphine)palladium(0) (46 mg, 0.04 mmol), 2-dicyclohexylphosphino-2',4',6'-triisopropylbiphenyl (Xphos) (81 mg, 0.17 mmol) and potassium phosphate tribasic (2.26 g, 5 eq.) were added and the mixture was stirred under nitrogen gas at 85° C. for 15 hours. The reaction mixture was cooled and the solvent was removed under reduced pressure. Ethyl acetate was added and the organic layer was washed with water. The organic layer was dried, filtered and the solvent was removed under reduced pressure. A mixture of the methylester and the carboxylic acid was obtained. The two compounds were separated by flash column chromatography over silica gel using heptane and ethyl acetate as eluents (gradient elution from 0% to 100% ethyl acetate). The product fractions were collected and the solvent was removed under reduced pressure. The carboxylic acid was used in the next step.

Yield: 735 g of intermediate 102 (65%)

Preparation of Intermediate 103

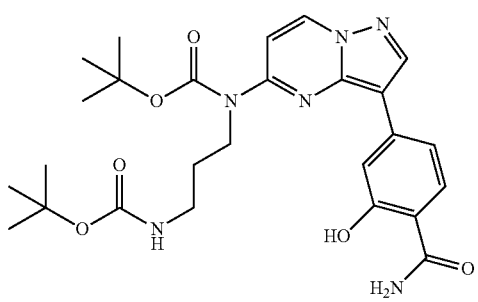 [SMILES: CC(C)(C)OC(=O)NCCCN(C(=O)OC(C)(C)C)c1ccn2ncc(-c3ccc(C(N)=O)c(O)c3)c2n1]

1-Hydroxybenzotriazole (243 mg, 1.80 mmol) was added to a solution of intermediate 102 (631 mg, 1.20 mmol), ammoniumchloride (100 mg, 1.80 mmol) and N,N'-diisopropylmethanediimine (280 µl, 1.80 mmol) in N,N-dimethylformamide (3.60 ml). The reaction mixture was stirred at room temperature for 16 hours. The reaction mixture was diluted with ethyl acetate and washed with a saturated aqueous sodium bicarbonate solution. The organic layer was dried, filtered and the solvent was removed under reduced pressure. The residue was purified by flash column chromatography over silica gel using heptane and ethyl acetate as eluents (gradient elution from 0% to 100% ethyl acetate). The product fractions were collected and the solvent was removed under reduced pressure.

Yield: 568 mg of example 103 (90%)

LCMS method 2: MH$^+$=427 (MW-Boc), RT=1.095 min

Preparation of Intermediate 104

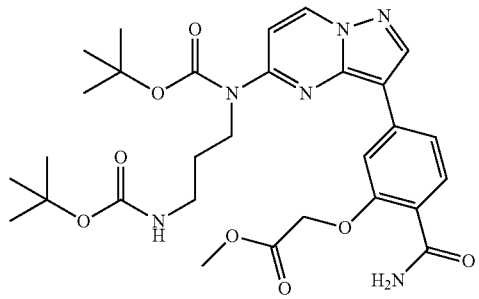 [SMILES: COC(=O)COc1cc(-c2cnn3ccc(N(CCCNC(=O)OC(C)(C)C)C(=O)OC(C)(C)C)nc23)ccc1C(N)=O]

A mixture of intermediate 103 (518 mg, 0.98 mmol), methyl 2-bromoacetate (140 mg, 1.47 mmol) and potassium carbonate (271 mg, 1.96 mmol) in N,N-dimethylformamide (2.94 ml) was stirred at 80° C. for 3 hours. Ethyl acetate was added and the organic layer was washed with water. The precipitate in the organic phase was filtered. The organic layer was dried, filtered and the solvent was removed under reduce pressure. Methanol was added and the precipitate was filtered and dried. The two precipitates were joined.

Yield: 0.337 mg of intermediate 104 (57%)

LCMS method 1: MH$^+$=599, RT=1.053 min

Preparation of Intermediate 105

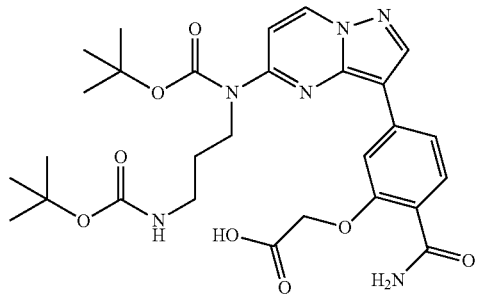 [SMILES: CC(C)(C)OC(=O)NCCCN(C(=O)OC(C)(C)C)c1ccn2ncc(-c3ccc(C(N)=O)c(OCC(=O)O)c3)c2n1]

Intermediate 104 (287 mg, 0.48 mmol) and lithium hydroxide monohydrate (40 mg, 0.96 mmol) were suspended in a mixture of tetrahydrofurane, methanol and water (2:2:1, 1.44 ml). The mixture was stirred at room temperature for 3 hours. The solvent was removed under reduced pressure and the product was used without further purification in the next step.

LCMS method 1: MH$^+$=585, RT=0.936 min

Preparation of Intermediate 106

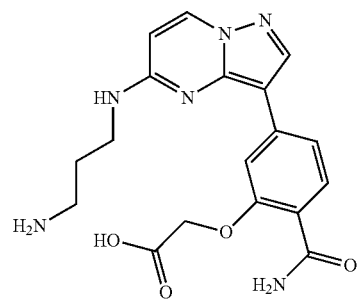 [SMILES: NCCCNc1ccn2ncc(-c3ccc(C(N)=O)c(OCC(=O)O)c3)c2n1]

Intermediate 105 (327 mg, 0.56 mmol) was stirred for 6 hours at room temperature in a 4N HCl solution in 1,4-dioxane (1.68 ml). The solvent was removed under reduced pressure. Toluene was added and removed under reduced pressure. The product was used without further purification in the next step.

LCMS method 1: MH$^+$=385, RT=0.286 min

Preparation of Example 61

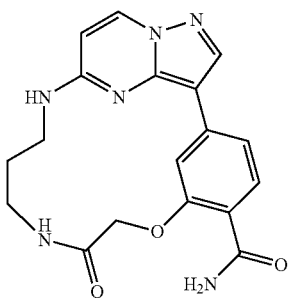 [SMILES: NC(=O)c1ccc2cc1OCC(=O)NCCCNc1ccn3ncc-2c3n1]

A solution of intermediate 106 (168 mg, 0.40 mmol) in N,N-dimethylformamide (12 ml) was added drop wise to a solution of O-(benzotriazol-1-yl)-N,N,N',N'-tetramethyluronium hexafluorophosphate (HBTU) (460 mg, 1.20 mmol) and N,N-diisopropylethylamine (1012 µl, 6.00 mmol) in N,N-dimethylformamide (28 ml). The reaction mixture was stirred at room temperature for 1 hour. The solvent was removed under reduced pressure. The residue was purified by reversed phase HPLC (HPLC method A). The product fractions were collected and the solvent was removed under reduced pressure.

Yield: 40 mg of example 61 (27%)
LCMS method 2: MH$^+$=367, RT=1.771 min

Example 62

Preparation of Example 62

Example 62 is prepared following general scheme 4.

Preparation of Intermediate 107

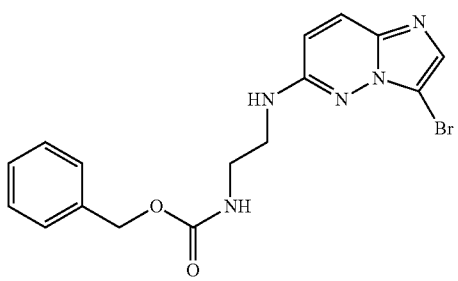 [SMILES: O=C(NCCNc1ccc2ncc(Br)n2n1)OCc1ccccc1]

A mixture of 3-bromo-6-chloro-imidazo[2,1-f]pyridazine (3.00 g, 12.90 mmol), benzyl N-(2-aminoethyl)carbamate hydrochloride (11.90 g, 51.60 mmol) and N,N-diisopropylethylamine (13.52 ml, 77.40 mmol) in n-butanol (38.7 ml) was heated for 72 hours at 150° C. in a sealed tube. The reaction mixture was cooled and ethyl acetate was added. The organic layer was washed with a 1N aqueous HCl solution, water and brine. The organic layer was dried, filtered and the solvent was removed under reduced pressure. The residue was purified by flash column chromatography over silica gel using dichloromethane and methanol as eluents (gradient elution from 0% to 3% methanol). The product fractions were collected and the solvent was evaporated.

Yield: 2.70 g of intermediate 107 (54%)
LCMS method 1: MH$^+$=391, RT=0.650 min

Preparation of Intermediate 108

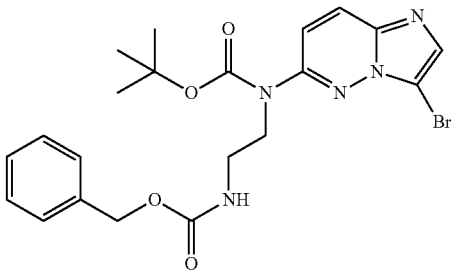 [SMILES: CC(C)(C)OC(=O)N(CCNC(=O)OCc1ccccc1)c1ccc2ncc(Br)n2n1]

Tert-butoxycarbonyl anhydride (760 mg, 3.48 mmol) was added to a solution of intermediate 107 (1.13 g, 2.90 mmol) in tetrahydrofuran (8.70 ml). The reaction mixture was stirred at room temperature for 3 days. The solvent was removed under reduced pressure. The residue was purified by flash column chromatography over silica gel using heptane and ethyl acetate as eluents (gradient elution from 0% to 50% ethyl acetate). The product fractions were collected and the solvent was removed under reduced pressure.

Yield: 840 mg of intermediate 108 (59%)
LCMS method 2: MH$^+$=490, RT=1.062 min

Preparation of Intermediate 109

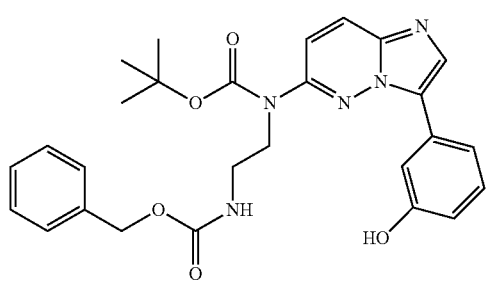 [SMILES: CC(C)(C)OC(=O)N(CCNC(=O)OCc1ccccc1)c1ccc2ncc(-c3cccc(O)c3)n2n1]

Intermediate 108 (840 mg, 1.71 mmol), (3-hydroxyphenyl)boronic acid (350 mg, 1.50 mmol), 2-dicyclohexylphosphino-2',4',6'-triisopropylbiphenyl (Xphos) (67 mg, 0.14 mmol) and potassium phosphate tribasic (1.80 g, 5 eq.) were dissolved in a mixture of 1,4-dioxane and water (3:1, 5.13 ml) and the mixture was degassed by bubbling nitrogen gas through. Tetrakis(triphenylphosphine)palladium(0) (81 mg, 0.07 mmol) was added and the mixture was stirred under nitrogen gas at 70° C. for 18 hours. The reaction mixture was cooled and ethyl acetate was added. The organic layer was washed with water and brine. The organic layer was dried, filtered and the solvent was removed under reduced pressure. The product was triturated with dichloromethane, filtered and dried under reduced pressure. The product was purified by flash column chromatography over silica gel using dichloromethane and methanol as eluents (gradient elution from 0% to 2% methanol). The product fractions were collected and the solvent was removed under reduced pressure.

Yield: 740 g of intermediate 109 (86%)
LCMS method 1: $MH^+$=504, RT=0.948 min

Preparation of Intermediate 110

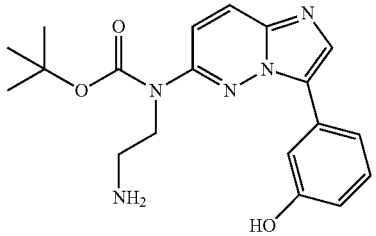 [SMILES: CC(C)(C)OC(=O)N(CCN)c1ccc2ncc(-c3cccc(O)c3)n2n1]

Intermediate 109 was dissolved in a mixture of methanol and tetrahydrofurane (3:1, 30 ml), degassed by bubbling nitrogen gas through the mixture and palladium (160 mg, 1.47 mmol) was added. The reaction mixture was stirred at room temperature under hydrogen atmosphere for 7 hours. The reaction mixture was filtered over decalite and washed with methanol. The solvent was removed under reduced pressure. The product was without further purification used in the next step.

LCMS method 1: $MH^+$=370, RT=0.451 min

Preparation of Intermediate 111

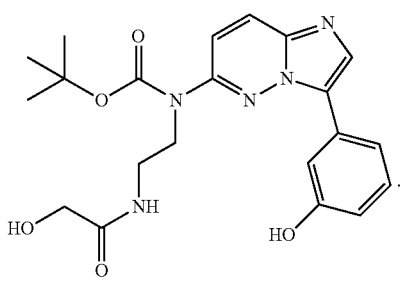 [SMILES: CC(C)(C)OC(=O)N(CCNC(=O)CO)c1ccc2ncc(-c3cccc(O)c3)n2n1]

Intermediate 110 (460 mg, 1.25 mmol), 2-hydroxyacetic acid (100 mg, 1.38 mmol) and N,N-diisopropylethylamine (328 µl, 1.88 mmol) were dissolved in N,N-dimethylformamide (3.75 ml). O-(Benzotriazol-1-yl)-N,N,N',N'-tetramethyluronium hexafluorophosphate (HBTU) (569 mg, 1.38 mmol) was added and the reaction mixture was stirred at room temperature for 4 hours. The reaction mixture was poured into water and the water layer was extracted with ethyl acetate. The organic layer was washed with water and brine, dried, filtered and the solvent was removed under reduced pressure. The product was purified by flash column chromatography over silica gel using dichloromethane and methanol as eluents (gradient elution from 0% to 5% methanol). The product fractions were collected and the solvent was removed under reduced pressure.

Yield: 150 mg of intermediate 111 (28%)
LCMS method 1: $MH^+$=428, RT=0.586 min

Preparation of Intermediate 112

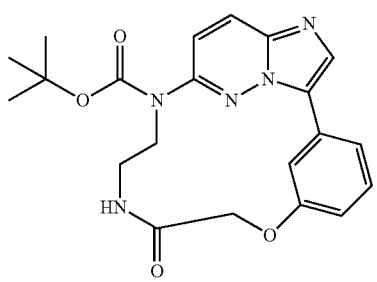 [SMILES: CC(C)(C)OC(=O)N1CCNC(=O)COc2cccc(c2)-c2cnc3ccc1nn23]

All solutions were degassed by bubbling nitrogen gas through the solutions. A solution of intermediate 111 (150 mg, 0.35 mmol) in 2-methyltetrahydrofuran (20 ml/mmol) and a solution of diisopropyl azodicarboxylate (210 µl, 1.05 mmol) in toluene (20 ml/mmol) were added simultaneously over a period of 2 hours to a solution of triphenylphosphine (275 mg, 1.05 mmol) in toluene (75 ml/mmol of intermediate 111) at 90° C. The mixture was stirred at 90° C. for 1 hour. More triphenylphosphine (275 mg, 1.05 mmol) was added and diisopropyl azodicarboxylate (210 µl, 1.05 mmol) was added drop wise. The mixture was stirred at 90° C. for 2 hours. The reaction mixture was cooled and the solvent was removed under reduced pressure. The residue was purified by reversed phase HPLC (HPLC method A). The product fractions were collected and the solvent was evaporated.

Yield: 15 mg of intermediate 112 (10%)
LCMS method 1: $MH^+$=410, RT=2.432 min

Preparation of Example 62

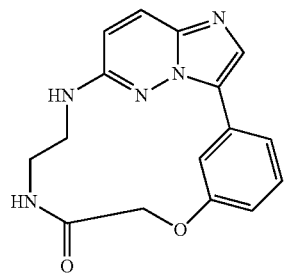 [SMILES: O=C1COc2cccc(c2)-c2cnc3ccc(nn23)NCCN1]

Intermediate 112 (15 mg, 0.04 mmol) was stirred for 3 hours at room temperature in a 4N HCl solution in 1,4-dioxane (200 µl). The solvent was removed under reduced pressure. Diethyl ether was added and the solvent was removed under reduced pressure.

Yield: 10 mg of example 62 (81%)
LCMS method 2: $MH^+$=310, RT=1.168 min

Example 63

Preparation of Example 63

Example 63 is prepared following general scheme 2.

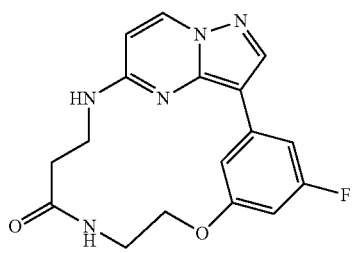 [SMILES: O=C1CCNc2ccn3ncc(c3n2)-c2cc(F)cc(c2)OCCN1]

Example 63 was prepared according to similar procedures as the ones applied to obtain example 3 except that for the Suzuki coupling (3-fluoro-5-hydroxy-phenyl)boronic acid was being used. The ring closure was effected according to following procedure. A solution of 3-[[3-[3-(2-aminoethoxy)-5-fluoro-phenyl]pyrazolo[1,5-a]pyrimidin-5-yl]amino]propanoic acid (27 mg, 0.08 mmol) in N,N-dimethylformamide (0.9 ml) was added drop wise to a solution of O-(benzotriazol-1-yl)-N,N,N',N'-tetramethyluronium hexafluorophosphate (HBTU) (30 mg, 0.08 mmol) and N,N-diisopropylethylamine (204 μl, 1.20 mmol) in N,N-dimethylformamide (1.9 ml). The reaction mixture was stirred at room temperature for 1 hour. The solvent was removed under reduced pressure. The residue was purified by reversed phase HPLC (HPLC method A). The product fractions were collected and the solvent was removed under reduced pressure.

Yield: 5 mg of example 63 (18%)
LCMS method 2: MH$^+$=342, RT=2.556 min

Example 64

Preparation of Example 64

Example 64 is prepared following general scheme 1.

Preparation of Intermediate 113

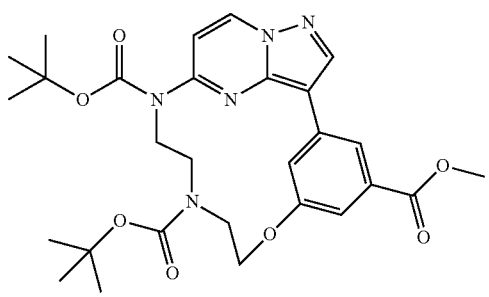 [SMILES: COC(=O)c1cc2cc(c1)-c1cnn3ccc(nc13)N(C(=O)OC(C)(C)C)CCN(C(=O)OC(C)(C)C)CCO2]

Intermediate 113 is prepared according to similar procedures that have been applied to obtain 10,13-di-tert-butyl 7-oxa-10,13,17,18,21-pentaazatetracyclo[12.5.2.1^{2,6}.0^{17,20}]docosa-1(20),2(22),3,5,14(21),15,18-heptaene-10,13-dicarboxylate except that (3-hydroxy-5-methoxycarbonyl-phenyl)boronic acid was used for the Suzuki coupling. The ring closure was effected according to following procedure. A solution of methyl 3-[5-[tert-butoxycarbonyl-[2-(tert-butoxycarbonyl(2-hydroxyethyl)amino)ethyl]amino]pyrazolo[1,5-a]pyrimidin-3-yl]-5-hydroxy-benzoate (8.946 g, 15.65 mmol) in 2-methyltetrahydrofuran (20 ml/mmol) and a solution of diisopropyl azodicarboxylate (9.31 ml, 46.95 mmol) in toluene (20 ml/mmol) were added simultaneously over a period of 3 hours to a solution of triphenylphosphine (12.315 g, 46.95 mmol) in toluene (75 ml/mmol) at 90° C. The mixture was stirred at 90° C. for 30 minutes. The reaction mixture was cooled and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure.

Yield: 7.698 mg of intermediate 113 (89%)
LCMS method 1: MH$^+$=554, RT=1.470 min Preparation of Intermediate 114

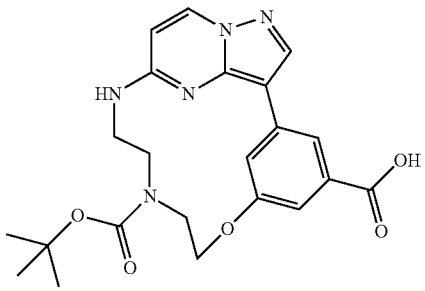 [SMILES: CC(C)(C)OC(=O)N1CCNc2ccn3ncc(c3n2)-c2cc(cc(C(=O)O)c2)OCC1]

Intermediate 113 (2.00 g, 3.61 mmol) and lithium hydroxide monohydrate (450 mg, 10.83 mmol) in a mixture tetrahydrofuran/methanol/water (2:2:1, 40 ml) were stirred at 50° C. for 15 hours. The solvent was removed under reduced pressure. Water was added and 1N HCl was added to acidify the solution to pH 5-6. The precipitate was filtered, washed with methanol and dried under reduced pressure. The residue was used in the next step without further purification.

LCMS method 1: MH$^+$=440, RT=0.860 min

Preparation of Intermediate 115

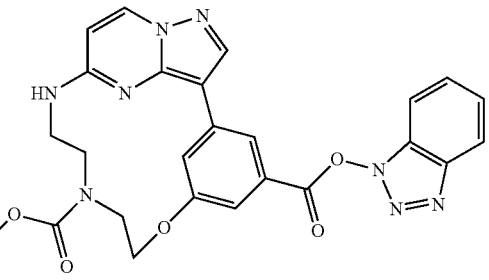

1-Hydroxybenzotriazole (600 mg, 3.84 mmol) was added to a solution of intermediate 114 (1.123 g, 2.56 mmol) in dry tetrahydrofurane (7.68 ml). N,N'-diisopropylmethanediimine (598 μl, 3.84 mmol) was added and the reaction mixture was stirred at room temperature for 3 hours. Water was added and the aqueous layer was extracted with ethyl acetate. The organic layer was dried, filtered and the solvent was removed Preparation of Intermediate 116

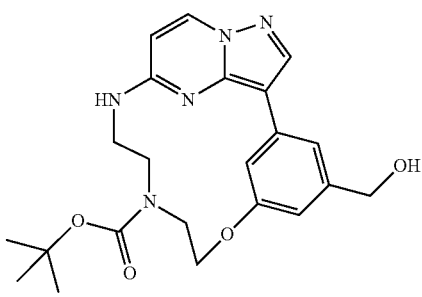 [SMILES: CC(C)(C)OC(=O)N1CCNc2ccn3ncc(c3n2)-c2cc(CO)cc(c2)OCC1]

Sodium borohydride (100 mg, 2.56 mmol) was added at 0° C. to a suspension of intermediate 115 (1.42 g, 2.56 mmol) in dry tetrahydrofuran (7.68 ml). The mixture was stirred at room temperature for 3 hours. More sodium borohydride (20 mg, 0.512 mmol) was added and the mixture was stirred at room temperature for 1 more hour. Water was added and the product was extracted with ethyl acetate. The organic layer was dried, filtered and the solvent was removed under reduced pressure. The residue was purified by flash column chromatography over silica gel using heptane and ethyl acetate as eluents (gradient elution from 0% to 100% ethyl acetate). The product fractions were collected and the solvent was removed under reduced pressure.

Yield: 357 mg of intermediate 116 (33%)
LCMS method 1: MH$^+$=426, RT=0.792 min

Preparation of Intermediate 117

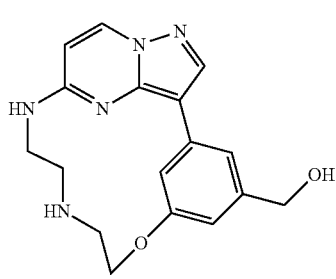 [SMILES: OCc1cc2cc(c1)-c1cnn3ccc(nc13)NCCNCCO2]

Intermediate 116 (482 mg, 1.13 mmol) was stirred in 4N HCl in 1,4-dioxane (4 ml/mmol) at room temperature for 3 hours. The solvent was removed under reduced pressure. Toluene was added and removed under reduced pressure. The product was without further purification used in the next step.

LCMS method 2: MH$^+$=362, RT=1.391 min

Preparation of Intermediate 118

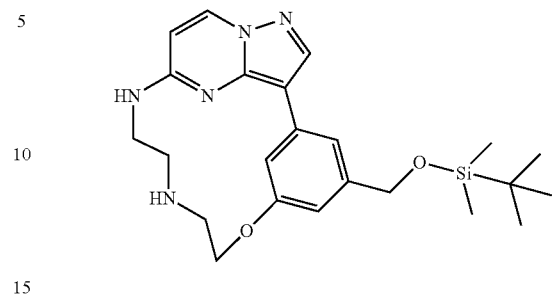

Tert-butyldimethylsilyl chloride (180 mg, 1.19 mmol) was added portion wise to a solution of intermediate 117 (358 mg, 0.99 mmol) and triethylamine (441 µl, 3.17 mmol) in N,N-dimethylformamide (2.97 ml). The mixture was stirred at room temperature for 16 hours. More tert-butyldimethylsilyl chloride (180 mg, 1.19 mmol) and triethylamine (441 µl, 3.17 mmol) was added. The mixture was stirred at room temperature for another 17 hours. The reaction mixture was diluted with ethyl acetate. The organic layer was dried, filtered and the solvent was removed under reduced pressure. The residue was purified by flash column chromatography using dichloromethane and methanol as eluents (gradient elution from 0% to 10% methanol). The product fractions were collected and the solvent was evaporated.

Yield: 356 mg of intermediate 118 (82%)
LCMS method 1: MH$^+$=440, RT=0.823 min

Preparation of Intermediate 119

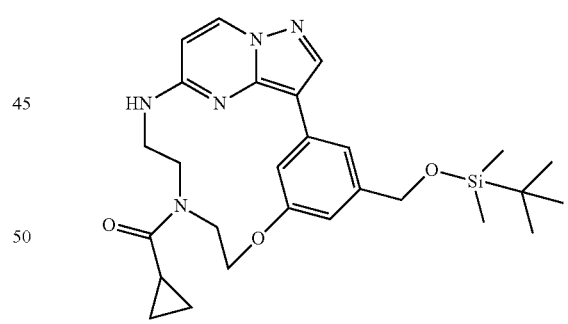

A mixture of intermediate 118 (356 mg, 0.81 mmol) and triethylamine (170 µl, 1.22 mmol) in dry tetrahydrofuran (2.43 ml) was stirred and cyclopropanecarbonyl chloride (80 µl, 0.89 mmol) was added. The mixture was stirred at room temperature for 2 hours. The solvent was removed under reduced pressure and the residue was triturated in methanol, filtered and dried under reduced pressure.

Yield: 343 mg of intermediate 119 (83%)
LCMS method 2: MH$^+$=508, RT=4.608 min

Preparation of Example 64

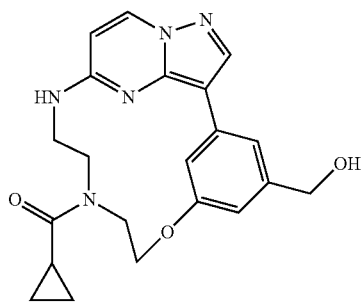 [SMILES: O=C(C1CC1)N1CCNc2ccn3ncc(c3n2)-c2cc(CO)cc(c2)OCC1]

A solution of tetrabutyl ammonium fluoride (1M solution in tetrahydrofuran, 0.48 ml, 0.48 mmol) and intermediate 119 (224 mg, 0.44 mmol) in tetrahydrofuran (1.32 ml) was stirred at room temperature for 2 hours. The solvent was removed under reduced pressure. The residue was triturated in methanol, filtered and dried under reduced pressure.

Yield: 158 mg of example 64 (91%)

LCMS method 2: $MH^+$=394, RT=2.426 min

Example 65

Preparation of Example 65

Example 65 is prepared following general scheme 1.

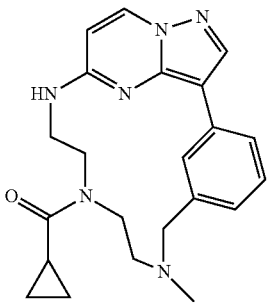 [SMILES: CN1CCN(C(=O)C2CC2)CCNc2ccn3ncc(c3n2)-c2cccc(c2)C1]

A mixture of example 38 (52 mg, 0.14 mmol) and formaldehyde (37% solution, 5.4 µl, 1.17 mmol) in 1,2-dichloroethane (0.42 ml) was stirred at room temperature for 1 hour. Sodium triacetoxyborohydride (59 mg, 0.28 mmol) was added and the mixture was stirred at room temperature for 3 hours. The solvent was removed under reduced pressure. A saturated aqueous sodium bicarbonate solution was added and the product was extracted with a mixture of dichloromethane and methanol (9:1). The organic layer was dried, filtered and the solvent was removed under reduce pressure. The residue was purified by flash column chromatography over silica gel using dichloromethane and methanol as eluents (gradient elution from 0% to 10% methanol). The product fractions were collected and the solvent was removed under reduced pressure.

Yield: 28 mg of example 65 (51%)

LCMS method 1: $MH^+$=391, RT=0.314 min

Example 66

Preparation of Example 66

Example 66 is prepared following general scheme 2.

Preparation of Intermediate 120

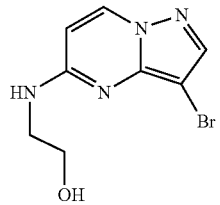 [SMILES: OCCNc1ccn2ncc(Br)c2n1]

2-Aminoethanol (570 µl, 9.46 mmol) was added to a solution of 3-bromo-5-chloro-pyrazolo[1,5-a]pyrimidine (2.00 g, 8.60 mmol) and N,N-diisopropylethylamine (1.803 ml, 10.32 mmol) in acetonitrile (25.80 ml). The reaction mixture was refluxed overnight. The solvent was removed under reduced pressure and the residue was purified by flash column chromatography over silica gel using dichloromethane and methanol as eluents. The product fractions were collected and the solvent was evaporated.

Yield: 2.10 g of intermediate 120 (95%)

LCMS method 1: $MH^+$=258, RT=0.386 min

Preparation of Intermediate 121

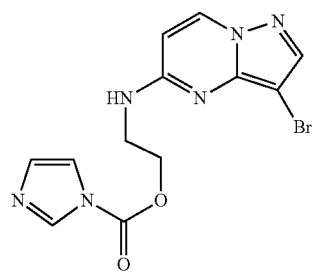 [SMILES: O=C(OCCNc1ccn2ncc(Br)c2n1)n1ccnc1]

To a solution of intermediate 120 (2.10 g, 8.17 mmol) in dichloromethane (24.51 ml) was added di(imidazol-1-yl)methanone (1.99 g, 12.25 mmol) and the mixture was stirred at room temperature for 1 hour. The precipitate was filtered, washed with dichloromethane and dried under reduced pressure. The product was without further purification used in the next step.

Yield: 2.26 g of intermediate 121 (79%)

Preparation of Intermediate 122

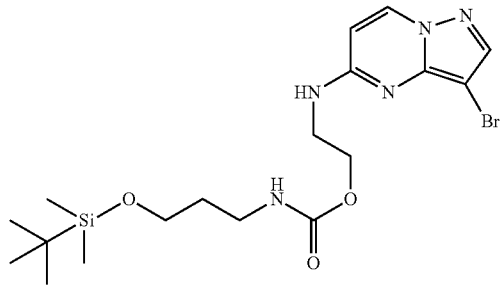 [SMILES: CC(C)(C)[Si](C)(C)OCCCNC(=O)OCCNc1ccn2ncc(Br)c2n1]

3-(Tert-butyl(dimethyl)silyl)oxypropan-1-amine (1.08 g, 5.70 mmol) was added to a suspension of intermediate 121 (1.00 g, 2.85 mmol), triethylamine (317 µl, 3.13 mmol) and N,N-dimethylpyridin-4-amine (17 mg, 0.14 mmol) in tetrahydrofurane (8.55 ml). The reaction mixture was stirred at room temperature overnight. The mixture was diluted with ethyl acetate and the organic layer was washed with water and brine. The organic layer was dried, filtered and the solvent was removed under reduced pressure. The residue was purified by flash column chromatography over silica gel using dichloromethane and methanol as eluents. The product fractions were collected and the solvent was evaporated.

Yield: 1.16 g of intermediate 122 (86%)
LCMS method 1: MH$^+$=472, RT=1.156 min

Preparation of Intermediate 123

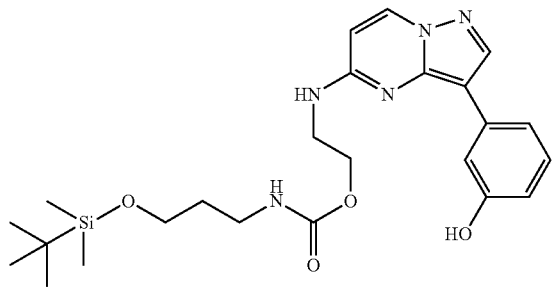 [SMILES: CC(C)(C)[Si](C)(C)OCCCNC(=O)OCCNc1ccn2ncc(-c3cccc(O)c3)c2n1]

A mixture of 1,4-dioxane and water (3:1, 25 ml) was degassed by bubbling nitrogen gas through the mixture. Intermediate 122 (1.16 g, 2.46 mmol), (3-hydroxyphenyl)boronic acid (440 mg, 3.20 mmol), tetrakis(triphenylphosphine)palladium(0) (58 mg, 0.05 mmol), 2-dicyclohexyl phosphino-2',4',6'-triisopropylbiphenyl (Xphos) (95 mg, 0.20 mmol) and potassium phosphate tribasic (2.60 g, 5 eq.) were added and the mixture was stirred under nitrogen gas at 80° C. for 2 hours. The reaction mixture was cooled, diluted with ethyl acetate and the organic layer was washed with brine. The organic layer was dried, filtered and the solvent was removed under reduced pressure. The residue was purified by flash column chromatography over silica gel using dichloromethane and methanol as eluents. The product fractions were collected and the solvent was evaporated.

Yield: 1.10 g of intermediate 123 (92%)
LCMS method 1: MH$^+$=486, RT=1.118 min

Preparation of Intermediate 124

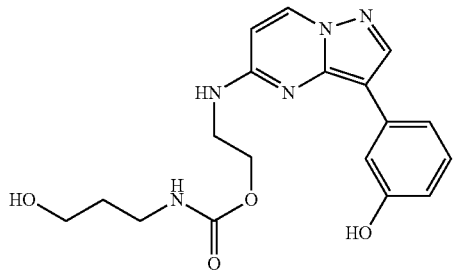 [SMILES: O=C(NCCCO)OCCNc1ccn2ncc(-c3cccc(O)c3)c2n1]

Tetrabutyl ammonium fluoride (1M solution in tetrahydrofuran, 3.40 ml, 3.39 mmol) was added to a solution of intermediate 123 (1.10 g, 2.26 mmol) in tetrahydrofuran (6.78 ml) and the mixture was stirred at room temperature overnight. The solvent was removed under reduced pressure. The residue was diluted with ethyl acetate and washed with water (3×) and brine. The organic layer was dried, filtered and the solvent was removed under reduced pressure. The residue was used in the next step without further purification.

LCMS method 1: MH$^+$=372, RT=0.459 min

Preparation of Example 66

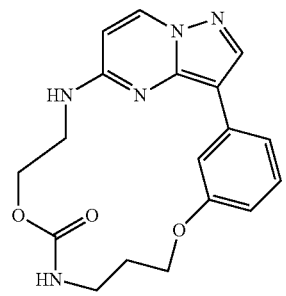 [SMILES: O=C1NCCCOc2cccc(c2)-c2cnn3ccc(nc23)NCCO1]

A solution of intermediate 124 (408 mg, 1.10 mmol) in 2-methyltetrahydrofuran (20 ml/mmol) and a solution of diisopropyl azodicarboxylate (650 µl, 3.30 mmol) in toluene (20 ml/mmol) were added simultaneously over a period of 2 hours to a solution of triphenylphosphine (866 mg, 3.30 mmol) in toluene (75 ml/mmol of intermediate 124) at 90° C. The mixture was stirred at 90° C. for 1 hour. The reaction mixture was cooled and the solvent was removed under reduced pressure. The residue was purified by flash column chromatography over silica gel using dichloromethane and methanol as eluents. The product fractions were collected and the solvent was evaporated. The product was triturated with methanol, filtered and dried under reduced pressure.

LCMS method 2: MH$^+$=354, RT=2.785 min

Example 67

Preparation of Example 67

Example 67 is prepared following general scheme 2.

Preparation of Intermediate 125

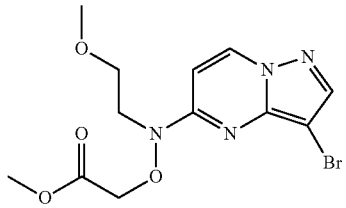 [SMILES: COCCN(OCC(=O)OC)c1ccn2ncc(Br)c2n1]

A mixture of 3-bromo-5-chloro-pyrazolo[1,5-a]pyrimidine (1.55 g, 6.67 mmol), methyl 3-(2-methoxyethylamino)propanoate (1.08 g, 6.67 mmol) and N,N-diisopropylethylamine (1.394 ml, 8.00 mmol) in acetonitrile (20 ml) was refluxed overnight. The reaction mixture was cooled, the solvent was removed under reduced pressure and ethyl acetate was added. The organic layer was washed with water and brine. The organic layer was dried, filtered and the solvent was removed under reduced pressure. The residue was purified by flash column chromatography over silica gel using heptane and ethyl acetate as eluents (gradient elution from 5% to 70% ethyl acetate). The product fractions were collected and the solvent was evaporated.

Yield: 1.05 g of intermediate 125 (44%)
LCMS method 1: MH$^+$=358, RT=1.072 min

Preparation of Intermediate 126

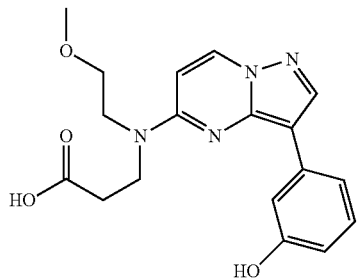 [SMILES: COCCN(CCC(=O)O)c1ccn2ncc(-c3cccc(O)c3)c2n1]

A mixture of 1,4-dioxane and water (3:1, 7.92 ml) was degassed by bubbling nitrogen gas through. Intermediate 125 (943 mg, 2.64 mmol), (3-hydroxyphenyl)boronic acid (470 mg, 3.43 mmol), 2-dicyclohexylphosphino-2',4',6'-triisopropylbiphenyl (Xphos) (100 mg, 0.21 mmol), tetrakis(triphenylphosphine)palladium(0) (58 mg, 0.05 mmol) and potassium phosphate tribasic (3.40 g, 5 eq.) The reaction mixture was stirred under nitrogen atmosphere at 70° C. overnight. The reaction mixture was cooled and ethyl acetate was added. The organic layer was washed with water and brine. The organic layer was dried, filtered and the solvent was removed under reduced pressure. The residue was purified by flash column chromatography over silica gel using dichloromethane and methanol as eluents (gradient elution from 0% to 10% methanol). The product fractions were collected and the solvent was removed under reduced pressure. The carboxylic acid was obtained.

Yield: 484 mg of intermediate 126 (51%)
LCMS method 1: MH$^+$=357, RT=0.600 min

Preparation of Intermediate 127

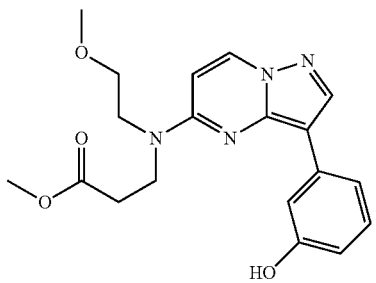 [SMILES: COCCN(CCC(=O)OC)c1ccn2ncc(-c3cccc(O)c3)c2n1]

Sulfuric acid (80 µl, 1.51 mmol) was added drop wise at 0° C. to a solution of intermediate 126 (538 mg, 1.51 mmol) in methanol (4.53 ml). The reaction mixture was refluxed for 4 hours. The solvent was removed under reduced pressure. The residue was purified by flash column chromatography over silica gel using dichloromethane and methanol as eluents (gradient elution from 0% to 5% methanol). The product fractions were collected and the solvent was removed under reduced pressure. The carboxylic acid was obtained.

Yield: 338 mg of intermediate 127 (60%)
LCMS method 2: MH$^+$=371, RT=2.839 min

Preparation of Intermediate 128

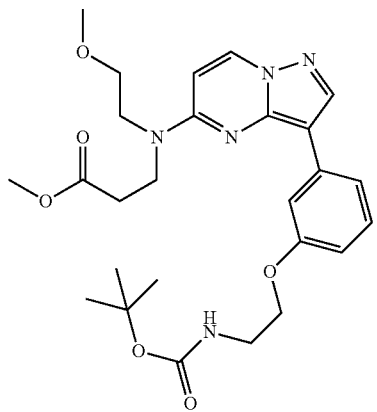 [SMILES: COCCN(CCC(=O)OC)c1ccn2ncc(-c3cccc(OCCNC(=O)OC(C)(C)C)c3)c2n1]

Intermediate 127 (271 mg, 0.73 mmol), tert-butyl N-(2-hydroxyethyl)carbamate (160 mg, 1.02 mmol) and triphenylphosphine (365 mg, 1.39 mmol) were suspended in dry tetrahydrofurane (5.84 ml). Diisopropyl azodicarboxylate (274 µl, 1.39 mmol) was added and the reaction mixture was stirred at room temperature for 3 hours. More tert-butyl N-(2-hydroxyethyl)carbamate (160 mg, 1.02 mmol), triphenylphosphine (365 mg, 1.39 mmol) and diisopropyl azodicarboxylate (274 µl, 1.39 mmol) were added the reaction mixture was stirred at room temperature for 2 days. The solvent was removed under reduced pressure and the residue was purified by flash column chromatography over silica gel using heptane and ethyl acetate as eluents (gradient elution from 10% to 90% ethyl acetate). The product fractions were collected and the solvent was evaporated.

Yield: 211 mg of intermediate 128 (56%)
LCMS method 1: MH$^+$=514, RT=1.873 min

Preparation of Intermediate 129

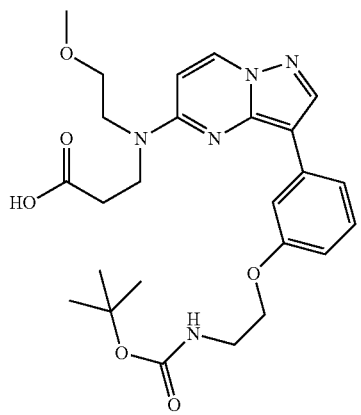 [SMILES: COCCN(CCC(=O)O)c1ccn2ncc(-c3cccc(OCCNC(=O)OC(C)(C)C)c3)c2n1]

Lithium hydroxide monohydrate (10 mg, 0.35 mmol) was added to a solution of intermediate 128 (178 mg, 0.35 mmol) in a mixture tetrahydrofuran/methanol/water (2:2:1, 1.05 ml) and the reaction mixture was stirred at room temperature overnight. The solvent was removed under reduced pressure. Toluene was added and evaporated twice. The residue was used in the next step without further purification.

LCMS method 1: $MH^+=500$, RT=0.890 min

Preparation of Intermediate 130

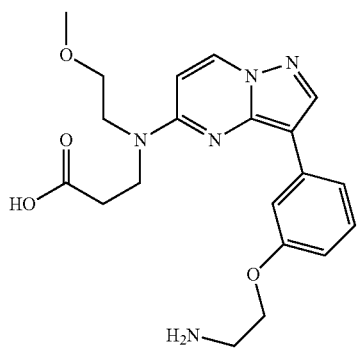 [SMILES: COCCN(CCC(=O)O)c1ccn2ncc(-c3cccc(OCCN)c3)c2n1]

Intermediate 129 (175 mg, 0.35 mmol) was stirred in 4N HCl in 1,4-dioxane (4 ml/mmol) at room temperature overnight. The solvent was removed under reduced pressure. Toluene was added and removed under reduced pressure. The product was without further purification used in the next step.

LCMS method 1: $MH^+=400$, RT=0.471 min

Preparation of Example 67

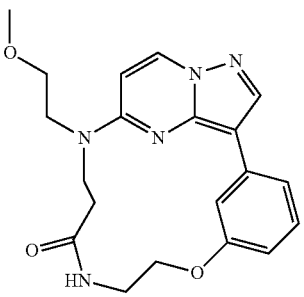 [SMILES: COCCN1CCC(=O)NCCOc2cccc(c2)-c2cnn3ccc1nc23]

A solution of intermediate 130 (140 mg, 0.35 mmol) in N,N-dimethylformamide (23 ml) was added drop wise over a period of 30 minutes to a solution of O-(benzotriazol-1-yl)-N,N,N',N'-tetramethyluronium hexafluorophosphate (HBTU) (400 mg, 1.05 mmol) and N,N-diisopropylethylamine (917 µl, 5.25 mmol) in N,N-dimethylformamide (12 ml). The reaction was stirred at room temperature for 1 hour. The solvent was removed under reduced pressure. The residue was purified by flash column chromatography over silica gel using dichloromethane and methanol as eluents (gradient elution from 0% to 5% methanol). The product fractions were collected and the solvent was removed under reduced pressure. The product was further purified by reversed phase HPLC (HPLC method A). The product fractions were collected and the solvent was evaporated.

Yield: 15 mg of example 67 (11%)

LCMS method 2: $MH^+=382$, RT=2.548 min

The compounds in Table 1 were prepared by analogy to one of the procedures described above.

TABLE 1

| | |
|---|---|
| [structure] | Compound 1, Example 1 |
| [structure] | Compound 2, Example 2 |
| [structure] | Compound 3, Example 3 |
| [structure] | Compound 4, Example 4 |
| [structure] | Compound 5, Example 5 |

TABLE 1-continued
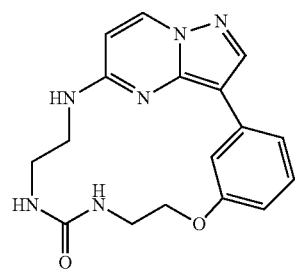 [SMILES: O=C1NCCNc2ccn3ncc(c3n2)-c2cccc(c2)OCCN1]
Compound 6, Example 6
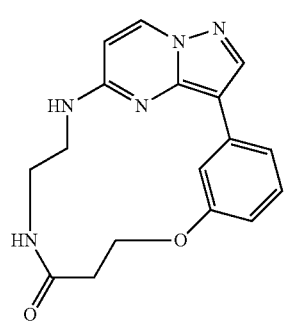 [SMILES: O=C1CCOc2cccc(c2)-c2cnn3ccc(nc23)NCCN1]
Compound 7, Example 7
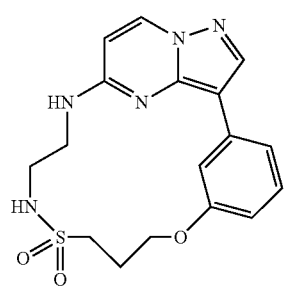 [SMILES: O=S1(=O)CCCOc2cccc(c2)-c2cnn3ccc(nc23)NCCN1]
Compound 8, Example 8
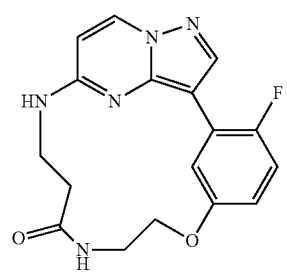 [SMILES: O=C1CCNc2ccn3ncc(c3n2)-c2cc(ccc2F)OCCN1]
Compound 9
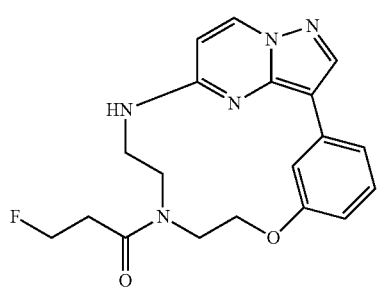 [SMILES: O=C(CCF)N1CCNc2ccn3ncc(c3n2)-c2cccc(c2)OCC1]
Compound 10, Example 9
TABLE 1-continued
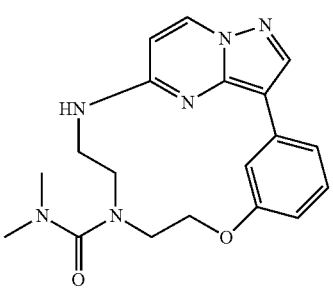 [SMILES: CN(C)C(=O)N1CCNc2ccn3ncc(c3n2)-c2cccc(c2)OCC1]
Compound 11, Example 10
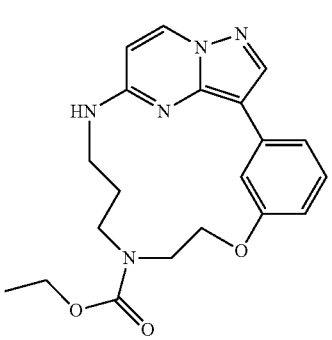 [SMILES: CCOC(=O)N1CCCNc2ccn3ncc(c3n2)-c2cccc(c2)OCC1]
Compound 12, Example 11
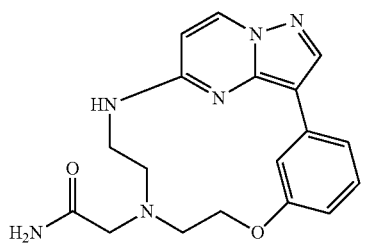 [SMILES: NC(=O)CN1CCNc2ccn3ncc(c3n2)-c2cccc(c2)OCC1]
Compound 13, Example 12
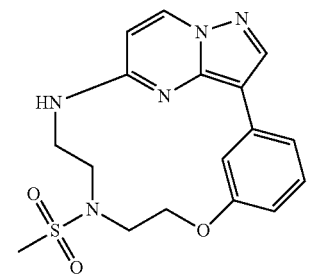 [SMILES: CS(=O)(=O)N1CCNc2ccn3ncc(c3n2)-c2cccc(c2)OCC1]
Compound 14, Example 13
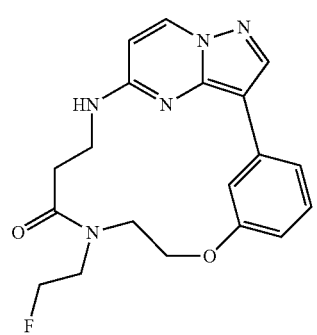 [SMILES: O=C1CCNc2ccn3ncc(c3n2)-c2cccc(c2)OCCN1CCF]
Compound 15

TABLE 1-continued
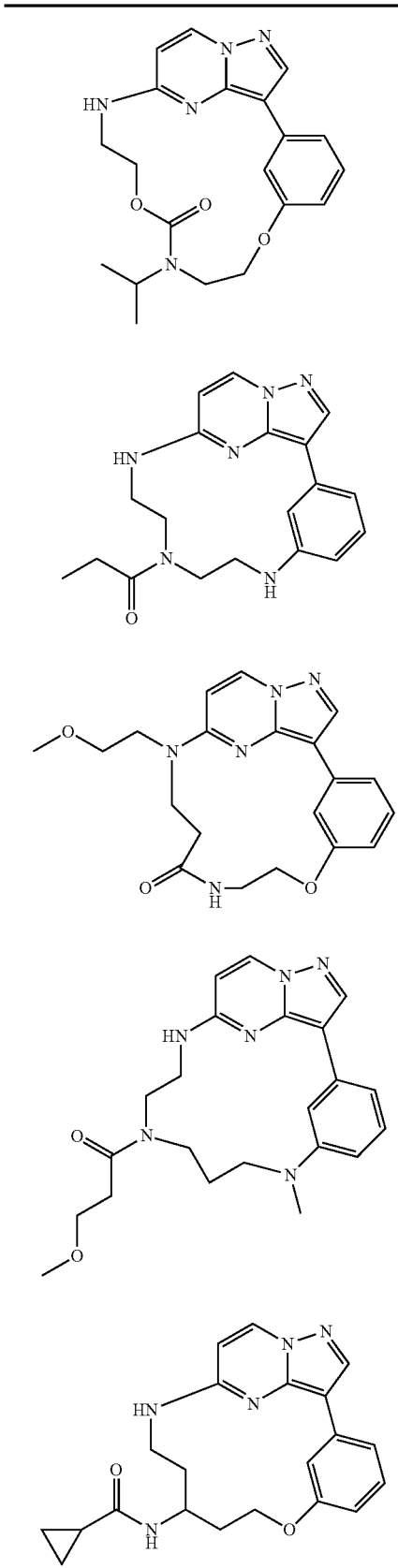
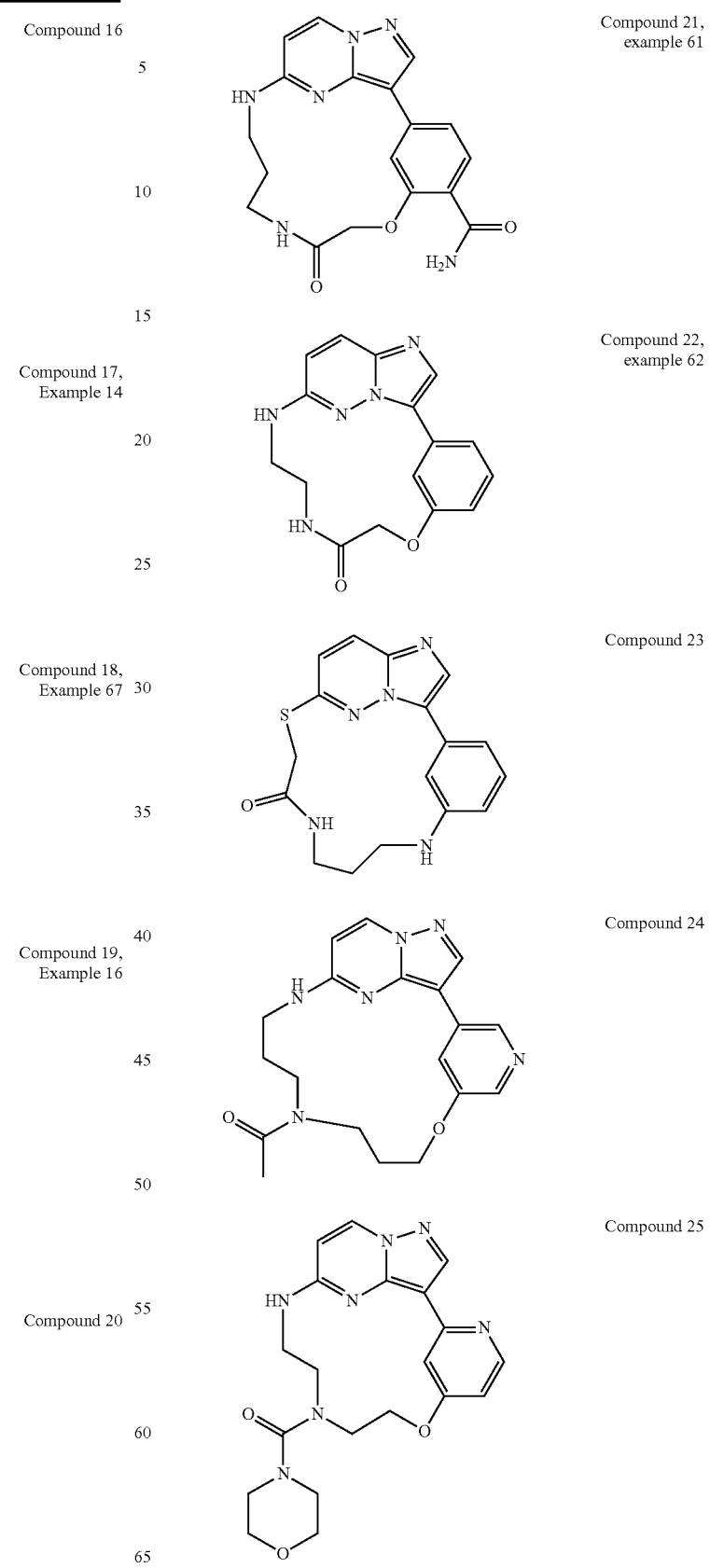

TABLE 1-continued

| Compound | |
|---|---|
| Compound 26 | |
| Compound 27 | |
| Compound 28 | |
| Compound 29, Example 17 | |
| Compound 30, Example 15 | |
| Compound 31, Example 18 | |
| Compound 32, Example 19 | |
| Compound 33, Example 20 | |
| Compound 34, Example 21 | |

TABLE 1-continued
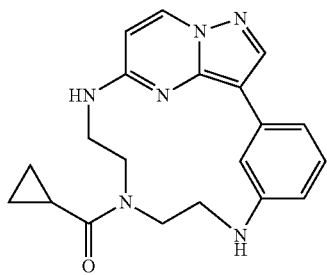 [SMILES: O=C(C1CC1)N1CCNc2cccc(c2)-c2cnn3ccc(nc23)NCC1] Compound 35, Example 22
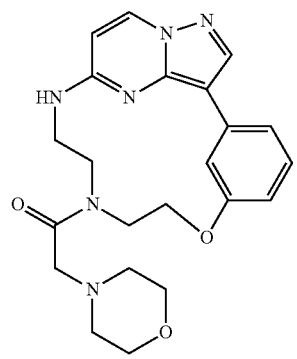 [SMILES: O=C(CN1CCOCC1)N1CCNc2ccn3ncc(c3n2)-c2cccc(c2)OCC1] Compound 36, Example 23
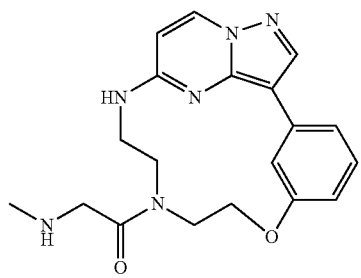 [SMILES: CNCC(=O)N1CCNc2ccn3ncc(c3n2)-c2cccc(c2)OCC1] Compound 37, Example 24
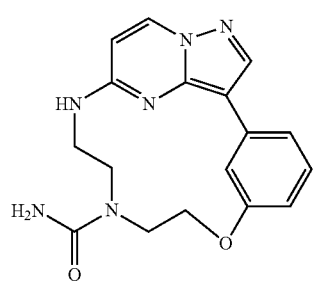 [SMILES: NC(=O)N1CCNc2ccn3ncc(c3n2)-c2cccc(c2)OCC1] Compound 38, Example 25
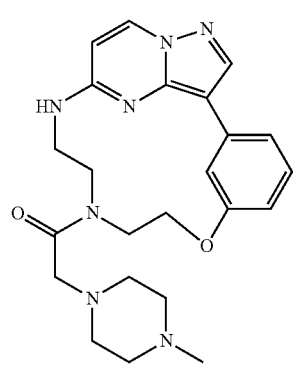 [SMILES: CN1CCN(CC(=O)N2CCNc3ccn4ncc(c4n3)-c3cccc(c3)OCC2)CC1] Compound 39, Example 26
TABLE 1-continued
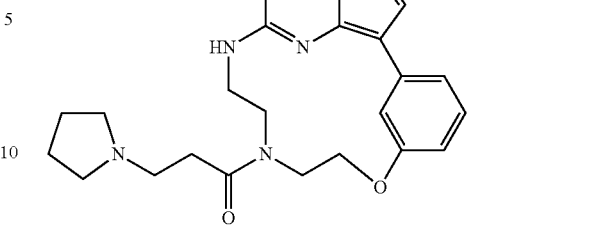 Compound 40, Example 27
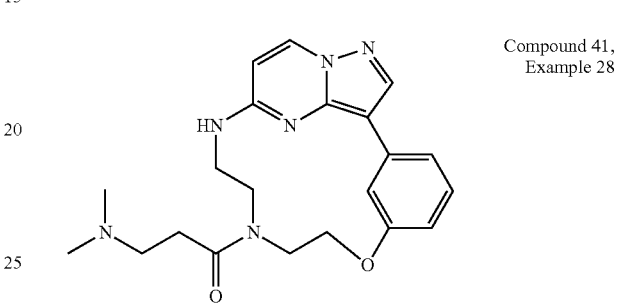 Compound 41, Example 28
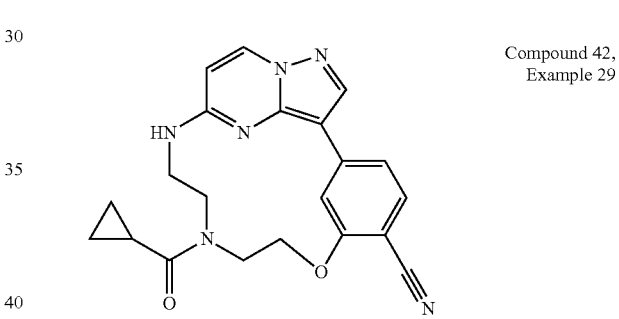 Compound 42, Example 29
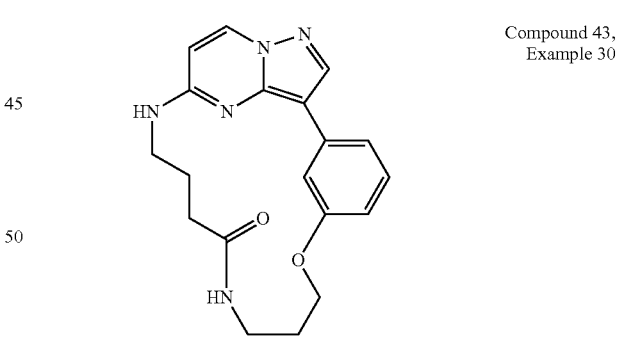 Compound 43, Example 30
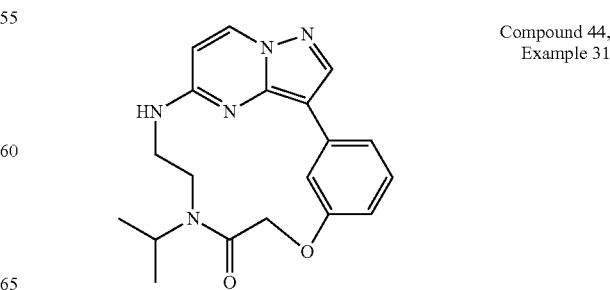 Compound 44, Example 31

TABLE 1-continued
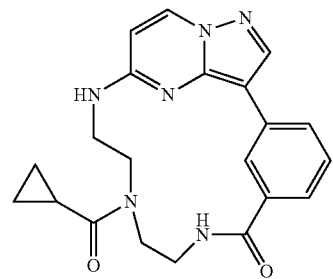 [SMILES: O=C1NCCN(C(=O)C2CC2)CCNc2ccn3ncc(c3n2)-c2cccc1c2]
Compound 45, Example 32
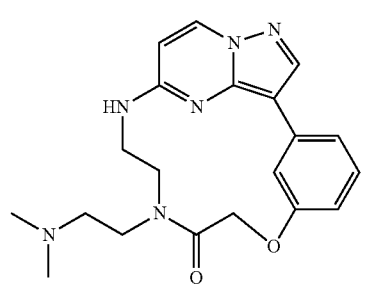 [SMILES: CN(C)CCN1CCNc2ccn3ncc(c3n2)-c2cccc(c2)OCC1=O]
Compound 46, Example 33
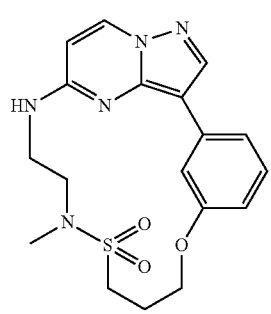 [SMILES: CN1CCNc2ccn3ncc(c3n2)-c2cccc(c2)OCCCS1(=O)=O]
Compound 47, Example 34
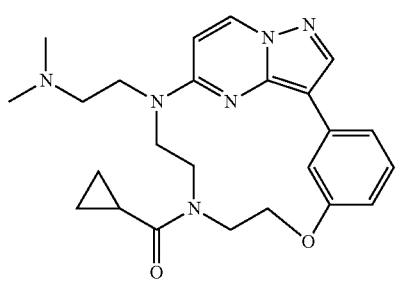 [SMILES: CN(C)CCN1CCN(C(=O)C2CC2)CCOc2cccc(c2)-c2cnn3ccc1nc23]
Compound 48, Example 35
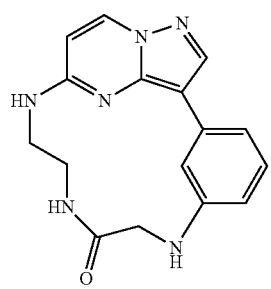 [SMILES: O=C1CNc2cccc(c2)-c2cnn3ccc(nc23)NCCN1]
Compound 49, Example 36
TABLE 1-continued
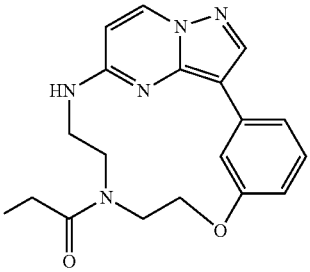
Compound 50, Example 37
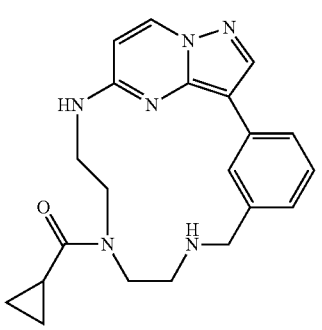 [SMILES: O=C(C1CC1)N1CCNCc2cccc(c2)-c2cnn3ccc(nc23)NCC1]
Compound 51, Example 38
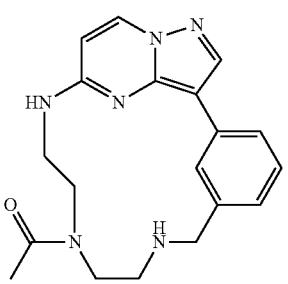 [SMILES: CC(=O)N1CCNCc2cccc(c2)-c2cnn3ccc(nc23)NCC1]
Compound 52, Example 39
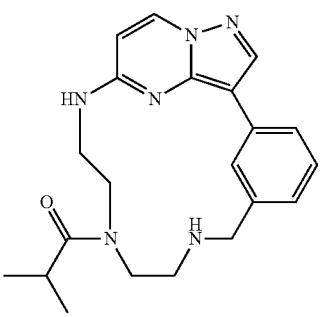 [SMILES: CC(C)C(=O)N1CCNCc2cccc(c2)-c2cnn3ccc(nc23)NCC1]
Compound 53, Example 40
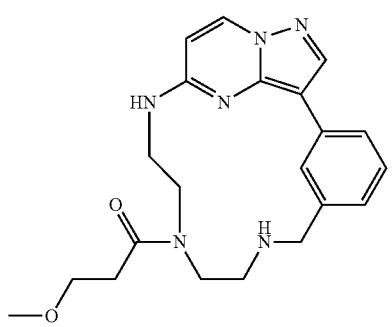 [SMILES: COCCC(=O)N1CCNCc2cccc(c2)-c2cnn3ccc(nc23)NCC1]
Compound 54, Example 41

TABLE 1-continued
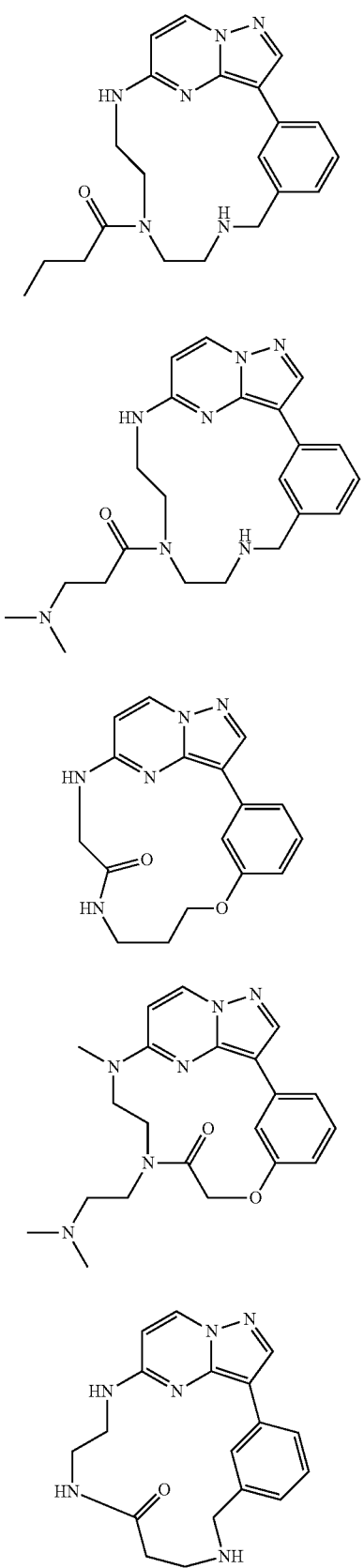
Compound 55, Example 42
Compound 56, Example 43
Compound 57, Example 44
Compound 58, Example 45
Compound 59, Example 46
TABLE 1-continued
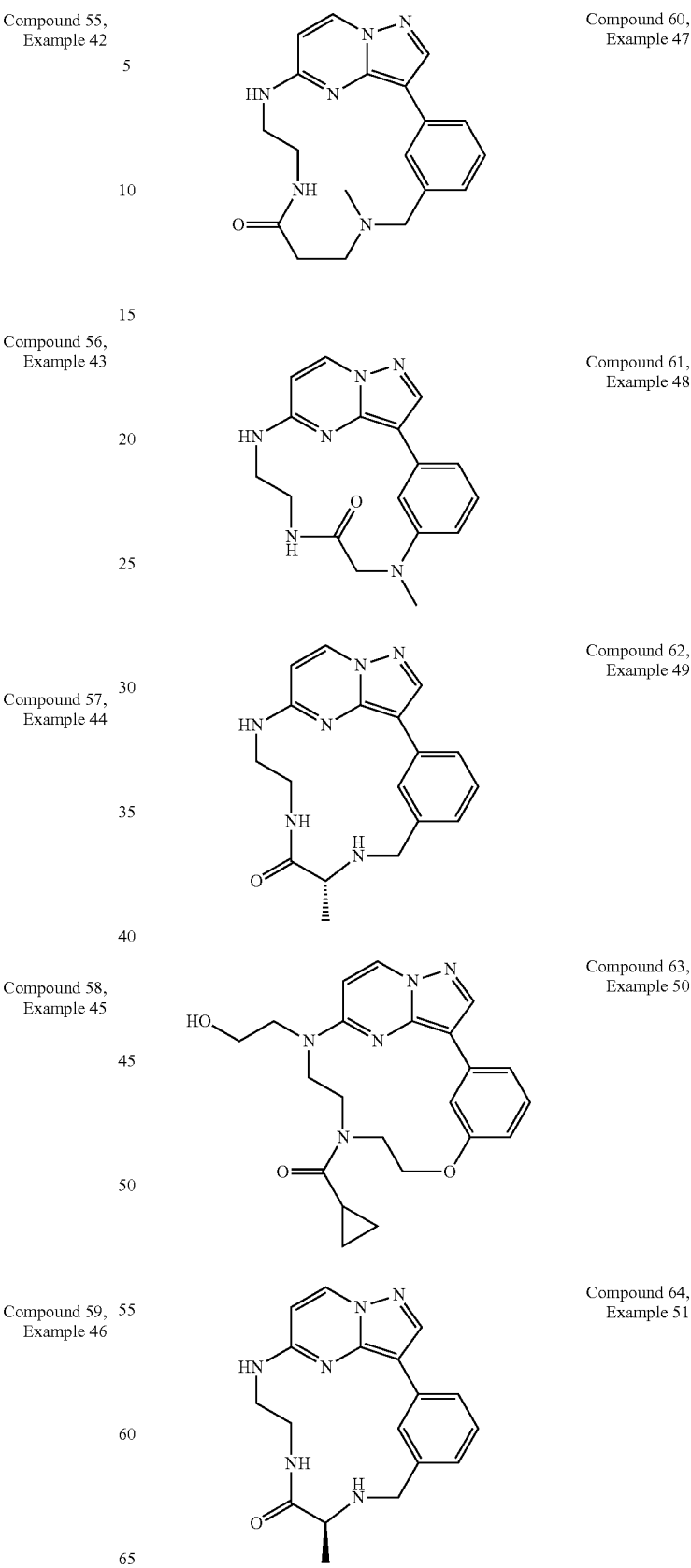
Compound 60, Example 47
Compound 61, Example 48
Compound 62, Example 49
Compound 63, Example 50
Compound 64, Example 51

TABLE 1-continued
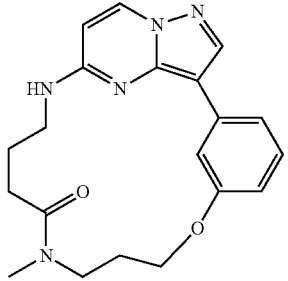 [SMILES: CN1CCCOc2cccc(c2)-c2cnn3ccc(nc23)NCCCC1=O] Compound 65, Example 52
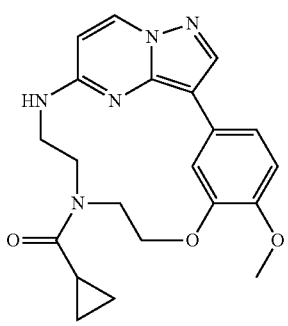 [SMILES: COc1ccc2cc1OCCN(C(=O)C1CC1)CCNc1ccn3ncc-2c3n1] Compound 66, Example 53
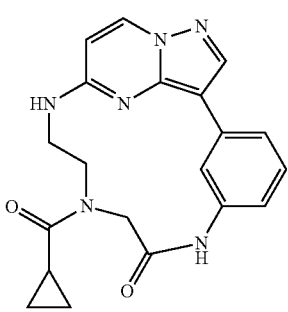 [SMILES: O=C1CN(C(=O)C2CC2)CCNc2ccn3ncc(c3n2)-c2cccc(c2)N1] Compound 67, Example 54
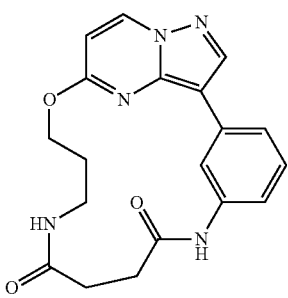 [SMILES: O=C1CCC(=O)Nc2cccc(c2)-c2cnn3ccc(nc23)OCCCN1] Compound 68, Example 55
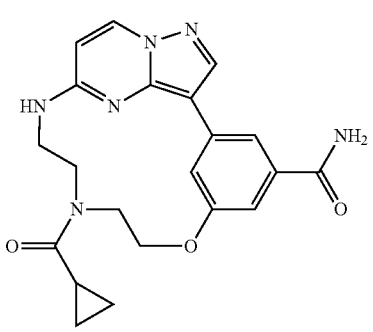 [SMILES: NC(=O)c1cc2cc(c1)-c1cnn3ccc(nc13)NCCN(C(=O)C1CC1)CCO2] Compound 69, Example 56
TABLE 1-continued
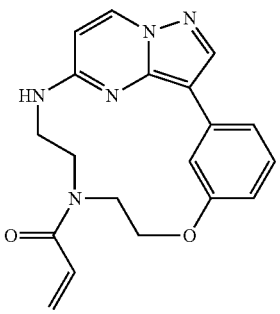 [SMILES: C=CC(=O)N1CCNc2ccn3ncc(c3n2)-c2cccc(c2)OCC1] Compound 70, Example 57
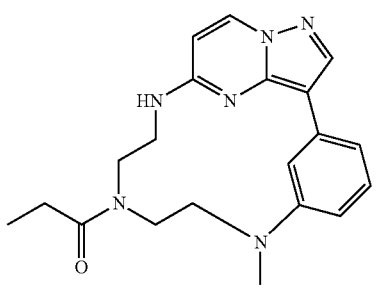 [SMILES: CCC(=O)N1CCNc2ccn3ncc(c3n2)-c2cccc(c2)N(C)CC1] Compound 71, Example 58
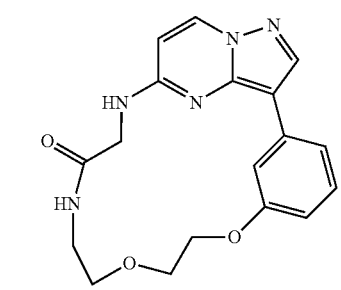 [SMILES: O=C1CNc2ccn3ncc(c3n2)-c2cccc(c2)OCCOCCN1] Compound 72, Example 59
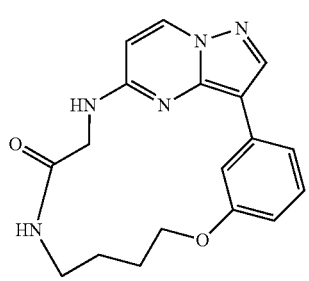 [SMILES: O=C1CNc2ccn3ncc(c3n2)-c2cccc(c2)OCCCCN1] Compound 73, Example 60
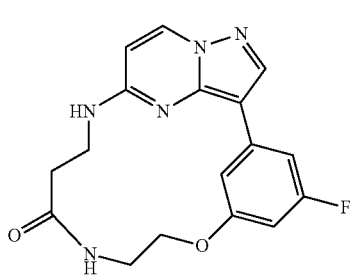 [SMILES: O=C1CCNc2ccn3ncc(c3n2)-c2cc(F)cc(c2)OCCN1] Compound 74, Example 63

TABLE 1-continued

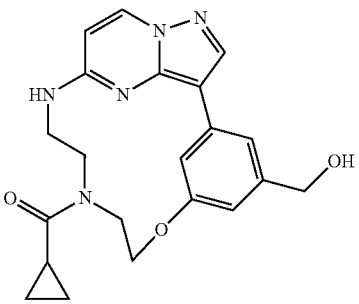 [SMILES: O=C(C1CC1)N1CCNc2ccn3ncc(c3n2)-c2cc(CO)cc(c2)OCC1]

Compound 75, Example 64

Compound 76, Example 65

Compound 77, Example 66

Compound Identification
Melting Points

For the melting point determination of the compounds of the present invention, the following method was used.

Melting Point Method

For a number of compounds, melting points (m.p.) were determined in open capillary tubes on a Mettler FP62 apparatus. Melting points were measured with a temperature ranging from 50° C. to 300° C., using a gradient of 10° C./minute. The melting point value was read from a digital display and was not corrected.

TABLE 2

Melting points

| COMPOUND No | MELTING POINT (° C.) |
|---|---|
| 1 | >300 |
| 2 | >300 |
| 3 | >300 |
| 4 | >300 |
| 5 | >300 |
| 6 | ND* |
| 7 | ND* |
| 8 | 269 |
| 10 | >300 |
| 11 | >300 |
| 12 | ND* |
| 13 | >300 |

TABLE 2-continued

Melting points

| COMPOUND No | MELTING POINT (° C.) |
|---|---|
| 14 | ND* |
| 17 | >300 |
| 18 | 251.7 |
| 19 | >300 |
| 21 | >300 |
| 22 | ND* |
| 29 | ND* |
| 30 | 185.2 |
| 31 | ND* |
| 32 | >300 |
| 33 | >300 |
| 34 | ND* |
| 35 | >300 |
| 36 | 270.4 |
| 37 | ND* |
| 38 | >300 |
| 39 | 230.7 |
| 40 | >300 |
| 41 | 295 |
| 42 | >300 |
| 43 | ND* |
| 44 | ND* |
| 45 | ND* |
| 46 | ND* |
| 47 | 258.1 |
| 48 | 279.1 |
| 49 | >300 |
| 50 | >300 |
| 51 | ND* |
| 52 | >300 |
| 53 | 275 |
| 54 | ND* |
| 55 | ND* |
| 56 | 179.9 |
| 57 | >300 |
| 58 | >300 |
| 59 | >300 |
| 60 | 239.1 |
| 61 | >300 |
| 62 | >300 |
| 63 | 286.8 |
| 64 | >300 |
| 65 | ND* |
| 66 | ND* |
| 67 | ND* |
| 68 | 295.1 |
| 69 | >300 |
| 70 | >300 |
| 71 | >300 |
| 72 | 272.5 |
| 73 | >300 |
| 74 | ND* |
| 75 | ND* |
| 76 | ND* |
| 77 | ND* |

*Not determined

LCMS

For LCMS-characterization of the compounds of the present invention, the following method was used.

General Procedure LCMS

All analyses were performed using an Agilent 6110 series LC/MSD quadrupole coupled to an Agilent 1290 series liquid chromatography (LC) system consisting of a binary pump with degasser, autosampler, thermostated column compartment and diode array detector. The mass spectrometer (MS) was operated with an atmospheric pressure electro-spray ionisation (API-ES) source in positive ion mode. The capillary voltage was set to 3000 V, the fragmentor voltage to 70 V and the quadrupole temperature was maintained at 100° C. The drying gas flow and temperature values were 12.0 L/min and 350° C. respectively. Nitrogen was used as the nebulizer gas, at a pressure of 35 psig. Data acquisition was performed with Agilent Chemstation software.

LCMS Method 1

In addition to the general procedure LCMS1: Analyses were carried out on a Phenomenex Kinetex C18 column (50 mm long×2.1 mm i.d.; 1.7 µm particles) at 60° C., with a flow rate of 1.5 mL/min. A gradient elution was performed from 90% (water+0.1% formic acid)/10% Acetonitrile to 10% (water+0.1% formic acid)/90% acetonitrile in 1.50 minutes, then the final mobile phase composition was held for an additional 0.40 min. The standard injection volume was 2 µL. Acquisition ranges were set to 254 nm for the UV-PDA detector and 80-800 m/z for the MS detector.

LCMS Method 2

In addition to the general procedure LCMS1: Analyses were carried out on a YMC pack ODS-AQ C18 column (50 mm long×4.6 mm i.d.; 3 µm particles) at 35° C., with a flow rate of 2.6 mL/min. A gradient elution was performed from 95% (water+0.1% formic acid)/5% Acetonitrile to 5% (water+0.1% formic acid)/95% Acetonitrile in 4.80 minutes, then the final mobile phase composition was held for an additional 1.00 min. The standard injection volume was 2 µL. Acquisition ranges were set to 190-400 nm for the UV-PDA detector and 100-1400 m/z for the MS detector.

TABLE 3

LCMS data

| COMPOUND NUMBER | MASS (MH)+ PEAK | RETENTION TIME (min) | LCMS METHOD |
|---|---|---|---|
| 1 | 364 | 3.022 | 2 |
| 2 | 338 | 2.267 | 2 |
| 3 | 365 | 2.285 | 2 |
| 4 | 368 | 2.433 | 2 |
| 5 | 324 | 2.097 | 2 |
| 6 | 339 | 1.528 | 2 |
| 7 | 324 | 2.275 | 2 |
| 8 | 374 | 2.590 | 2 |
| 10 | 370 | 2.917 | 2 |
| 11 | 367 | 2.939 | 2 |
| 12 | 382 | 3.414 | 2 |
| 13 | 353 | 1.889 | 2 |
| 14 | 374 | 3.011 | 2 |
| 17 | 351 | 2.700 | 2 |
| 18 | 382 | 2.548 | 2 |
| 19 | 409 | 2.224 | 2 |
| 21 | 367 | 1.771 | 2 |
| 22 | 310 | 1.168 | 2 |
| 29 | 454 | 2.032 | 2 |
| 30 | 395 | 1.910 | 2 |
| 31 | 382 | 2.813 | 2 |
| 32 | 389 | 3.208 | 2 |
| 33 | 391 | 2.988 | 2 |
| 34 | 400 | 3.288 | 2 |
| 35 | 363 | 2.740 | 2 |
| 36 | 423 | 1.942 | 2 |
| 37 | 367 | 1.875 | 2 |
| 38 | 339 | 2.412 | 2 |
| 39 | 436 | 1.930 | 2 |
| 40 | 421 | 2.050 | 2 |
| 41 | 395 | 1.977 | 2 |
| 42 | 389 | 3.056 | 2 |
| 43 | 352 | 2.612 | 2 |
| 44 | 352 | 2.507 | 2 |
| 45 | 391 | 2.410 | 2 |
| 46 | 381 | | 2 |
| 47 | 388 | 2.887 | 2 |
| 48 | 435 | 2.265 | 2 |
| 49 | 309 | 1.757 | 2 |
| 50 | 356 | 2.790 | 2 |
| 51 | 377 | 1.685 | 2 |
| 52 | 351 | 1.073 | 2 |
| 53 | 379 | 1.911 | 2 |
| 54 | 395 | 1.623 | 2 |
| 55 | 379 | 1.206 | 2 |
| 56 | 408 | 0.733 | 2 |
| 57 | 324 | 1.071 | 2 |
| 58 | 395 | 1.225 | 2 |
| 59 | 337 | 0.998 | 2 |
| 60 | 351 | 1.036 | 2 |
| 61 | 323 | 1.605 | 2 |
| 62 | 337 | 1.090 | 2 |
| 63 | 408 | 2.247 | 2 |
| 64 | 337 | 1.074 | 2 |
| 65 | 366 | 2.150 | 2 |
| 66 | 394 | 2.788 | 2 |
| 67 | 377 | 2.331 | 2 |
| 68 | 366 | 2.158 | 2 |
| 69 | 407 | 2.276 | 2 |
| 70 | 350 | 2.915 | 2 |
| 71 | 365 | 3.060 | 2 |
| 72 | 354 | 2.218 | 2 |
| 73 | 338 | 2.425 | 2 |
| 74 | 342 | 2.556 | 2 |
| 75 | 394 | 2.426 | 2 |
| 76 | 391 | 0.314 | 1 |
| 77 | 354 | 2.785 | 2 |

B. Kinase Activity Assay

The inhibition of LRRK2 and LRRK1 kinase was assessed using LRRK2 and LRRK1 recombinant protein in an in vitro peptide-based kinase assay.

Protocol 1

Expression and Purification of Recombinant LRRK2 Protein

LRRK2 protein is prepared as described in Daniëls et al. ((2011) *J Neurochem* 116, 304-315.). HEK293T cells are transfected with pCHMWS-3xflag-LRRK2 plasmid using polyethyleneimine and lysed after 48-72 hours in lysis buffer (Tris 20 mM pH 7.5, NaCl 150 mM, EDTA 1 mM, Triton 1%, Glycerol 10%, protease inhibitor cocktail). Lysates are cleared by centrifugation at 20,000 g for 10 minutes and incubated with normal mouse IgGs bound to agarose beads to remove proteins aspecifically binding to agarose or mouse IgGs. After removal of the IgG bead slurry, lysates are incubated for 3 to 18 hours with flagM2 bound to agarose beads. Beads are washed 4 times with wash buffer (Tris 25 mM pH 7.5, NaCl 400 mM, Triton 1%) and rinsed in kinase buffer (Tris-HCl 25 mM pH 7.5, 10 mM MgCl$_2$, 2 mM dithiothreitol (DTT), 0.02% triton, 5 mM beta-glycerophosphate, 0.1 mM Na$_3$VO$_4$). Proteins are eluted in 5 volumes of kinase buffer containing 100 µg/ml 3xflag peptide. For assays using purified protein bound to affinity resin, affinity beads are resuspended in an equal volume of kinase buffer unless otherwise indicated. Purity and concentration are assessed by SDS-PAGE (3-8% tris-acetate SDS gel) and Coomassie Brilliant Blue staining or silver staining. Alternatively, a truncated LRRK2 enzyme (GST tagged LRRK2 of amino acids 970-2527) and a truncated LRRK2-G2019S (GST tagged LRRK2-G2019S of amino acids 970-2527) are used.

Kinase Assay LRRK2

For Lrrktide phosphorylation, recombinant LRRK2 is incubated with 6 µCi of $_{32}$P-ATP (3000 Ci/mmol), 200 µM Lrrktide, 10 µM ATP and compound or solvent per 40 µl reaction for 30 minutes at 30° C. Compounds are tested at concentrations ranging from 10 µM to 10 µM; the final amount of DMSO in the kinase reaction is 1%. Reactions are stopped and spotted to P81 phosphocellulose paper and washed 4×10 minutes in 75 mM phosphoric acid. Lrrktide phosphorylation levels are measured via autoradiography. Kinase assays are performed for each condition in triplicate.

LRRKtide phosphorylation levels are plotted vs. the log of the compound concentration and inhibition curves are fitted from which IC50 values are derived.

Protocol 2

A radiometric protein kinase assay ($^{33}$PanQinase® Activity Assay) is used for measuring the kinase activity. All assays are performed in 96-well FlashPlates™ from Perkin Elmer in a 50 µl reaction volume. The reaction cocktail is pipetted in 4 steps in the following order:

10 µl of non-radioactive ATP solution (in H2O)
25 µl of assay buffer/[γ-$^{33}$P]-ATP mixture
5 µl of test sample in 10% DMSO
10 µl of enzyme/substrate mixture The assay contains 70 mM HEPES-NaOH pH 7.5, 3 mM MgCl$_2$, 3 mM MnCl$_2$, 3 µM Na-orthovanadate, 1.2 mM DTT, ATP (0.3 µM), [γ-$^{33}$P]-ATP (approx. 4×1005 cpm per well), protein kinase (7.3 nM) and substrate (GSK3(14-27), 1.0 µg/50 µl).

The kinase is obtained from Invitrogen Corporation.

The reaction cocktails were incubated at 30° C. for 60 minutes. The reaction was stopped with 50 µl of 2% (v/v) H$_3$PO$_4$, plates were aspirated and washed two times with 200 µl 0.9% (w/v) NaCl. Incorporation of $^{33}$Pi (counting of "cpm") was determined with a microplate scintillation counter.

Compounds

The compounds are dissolved to 10 mM in DMSO. Where needed, solutions are sonicated in a bath sonicator. Compounds are aliquoted and stored at −20° C.

Table 4 provides the IC$_{50}$ values of the compounds according to the invention, obtained using the above mentioned kinase assay.

TABLE 4

| Compound No | IC$_{50}$ for full-length LRRK2 | IC$_{50}$ for truncated LRRK2 | IC$_{50}$ for truncated LRRK2-G2019S | Protocol |
|---|---|---|---|---|
| 1 | N/A | +++ | +++ | 1 |
| 2 | +++ | ++ | ++ | 1 |
| 3 | +++ | +++ | +++ | 1 |
| 4 | N/A | +++ | +++ | 1 |
| 5 | ++ | ++ | ++ | 1 |
| 6 | N/A | N/A | N/A | |
| 7 | N/A | N/A | N/A | |
| 8 | N/A | N/A | N/A | |
| 10 | N/A | +++ | N/A | 2 |
| 11 | N/A | +++ | N/A | 2 |
| 12 | N/A | ++ | N/A | 2 |
| 13 | N/A | +++ | N/A | 2 |
| 14 | N/A | ++ | N/A | 2 |
| 17 | N/A | +++ | N/A | 2 |
| 18 | N/A | N/A | N/A | |
| 19 | N/A | ++ | N/A | 2 |
| 21 | N/A | N/A | N/A | 2 |
| 22 | N/A | N/A | N/A | 2 |
| 29 | N/A | ++ | N/A | 2 |
| 30 | N/A | +++ | N/A | 2 |
| 31 | N/A | ++ | N/A | 2 |
| 32 | N/A | +++ | N/A | 2 |
| 33 | N/A | +++ | N/A | 2 |
| 34 | N/A | ++ | N/A | 2 |
| 35 | N/A | +++ | N/A | 2 |
| 36 | N/A | ++ | N/A | 2 |
| 37 | N/A | +++ | N/A | 2 |
| 38 | N/A | +++ | N/A | 2 |
| 39 | N/A | ++ | N/A | 2 |
| 40 | N/A | +++ | N/A | 2 |
| 41 | N/A | +++ | N/A | 2 |
| 42 | N/A | +++ | N/A | 2 |
| 43 | N/A | ++ | N/A | 2 |
| 44 | N/A | + | N/A | 2 |
| 45 | N/A | ++ | N/A | 2 |
| 46 | N/A | + | N/A | 2 |
| 47 | N/A | ++ | N/A | 2 |
| 48 | N/A | ++ | N/A | 2 |
| 49 | N/A | ++ | N/A | 2 |
| 50 | N/A | +++ | N/A | 2 |
| 51 | N/A | ++ | N/A | 2 |
| 52 | N/A | ++ | N/A | 2 |
| 53 | N/A | + | N/A | 2 |
| 54 | N/A | ++ | N/A | 2 |
| 55 | N/A | + | N/A | 2 |
| 56 | N/A | + | N/A | 2 |
| 57 | N/A | + | N/A | 2 |
| 58 | N/A | + | N/A | 2 |
| 59 | N/A | + | N/A | 2 |
| 60 | N/A | +++ | N/A | 2 |
| 61 | N/A | + | N/A | 2 |
| 62 | N/A | + | N/A | 2 |
| 63 | N/A | ++ | N/A | 2 |
| 64 | N/A | + | N/A | 2 |
| 65 | N/A | + | N/A | 2 |
| 66 | N/A | ++ | N/A | 2 |
| 67 | N/A | + | N/A | 2 |
| 68 | N/A | + | N/A | 2 |
| 69 | N/A | + | N/A | 2 |
| 70 | N/A | +++ | N/A | 2 |
| 71 | N/A | N/A | N/A | |
| 72 | N/A | N/A | N/A | |
| 73 | N/A | N/A | N/A | |
| 74 | N/A | N/A | N/A | |
| 75 | N/A | N/A | N/A | |
| 76 | N/A | N/A | N/A | |
| 77 | N/A | N/A | N/A | |

+ indicates an IC50 > 1 µM,
++ indicates an IC50 of between 100 nM and 1 µM,
and +++ indicates an IC50 < 100 nM
N/A indicates not available Expression and Purification of Recombinant LRRK1 Protein LRRK1 protein is prepared essentially as described by Daniëls et al. ((2011) *J Neurochem* 116, 304-315.). HEK293T cells are transfected with pCHMWS-3xflag-LRRK1 plasmid using polyethyleneimine and lysed after 48-72 hours in lysis buffer (Tris 20 mM pH 7.5, NaCl 150 mM, EDTA 1 mM, Triton 1%, Glycerol 10%, protease inhibitor cocktail). Lysates are cleared by centrifugation at 20,000 g for 10 minutes and incubated with normal mouse IgGs bound to agarose beads to remove proteins aspecifically binding to agarose or mouse IgGs. After removal of the IgG bead slurry, lysates are incubated for 3-18 hours with flagM2 bound to agarose beads. Beads are washed 4 times with wash buffer (Tris 25 mM pH 7.5, NaCl 400 mM, Triton 1%) and rinsed in kinase buffer (Tris-HCl 25 mM pH 7.5, 10 mM MgCl$_2$, 2 mM dithiothreitol (DTT), 0.02% triton, 5 mM beta-glycerophosphate, 0.1 mM Na$_3$VO$_4$). Proteins are eluted in 5 volumes of kinase buffer containing 100 µg/ml 3xflag peptide. Purity and concentration are assessed by SDS-PAGE (3-8% tris-acetate SDS gel;) and Coomassie Brilliant Blue staining or silver staining.

Kinase Assay LRRK1

To assay autophosphorylation, recombinant LRRK1 is incubated with 6 µCi $^{32}$P-ATP (3000 Ci/mmol), 10 µM ATP and 1 µM compound or solvent per 40 µl reaction for 30 minutes at 30° C. Reactions are terminated by adding SDS loading buffer. Samples are loaded onto pre-cast Tris-acetate 3-8% gels or Tris-glycine 4-20% gels and transferred onto polyvinylidene fluoride membranes. Incorporated $^3$P-ATP is detected by autoradiography using a Storm 840 phosphorescence plate scanner. The same membranes are probed with DR4A/3EDD in house anti-LRRK2 kinase domain antibody to confirm the presence of LRRK1. Densitometric analysis of the bands on the blot autoradiograms and immunoreactivity is performed using Aida analyzer v1.0 (Raytest, Straubenhardt, Germany) or ImageJ software (NIH, USA). Autophosphorylation levels are calculated as the ratio of the autoradiographic signal over the immunoreactivity level. The results of the autophosphorylation assay of LRRK1 are shown in FIG. 1.

Effect on LRRK1 and LRRK2 Phosphorylation Levels in Cells

Figure 2:
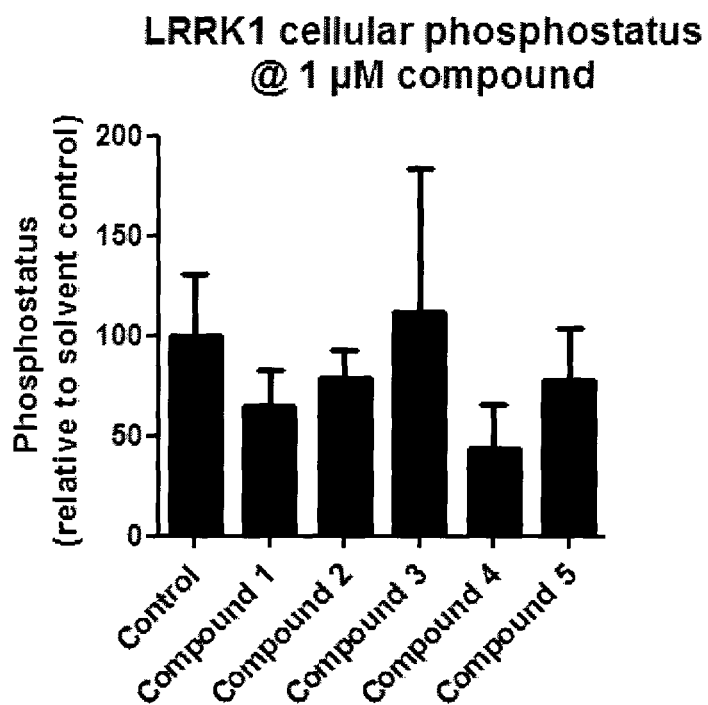
FIG. 2: Cellular phosphostatus of LRRK1 in the presence of 1 μM compound (mean+/−SD, N=3)
Figure 3:
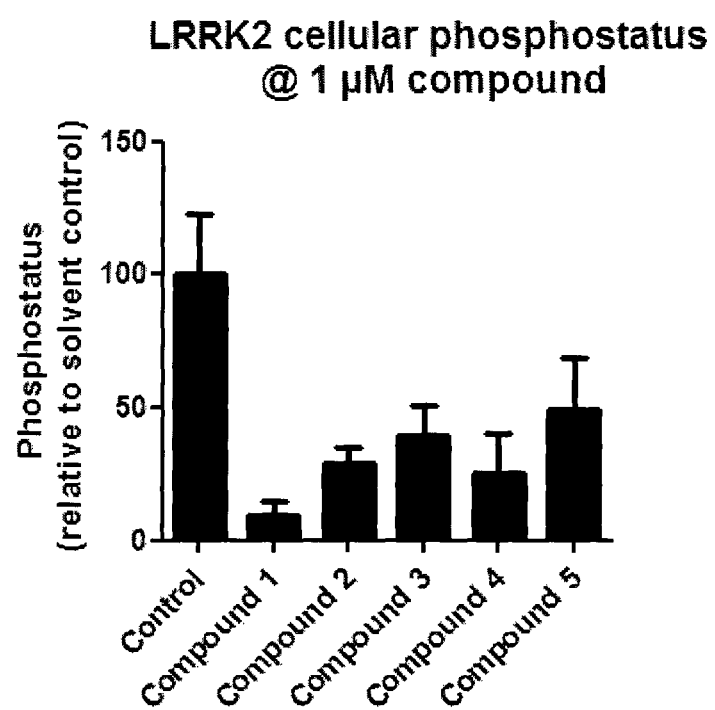
FIG. 3: Cellular phosphostatus of LRRK2 in the presence of 1 μM compound (mean+/−SD, N=4)

For labelling of intact cells, LRRK1 or LRRK2 are expressed in HEK293T cells. Cells are rinsed 2× in DMEM without phosphates and then metabolically labelled with 5 µCi/cm$^2$ orthophosphate-P$^{32}$ in DMEM without phosphates at 37° C. Following 4-8 hours labelling, cells are treated with compound at 1 µM or solvent for 2 hours. Treated cells are then lysed and LRRK1 or LRRK2 is immunoprecipitated using flag-M2 agarose beads. Immunoprecipitated protein is resolved on 3-8% SDS-PAGE gels and blotted to pvdf membranes. Membranes are processed as described above for the autophosphorylation assay. All conditions are tested in triplicate and the results are shown in FIGS. 2 and 3.

The invention claimed is:

1. A method of treating Parkinson's disease comprising administering to a subject in need thereof a therapeutically effective amount of a compound of Formula I

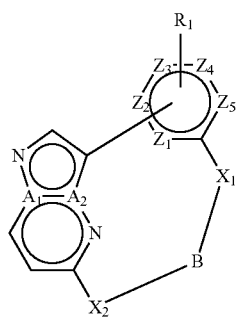

I or a stereoisomer, tautomer, racemate, pharmaceutical salt, or N-oxide thereof, wherein:

$A_1$ and $A_2$ are each individually C or N; wherein when $A_1$ is C, then $A_2$ is N, and when $A_2$ is C, then $A_1$ is N;

$X_1$ is —$C_{1-6}$ alkyl-, —O—$C_{1-6}$ alkyl-, —S—$C_{1-6}$ alkyl-, —(C=O)—, —NR$_3$—(C=O)—NR$_3$—(C=O)—$C_{1-6}$ alkyl-, —(C=O)—NR$_3$—$C_{1-6}$ alkyl-, —NR$_3$—$C_{1-6}$ alkyl-, —$C_{1-6}$ alkyl-NR$_3$—$C_{1-6}$ alkyl-, or —SO$_2$—NR$_3$—;

wherein said $C_{1-6}$ alkyl group is unsubstituted or substituted with 1 to 3 substituents independently selected from -halo, —OH, —$C_{1-6}$ alkyl, —O—$C_{1-6}$ alkyl, —S—$C_{1-6}$ alkyl, and —NR$_{37}$R$_{38}$;

$X_2$ is —$C_{1-6}$ alkyl-, —O—$C_{1-6}$ alkyl-, —O—$C_{1-6}$ alkyl-O—$C_{1-6}$ alkyl-, —S—$C_{1-6}$ alkyl-, —(C=O)—, —(C=O)—NR$_2$—, —NR$_2$—$C_{1-6}$ alkyl-, —NR$_2$—, or —SO$_2$—NR$_2$—; wherein said $C_{1-6}$ alkyl group is unsubstituted or substituted with 1 to 3 substituents independently selected from -halo, —OH, —$C_{1-6}$ alkyl, —O—$C_{1-6}$ alkyl, —S—$C_{1-6}$ alkyl, and —NR$_{39}$R$_{40}$;

B is —(C=O)—, —(C=N)—R$_{39}$—, —(SO$_2$)—, —(C=O)—NR$_5$—, —(C=S)—NR$_5$—, —NR$_5$—(C=O)—NR$_7$—, —NR$_5$—(C=S)—NR$_7$—, —SO$_2$—NR$_5$—, —NR$_6$—, —NR$_5$—(C=O)—O—, —NR$_5$—(C=O)—O—, or —CHR$_8$—;

$R_1$ is —H, -halo, —OH, —$C_{1-6}$ alkyl, —$C_{3-6}$ cycloalkyl, —O—$C_{1-6}$ alkyl, —S—$C_{1-6}$ alkyl, —NR$_9$R$_{10}$, —(C=O)—R$_4$, —SO$_2$—R$_4$, —CN, —NR$_9$—SO$_2$—R$_4$, or -Het$_1$; wherein said $C_{1-6}$ alkyl group is unsubstituted or substituted with 1 to 3 substituents independently selected from -halo, —OH, —NR$_{11}$R$_{12}$, —O—$C_{1-6}$ alkyl, and —S—$C_{1-6}$ alkyl;

$R_2$ is —H, -halo, —OH, —$C_{1-6}$ alkyl, —$C_{3-6}$cycloalkyl, —O—$C_{1-6}$ alkyl, —S—$C_{1-6}$ alkyl, —(C=O)—$C_{1-6}$ alkyl, —(C=O)—O—$C_{1-6}$ alkyl, —(C=O)—NR$_{27}$R$_{28}$, -Het$_3$, —(C=O)-Het$_3$, or —SO$_2$—$C_{1-6}$ alkyl; wherein said $C_{1-6}$ alkyl group is unsubstituted or substituted with 1 to 3 substituents independently selected from -halo, —OH, —O—$C_{1-6}$ alkyl, —S—$C_{1-6}$ alkyl, -Het$_3$, —Ar$_2$, and —NR$_{13}$R$_{14}$;

$R_3$ is —H, -halo, —OH, —$C_{1-6}$ alkyl, —$C_{3-6}$ cycloalkyl, —O—$C_{1-6}$ alkyl, —S—$C_{1-6}$ alkyl, —(C=O)—$C_{1-6}$ alkyl, —(C=O)—O—$C_{1-6}$ alkyl, -Het$_2$, —(C=O)-Het$_2$, —(C=O)—NR$_{29}$R$_{30}$, or —SO$_2$—$C_{1-6}$ alkyl;

wherein said $C_{1-6}$ alkyl group is unsubstituted or substituted with 1 to 3 substituents independently selected from -halo, —OH, —OC$_{1-6}$ alkyl, —SC$_{1-6}$ alkyl, —NR$_{15}$R$_{16}$, -Het$_2$, and —Ar$_4$;

$R_4$ is -halo, —OH, —$C_{1-6}$ alkyl, —O—$C_{1-6}$ alkyl, —S—$C_{1-6}$ alkyl, —NR$_{17}$R$_{18}$, or -Het$_4$;

$R_5$ and $R_7$ are each independently —H, -halo, —$C_{1-6}$ alkyl, —OC$_{1-6}$ alkyl, —S—$C_{1-6}$ alkyl, -Het$_5$, —Ar$_1$, $C_{3-6}$ cycloalkyl, —SO$_2$—Ar$_3$, —SO$_2$, —SO$_2$—$C_{1-6}$ alkyl, —(C=O), —(C=O)—$C_{1-6}$ alkyl, —O—(C=O)—$C_{1-6}$ alkyl, or —(C=O)—O—$C_{1-6}$ alkyl; wherein said $C_{1-6}$ alkyl group is unsubstituted or substituted with 1 to 3 substituents independently selected from -halo, —OH, —OC$_{1-6}$ alkyl, —SC$_{1-6}$ alkyl, -Het$_5$, and —NR$_{23}$R$_{24}$;

$R_6$ is —SO$_2$, —SO$_2$—$C_{1-6}$ alkyl, —(C=O), —(C=S), —(C=O)—O—$C_{1-6}$ alkyl, —(C=S)—O—$C_{1-6}$ alkyl, —(C=O)—$C_{1-6}$ alkyl, —(C=O)—$C_{2-6}$ alkenyl, —(C=S)—$C_{1-6}$ alkyl, —(C=S)—$C_{2-6}$ alkenyl, —$C_{1-6}$ alkyl-(C=O)—NR$_{31}$R$_{32}$, —$C_{1-6}$ alkyl-(C=S)—NR$_{31}$R$_{32}$, —$C_{1-6}$ alkyl-NR$_{33}$(C=O)—NR$_{31}$R$_{32}$, —$C_{1-6}$ alkyl-NR$_{33}$(C=S)—NR$_{31}$R$_{32}$, —SO$_2$—$C_{3-5}$ cycloalkyl, —(C=O)—$C_{3-5}$ cycloalkyl, —(C=S)—$C_{3-5}$ cycloalkyl, —(C=O)—NR$_{31}$R$_{32}$, —(C=S)—NR$_{31}$R$_{32}$, —(C=O)-Het$_5$, —(C=S)-Het$_5$, —(C=O)—Ar$_6$, —(C=S)—Ar$_6$, or —(C=O)—NR$_{31}$—(C=O)—R$_{32}$; wherein said $C_{1-6}$ alkyl group is unsubstituted or substituted with 1 to 3 substituents independently selected from -halo, —OH, —OC$_{1-6}$ alkyl, —SC$_{1-6}$ alkyl, -Het$_5$, and —NR$_{25}$R$_{26}$;

$R_8$ is —NR$_{34}$—(C=O)—R$_{35}$, —NR$_{36}$—(C=O)—NR$_{34}$R$_{35}$, —NR$_{34}$—(SO$_2$)—R$_{35}$, —NR$_{34}$—(C=O)—O—R$_{35}$, or —O—(C=O)—NR$_{34}$R$_{35}$;

$R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{37}$, $R_{38}$, $R_{39}$ and $R_{40}$ are each independently —H, -halo, —O, —OH, —O—$C_{1-6}$ alkyl, —$C_{1-6}$ alkyl, —$C_{3-6}$cycloalkyl or -Het$_1$; wherein said $C_{1-6}$ alkyl group is unsubstituted or substituted with 1 to 3 substituents independently selected from -halo, —OH, —O—$C_{1-6}$ alkyl, —S—$C_{1-6}$ alkyl, -Het$_6$, and —Ar$_5$;

Ar$_1$, Ar$_2$, Ar$_3$, Ar$_4$, Ar$_5$, and Ar$_6$ are each independently a 5- or 6-membered-aryl or a 5- or 6-membered heteroaryl comprising 1 or 2 heteroatoms which are independently O, N or S; each of said $Ar_1$, $Ar_2$, $Ar_3$, $Ar_4$, and $Ar_5$ being unsubstituted or substituted with 1 to 3 substituents independently selected from $-NR_{19}R_{20}$, $-C_{1-6}$ alkyl, $-O-C_{1-6}$ alkyl, and $-S-C_{1-6}$ alkyl;

$Het_1$, $Het_2$, $Het_3$, $Het_4$, $Het_5$, and $Het_6$ are each independently a 5- or 6-membered monocyclic heterocycle having from 1 to 3 heteroatoms which are independently O, N or S; each heterocycle being unsubstituted or substituted with 1 to 3 substituents independently selected from -halo, $-C_{1-6}$ alkyl, $-OC_{1-6}$ alkyl, $-SC_{1-6}$ alkyl, and $-NR_{21}R_{22}$; and each $-C_{1-6}$ alkyl group being unsubstituted or substituted with 1 to 3 halo substituents; and $Z_1$, $Z_2$, $Z_3$, $Z_4$ and $Z_5$ are each independently C or N.

2. The method of claim 1, wherein $X_1$ is $-O-CH_2-$ and $R_5$ is not $-H$.

3. The method of claim 1, wherein:

$A_1$ is N;

$A_2$ is C;

$X_1$ is $-C_{1-6}$ alkyl-, $-O-C_{1-6}$ alkyl-, $-S-C_{1-6}$ alkyl-, $-(C=O)-$, $-NR_3-(C=O)-$, $-NR_3-(C=O)-C_{1-6}$ alkyl, $-(C=O)-NR_3-C_{1-6}$ alkyl-, $-C_{1-6}$ alkyl-$NR_3-C_{1-6}$ alkyl-, or $-SO_2-NR_3-$; wherein said $C_{1-6}$ alkyl group is unsubstituted or substituted with 1 to 3 substituents independently selected from -halo, $-OH$, $-C_{1-6}$ alkyl, $-O-C_{1-6}$ alkyl, $-S-C_{1-6}$ alkyl, and $-NR_{37}R_{38}$;

$X_2$ is $-C_{1-6}$ alkyl-, $-O-C_{1-6}$ alkyl-, $-S-C_{1-6}$ alkyl-, $-(C=O)-$, $-(C=O)-NR_2-NR_2-C_{1-6}$ alkyl-, $-NR_2-$, or $-SO_2-NR_2-$; wherein said $C_{1-6}$ alkyl group is unsubstituted or substituted with 1 to 3 substituents independently selected from -halo, $-OH$, $-C_{1-6}$ alkyl, $-O-C_{1-6}$ alkyl, $-S-C_{1-6}$ alkyl, and $-NR_{39}R_{40}$;

B is $-(C=O)-$, $-(C=N)R_{39}-$, $-(SO_2)-$, $-(C=O)-NR_5-$, $-(C=S)-NR_5-$, $-NR_5-(C=O)-NR_7-$, $-NR_5-(C=S)-NR_7-$, $-SO_2-NR_5-$, $-NR_6-$, $-NR_5-(C=S)-O-$, or $-CHR_8-$;

$R_1$ is $-H$, $-OH$, $-C_{1-6}$ alkyl, $-C_{3-6}$ cycloalkyl, $-O-C_{1-6}$ alkyl, $-S-C_{1-6}$ alkyl, $-NR_9R_{10}$, $-SO_2-R_4$, $-CN$, $-NR_9-SO_2-R_4$, or $-Het_1$; wherein said $C_{1-6}$ alkyl group is unsubstituted or substituted with 1 to 3 substituents independently selected from -halo, $-OH$, $-NR_{11}R_{12}$, $-O-C_{1-6}$ alkyl, and $-S-C_{1-6}$ alkyl;

$R_5$ and $R_7$ are each independently $-H$, -halo, $-C_{1-6}$ alkyl, $-OC_{1-6}$ alkyl, $-S-C_{1-6}$ alkyl, $-Het_5$, $-Ar_1$, $-C_{3-6}$ cycloalkyl, $-SO_2-Ar_3$, $-SO_2$, $-SO_2-C_{1-6}$ alkyl, $-(C=O)$, $-(C=O)-C_{1-6}$ alkyl, $-O-(C=O)-C_{1-6}$ alkyl, or $-(C=O)-O-C_{1-6}$ alkyl; wherein said $C_{1-6}$ alkyl group is unsubstituted or substituted with 1 to 3 substituents independently selected from $-OH$, $-OC_{1-6}$ alkyl, $-SC_{1-6}$ alkyl, $-Het_5$, and $-NR_{23}R_{24}$;

$R_6$ is $-SO_2$, $-(C=O)$, $-(C=S)$, $-(C=O)-O-C_{1-6}$ alkyl, $-(C=O)-C_{2-6}$ alkenyl, $-(C=S)-O-C_{1-6}$ alkyl, $(C=O)-C_{1-6}$ alkyl, $-(C=S)-C_{1-6}$ alkyl, $-(C=S)-C_{2-6}$ alkenyl, $-C_{1-6}$ alkyl-$(C=S)-NR_{31}R_{32}$, $-C_{1-6}$ alkyl-$NR_{33}(C=O)-NR_{31}R_{32}$, $-C_{1-6}$ alkyl-$NR_{33}(C=S)-NR_{31}R_{32}$, $-(C=S)-C_{3-5}$ cycloalkyl, $-(C=S)-NR_{31}R_{32}$, $-(C=O)-Het_5$, $-(C=S)-Het_5$, or $-(C=O)-NR_{31}-(C=O)-R_{32}$; wherein said $C_{1-6}$ alkyl group is unsubstituted or substituted with 1 to 3 substituents independently selected from $-OH$, $-OC_{1-6}$ alkyl, $-SC_{1-6}$ alkyl, $-Het_5$, and $-NR_{25}R_{26}$;

$R_9$ is $-NR_{36}-(C=O)-NR_{34}R_{35}$, $-NR_{34}-(SO_2)-R_{35}$, $-NR_{34}-(C=O)-O-R_{35}$, or $-O-(C=O)-NR_{34}R_{35}$; and $Z_1$, $Z_2$, $Z_3$, $Z_4$ and $Z_5$ are each C.

4. The method of claim 1, wherein:

$X_1$ is $-O-C_{1-6}$ alkyl-, $-NR_3-(C=O)-C_{1-6}$ alkyl-, $-(C=O)-NR_3-C_{1-6}$ alkyl-, $-NR_3-C_{1-6}$ alkyl-, $-C_{1-6}$ alkyl-$NR_3-C_{1-6}$ alkyl-, or $-SO_2-NR_3-$; wherein said $C_{1-6}$ alkyl group is unsubstituted or substituted with 1 to 3 $-C_{1-6}$ alkyl groups;

$X_2$ is $-O-C_{1-6}$ alkyl-, $-S-C_{1-6}$ alkyl-, or $-NR_2-C_{1-6}$ alkyl-;

B is $-(C=O)-NR_5-$, $-NR_5-(C=O)-NR_7-$, $-SO_2-NR_5-$, $-NR_6-$, $-NR_5-(C=O)-O-$, or $-CHR_8-$;

$R_1$ is $-H$, -halo, $-C_{1-6}$ alkyl, $-O-C_{1-6}$ alkyl, $-(C=O)-R_4$, or $-CN$; wherein said $C_{1-6}$ alkyl group is unsubstituted or substituted with 1 to 3 $-OH$ groups;

$R_2$ is $-H$ or $-C_{1-6}$ alkyl; wherein said $C_{1-6}$ alkyl is unsubstituted or substituted with 1 to 3 substituents independently selected from $-OH$, $-O-C_{1-6}$ alkyl, and $-NR_{13}R_{14}$;

$R_3$ is $-H$ or $-C_{1-6}$ alkyl;

$R_4$ is $-NR_{17}R_{18}$;

$R_5$ and $R_7$ are each independently $-H$ or $-C_{1-6}$ alkyl; wherein said $C_{1-6}$ alkyl is unsubstituted or substituted with 1 to 3 substituents independently selected from -halo and $-NR_{23}R_{24}$;

$R_6$ is $-SO_2$, $-(C=O)-O-C_{1-6}$ alkyl, $-(C=O)-C_{1-6}$ alkyl, $-(C=O)-C_{2-6}$ alkenyl, $-C_{1-6}$ alkyl-$(C=O)-NR_{31}R_{32}$, $-SO_2-C_{3-5}$ cycloalkyl, $-(C=O)-C_{3-5}$ cycloalkyl, $-(C=O)-NR_{31}R_{32}$, $-(C=O)-Het_5$, or $-(C=O)-Ar_6$; wherein said $C_{1-6}$ alkyl group is unsubstituted or substituted with 1 to 3 substituents independently selected from -halo, $-OH$, $-OC_{1-6}$ alkyl, $-Het_5$, and $-NR_{25}R_{26}$;

$R_8$ is $-NR_{34}-(C=O)-R_{35}$;

$R_{13}$, $R_{14}$, $R_{17}$, $R_{18}$, $R_{23}$, $R_{24}$, $R_{25}$, $R_{26}$, $R_{31}$, $R_{32}$, $R_{34}$, and $R_{35}$ are each independently $-H$, $-C_{1-6}$ alkyl, or $-C_{3-6}$ cycloalkyl;

$Ar_6$ is a 5- or 6-membered aryl or a 5- or 6-membered heteroaryl comprising 1 or 2 heteroatoms which are independently O, N or S; and $Het_5$ is a 5- or 6-membered monocyclic heterocycle having 1 to 3 heteroatoms which are independently O, N or S, wherein said heterocycle is unsubstituted or substituted with from 1 to 3 $-C_{1-6}$ alkyl groups; each said $-C_{1-6}$ alkyl group being unsubstituted or substituted with 1 to 3 -halo substituents.

5. The method of claim 1, wherein $A_1$ is N;

$A_2$ is C;

$X_1$ is $-O-C_{1-6}$ alkyl or $-NR_3-C_{1-6}$ alkyl-;

$X_2$ is $-NR_2-C_{1-6}$ alkyl-;

B is $-(C=O)-NR_5-$ or $-NR_6-$;

$R_1$, $R_2$, $R_3$ and $R_5$ are each $-H$;

$R_6$ is $-(C=O)-C_{1-6}$ alkyl, $-(C=O)-C_{3-5}$ cycloalkyl, or $-(C=O)-NR_{31}R_{32}$; wherein said $C_{1-6}$ alkyl group is unsubstituted or substituted with 1 to 3 $-NR_{25}R_{26}$ groups;

$R_{25}$ and $R_{26}$, are each independently $-H$ or $-C_{1-6}$ alkyl;

$R_{31}$ and $R_{32}$ are each $-H$; and $Z_1$, $Z_2$, $Z_3$, $Z_4$ and $Z_5$ are each C.

6. A method of claim 1, wherein said compound is:

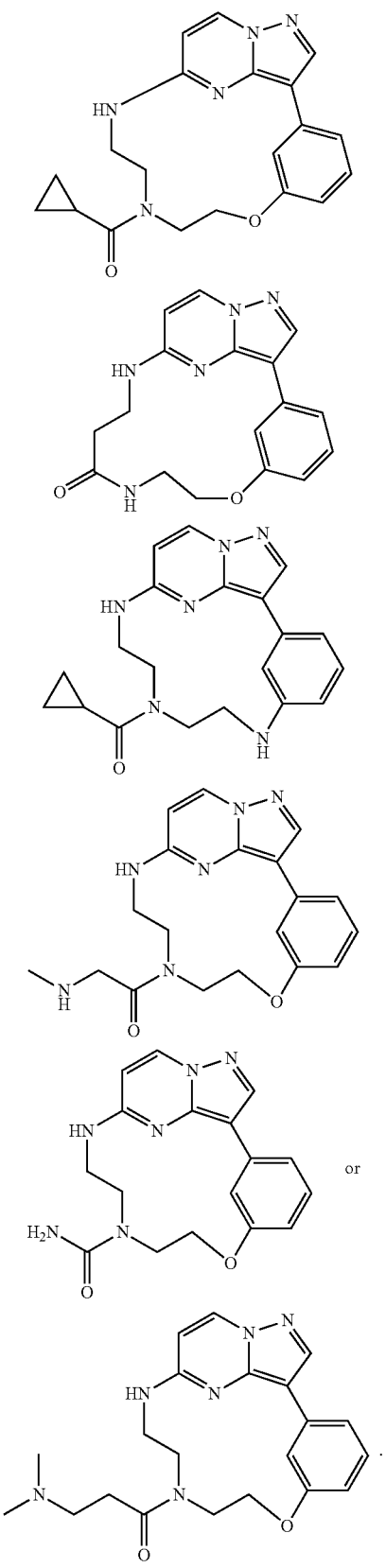

7. The method of claim 1, wherein the bicyclic ring including $A_1$ and $A_2$ is linked to the ring including $Z_1$-$Z_5$ at position $Z_1$ or $Z_2$.

8. The method of claim 1, wherein $R_1$ is linked to the ring including $Z_1$-$Z_5$ at position $Z_3$, $Z_4$ or $Z_5$.

9. A method of treating Parkinson's disease comprising administering to a subject in need thereof a therapeutically effective amount of a compound, wherein said compound is

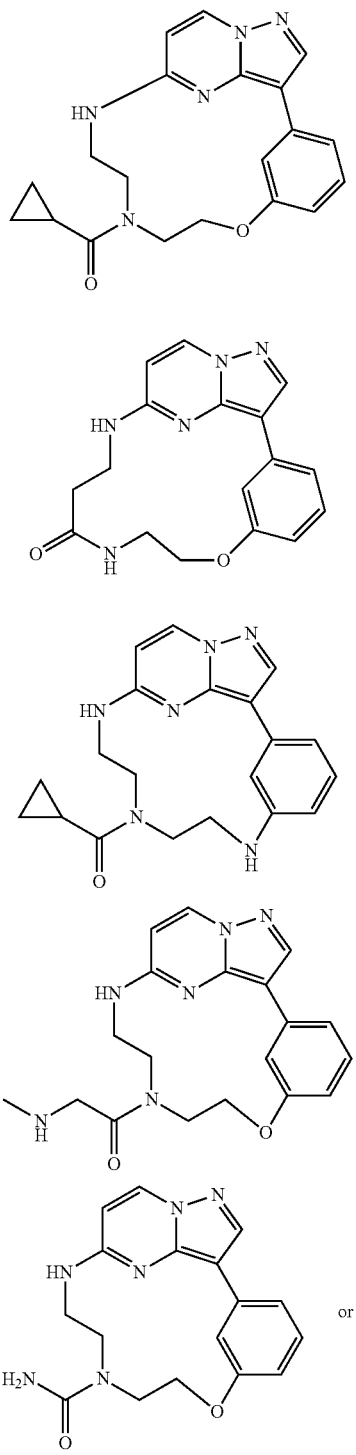

-continued
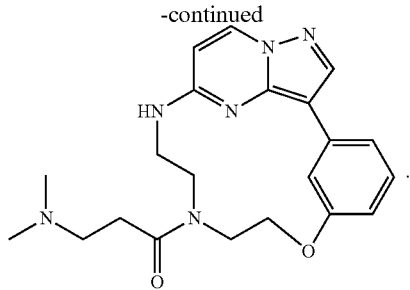
* * * * *